(12) United States Patent
Davidson et al.

(10) Patent No.: US 12,194,230 B2
(45) Date of Patent: Jan. 14, 2025

(54) METHODS, DEVICES AND SYSTEMS FOR PULMONARY DELIVERY OF ACTIVE AGENTS

(71) Applicant: Syqe Medical Ltd., Tel-Aviv (IL)

(72) Inventors: Perry Davidson, Tel-Aviv (IL); Shlomo Almog, Reut (IL); Seth Kindler, Tel-Aviv (IL)

(73) Assignee: Syqe Medical Ltd., Tel-Aviv (IL)

( * ) Notice: Subject to any disclaimer, the term of this patent is extended or adjusted under 35 U.S.C. 154(b) by 131 days.

(21) Appl. No.: 17/694,764

(22) Filed: Mar. 15, 2022

(65) Prior Publication Data

US 2022/0211958 A1 Jul. 7, 2022

Related U.S. Application Data

(63) Continuation of application No. 16/030,967, filed on Jul. 10, 2018, now Pat. No. 11,298,477, which is a (Continued)

(51) Int. Cl.
*A61M 15/00* (2006.01)
*A61K 9/00* (2006.01)
(Continued)

(52) U.S. Cl.
CPC ......... *A61M 15/0028* (2013.01); *A61K 9/007* (2013.01); *A61K 9/0073* (2013.01); (Continued)

(58) Field of Classification Search
CPC ............... A61M 16/14; A61M 16/20; A61M 2205/0216; A61M 2205/3303; (Continued)

(56) References Cited

U.S. PATENT DOCUMENTS 3,203,432 A 8/1965 Green et al.
3,894,544 A 7/1975 Egri
(Continued)

FOREIGN PATENT DOCUMENTS

AU 199641966 5/1996
AU 708269 7/1999
(Continued)

OTHER PUBLICATIONS

"IPhone 4 Technical Specifications", published Feb. 12, 2014, Apple, Inc.*
(Continued)

*Primary Examiner* — Valerie L Woodward

(57) ABSTRACT

Provided herein is a method of pulmonary delivering to a subject at least one pharmacologically active agent being in a plant material, which is effected by pulmonary delivering the agent to the subject using a metered dose inhaler device that is configured to vaporize at least one pre-determined vaporized amount of the agent upon controllably heating the plant material, wherein the pre-determined vaporized amount is selected so as to achieve at least one pre-determined pharmacokinetic effect and/or at least one pre-determined pharmacodynamic effect induced by the agent in the subject.

19 Claims, 21 Drawing Sheets

Related U.S. Application Data continuation of application No. 15/375,098, filed on Dec. 11, 2016, now Pat. No. 10,118,006, which is a continuation of application No. PCT/IL2015/050674, filed on Jun. 30, 2015, and a continuation of application No. PCT/IL2015/050675, filed on Jun. 30, 2015, and a continuation of application No. PCT/IL2015/050676, filed on Jun. 30, 2015.

(60) Provisional application No. 62/164,710, filed on May 21, 2015, provisional application No. 62/086,208, filed on Dec. 2, 2014, provisional application No. 62/085,772, filed on Dec. 1, 2014, provisional application No. 62/035,588, filed on Aug. 11, 2014, provisional application No. 62/019,225, filed on Jun. 30, 2014.

(51) Int. Cl.

| | | |
|---|---|---|
| *A61K 31/05* | (2006.01) | |
| *A61K 31/352* | (2006.01) | |
| *A61K 31/465* | (2006.01) | |
| *A61K 36/185* | (2006.01) | |
| *A61K 36/81* | (2006.01) | |
| *A61M 11/02* | (2006.01) | |
| *A61M 11/04* | (2006.01) | |
| *A61M 15/06* | (2006.01) | |
| *A61M 16/14* | (2006.01) | |
| *A61M 16/20* | (2006.01) | |
| *H05B 1/02* | (2006.01) | |

(52) U.S. Cl.
CPC ............ *A61K 31/05* (2013.01); *A61K 31/352* (2013.01); *A61K 31/465* (2013.01); *A61K 36/185* (2013.01); *A61K 36/81* (2013.01); *A61M 11/041* (2013.01); *A61M 11/042* (2014.02); *A61M 15/0001* (2014.02); *A61M 15/0003* (2014.02); *A61M 15/0013* (2014.02); *A61M 15/0015* (2014.02); *A61M 15/002* (2014.02); *A61M 15/0045* (2013.01); *A61M 15/005* (2014.02); *A61M 15/0051* (2014.02); *A61M 15/0065* (2013.01); *A61M 15/0066* (2014.02); *A61M 15/06* (2013.01); *A61M 16/14* (2013.01); *A61M 16/20* (2013.01); *H05B 1/025* (2013.01); *A61M 11/02* (2013.01); *A61M 15/0021* (2014.02); *A61M 15/0091* (2013.01); *A61M 2205/0216* (2013.01); *A61M 2205/3303* (2013.01); *A61M 2205/3331* (2013.01); *A61M 2205/3334* (2013.01); *A61M 2205/3368* (2013.01); *A61M 2205/3569* (2013.01); *A61M 2205/3592* (2013.01); *A61M 2205/36* (2013.01); *A61M 2205/502* (2013.01); *A61M 2205/52* (2013.01)

(58) Field of Classification Search
CPC .. A61M 2205/3331; A61M 2205/3334; A61M 2205/3368; A61M 2205/3569; A61M 2205/3592; A61M 2205/36; A61M 2205/502; A61M 2205/52; H05B 1/025; A61K 9/007; A61K 9/0073; A61K 31/05; A61K 31/352; A61K 31/465; A61K 36/185; A61K 36/81

See application file for complete search history.

(56) References Cited

U.S. PATENT DOCUMENTS

| | | |
|---|---|---|
| 4,603,030 A | 7/1986 | McCarthy |
| 4,735,358 A | 4/1988 | Morita et al. |
| 4,966,171 A | 10/1990 | Serrano et al. |
| 4,969,477 A | 11/1990 | Yagisawa |
| 5,023,020 A | 6/1991 | Machida et al. |
| 5,086,978 A | 2/1992 | Fertig |
| 5,105,838 A | 4/1992 | White et al. |
| 5,301,666 A | 4/1994 | Lerk et al. |
| 5,333,106 A | 7/1994 | Lanpher et al. |
| 5,388,594 A | 2/1995 | Counts et al. |
| 5,404,871 A | 4/1995 | Goodman et al. |
| 5,443,606 A | 8/1995 | Hassenboehler, Jr. et al. |
| 5,479,948 A | 1/1996 | Counts et al. |
| 5,503,869 A | 4/1996 | Van Oort |
| 5,546,965 A | 8/1996 | White |
| 5,565,148 A | 10/1996 | Pendergrass, Jr. |
| 5,649,554 A | 7/1997 | Sprinkel et al. |
| 5,655,520 A | 8/1997 | Howe et al. |
| 5,792,057 A | 8/1998 | Rubsamen et al. |
| 5,805,768 A | 9/1998 | Schwartz et al. |
| 5,819,756 A | 10/1998 | Miclordt |
| 5,855,564 A | 1/1999 | Ruskcwicz |
| 6,547,229 B1 | 4/2003 | Hanson et al. |
| 6,703,418 B2 | 3/2004 | Plasse |
| 6,713,024 B1 | 3/2004 | Arnell et al. |
| 6,761,164 B2 | 7/2004 | Amirpour et al. |
| 6,871,647 B2 | 3/2005 | Allan et al. |
| 7,088,914 B2 | 8/2006 | Whittle et al. |
| 7,169,378 B2 | 1/2007 | Rabinowitz et al. |
| 7,287,530 B1 | 10/2007 | Stuart |
| 7,376,344 B2 | 5/2008 | Manne |
| 7,389,943 B2 | 6/2008 | Jaworski |
| 7,537,005 B2 | 5/2009 | Dave |
| 7,690,076 B2 | 6/2010 | Tannous |
| 7,987,846 B2 | 8/2011 | Hale et al. |
| 8,235,037 B2 | 8/2012 | Hale et al. |
| 8,408,200 B2 | 4/2013 | Clark et al. |
| 8,490,627 B2 | 7/2013 | Levin et al. |
| 8,615,407 B2 | 12/2013 | Hyde et al. |
| 9,775,379 B2 | 10/2017 | Davidson et al. |
| 9,802,011 B2 | 10/2017 | Davidson et al. |
| 9,943,114 B2 | 4/2018 | Batista |
| 9,993,602 B2 | 6/2018 | Davidson et al. |
| 10,080,851 B2 | 9/2018 | Davidson et al. |
| 10,179,215 B2 | 1/2019 | Raichman |
| 10,299,515 B2 | 5/2019 | Krietzmam |
| 11,006,661 B2 | 5/2021 | Valadi |
| 11,044,950 B2 | 6/2021 | Collett et al. |
| 11,071,712 B2 | 7/2021 | Davidson et al. |
| 2001/0027789 A1 | 10/2001 | Goede et al. |
| 2002/0078951 A1 | 6/2002 | Nichols et al. |
| 2002/0168322 A1 | 11/2002 | Clark et al. |
| 2003/0037785 A1 | 2/2003 | Sonntag |
| 2003/0041859 A1 | 3/2003 | Abrams et al. |
| 2003/0049025 A1 | 3/2003 | Neumann et al. |
| 2003/0062042 A1 | 4/2003 | Wensley et al. |
| 2003/0136420 A1 | 7/2003 | Kraker |
| 2003/0163099 A1 | 8/2003 | Wermeling et al. |
| 2003/0168057 A1 | 9/2003 | Snyder et al. |
| 2003/0200964 A1 | 10/2003 | Blakley et al. |
| 2004/0045567 A1 | 3/2004 | Lewis et al. |
| 2004/0069798 A1 | 4/2004 | Grey et al. |
| 2004/0084044 A1 | 5/2004 | Childers et al. |
| 2004/0099266 A1 | 5/2004 | Cross et al. |
| 2004/0188546 A1 | 9/2004 | Tabata et al. |
| 2004/0192760 A1 | 9/2004 | Whittle et al. |
| 2004/0234699 A1 | 11/2004 | Hale et al. |
| 2005/0063686 A1 | 3/2005 | Whittle et al. |
| 2005/0126562 A1 | 6/2005 | Rabinowitz et al. |
| 2005/0244521 A1 | 11/2005 | Strickland et al. |
| 2005/0268909 A1 | 12/2005 | Bonney et al. |
| 2005/0268911 A1 | 12/2005 | Cross et al. |
| 2006/0102175 A1 | 5/2006 | Nelson |
| 2006/0120962 A1 | 6/2006 | Rabinowitz et al. |
| 2006/0157491 A1 | 7/2006 | Whittle et al. |
| 2006/0167084 A1 | 7/2006 | Dudley |
| 2006/0258738 A1 | 11/2006 | Dieterich |
| 2007/0023060 A1 | 2/2007 | Ra |
| 2007/0072938 A1 | 3/2007 | Rose |
| 2007/0122353 A1 | 3/2007 | Hale et al. |
| 2007/0074721 A1 | 4/2007 | Harmer et al. |

(56) References Cited

U.S. PATENT DOCUMENTS

| | | |
|---|---|---|
| 2007/0102013 A1 | 5/2007 | Adams et al. |
| 2007/0163580 A1 | 7/2007 | Braithwaite |
| 2007/0209661 A1 | 9/2007 | Smyth et al. |
| 2007/0240712 A1 | 10/2007 | Fleming et al. |
| 2007/0286816 A1 | 12/2007 | Hale et al. |
| 2008/0072898 A1 | 3/2008 | Quoniam |
| 2008/0078382 A1 | 4/2008 | LeMahieu et al. |
| 2008/0140250 A1 | 6/2008 | Dave |
| 2008/0159961 A1 | 7/2008 | Woolfe et al. |
| 2008/0176885 A1 | 7/2008 | Holtman et al. |
| 2008/0181942 A1 | 7/2008 | Zajicek |
| 2008/0199161 A1 | 8/2008 | Hickey et al. |
| 2008/0202515 A1 | 8/2008 | Hodson et al. |
| 2008/0299048 A1 | 12/2008 | Hale et al. |
| 2008/0308101 A1 | 12/2008 | Spandorfer |
| 2008/0311176 A1 | 12/2008 | Hale et al. |
| 2009/0060287 A1* | 3/2009 | Hyde .............. A61B 5/7435 382/118 |
| 2009/0084865 A1 | 4/2009 | Maharajh |
| 2009/0151722 A1 | 6/2009 | Eason et al. |
| 2009/0194105 A1 | 8/2009 | Besseller et al. |
| 2009/0197941 A1 | 8/2009 | Guy et al. |
| 2009/0241949 A1 | 10/2009 | Smutney et al. |
| 2009/0281398 A1* | 11/2009 | Hogan ................ A61B 5/162 463/7 |
| 2009/0293888 A1 | 12/2009 | Williams et al. |
| 2009/0293892 A1 | 12/2009 | Williams et al. |
| 2009/0308390 A1 | 12/2009 | Smutney et al. |
| 2009/0320836 A1 | 12/2009 | Baker, Jr. |
| 2010/0012118 A1 | 1/2010 | Storz |
| 2010/0035978 A1 | 2/2010 | Guy et al. |
| 2010/0154795 A1 | 6/2010 | Pentafragas |
| 2010/0168228 A1 | 7/2010 | Bose |
| 2010/0181387 A1 | 7/2010 | Zaffaroni et al. |
| 2010/0204602 A1 | 8/2010 | Addington et al. |
| 2010/0250280 A1 | 9/2010 | Sutherland |
| 2010/0294278 A1 | 11/2010 | Mosier et al. |
| 2010/0300442 A1 | 12/2010 | Houzego et al. |
| 2010/0326438 A1 | 12/2010 | Dunne |
| 2011/0030706 A1 | 2/2011 | Gibson et al. |
| 2011/0036346 A1 | 2/2011 | Cohen et al. |
| 2011/0038958 A1 | 2/2011 | Kikuchi et al. |
| 2011/0126831 A1 | 6/2011 | Fernandez Pernia |
| 2011/0240011 A1 | 10/2011 | Caldwell |
| 2011/0244020 A1 | 10/2011 | Hale et al. |
| 2011/0265806 A1 | 11/2011 | Alarcon et al. |
| 2012/0003318 A1 | 1/2012 | Schuler et al. |
| 2012/0006700 A1 | 1/2012 | Geboers et al. |
| 2012/0116241 A1 | 5/2012 | Shie et al. |
| 2012/0252885 A1 | 10/2012 | Barbato |
| 2012/0255546 A1 | 10/2012 | Goetz et al. |
| 2012/0291781 A1 | 11/2012 | Kaufmann et al. |
| 2012/0291791 A1 | 11/2012 | Pradeep |
| 2012/0304990 A1 | 12/2012 | Todd |
| 2012/0325227 A1 | 12/2012 | Robinson et al. |
| 2013/0032139 A1 | 2/2013 | Hale et al. |
| 2013/0053719 A1 | 2/2013 | Wekell |
| 2013/0081623 A1 | 4/2013 | Buchberger |
| 2013/0087144 A1 | 4/2013 | Todd |
| 2013/0112197 A1 | 5/2013 | Kruener et al. |
| 2013/0213397 A1 | 8/2013 | Curtis et al. |
| 2013/0218588 A1 | 8/2013 | Kchr et al. |
| 2013/0269694 A1 | 10/2013 | Patton et al. |
| 2013/0276799 A1* | 10/2013 | Davidson .......... A61M 15/0051 131/273 |
| 2013/0304502 A1* | 11/2013 | Cederlund ........ G06Q 30/0203 705/2 |
| 2013/0304990 A1 | 11/2013 | Bass et al. |
| 2013/0333700 A1 | 12/2013 | Buchberger |
| 2014/0037794 A1 | 2/2014 | Patera et al. |
| 2014/0060525 A1 | 3/2014 | Hale et al. |
| 2014/0088045 A1 | 3/2014 | Rigas et al. |
| 2014/0100249 A1 | 4/2014 | Sears et al. |
| 2014/0106324 A1 | 4/2014 | Adams et al. |
| 2014/0144429 A1 | 5/2014 | Wensley et al. |
| 2014/0190496 A1* | 7/2014 | Wensley .............. A61M 11/042 131/273 |
| 2014/0202454 A1 | 7/2014 | Buchberger |
| 2014/0209105 A1 | 7/2014 | Sears et al. |
| 2014/0238423 A1 | 8/2014 | Tucker et al. |
| 2014/0366898 A1 | 12/2014 | Monsees et al. |
| 2015/0064672 A1 | 3/2015 | Bars |
| 2015/0075521 A1 | 3/2015 | Lee et al. |
| 2015/0090253 A1 | 4/2015 | Farrow |
| 2015/0122252 A1 | 5/2015 | Frija |
| 2015/0136124 A1 | 5/2015 | Aronie et al. |
| 2015/0237913 A1 | 8/2015 | Suzuki et al. |
| 2016/0007653 A1 | 1/2016 | Tu |
| 2016/0044960 A1 | 2/2016 | O'Connor |
| 2016/0089508 A1* | 3/2016 | Smith ............... A61M 15/0085 128/202.21 |
| 2016/0100624 A1 | 4/2016 | Yilmaz et al. |
| 2016/0121057 A1 | 5/2016 | Dyche et al. |
| 2016/0166564 A1 | 6/2016 | Myers et al. |
| 2016/0166786 A1 | 6/2016 | Kinzer |
| 2016/0171164 A1 | 6/2016 | Kinzer |
| 2016/0183589 A1 | 6/2016 | Born et al. |
| 2016/0219938 A1 | 8/2016 | Mamoun et al. |
| 2016/0271347 A1 | 9/2016 | Raichman |
| 2016/0286860 A1 | 10/2016 | Flayler |
| 2016/0295922 A1 | 10/2016 | John et al. |
| 2016/0309774 A1 | 10/2016 | Wand |
| 2016/0309784 A1 | 10/2016 | Silvestrini et al. |
| 2016/0331022 A1 | 11/2016 | Cameron |
| 2016/0331913 A1 | 11/2016 | Bourque |
| 2016/0345630 A1 | 12/2016 | Mironov et al. |
| 2016/0354573 A1 | 12/2016 | Buswell et al. |
| 2017/0072145 A1* | 3/2017 | Hadash .............. A61M 15/009 |
| 2017/0095624 A1 | 4/2017 | Davidson et al. |
| 2017/0106153 A1 | 4/2017 | Davidson et al. |
| 2017/0119979 A1 | 5/2017 | Davidson et al. |
| 2017/0119981 A1 | 5/2017 | Davidson et al. |
| 2017/0127727 A1 | 5/2017 | Davidson et al. |
| 2017/0136196 A1 | 5/2017 | Davidson et al. |
| 2017/0150755 A1 | 6/2017 | Batista |
| 2017/0157341 A1 | 6/2017 | Pandya |
| 2017/0157343 A1 | 6/2017 | Davidson et al. |
| 2017/0164657 A1 | 6/2017 | Batista |
| 2017/0203058 A1 | 7/2017 | Davidson et al. |
| 2017/0295848 A1 | 10/2017 | LaMothe |
| 2017/0304567 A1 | 10/2017 | Adelson |
| 2017/0360089 A1 | 12/2017 | Davidson et al. |
| 2018/0043115 A1 | 2/2018 | Gould et al. |
| 2018/0110943 A1 | 4/2018 | Raichman |
| 2018/0263288 A1 | 9/2018 | Goldstein et al. |
| 2018/0318529 A1 | 11/2018 | Davidson et al. |
| 2018/0344954 A1 | 12/2018 | Davidson et al. |
| 2019/0001087 A1 | 1/2019 | Davidson et al. |
| 2019/0009039 A1 | 1/2019 | Davidson et al. |
| 2019/0015382 A1 | 1/2019 | Davidson et al. |
| 2019/0124982 A1 | 5/2019 | Atkins et al. |
| 2019/0183185 A1 | 6/2019 | Manas et al. |
| 2019/0290862 A1 | 9/2019 | Davidson et al. |
| 2021/0023316 A1 | 1/2021 | Schorr et al. |
| 2021/0236414 A1 | 8/2021 | Davidson et al. |
| 2021/0402109 A1 | 12/2021 | Landa et al. |
| 2022/0031972 A1 | 2/2022 | Davidson et al. |
| 2022/0096760 A1 | 3/2022 | Schwartz et al. |
| 2022/0183962 A1 | 6/2022 | Davidson et al. |
| 2022/0241523 A1 | 8/2022 | Davidson et al. |
| 2023/0390186 A1 | 12/2023 | Davidson et al. |

FOREIGN PATENT DOCUMENTS

| | | |
|---|---|---|
| CA | 2599022 | 9/2005 |
| CA | 3025407 | 11/2017 |
| CN | 1323231 | 11/2001 |
| CN | 2816102 | 9/2006 |
| CN | 1925883 | 3/2007 |
| CN | 101053685 | 10/2007 |
| CN | 101130121 | 2/2008 |
| CN | 101132823 | 2/2008 |
| CN | 101360528 | 2/2009 |
| CN | 101415457 | 4/2009 |

(56) References Cited

FOREIGN PATENT DOCUMENTS

| | | |
|---|---|---|
| CN | 101980743 | 2/2011 |
| CN | 102355914 | 2/2012 |
| CN | 102438602 | 5/2012 |
| CN | 203166473 | 8/2013 |
| CN | 106659858 | 5/2017 |
| CN | 108260855 | 7/2018 |
| CN | 108712918 | 10/2018 |
| EA | 201100197 | 3/2012 |
| EP | 0216926 | 3/1991 |
| EP | 0539674 | 5/1993 |
| EP | 0547429 | 6/1993 |
| EP | 1358902 | 11/2003 |
| EP | 2145643 | 1/2010 |
| EP | 2292108 | 3/2011 |
| EP | 3160553 | 5/2017 |
| GB | 2108390 | 5/1983 |
| GB | 2340758 | 3/2000 |
| GB | 2456183 | 7/2009 |
| GB | 2495771 | 4/2013 |
| JP | 2002-527151 | 8/2002 |
| JP | 2003-503117 | 1/2003 |
| JP | 2003-079731 | 3/2003 |
| JP | 2003-275214 | 9/2003 |
| JP | 2004-283609 | 10/2004 |
| JP | 2004-298331 | 10/2004 |
| JP | 2005-503846 | 2/2005 |
| JP | 2005-516644 | 6/2005 |
| JP | 2005-516647 | 6/2005 |
| JP | 2006-507909 | 3/2006 |
| JP | 2007-0516015 | 6/2007 |
| JP | 2008-501406 | 1/2008 |
| JP | 2008-525108 | 7/2008 |
| JP | 2008-301847 | 12/2008 |
| JP | 2009-509523 | 3/2009 |
| JP | 2009-131686 | 6/2009 |
| JP | 2011-508765 | 3/2011 |
| JP | 2012-110499 | 6/2012 |
| JP | 2012-527329 | 11/2012 |
| JP | 2013-521074 | 6/2013 |
| JP | 2013-521075 | 6/2013 |
| JP | 2013-523395 | 6/2013 |
| JP | 2017-523828 | 8/2017 |
| JP | 2020-062479 | 4/2020 |
| KR | 10-1319228 | 10/2013 |
| KR | 10-2017-0024084 | 3/2017 |
| RU | 2413544 | 3/2011 |
| RU | 107026 | 8/2011 |
| RU | 2460677 | 9/2012 |
| RU | 2017102234 | 7/2018 |
| WO | WO 91/11120 | 8/1991 |
| WO | WO 94/09842 | 5/1994 |
| WO | WO 96/32854 | 10/1996 |
| WO | WO 98/04308 | 2/1998 |
| WO | WO 00/21594 | 4/2000 |
| WO | WO 00/21598 | 4/2000 |
| WO | WO 00/24362 | 5/2000 |
| WO | WO 01/00263 | 1/2001 |
| WO | WO 01/17595 | 3/2001 |
| WO | WO 03/020057 | 3/2003 |
| WO | WO 03/030979 A1 | 4/2003 |
| WO | WO 03/037412 | 5/2003 |
| WO | WO 2005/061033 | 7/2005 |
| WO | WO 2005/072719 | 8/2005 |
| WO | WO 2005/072792 | 8/2005 |
| WO | WO 2005/120614 | 12/2005 |
| WO | WO 2006/071512 | 7/2006 |
| WO | WO 2007/018568 | 2/2007 |
| WO | WO 2007/042941 | 4/2007 |
| WO | WO 2008/024408 | 2/2008 |
| WO | WO 2008/024490 | 2/2008 |
| WO | WO 2008/116165 | 9/2008 |
| WO | WO 2009/102976 | 8/2009 |
| WO | WO 2009/124552 | 10/2009 |
| WO | WO 2010/015260 | 2/2010 |
| WO | WO 2011/073306 | 6/2011 |
| WO | WO 2011/130183 | 10/2011 |
| WO | WO 2012/006125 | 1/2012 |
| WO | WO 2012/006126 | 1/2012 |
| WO | WO 2012/026963 | 3/2012 |
| WO | WO 2012/038903 | 3/2012 |
| WO | WO 2012/085919 | 6/2012 |
| WO | WO 2013/013808 | 1/2013 |
| WO | WO 2013/057185 | 4/2013 |
| WO | WO 2013/060781 | 5/2013 |
| WO | WO 2013/083636 | 6/2013 |
| WO | WO 2014/037794 | 3/2014 |
| WO | WO 2014/053242 | 4/2014 |
| WO | WO 2014/061477 | 4/2014 |
| WO | WO 2014/085719 | 6/2014 |
| WO | WO 2015/123064 | 8/2015 |
| WO | WO 2015/123317 | 8/2015 |
| WO | WO 2015/175979 | 11/2015 |
| WO | WO 2016/001921 | 1/2016 |
| WO | WO 2016/001922 | 1/2016 |
| WO | WO 2016/001923 | 1/2016 |
| WO | WO 2016/001924 | 1/2016 |
| WO | WO 2016/001925 | 1/2016 |
| WO | WO 2016/001926 | 1/2016 |
| WO | WO 2016/090303 | 6/2016 |
| WO | WO 2016/147188 | 9/2016 |
| WO | WO 2016/172802 | 11/2016 |
| WO | WO 2016/187695 | 12/2016 |
| WO | WO 2016/187696 | 12/2016 |
| WO | WO 2017/118980 | 7/2017 |
| WO | WO 2017/122196 | 7/2017 |
| WO | WO 2017/122201 | 7/2017 |
| WO | WO 2017/178958 | 10/2017 |
| WO | WO 2017/185051 | 10/2017 |
| WO | WO 2018/019855 | 2/2018 |
| WO | WO 2019/159170 | 8/2019 |
| WO | WO 2020/089890 | 5/2020 |
| WO | WO 2020/161721 | 8/2020 |
| WO | WO 2013/052586 | 3/2021 |

OTHER PUBLICATIONS

Requisition by the Examiner Dated May 25, 2022 From the Innovation, Science and Economic Development Canada, Canadian Intellectual Property Office Re. Application No. 3,114,582. (3 Pages).
Ground(s) of Reason of Rejection Dated Nov. 21, 2022 From the Korean Intellectual Property Office Re. Application No. 10-2022-7038127 and its Translation into English. (5 Pages).
Requisition by the Examiner Dated Nov. 28, 2022 From the Innovation, Science and Economic Development Canada, Canadian Intellectual Property Office Re. Application No. 2,953,069 with Claims. (17 Pages).
Requisition by the Examiner Dated Nov. 28, 2022 From the Innovation, Science and Economic Development Canada, Canadian Intellectual Property Office Rc. Application No. 2,953,073. (3 Pagcs).
Official Action Dated Dec. 20, 2023 from the US Patent and Trademark Office Re. U.S. Appl. No. 16/969,612. (61 pages).
Request for Examination and Search Report Dated Nov. 16, 2023 From the (ROSPATENT), Federal Government Institution of Industrial Property of the Federal Service of Intellectual Property, Patents and Trademark of the Russian Federation Re. Application No. 2021125574 and It's Machine translation into English. (15 Pages).
Notice of Reason(s) for Rejection Dated Nov. 7, 2023 From the Japan Patent Office Re. Application No. 2021-522537. (4 Pages).
Official Action Dated Mar. 30, 2023 From the US Patent and Trademark Office Re. U.S. Appl. No. 17/679,190. (287 Pages).
Translation Dated Mar. 30, 2023 of Request for Examination and Search Report Dated Feb. 16, 2023 From the (ROSPATENT), Federal Government Institution of Industrial Property of the Federal Service of Intellectual Property, Patents and Trademark of the Russian Federation Re. Application No. 202111628 and its Summary in English.(7 Pages).
Notice of Reason(s) for Rejection Dated May 16, 2023 From the Japan Patent Office Re. Application No. 2021-522537 and Its Translation Into English. (9 Pages).

(56) References Cited

OTHER PUBLICATIONS

Requisition by the Examiner Dated Mar. 11, 2022 From the Innovation, Science and Economic Development Canada, Canadian Intellectual Property Office Re. Application No. 2,953,082. (6 Pages).
Official Action Dated Oct. 26, 2023 from the US Patent and Trademark Office Re. U.S. Appl. No. 17/679,190. (91 pages).
Examination Report Dated Oct. 19, 2023 From the Australian Government, IP Australia Re. Application No. 2022211900. (8 Pages).
Notification of Office Action Dated Jun. 23, 2022 From the State Intellectual Property Office of the People's Republic of China Re. Application No. 20200101980.3. (8 Pages).
Decision on Rejection Dated Apr. 23, 2023 From the State Intellectual Property Office of the People's Republic of China Re. Application No. 201980081175.0. (8 pages).
English Summary Dated Apr. 26, 2023 of Notification of Office Action Dated Apr. 19, 2023 From the State Intellectual Property Office of the People's Republic of China Re. Application No. 202080027182.5. (2 pages).
Notification of Office Action and Search Report Dated Apr. 13, 2023 From the State Intellectual Property Office of the People's Republic of China Re. Application No. 202080027182.5 (11 pages).
Examination Report Dated May 29, 2022 From the Servico Publico Federal, Ministerio da Economia, Instituto Nacional da Propriedade Industrial do Brasil RE Application No. BR12 2020 018207 5 with Pending Claims and its English Summary. (8 Pages).
Examination Report Dated Aug. 31, 2023 From the Australian Government, IP Australia Re. Application No. 2021204365. (4 Pages).
Translation Dated Sep. 26, 2023 of Grounds of Reason of Rejection Dated Sep. 14, 2023 From the Korean Intellectual Property Office Re. Application No. 10-2023-7025097. (5 Pages).
Notification of Office Action and Search Report Dated Oct. 25, 2022 From the State Intellectual Property Office of the People's Republic of China Re. Application No. 202110926270.5 and Its Translation of Office Action Into English. (7 Pages).
Official Action Dated Oct. 26, 2022 from the US Patent and Trademark Office Re. U.S. Appl. No. 17/238,278. (156 pages).
Grasscity "How to Make Hush?, Discussion in 'Apprentice Marijuana Consuption' started by Juggalobud", Grasscity Forums, Retrieved from the Internet, Nov. 1, 2002 (17 pages).
UNODC "Recommended Methods for the Identification and Analysis of Cannabis and Cannabis Products", United Nations Office on Drugs, Crime, United Nations Publications, 1-50, Sep. 2009.
Verilife "Cannabis Trichomes: What Are They & What They Do?", Retrieved from the Internet, Nov. 29, 2021 (4 pages).
Interview Summary Dated Sep. 12, 2022 From the US Patent and Trademark Office Re. U.S. Appl. No. 16/068,373. (2 Pages).
Notice of Reasons for Rejection Dated Aug. 30, 2022 From the Japan Patent Office Re. Application No. 2021-175408 and Its Translation Into English. (12 Pages).
Notice of Reason(s) for Rejection Dated Jun. 13, 2023 From the Japan Patent Office Re. Application No. 2022-115378. (4 pages).
Grounds of Reason of Rejection Dated Sep. 14, 2023 From the Korean Intellectual Property Office Re. Application No. 10-2023-7025097. (5 Pages).
Interview Summary Dated Dec. 24, 2021 From the US Patent and Trademark Office Re. U.S. Appl. No. 16/068,373. (3 Pages).
Requisition by the Examiner Dated Apr. 4, 2022 From the Innovation, Science and Economic Development Canada, Canadian Intellectual Property Office Re. Application No. 2,953,074 with Claims. (11 Pages).
Notification of Office Action and Search Report Dated Oct. 16, 2023 From the National Intellectual Property Administration of the People's Republic of China Re. Application No. 202080027182.5 (5 Pages).
Notice of Allowance Dated Jun. 28, 2023 Together with Interview Summary Dated Jun. 13, 2023 from the US Patent and Trademark Office Re. U.S. Appl. No. 16/068,373. (39 pages).

Requisition by the Examiner Dated Jun. 27, 2023 From the Innovation, Science and Economic Development Canada, Canadian Intellectual Property Office Re. Application No. 3,114,582. (3 pages).
Notification of Office Action and Search Report Dated Jun. 27, 2022 From the State Intellectual Property Office of the People's Republic of China Re. Application No. 201980081175.0. (13 Pages).
Official Action Dated Jul. 6, 2022 from US Patent and Trademark Office Re. U.S. Appl. No. 16/068,373. (40 pages).
Perry et al.
English Summary Dated Oct. 30, 2023 of Notification of Office Action and Search Report Dated Oct. 16, 2023 From the National Intellectual Property Administration of the People's Republic of China Re. Application No. 202080027182.5 (2 Pages).
Notice of Reason(s) for Rejection Dated Oct. 24, 2023 From the Japan Patent Office Re. Application No. 2021-545436 and Its Translation Into English. (10 Pages).
Request for Examination and Search Report Dated Mar. 10, 2023 From the (ROSPATENT), Federal Government Institution of Industrial Property of the Federal Service of Intellectual Property, Patents and Trademark of the Russian Federation Re. Application No. 2021125574. (9 Pages).
Request for Examination and Search Report Dated Feb. 16, 2023 From the (ROSPATENT), Federal Government Institution of Industrial Property of the Federal Service of Intellectual Property, Patents and Trademark of the Russian Federation Re. Application No. 202111628 and its Summary in English. (12 Pages).
Requisition by the Examiner Dated Dec. 13, 2022 From the Innovation, Science and Economic Development Canada, Canadian Intellectual Property Office Re. Application No. 2,953,074 with claims. (11 pages).
Grounds of Reason of Rejection Dated Mar. 24, 2022 From the Korean Intellectual Property Office Re. Application No. 10-2017-7002682 and Its Translation Into English. (14 Pages).
Notice of Reasons for Rejection Dated Mar. 22, 2022 From the Japan Patent Office Re. Application No. 2020-101083 and Its Translation Into English. (7 Pages).
Patent Examination Report Dated Mar. 18, 2022 From the Australian Government, IP Australia Re. Application No. 2021204703 with claims. (7 Pages).
Patent Examination Report Dated Mar. 22, 2022 From the Australian Government, IP Australia Re. Application No. 2020205271 with amended Claims. (8 Pages).
Requisition by the Examiner Dated Mar. 29, 2022 From the Innovation, Science and Economic Development Canada, Canadian Intellectual Property Office Re. Application No. 2,953,069 with Claims. (15 Pages).
Requisition by the Examiner Dated Mar. 30, 2022 From the Innovation, Science and Economic Development Canada, Canadian Intellectual Property Office Re. Application No. 2,953,073 with Claims. (18 Pages).
Notice of Reasons for Rejection Dated May 24, 2022 From the Japan Patent Office Re. Application No. 2020-134166 and Its Translation Into English. (10 Pages).
English Summary Dated May 4, 2023 of Decision on Rejection Dated Apr. 23, 2023 From the State Intellectual Property Office of the People's Republic of China Re. Application No. 201980081175.0 (1 page).
Grounds of Reason of Rejection Dated Apr. 20, 2023 From the Korean Intellectual Property Office Re. Application No. 10-2022-7045372 and Its Translation Into English. (9 Pages).
Notice of Allowance Dated May 2, 2023 From the US Patent and Trademark Office Re. U.S. Appl. No. 17/238,278. (33 Pages).
Supplementary European Search Report and the European Search Opinion Dated Jul. 12, 2022 From the European Patent Office Re. Application No. 19880500.4. (11 Pages).
English Summary Dated Jul. 20, 2022 of Notification of Office Action and Search Report Dated Jun. 27, 2022 From the State Intellectual Property Office of the People's Republic of China Re. Application No. 201980081175.0. (1 Page).
Final Official Action Dated Nov. 30, 2022 from the US Patent and Trademark Office Re. U.S. Appl. No. 16/068,373. (15 pages).

(56) References Cited

OTHER PUBLICATIONS

Translation Dated Apr. 10, 2023 of Request for Examination and Search Report Dated Mar. 10, 2023 From the (ROSPATENT), Federal Government Institution of Industrial Property of the Federal Service of Intellectual Property, Patents and Trademark of the Russian Federation Re. Application No. 2021125574. (5 Pages).
Requisition by the Examiner Dated Jul. 5, 2023 From the Innovation, Science and Economic Development Canada, Canadian Intellectual Property Office Re. Application No. 2,953,073. (3 pages).
Supplementary European Search Report and the European Search Opinion Dated Nov. 14, 2022 From the European Patent Office Re. Application No. 20751958.8 (8 pages).
Examination Report Dated Jan. 11, 2023 From the Australian Government, IP Australia Re. Application No. 2021204365. (4 Pages).
Notice of Reason(s) for Rejection Dated Mar. 7, 2023 From the Japan Patent Office Re. Application No. 2021-175408 and Its Translation Into English. (5 Pages).
Applicant-Initiated Interview Summary Dated Apr. 5, 2018 From the US Patent and Trademark Office Re. U.S. Appl. No. 15/391,896. (3 pages).
Applicant-Initiated Interview Summary Dated Jan. 5, 2018 From the US Patent and Trademark Office Re. U.S. Appl. No. 15/382,819. (3 pages).
Applicant-Initiated Interview Summary Dated Dec. 22, 2017 From the US Patent and Trademark Office Re. U.S. Appl. No. 15/312,647. (3 pages).
Applicant-Initiated Interview Summary Dated Dec. 22, 2017 From the US Patent and Trademark Office Re. U.S. Appl. No. 15/362,883. (3 pages).
Applicant-Initiated Interview Summary Dated Mar. 22, 2018 From the US Patent and Trademark Office Re. U.S. Appl. No. 15/308,370. (5 pages).
Applicant-Initiated Interview Summary Dated May 22, 2017 From the US Patent and Trademark Office Re. Application No. 15/386,182. (3 pages).
Applicant-Initiated Interview Summary Dated May 23, 2017 From the US Patent and Trademark Office Re. U.S. Appl. No. 15/362,841. (3 pages).
Applicant-Initiated Interview Summary Dated May 23, 2017 From the US Patent and Trademark Office Re. U.S. Appl. No. 15/362,883. (3pages).
Applicant-Initiated Interview Summary Dated May 23, 2017 From the US Patent and Trademark Office Re. U.S. Appl. No. 15/375,098. (3 pages).
Applicant-Initiated Interview Summary Dated May 23, 2017 From the US Patent and Trademark Office Re. U.S. Appl. No. 15/382,819. (3 pages).
Applicant-Initiated Interview Summary Dated Dec. 30, 2019 From the US Patent and Trademark Office Re. U.S. Appl. No. 15/690,323. (4 pages).
Communication Pursuant to Article 94(3) EPC Dated Sep. 2, 2020 From the European Patent Office Re. Application No. 15756490.7. (5 Pages).
Communication Pursuant to Article 94(3) EPC Dated Aug. 4, 2020 From the European Patent Office Re. Application No. 15815982.2. (5 Pages).
Communication Pursuant to Article 94(3) EPC Dated Sep. 5, 2018 From the European Patent Office Re. Application No. 15744363.1. (4 Pages).
Communication Pursuant to Article 94(3) EPC Dated Feb. 6, 2019 From the European Patent Office Re. Application No. 15753782.0. (6 Pages).
Communication Pursuant to Article 94(3) EPC Dated Nov. 12, 2018 From the European Patent Office Re. Application No. 15814472.5. (5 Pages).
Communication Pursuant to Article 94(3) EPC Dated Nov. 12, 2018 From the European Patent Office Re. Application No. 15815982.2. (4 Pages).
Communication Pursuant to Article 94(3) EPC Dated Jan. 19, 2018 From the European Patent Office Re. Application No. 15744363.1. (4 Pages).
Communication Pursuant to Article 94(3) EPC Dated Nov. 19, 2018 From the European Patent Office Re. Application No. 15756490.7. (4 Pages).
Communication Pursuant to Article 94(3) EPC Dated Jan. 22, 2018 From the European Patent Office Re. Application No. 15756490.7. (4 Pages).
Communication Pursuant to Article 94(3) EPC Dated Jun. 23, 2017 From the European Patent Office Re. Application No. 11815728.8. (5 Pages).
Communication Pursuant to Article 94(3) EPC Dated Apr. 26, 2018 From the European Patent Office Re. Application No. 11815728.8. (4 Pages).
Communication Pursuant to Article 94(3) EPC Dated Feb. 26, 2018 From the European Patent Office Re. Application No. 15753782.0. (6 Pages).
Communication Relating to the Results of the Partial International Search Dated May 18, 2012 From the International Searching Authority Re. Application No. PCT/IL2011/050071.
Communication Relating to the Results of the Partial International Search Dated Oct. 22, 2015 From the International Searching Authority Re. Application No. PCT/IL2015/050673.
Communication Relating to the Results of the Partial International Search Dated Sep. 24, 2015 From the International Searching Authority Re. Application No. PCT/IL2015/050677.
Decision of Rejection Dated Sep. 17, 2019 From the Japan Patent Office Re. Application No. 2016-576068 and Its Translation Into English. (12 Pages).
Decision of Rejection Dated Aug. 27, 2019 From the Japan Patent Office Re. Application No. 2016-576071 and Its Translation Into English. (8 Pages).
Decision to Grant a Patent for Invention and Search Report Dated Oct. 29, 2019 From the (ROSPATENT), Federal Government Institution of Industrial Property of the Federal Service of Intellectual Property, Patents and Trademark of the Russian Federation Re. Application No. 2019115942.and Its Translation Into English. (16 Pages).
Decision to Grant a Patent for Invention Dated Mar. 25, 2019 From the Federal Goverment Institution, Federal Institute of Industrial Property of the Federal Service for Intellectual Property, Patents and Trademarks, ROSPATENT of the Russian Federation Re. Application No. 2017102236 and Its Translation Into English. (18 Pages).
Decision to Grant a Patent for Invention Dated Mar. 25, 2019 From the Federal Government Institution, Federal Institute of Industrial Property of the Federal Service for Intellectual Property, Patents and Trademarks, ROSPATENT of the Russian Federation Re. Application No. 2017102235 and Its Translation Into English. (16 Pages).
Decision to Grant a Patent for Invention Dated Mar. 25, 2019 From the Federal Government Institution, Federal Institute of Industrial Property of the Federal Service of Intellectual Property, Patents and Trademarks, ROSPATENT of the Russian Federation Re. Application No. 2017102233 and Its Translation Into English. (17 Pages).
English Translation Dated Feb. 21, 2022 of Notification of Office Action and Search Report Dated Jan. 20, 2022 From the State Intellectual Property Office of the People's Republic of China Re. Application No. 202011200160.2.1 Pages).
European Search Report and the European Search Opinion Dated Oct. 11, 2021 From the European Patent Office Re. Application No. 21194394.9 (8 Pages).
European Search Report and the European Search Opinion Dated Jul. 5, 2019 From the European Patent Office Re. Application No. PCT/19165448.2. (7 Pages).
European Search Report and the European Search Opinion Dated Apr. 8, 2021 From the European Patent Office Re. Application No. 21159548.3. (7 Pages).
European Search Report and the European Search Opinion Dated Nov. 9, 2021 From the European Patent Office Re. Application No. 21199976.8. (8 Pages).
European Search Report and the European Search Opinion Dated Dec. 17, 2021 From the European Patent Office Re. Application No. 21196651.0. (7 Pages).

(56) References Cited

OTHER PUBLICATIONS

European Search Report and the European Search Opinion Dated Nov. 20, 2020 From the European Patent Office Re. Application No. 20192870.2. (7 Pages).
European Search Report and the European Search Opinion Dated Apr. 22, 2021 From the European Patent Office Re. Application No. 20192870.2. (14 Pages).
European Search Report and the European Search Opinion Dated Mar. 26, 2020 From the European Patent Office Re. Application No. 20150198.8. (9 Pages).
Examination Report Dated Feb. 5, 2020 From the Instituti Mexicano de la Propiedad Industrial, IMPI, Direccion Divisional de Patentes Re. Application No. MX/a/2017/000056 and Its Translation Into English. (4 Pages).
Examination Report Dated Aug. 6, 2021 From the Instituto Mexicano de la Propicdad Industrial, Dirccciou Divisional dc Patcntcs Rc. Application No. MX/a/2017/000057 and Its Translation Into English. (10 Pagcs).
Examination Report Dated Apr. 8, 2019 From the Australian Government, IP Australia Re. Application No. 2015283589. (5 Pages).
Examination Report Dated Jan. 13, 2021 From the Instituto Mexicano de la Propiedad Industrial, Secretario de Economia, Dioreccion Divisional de Patentes Re. Application No. MX/a/2017/000057. (6 Pages).
Examination Report Dated Sep. 14, 2020 From the Australian Government, IP Australia Re. Application No. 2019229369. (4 Pages).
Examination Report Dated Jan. 15, 2019 From the Australian Government, IP Australia Re. Application No. 2015283594. (4 Pages).
Examination Report Dated Apr. 20, 2021 From the Instituto Mexicano de la Propiedad Industrial, Direccion Divisional de Patentes Re. Application No. MX/a/2017/000057 and Its Summary in English. (5 Pages).
Examination Report Dated Feb. 20, 2020 From the Australian Government, IP Australia Re. Application No. 2015283590. (6 Pages).
Examination Rcport Datcd Jan. 21, 2019 From thc Australian Govcrnmcnt, IP Australia Re. Application No. 2015283593. (4 Pages).
Examination Report Dated Jan. 29, 2022 from the Australian Patent Office Re. Application No. 2021202185. (5 pages).
Examination Report Dated Mar. 29, 2019 From the Australian Government, IP Australia Re. Application No. 2015283590. (5 Pages).
Examination Report Dated Jan. 30, 2020 From the Instituto Mexicano de la Propiedade Industrial, IMPI, Direccion Divisional de Patentes Re. Application No. MX/a/2017/000055 and Its Translation Into English. (5 Pages).
Examiner-Initiated Interview Summary Dated Nov. 2, 2017 From the US Patent and Trademark Office Re. U.S. Appl. No. 15/382,819. (2 pages).
Final Official Action Dated Jul. 6, 2021 from the US Patent and Trademark Office Re. U.S. Appl. No. 16/068,373. (33 pages).
Final Official Action Dated Feb. 22, 2021 From the US Patent and Trademark Office Re. U.S. Appl. No. 16/131,079. (60 Pages).
Final Official Action Dated May 4, 2020 from the US Patent and Trademark Office Re. U.S. Appl. No. 15/690,323. (55 pages).
Ground(s) of Reason of Rejection Dated Jan. 21, 2022 From the Korean Intellectual Property Office Re. Application No. 10-2017-70023243 and its Translation into English. (13 Pages).
International Preliminary Report on Patentability Dated Jul. 2, 2013 From the International Preliminary Examining Authority Re. Application No. PCT/IL2011/050071.
International Preliminary Report on Patentability Dated May 6, 2021 From the International Bureau of WIPO Re. Application No. PCT/IL2019/051163. (6 Pages).
International Preliminary Report on Patentability Dated Jan. 12, 2017 From the International Bureau of WIPO Re. Application No. PCT/IL2015/050673. (15 Pages).
International Preliminary Report on Patentability Dated Jan. 12, 2017 From the International Bureau of WIPO Re. Application No. PCT/IL2015/050674. (11 Pages).
International Preliminary Report on Patentability Dated Jan. 12, 2017 From the International Bureau of WIPO Re. Application No. PCT/IL2015/050675. (8 Pages).
International Prcliminary Rcport on Patcntability Datcd Jan. 12, 2017 From thc International Bureau of WIPO Re. Application No. PCT/IL2015/050677. (13 Pages).
International Preliminary Report on Patentability Dated Jan. 12, 2017 From the International Bureau of WIPO Re. Application No. PCT/IL2015/050678. (12 Pages).
International Preliminary Report on Patentability Dated Jan. 12, 2017 From the International Bureau of WIPO Re. Application No. PCT/IL2015/50676. (11 Pages).
International Preliminary Report on Patentability Dated Aug. 19, 2021 From the International Bureau of WIPO Re. Application No. PCT/IL2020/050151. (7 Pages).
International Preliminary Report on Patentability Dated Jul. 19, 2018 From the International Bureau of WIPO Re. Application No. PCT/IL2017/050014. (10 Pages).
International Preliminary Report on Patentability Dated Aug. 27, 2020 From the International Bureau of WIPO Re. Application No. PCT/IL2019/050178. (8 Pages).
International Search Report and the Written Opinion Dated Feb. 2, 2016 From thc Intcrnational Scarching Authority Rc. Application No. PCT/IL2015/050673.
International Search Report and the Written Opinion Dated Dec. 3, 2015 From the International Searching Authority Re. Application No. PCT/IL2015/050677.
International Search Report and the Written Opinion Dated May 3, 2020 From the International Searching Authority Re. Application No. PCT/IL2020/050151. (18 Pages).
International Search Report and the Written Opinion Dated Jan. 7, 2016 From the International Searching Authority Re. Application No. PCT/IL2015/050675.
International Search Report and the Written Opinion Dated Dec. 10, 2015 From the International Searching Authority Re. Application No. PCT/IL2015/050674.
International Search Report and the Written Opinion Dated Oct. 19, 2012 From the International Searching Authority Re. Application No. PCT/IL2011/050071.
International Search Report and the Written Opinion Dated Jan. 20, 2016 From the International Searching Authority Re. Application No. PCT/IL2015/50676.
International Search Report and the Written Opinion Dated Oct. 22, 2015 From the International Searching Authority Re. Application No. PCT/IL2015/050678.
International Search Report and the Written Opinion Dated May 23, 2019 From the International Searching Authority Re. Application No. PCT/IL2019/050178. (15 Pages).
International Search Report and the Written Opinion Dated Mar. 27, 2017 From the International Searching Authority Re. Application No. PCT/IL2017/050014. (16 Pages).
International Search Report and the Written Opinion Dated Dec. 31, 2019 From the International Searching Authority Re. Application No. PCT/IL2019/051163. (16 Pages).
Interview Summary Dated Feb. 23, 2021 From the US Patent and Trademark Office Re. U.S. Appl. No. 16/068,373. (3 Pages).
Notice of Acceptance Dated Aug. 28, 2019 From the Australian Government, IP Australia Re. Application No. 2015283589. (4 Pages).
Notice of Allowance Dated Dec. 20, 2021 from US Patent and Trademark Office Re. U.S. Appl. No. 16/055,269. (158 pages).
Notice of Allowance Dated Dec. 1, 2021 from the US Patent and Trademark Office Re. U.S. Appl. No. 16/030,967. (21 pages).
Notice of Allowance Dated Jun. 1, 2017 From the US Patent and Trademark Office Re. U.S. Appl. No. 13/997,302. (24 Pages).
Notice of Allowance Dated Mar. 1, 2018 From the US Patent and Trademark Office Re. U.S. Appl. No. 15/312,647. (24 pages).
Notice of Allowance Dated Jun. 12, 2018 From the US Patent and Trademark Office Re. U.S. Appl. No. 15/308,370. (13 pages).

(56) References Cited

OTHER PUBLICATIONS

Notice of Allowance Dated Jun. 16, 2021 from the US Patent and Trademark Office Re. U.S. Appl. No. 16/131,079. (19 pages).
Notice of Allowance Dated Apr. 19, 2018 From the US Patent and Trademark Office Re. U.S. Appl. No. 15/375,098. (5 pages).
Notice of Allowance Dated Sep. 20, 2017 From the US Patent and Trademark Office Re. U.S. Appl. No. 15/362,841. (33 pages).
Notice of Allowance Dated Sep. 20, 2017 From the US Patent and Trademark Office Re. U.S. Appl. No. 15/386,182.(32 pages).
Notice of Allowance Dated Feb. 22, 2021 From the US Patent and Trademark Office Re. U.S. Appl. No. 15/690,323. (28 Pages).
Notice of Allowance Dated Apr. 23, 2018 From the US Patent and Trademark Office Re. U.S. Appl. No. 15/382,819. (17 pages).
Notice of Allowance Dated Oct. 23, 2018 From the US Patent and Trademark Office Re. U.S. Appl. No. 15/391,896. (16 pages).
Notice of Allowance Dated Nov. 24, 2021 from the US Patent and Trademark Office Re. U.S. Appl. No. 16/436,984. (124 pages).
Notice of Reason(s) for Rejection Dated Jun. 1, 2021 From the Japan Patent Office Re. Application No. 2020-1101083 and Its Translation Into English. (12 Pages).
Notice of Reason(s) for Rejection Dated Oct. 12, 2021 From the Japan Patent Office Re. Application No. 2020-101083 and Its Translation Into English. (17 Pages).
Notice of Reason(s) for Rejection Dated Oct. 12, 2021 From the Japan Patent Office Re. Application No. 2020-134166 and Its Translation Into English. (10 Pages).
Notice of Reason(s) for Rejection Dated Jan. 26, 2021 From the Japan Patent Office Re. Application No. 2019-231996 and Its Translation Into English. (10 Pages).
Notice of Reason(s) for Rejection Dated Jan. 26, 2021 From the Japan Patent Office Re. Application No. 2020-003761 and Its Translation Into English. (7 Pages).
Notice of Reasons for Rejection Dated Feb. 4, 2020 From the Japan Patent Office Re. Application No. 2016-576066 and Its Translation Into English. (6 Pages).
Notice of Reasons for Rejection Dated Jan. 7, 2020 From the Japan Patent Office Re. Application No. 2016-576067 and Its Translation Into English. (10 Pages).
Notice of Reasons for Rejection Dated May 7, 2019 From the Japan Patent Office Re. Application No. 2016-576067 and Its Translation Into English. (3 Pages).
Notice of Reasons for Rejection Dated May 7, 2019 From the Japan Patent Office Re. Application No. 2016-576068 and Its Translation Into English. (15 Pages).
Notice of Reasons for Rejection Dated May 7, 2019 From the Japan Patent Office Re. Application No. 2016-576071 and Its Translation Into English. (8 Pages).
Notice of Reasons for Rejection Dated Mar. 9, 2021 From the Japan Patent Office Re. Application No. 2016-576068 and Its Translation Into English. (17 Pages).
Notice of Reasons for Rejection Dated May 21, 2019 From the Japan Patent Office Re. Application No. 2016-576066 and Its Translation Into English. (12 Pages).
Notice of Reasons for Rejection Dated Feb. 22, 2022 From the Korean Intellectual Property Office Re. Application No. 10-2017-7002721 and Its Translation Into English. (5 Pages).
Notification of Office Action and Search Report Dated Mar. 1, 2021 From the State Intellectual Property Office of the People's Republic of China Re. Application No. 201580045151.1 and Its Translation of Office Action Into English. (8 Pages).
Notification of Office Action and Search Report Dated Feb. 3, 2020 From the State Intellectual Property Office of the People's Republic of China Re. Application No. 201580045151.1. 4 Pages).
Notification of Office Action and Search Report Dated Nov. 3, 2021 From the State Intellectual Property Office of the People's Republic of China Re. Application No. 202010701980.3. (10 Pages).
Notification of Office Action and Search Report Dated Sep. 3, 2019 From the State Intellectual Property Office of the People's Republic of China Re. Application No. 201580045136.7. (9 Pages).
Notification of Office Action and Search Report Dated Sep. 3, 2019 From the State Intellectual Property Office of the People's Republic of China Re. Application No. 201580045638.X. (15 Pages).
Notification of Office Action and Search Report Dated Sep. 4, 2019 From the State Intellectual Property Office of the People's Republic of China Re. Application No. 201580046016.9 and Its Translation Into English. (16 Pages).
Notification of Office Action and Search Report Dated Aug. 13, 2020 From the State Intellectual Property Office of the People's Republic of China Re. Application No. 201580045151.1 and Its Translation of Office Action Into English. (9 Pages).
Notification of Office Action and Search Report Dated Jan. 20, 2022 From the State Intellectual Property Office of the People's Republic of China Re. Application No. 202011200160.2. (6 Pages).
Notification of Office Action and Search Report Dated Dec. 30, 2019 From the China National Intellectual Property Administration Re. Application No. 201580045638.X. (11 Pages).
Notification of Office Action Dated Aug. 1, 2019 From the State Intellectual Property Office of the People's Republic of China Re. Application No. 201580045151.1 and Its Translation Into English. (8 Pages).
Notification of Office Action Dated Aug. 2, 2018 From the State Intellectual Property Office of the People's Republic of China Re. Application No. 201580045151.1 and Its Summary in English. (6 Pages).
Notification of Office Action Dated Feb. 3, 2019 From the State Intellectual Property Office of the People's Republic of China Re. Application No. 201580045136.7 and Its Translation Into English. (4 Pages).
Notification of Office Action Dated Jan. 3, 2020 From the China National Intellectual Property Administration Re. Application No. 201580046016.9 and Its Translation Into English. (13 Pages).
Notification of Office Action Dated Feb. 11, 2019 From the State Intellectual Property Office of the People's Republic of China Re. Application No. 201580045638.X and Its Translation Into English. (4 Pages).
Notification of Office Action Dated Feb. 11, 2019 From the State Intellectual Property Office of the People's Republic of China Re. Application No. 201580046016.9 and Its Translation Into English. (4 Pages).
Notification of Office Action Dated Dec. 27, 2019 From the State Intellectual Property Office of the People's Republic of China Re. Application No. 201580045136.7 and Its Translation Into English. (4 Pages).
Notification of Office Action Dated Feb. 27, 2019 From the State Intellectual Property Office of the People's Republic of China Re. Application No. 201580045151.1 and Its Translation into English. (6 Pages).
Office Action Dated Nov. 2, 2021 From the Israel Patent Office Re. Application No. 262376 and Its Translation Into English. (7 Pages).
Office Action Dated Apr. 15, 2019 From the Israel Patent Office Re. Application No. 249834 and Its Translation Into English. (5 Pages).
Office Action Dated Apr. 15, 2019 From the Israel Patent Office Re. Application No. 249835 and Its Translation Into English. (5 Pages).
Office Action Dated Jan. 17, 2019 From the Israel Patent Office Re. Application No. 260852 and Its Translation Into English. (6 Pages).
Office Action Dated Jan. 19, 2017 From the Israel Patent Office Re. Application No. 227102 and Its Translation Into English. (5 Pages).
Office Action Dated Dec. 21, 2017 From the Israel Patent Office Re. Application No. 227102 and Its Translation Into English. (4 Pages).
Office Action Dated Jun. 22, 2016 From the Israel Patent Office Re. Application No. 227102 and Its Translation Into English.
Office Action Dated Jan. 30, 2020 From the Israel Patent Office Re. Application No. 249836 and Its Translation Into English. (9 Pages).
Official Action Dated Jun. 1, 2017 From the US Patent and Trademark Office Re. U.S. Appl. No. 15/375,098. (42 pages).
Official Action Dated Nov. 1, 2017 From the US Patent and Trademark Office Re. U.S. Appl. No. 15/382,819. (45 pages).
Official Action Dated Feb. 4, 2019 From the US Patent and Trademark Office Re. U.S. Appl. No. 15/362,883. (53 pages).
Official Action Dated Aug. 5, 2021 from the US Patent and Trademark Office Re. U.S. Appl. No. 16/030,967. (163 pages).

(56) References Cited

OTHER PUBLICATIONS

Official Action Dated Apr. 6, 2017 From the US Patent and Trademark Office Re. U.S. Appl. No. 15/362,841. (35 pages).
Official Action Dated Mar. 9, 2017 From the US Patent and Trademark Office Re. U.S. Appl. No. 15/386,182. (24 pages).
Official Action Dated Sep. 1, 2020 from the US Patent and Trademark Office Re. U.S. Appl. No. 15/690,323. (14 pages).
Official Action Dated Apr. 10, 2017 From the US Patent and Trademark Office Re. U.S. Appl. No. 15/362,883. (33 pages).
Official Action Dated Dec. 12, 2017 From the US Patent and Trademark Office Re. U.S. Appl. No. 15/308,370. (27 pages).
Official Action Dated Mar. 13, 2017 From the US Patent and Trademark Office Re. U.S. Appl. No. 15/391,896. (22 pages).
Official Action Dated Mar. 14, 2018 From the US Patent and Trademark Office Re. U.S. Appl. No. 15/362,883. (21 pages).
Official Action Dated Aug. 18, 2017 From the US Patent and Trademark Office Re. U.S. Appl. No. 15/308,370. (56 pages).
Official Action Dated Apr. 20, 2017 From the US Patent and Trademark Office Re. U.S. Appl. No. 15/382,819. (30 pages).
Official Action Dated Sep. 22, 2017 From the US Patent and Trademark Office Re. U.S. Appl. No. 15/362,883. (43 pages).
Official Action Dated Jan. 25, 2018 From the US Patent and Trademark Office Re. U.S. Appl. No. 15/375,098. (37 pages).
Official Action Dated Dec. 26, 2017 From the US Patent and Trademark Office Re. U.S. Appl. No. 15/391,896. (53 pages).
Official Action Dated Jul. 28, 2020 from the US Patent and Trademark Office Re. U.S. Appl. No. 16/131,079. (102 pages).
Official Action Dated Sep. 28, 2017 From the US Patent and Trademark Office Re. U.S. Appl. No. 15/312,647. (57 pages).
Official Action Dated Jan. 30, 2017 From the US Patent and Trademark Office Re. U.S. Appl. No. 13/997,302. (23 pages).
Official Action Dated Sep. 30, 2016 From the US Patent and Trademark Office Re. U.S. Appl. No. 13/997,302.
Official Action Dated Sep. 30, 2019 From the US Patent and Trademark Office Re. U.S. Appl. No. 15/690,323. (123 pages).
Official Action Dated May 31, 2018 From the US Patent and Trademark Office Re. U.S. Appl. No. 15/391,896. (17 pages).
Official Action Dated Jan. 8, 2021 from the US Patent and Trademark Office Re. U.S. Appl. No. 16/068,373. (85 pages).
Patent Examination Report Dated Aug. 13, 2021 From the Australian Government, IP Australia Re. Application No. 2020205271. (7 Pages).
Patent Examination Report Dated Sep. 14, 2020 From the Australian Government, IP Australia Re. Application No. 2019275594. (4 Pages).
Patent Examination Report Dated Nov. 23, 2020 From the Australian Government, IP Australia Re. Application No. 2019229370. (4 Pages).
Patent Examination Report Dated Oct. 26, 2021 From the Australian Government, IP Australia Re. Application No. 2017204945. (3 Pages).
Pre-Appeal Examination Report Dated Feb. 6, 2020 From the Japan Patent Office Re. Application No. 2016-576068 and Its Translation Into English.
Request for Examination and Search Report Dated Feb. 4, 2021 From the Federal Government Institution, Federal Institute of Industrial Property of the Federal Service of Intellectual Property, Patents and Trademarks of the Russian Federation, FIPS Re. Application No. 2020130235 and Its Translation of Office Action Into English. (9 Pages).
Request for Examination and Search Report Dated Nov. 22, 2018 From the Federal Government Institution, Federal Institute of Industrial Property of the Federal Service for Intellectual Property, Patents and Trademarks of the Russian Federation Re. Application No. 2017102236 and Its Translation of Office Action Into English. (7 Pages).
Request for Examination and Search Report Dated Nov. 23, 2018 From the Federal Government Institution, Federal Institute of Industrial Property of the Federal Service for Intellectual Property, Patents and Trademarks of the Russian Federation Re. Application No. 2017102235 and Its Translation Into English. (9 Pages).
Request for Examination and Search Report Dated Feb. 26, 2020 From the Federal Government Institution, Federal Institute of Industrial Property of the Federal Service of Intellectual Property, Patents and Trademarks of the Russian Federation, FIPS Re. Application No. 2019115949 and Its Translation Into English. (11 Pages).
Request for Examination and Search Report Dated Nov. 27, 2018 From the Federal Government Institution, Federal Institute of Industrial Property of the Federal Service of Intellectual Property, Patents and Trademarks of the Russian Federation Re. Application No. 2017102233 and Its Translation of Office Action Into English. (8 Pages).
Request for Examination Dated Feb. 4, 2021 From the (ROSPATENT), Federal Government Institution of Industrial Property of the Federal Service of Intellectual Property, Patents and Trademark of the Russian Federation Re. Application No. 2020130235. (5 Pages).
Request for Examination Dated Dec. 12, 2018 From the Federal Government Institution, Federal Institute of Industrial Property of the Federal Service or Intellectual Property, Patents and Trademark of the Russian Federation Re. Application No. 2017102234 and its Translation Into English. (9 Pages).
Request for Examination Dated Jan. 28, 2020 From the Federal Government Institution, Federal Institute of Industrial Property of the Federal Service or Intellectual Property, Patents and Trademark of the Russian Federation Re. Application No. 2017102234 and Its Translation Into English. (14 Pages).
Requisition by the Examiner Dated Nov. 2, 2018 From the Innovation, Science and Economic Development Canada, Canadian Intellectual Property Office Re. Application No. 2,822,738. (4 Pages).
Requisition by the Examiner Dated Aug. 6, 2019 From the Innovation, Science and Economic Development Canada, Canadian Intellectual Property Office Re. Application No. 2,822,738.(4 Pages).
Requisition by the Examiner Dated Aug. 13, 2020 From the Innovation, Science and Economic Development Canada, Canadian Intellectual Property Office Re. Application No. 2,822,738. (3 Pages).
Requisition by the Examiner Dated Nov. 16, 2017 From the Innovation, Science and Economic Development Canada, Canadian Intellectual Property Office Re. Application No. 2,822,738. (4 Pages).
Requisition by the Examiner Dated Aug. 19, 2021 From the Innovation, Science and Economic Development Canada, Canadian Intellectual Property Office Re. Application No. 2,953,074. (16 Pages).
Requisition by the Examiner Dated Aug. 26, 2021 From the Innovation, Science and Economic Development Canada, Canadian Intellectual Property Office Re. Application No. 2,953,082. (28 Pages).
Requisition by the Examiner Dated Sep. 28, 2021 From the Innovation, Science and Economic Development Canada, Canadian Intellectual Property Office Re. Application No. 2,953,069. (4 Pages).
Requisition by the Examiner Dated Sep. 28, 2021 From the Innovation, Science and Economic Development Canada, Canadian Intellectual Property Office Re. Application No. 2,953,073. (4 Pages).
Restriction Official Action Dated Aug. 7, 2017 From the US Patent and Trademark Office Re. U.S. Appl. No. 15/312,647. (8 pages).
Restriction Official Action Dated Jul. 8, 2016 From the US Patent and Trademark Office Re. U.S. Appl. No. 13/997,302.
Restriction Official Action Dated Sep. 17, 2020 from the US Patent and Trademark Office Re. U.S. Appl. No. 16/068,373. (8 pages).
Search Report and Explanation Dated Mar. 24, 2020 From the Servico Publico Federal, Ministerio da Economia, Instituto Nacional da Propriedade Industrial do Brasil Re. Application No. BR112016030944-8 and Its Summary in English. (5 Pages).
Search Report and Explanation Dated Mar. 24, 2020 From the Servico Publico Federal, Ministerio da Economia, Instituto Nacional da Propriedade Industrial do Brasil Re. Application No. BR112016030952-9 and Its Summary in English. (5 Pages.

(56) References Cited

OTHER PUBLICATIONS

Search Report and Explanation Dated Mar. 24, 2020 From the Sevico Publico Federal, Ministerio da Economia, Instituto Nacional da Propriedade Industrial do Brasil Re. Application No. BR112016030955-3 and Its Summary in English. (5 Pages).
Search Report and Explanations Dated Apr. 15, 2020 From the Servico Publico Federal, Ministerio da Economia, Instituto Nacional da Propriedade Industrial do Brasil Re. Application No. BR112016030829-8 and Its Summary in English. (5 Pages).
Summons to Attend Oral Proceedings Pursuant to Rule 115(1) EPC Dated Sep. 24, 2020 From the European Patent Office Re. Application No. 15814472.5. (6 Pages).
Supplementary European Search Report and the European Search Opinion Dated Dec. 16, 2021 From the European Patent Office Re. Application No. 19754583.3. (6 Pages).
Supplementary European Search Report and the European Search Opinion Dated Aug. 19, 2019 From the European Patent Office Re. Application No. 17735927.0. (8 Pages).
Supplementary European Search Report and the European Search Opinion Dated Mar. 19, 2018 From the European Patent Office Re. Application No. 15814472.5. (9 Pages).
Supplementary European Search Report and the European Search Opinion Dated Mar. 19, 2018 From the European Patent Office Re. Application No. 15815982.2. (8 Pages).
Translation Dated Oct. 1, 2019 of Notification of Office Action Dated Sep. 3, 2019 From the State Intellectual Property Office of the People's Republic of China Re. Application No. 201580045638.X. (13 Pages).
Translation Dated Aug. 14, 2018 of Notification of Office Action Dated Aug. 2, 2018 From the State Intellectual Property Office of the People's Republic of China Re. Application No. 201580045151.1. (3 Pages).
Translation Dated Sep. 18, 2019 of Notification of Office Action Dated Sep. 3, 2019 From the State Intellectual Property Office of the People's Republic of China Re. Application No. 201580045136.7. (5 Pages).
Translation Dated Feb. 20, 2020 of Notification of Office Action Dated Feb. 3, 2020 From the State Intellectual Property Office of the People's Republic of China Re. Application No. 201580045. (4 Pages).
Translation Dated Jan. 22, 2020 of Notification of Office Action Dated Dec. 30, 2019 From the China National Intellectual Property Administration Re. Application No. 201580045638.X. (9 Pages).
Written Opinion Dated Apr. 22, 2013 From the International Preliminary Examining Authority Re. Application No. PCT/IL2011/050071.
AAAAI "Inhaled Asthma Medications: Tips to Remember", American Academy of Allergy Asthma & Immunology, AAAAI, 4 P., 2013.
Abrams et al. "Vaporization as a Smokeless Cannabis Delivery System: A Pilot Study", Clinical Pharmacology & Therapeutics, 82(5): 572-578, Advance Online Publication Apr. 11, 2007.
Almog et al. "The Pharmacokinetics, Efficacy, and Safety of a Novel Selective-Dose Cannabis Inhaler in Patients With Chronic Pain: A Randomized, Double-Blineed, Placebo-Controlled Trial", European Journal of Pain, 24(8): 1505-1516, Published Online Jun. 12, 2020.
Assaf et al. "Pre- and Post-Conditioning Treatment With an Ultra-Low Dose of [Delta]$^\wedge$sup9$^\wedge$-Tetrahydrocannabinol (THC) Protects Against Pentylenetetrazole (PTZ)-Induced Cognitive Damage", Behavioral Brain Research, 220(1): 194-201, Jun. 2011.
Bhattacharyya et al. "Opposite Effects of Delta-9-Tetrahydrocannabinol and Cannabidiol on Human Brain Function and Psychopathology", Neuropsychopharmacology, 35: 764-774, 2010.
Boden et al. "The Effects of Cannabis Use Expectancies on Self-Initiated Cannabis Cessation", Addiction, 108: 1649-1657, 2013.
Carter et al. "Medicinal Cannabis: Rational Guidelines for Dosing", IDrugs, 7(5): 464-470, May 2004.
Cohen et al. "Modelling of the Concentration-Effect Relationship of THC on Central Nervous System Parameters and Heart Rate—Insight Into Its Mechanisms of Action and a Tool for Clinical Research and Development of Cannabinoids", Journal of Pharmacology, 22(7): 717-726, Sep. 2008.
Das et al. "Effects of 9-Ene-Tetrahydrocannabinol on Expression of Beta-Type Transforming Growth Factors, Insulin-Like Growth Factor-I and C-Myc Genes in the Mouse Uterus", The Journal of Steroid Biochemistry and Molecular Biology, 45(6): 459-465, 1993.
Eisenberg et al. "The Pharmacokinetics, Efficacy, Safety, and Ease of Use of a Novel Portable Metered-Dose Cannabis Inhaler in Patients With Chronic Neuropathic Pain: A Phase 1a Study", Journal of Pain & Palliative Care Pharmacotherapy, 28(3): 216-225, Published Online Aug. 13, 2014.
Farrimond et al. "Cannabinol and Cannabidiol Exert Opposing Effects on Rat Feeding Patterns", Psychopharmacology, 223: 117-129, 2012.
FDA "Guidance for Industry. Population Pharmacokinetics", U.S. Department of Health and Human Services, Food and Drug Administration (FDA), Center for Drug Evaluation and Research (CDER), Center for Biological Evaluation and Research (CBER), CP 1: 1-31, Feb. 1999.
Fishbein et al. "Long-Term Behavioral and Biochemical Effects of an Ultra-Low Dose of [Delta]$^\wedge$sup9$^\wedge$-Tetrahydrocannabinol (THC): Neuroprotection and ERK Signaling", Experimental Brain Research, 221(4): 437-448, Published Online Jul. 22, 2012.
Green Machine "Structure of a leaf—Internal & External", Retrieved from google.com, 6 Pages, Sep. 2019.
Hazekamp et al. "Bedrocan®—Stimulating the Development of Herbal Cannabis-Based Products", Bedromedical Presentation, 2013.
Hazekamp et al. "Evaluation of a Vaporizing (Volcano®) for the Pulmonary Administration of Tetrahydrocannabinol", Journal of Pharmaceutical Sciences, 95(6): 1308-1317, Jun. 2006.
Hazekamp et al. "The Medicinal Use of Cannabis and Cannabinoids—An International Cross-Sectional Survey on Administration Forms", Journal of Psychoactive Drugs, 45(3): 199-210, 2013.
Herbalizer "Herbalizer, the New Vaporization Experience", 6 P., Jun. 7, 2013.
Ibrahim et al. "Inhalation Drug Delivery Devices: Technology Update", Medical Devices: Evidence and Research, 8: 131-139, Feb. 12, 2015.
Jamontt et al. "The Effects of Delta[9]-Tetrahydrocannabinol and Cannabidiol Alone and in Combination on Damage, Inflammation and In Vitro Motility Disturbances in Rat Colitis", British Journal of Pharmacology, 160: 712-723, 2010.
Jang et al. "Thermophysical Properties of Porous SiC Ceramics Fabricated by Pressureless Sintering", Science and Technology of Advanced Materials, 8(7): 655-659, Nov. 30, 2007.
Lanz et al. "Medicinal Cannabis: In Vitro Validation of Vaporizers for the Smoke-Free Inhalation of Cannabis", PLOS One, 11(1): e0147286-1-e0147286-18, Jan. 19, 2016.
McPartland et al. "Affinity and Efficacy Studies of Tetrahydrocannabinolic Acid A at Cannabinoid Receptor Types One and Two", Cannabis and Cannabinoid Research, 2(1): 87-95, May 2017.
McPartland et al. "Are Cannabidiol and Delta9-Tetrahydrocannabivarin Negative Modulators of the Endocannabinoid System? A Systematic Review", British Journal of Pharmacology, 172(3): 737-753, Published Online Jan. 8, 2015.
McPartland et al. "Cannabis and Cannabis Extracts: Greater Than the Sum of Their Parts?", Journal of Cannabis Therapeutics, 1(3-4):103-132, Jun. 1, 2001.
Mechoulam et al. "Cannabidiol—Recent Advances", Chemistry & Biodiversity, 4: 1678-1692, 2007.
Moreno-Sanz "Can You Pass the Acid Test? Critical Review and Novel Therapeutic Perspectives of Delta9-Tetrahydrocannabinolic Acid A", Cannabis and Cannabinoid Research, 1(1): 124-130, Published Online Jun. 1, 2016.
Norwood et al. "Best Practices for Extractables and Leachables in Orally Inhaled and Nasal Drug Products: An Overview of the PQRI Recommendations", Pharmaceutical Research, 25(4): 727-739, Published Online Jan. 9, 2008.
Ormrod et al. "A Survey of Weed Leaf Stomata and Trichomes", Canadian Journal of Plant Science, 48(2): 197-209, 1968.
Pertwee "The Diverse CB1 and CB2 Receptor Pharmacology of Three Plant Cannabinoids: Delta[9]-Tetrahydrocannabinol, Can-

(56) References Cited

OTHER PUBLICATIONS nabidiol and Delta[9]-Tetrahydrocannabivarin", British Journal of Pharmacology, 153: 199-215, 2008.
Pomahacova et al. "Cannabis Smoke Condensate III: The Cannabinoid Content of Vaporised Cannabis Sativa", Inhalation Toxicology, 21(13): 1108-1112, Nov. 1, 2009.
Rabinowitz et al. "Fast Onset Medications Through Thermally Generated Aerosols", The Journal of Pharmacological and Experimental Therapeutics, 309(2): 769-775, Published Online Jan. 29, 2004.
Rau "The Inhalation of Drugs: Advantages and Problems", Respiratory Care, 50(3): 367-382, Mar. 2005.
Science "Nettle leaf trichromes", Retrieved fromsciencesource.com, 1 Page, Sep. 2019.
Syqe Medical "The World's First Metered Dose Pharmaceutical Grade Medical Cannabis Inhaler", Syqe Medical™, Press Kit, p. 1-8, 2015.
Van Gerven "Biomarkers to Assess Adverse Drug Effects on the CNS", Centre for Human Drug Research, CHDR, Poster-Session, Slide-Show, 25 P., 2013.
Van Hell et al. "Evidence for Involvement of the Insula in the Psychotropic Effects of THC in Humans: A Double-Blind, Randomized Pharamcological MRI Study", International Journal of Neuropharmacology, 14: 1377-1388, 2011.
Vann et al. "Divergent Effects of Cannabidiol on the Discriminative Stimulus and Place Conditioning Effects of Delta 9-Tetrahydrocannabiol", Drug and Alcohol Dependence, 94(1-3): 191-198, Apr. 1, 2008.
Vemuri et al. "Pharmacotherapeutic Targeting of the Endocannabinoid Signaling System: Drugs for Obesity and the Metabolic Syndrome", Physiology & Behavior, 93: 671-686, 2008.
Wallace et al. "Efficacy of Inhaled Cannabis on Painful Diabetic Neuropathy", The Journal of Pain, 169(7): 616-627, Published Online Apr. 3, 2015.
Ware et al. "Smoked Cannabis for Chronic Neuropathic Pain: A Randomized Controlled Trial", Canadian Medical Association Journal, CMAJ, 182(14): E694-E701, Published Online Aug. 30, 2010.
Wilscy et al. "A Randomized, Placebo-Controlled, Crossover Trial of Cannabis Cigarettes in Neuropathic Pain", The Journal of Pain, 9(6): 506-521, Published Online Apr. 10, 2008.
Wilsey et al. "Low-Dose Vaporized Cannabis Significantly Improves Neuropathic Pain", The Journal of Pain, 14(2): 136-148, Published Online Dec. 13, 2012. 'Discussion', Last Para.
Zuurman et al. "Biomarkers for the Effects of Cannabis and THC in Healthy Volunteers", British Journal of Clinical Pharmacology, 67(1): 5-21, 2008.
Zuurman et al. "Effect of Intrapulmonary Tetrahydrocannabinol Administration in Humans", Journal of Psychopharmacology, 22(7): 707-716, 2008.
Translation Dated Jun. 23, 2023 of Notice of Reason(s) for Rejection Dated Jun. 13, 2023 From the Japan Patent Office Re. Application No. 2022-115378. (4 pages).
Request for Examination Dated Oct. 18, 2023 From the (ROSPATENT), Federal Government Institution of Industrial Property of the Federal Service of Intellectual Property, Patents and Trademark of the Russian Federation Re. Application No. 2021114565. (9 Pages).
Final Notice of Rejection Dated Oct. 30, 2023 From the Korean Intellectual Property Office Re. Application No. 10-2022-7045372 and Its Translation Into English. (7 Pages).
Official Action Dated Aug. 3, 2023 from the US Patent and Trademark Office Re. U.S. Appl. No. 16/969,612. (271 pages).
Requisition by the Examiner Dated Dec. 22, 2022 From the Innovation, Science and Economic Development Canada, Canadian Intellectual Property Office Re. Application No. 3,009,599.(10 pages).
Translation for the Rejection of Claim 1 Dated May 11, 2023 of Notification of Office Action Dated Apr. 13, 2023 From the State Intellectual Property Office of the People's Republic of China Re. Application No. 202080027182.5. (1 Page).
Requisition by the Examiner Dated Aug. 17, 2023 From the Innovation, Science and Economic Development Canada, Canadian Intellectual Property Office Re. Application No. 3,009,599. (3 Pages).
Communication Pursuant to Article 94(3) EPC Dated Feb. 6, 2023 From the European Patent Office Re. Application No. 20150198.8 (7 Pages).
Grounds of Reason of Rejection Dated May 22, 2023 From the Korean Intellectual Property Office Re. Application No. 10-2022-7036865 and Its Translation Into English. (6 Pages).
Communication Pursuant to Article 94(3) EPC Dated Dec. 12, 2023 From the European Patent Office Re. Application No. 21159548.3. (4 Pages).
Translation Dated Dec. 12, 2023 of Request for Examination Dated Oct. 18, 2023 From the (ROSPATENT), Federal Government Institution of Industrial Property of the Federal Service of Intellectual Property, Patents and Trademark of the Russian Federation Re. Application No. 2021114565. (7 Pages).
Communication Pursuant to Article 94(3) EPC Dated Dec. 19, 2023 From the European Patent Office Re. Application No. 21196651.0. (5 Pages).
Interview Summary Dated Apr. 12, 2024 from the US Patent and Trademark Office Re. U.S. Appl. No. 16/969,612. (8 pages).
Examination Report Dated Dec. 21, 2023 From the Australian Government, IP Australia Re. Application No. 2022256225. (5 Pages).
Notice of Reason(s) for Rejection Dated Jan. 30, 2024 From the Japan Patent Office Re. Application No. 2023-139046 and Its Translation Into English. (12 Pages).
Notice of Allowance Dated Feb. 12, 2024 from the US Patent and Trademark Office Re. U.S. Appl. No. 17/679,190. (13 pages).
Restriction Official Action Dated Mar. 27, 2024 From the US Patent and Trademark Office Re. U.S. Appl. No. 17/428,706. (8 pages).
Communication Pursuant to Article 94(3) EPC Dated Dec. 15, 2023 From the European Patent Office Re. Application No. 21194394.9 (6 Pages).
Communication Pursuant to Article 94(3) EPC Dated Jan. 3, 2024 From the European Patent Office Re. Application No. 19754583.3 (5 Pages).
Examination Report Dated Jan. 18, 2024 From the Australian Government, IP Australia Re. Application No. 2019221321. (4 Pages).
Notice of Reason(s) for Rejection Dated Jan. 9, 2024 From the Japan Patent Office Re. Application No. 2023-061198 and Its Machine Translation Into English. (7 Pages).
Request for Examination and Search Report Dated Feb. 16, 2023 From the (ROSPATENT), Federal Government Institution of Industrial Property of the Federal Service of Intellectual Property, Patents and Trademark of the Russian Federation Re. Application No. 2021114565 and its Summary in English.(12 Pages).
Translation Dated Mar. 30, 2023 of Request for Examination and Search Report Dated Feb. 16, 2023 From the (ROSPATENT), Federal Government Institution of Industrial Property of the Federal Service of Intellectual Property, Patents and Trademark of the Russian Federation Re. Application No. 2021114565 and its Summary in English.(7 Pages).
Communication Pursuant to Article 94(3) EPC Dated Jan. 9, 2024 From the European Patent Office Re. Application No. 21199976.8. (5 Pages).
Grounds of Reason of Rejection Dated Apr. 23, 2024 From the Korean Intellectual Property Office Re. Application No. 10-2021-7015766. (8 Pages).
Requisition by the Examiner Dated Apr. 25, 2024 From the Innovation, Science and Economic Development Canada, Canadian Intellectual Property Office Re. Application No. 2,953,073. (3 Pages).
Translation Dated May 2, 2024 of Grounds of Reason of Rejection Dated Apr. 23, 2024 From the Korean Intellectual Property Office Re. Application No. 10-2021-7015766. (6 Pages).

* cited by examiner

METHODS, DEVICES AND SYSTEMS FOR PULMONARY DELIVERY OF ACTIVE AGENTS

RELATED APPLICATIONS

This application is a continuation of U.S. patent application Ser. No. 16/030,967 filed on Jul. 10, 2018, which is a continuation of U.S. patent application Ser. No. 15/375,098 filed on Dec. 11, 2016, now U.S. Pat. No. 10,118,006, which is a continuation of PCT Patent Application No. PCT/IL2015/050676 filed on Jun. 30, 2015, which claims the benefit of priority under 35 USC § 119(e) of U.S. Provisional Patent Application Nos. 62/019,225 filed on Jun. 30, 2014, 62/035,588 filed on Aug. 11, 2014, 62/085,772 filed on Dec. 1, 2014, 62/086,208 filed on Dec. 2, 2014 and 62/164,710 filed on May 21, 2015.

U.S. patent application Ser. No. 15/375,098 filed on Dec. 11, 2016, now U.S. Pat. No. 10,118,006, is also a continuation of PCT Patent Application No. PCT/IL2015/050674 filed on Jun. 30, 2015, which claims the benefit of priority under 35 USC § 119(e) of U.S. Provisional Patent Application Nos. 62/019,225 filed on Jun. 30, 2014, 62/035,588 filed on Aug. 11, 2014, 62/085,772 filed on Dec. 1, 2014, 62/086, 208 filed on Dec. 2, 2014 and 62/164,710 filed on May 21, 2015.

U.S. patent application Ser. No. 15/375,098 filed on Dec. 11, 2016, now U.S. Pat. No. 10,118,006, is also a continuation of PCT Patent Application No. PCT/IL2015/050675 filed on Jun. 30, 2015, which claims the benefit of priority under 35 USC § 119(e) of U.S. Provisional Patent Application Nos. 62/019,225 filed on Jun. 30, 2014, 62/035,588 filed on Aug. 11, 2014, 62/085,772 filed on Dec. 1, 2014, 62/086, 208 filed on Dec. 2, 2014 and 62/164,710 filed on May 21, 2015.

The contents of the above applications are all incorporated by reference as if fully set forth herein in their entirety.

FIELD AND BACKGROUND OF THE INVENTION

The present invention, in some embodiments thereof, relates to pharmacology and, more particularly, but not exclusively, to methods, devices and systems for controlled pulmonary delivery of active agents.

Natural substances, such as plant materials, offer a plethora of pharmaceutically active agents which can provide a wide range of therapeutic and other beneficial effects; however, the use of many such substances for direct pharmacological purposes have been limited for technical and cultural reasons, primarily since practitioners and pharmacologists, which are aware of the beneficial effects of those substances, are reluctant to prescribe a natural substance, since the active agents contained therein are difficult to quantify and thus difficult to administer controllably.

One of the most used and studied natural substance is cannabis, which has been shown to have a beneficial effect in treating nausea and vomiting, multiple sclerosis and other neurological conditions, loss of appetite and weight in cancer and AIDS, neurological pain, insomnia, anxiety and depression, epilepsy and other seizures, asthma, opioid withdrawal, inhibition of primary tumor growth, as well as being effective in antipyretic and anti-inflammatory, antihelmintic, antimigraine and oxytocic applications.

Nonetheless, cannabis as a "main stream" pharmaceutical has been a matter of controversy for years due to difficulties with its administration according to a typical medical model of drug prescription.

Lack of accurate and precise dosing capabilities is one of the major obstacles for the addition of cannabis as a major player in the armamentarium of drugs available for, e.g., pain management. Moreover, lacking a method of administering cannabis in a pharmaceutical fashion makes it difficult for doctors to prescribe and monitor treatment, further blurring the line between medical use and recreational use. Hence, authorities in many countries refrain from approving cannabis for medical use. Indeed, even to date, cannabis is not conceived by the public as a safe substance, and is mostly treated as an illicit substance in most countries around the world.

For natural substances, such as cannabis, to be used as "main stream" pharmaceuticals, these natural substances should be made available in such a way that the use of their active agents can follow customary pharmaceutical standards and practices in terms of dosing and regimen.

The problems associated with the use of cannabis as a natural substance can be exemplified by a recent survey on the patterns and prevalence of the medicinal use of cannabis, completed by 953 participants from 31 countries. The survey showed that pulmonary delivery of cannabis is the most preferred route of administration used by 86.6% (62.9% for smoking and 23.7% for vaporizing) of the participants. The oral mode of delivery of cannabis in edibles had been used by 10.3% of the participants, whereas only 2.3% participants used either cannabis extracts delivered by oromucosal route (Sativex®) or synthetic cannabinoids (Marinol® and Nabilone®) delivered orally in tablet forms. This can be partially attributed to the slow and erratic absorption of cannabinoids with oral administration, leading to delayed onset and often unsatisfactory magnitude of analgesia. A randomized, controlled, double-blind, double-dummy study on oromucosal administration of cannabis revealed a pharmacokinetic pattern similar to that of oral use.

Smoking products of the cannabis plant proves a rapid and efficient method of cannabinoid delivery. During smoking products of cannabis, THC plasma levels increase rapidly, whereas peak concentrations typically occur at 1-3 minutes, resulting in first onset of effects after about 7 minutes. However, variability in the depth of inhalation, puff duration and breath-hold time, and the fact that about 30% of the THC dose is assumed to be destroyed by pyrolysis during smoking, lead to heterogeneous bioavailability following the smoking route, which ranges between 2-56%. In addition to the variable bioavailability, the smoking-related pyrolytic byproducts, which may cause various diseases, render smoking an undesirable delivery methodology of cannabinoids.

A step forward has been made by developing cannabis vaporization techniques aimed at delivering inhaled cannabinoids while avoiding the respiratory hazards of smoking. While the temperature at the center of a burning cigarette is 750-800° C., vaporization of cannabis can be performed at 170-190° C. At such a temperature range, active cannabinoids, as well as flavonoids and terpenoids vapors, are formed below the point of combustion (230-235° C.), at which pyrolytic toxic compounds are generated. It has been shown that a vaporization technique reduces formation of carbon monoxide and highly carcinogenic compounds such as polynuclear aromatic hydrocarbons (PAHs), benzene and tar.

Recent clinical trials, which enrolled a population of patients suffering from chronic neuropathic pain of various etiologies, pointed to low doses of $\Delta^9$-THC as having a favorable risk-benefit ratio. Ware et al. [in Canadian Medical Association CMAJ. 2010; 182(14):E694-701] reported that compared to placebo, a single smoke inhalation of 25±1 mg cannabis, containing 9.4% $\Delta^9$-THC (an estimated dose of 2.35 mg based on the total available $\Delta^9$-THC), given three times a day for 5 days, was associated with mean $C_{max}$ elevation of 45 ng/ml and 11.4% decrease in average daily pain intensity. In another clinical trial, Wilsey et al. [in J Pain. 2013; 14(2):136-48] reported that inhalation of vaporized 10.3 mg total available $\Delta^9$-THC, divided to two sessions, separated by interval of two hours, is associated with 31% and 25% reduction of pain intensity, 3 and 5 hours, respectively. Increasing the THC dose to 28.2 mg produced equianalgesic response that remained stable at these time points. In a second clinical trial, Wilsey et al. [in J Pain. 2008; 9(6):506-21] reported that identical levels of analgesia were produced at each cumulative dose level by smoking either 19 mg (intermediate dose) or 34 mg of total available $\Delta^9$-THC (high dose), divided to 3 doses, reaching a plateau or "ceiling effect" of 45% reduction of neuropathic pain.

However none of the currently known smokeless vaporization devices can be utilized for administering cannabis under common pharmaceutical standards and practices. The pulmonary delivery of cannabinoids in the vapor phase varies within and between doses due to the subjective visual estimation of the dose amount loaded by the user, repeated asynchronous inhalations from the same loaded dose, inconsistent inhalation dynamics and a time-dependent condensation of vapors onto the inner surfaces of the device. Subsequently, vaporizers in use today make proper pharmaceutical dosing and medical regimen monitoring unrealistic or impractical.

Further to the ability to control the vaporized amount of pharmaceutically active agents from a natural plant substance in terms of accuracy and consistency, the problem of dosing and regimen associated with current methods for pulmonary delivery of such agents is typically solved by means of trial and error based on subjective perception of the user, as measuring pharmacokinetic and pharmacodynamic parameters remains beyond the reach of most users.

WO 2012/085919, by the present assignees, discloses an inhalation device for controlled extraction/vaporization of active agents from plant material by application of heat, wherein the plant material is organized as a cartridge and the device is configured to vaporize a precise amount of an agent in a highly reproducible manner. The inhaler comprises preloaded and pre-weighed plant material portions, each associated with a dedicated heating element designed to apply heat to the plant material matter to thereby vaporize one or more active substances from the plant material. Background art FIG. 1 presents a photograph of an example for such device.

Additional background art includes U.S. Patent Application publication No. 2005/0268911, which discloses devices and methods of entraining a substance within an airflow; and U.S. Patent Application publication No. 2011/0192399, which discloses a vaporizer for vaporizing a substance, as well as U.S. Patent Application publication Nos. 20050087189 and 20070240712 and U.S. Pat. Nos. 6,622,723, 6,830,046, 8,204,729, 8,333,197 and 8,474,453.

SUMMARY OF THE INVENTION

According to an aspect of some embodiments of the present disclosure there is provided a method of pulmonary delivering to a subject at least one pharmacologically active agent being in a plant material, the method comprising pulmonary delivering the agent to the subject using a metered dose inhaler device configured to vaporize at least one pre-determined vaporized amount of the agent upon controllably heating the plant material, wherein the at least one pre-determined vaporized amount of the agent is selected so as to achieve at least one pre-determined pharmacokinetic (PK) effect and/or at least one pre-determined pharmacodynamic (PD) effect induced by the agent in the subject.

According to some embodiments, the pre-determine vaporized amount is determined based on at least one PK effect and/or at least one PD effect relating to a population.

According to some embodiments, the method further includes adjusting the pre-determined vaporized amount to achieve the pre-determined PK effect and/or the pre-determined PD effect based on data indicative of at least one PK effect and/or at least one PD effect induced by the agent in the subject.

According to some embodiments, the method further includes generating the data by monitoring the at least one PK effect and/or the at least one PD effect induced by the agent in the subject.

According to some embodiments, the method includes pulmonary delivering at least two pre-determined vaporized amounts according to a pre-defined regimen.

According to some embodiments, the method includes adjusting the regimen to achieve the pre-determined PK effect and/or the pre-determined PD effect based on at least one PK effect and/or at least one PD effect induced by the agent in the subject.

According to some embodiments, the method further includes generating the data by monitoring the at least one PK effect and/or the at least one PD effect induced by the agent in the subject.

According to some embodiments, monitoring a PK effect and/or a PD effect includes receiving data indicative of at least one PD effect in the subject from at least one sensor being in communication with a controller associated with the inhaler device.

According to some embodiments, adjusting the pre-determined vaporized amount and/or the regimen is based on data received via a user interface device.

According to some embodiments, adjusting the pre-determined vaporized amount and/or the regimen is effected in real-time.

According to some embodiments, monitoring a PK effect and/or a PD effect induced by the agent in the subject is effected at pre-determined time intervals before, during and/or after the pulmonary delivering.

According to some embodiments, the PK effect includes a concentration of the agent in a given volume of a bodily fluid and a concentration of the agent in a given mass of a bodily tissue.

According to some embodiments, the PD effect includes a desired effect, an undesired effect, a therapeutic effect, an adverse effect and a level of a biomarker.

According to some embodiments, the method includes adjusting at least one of the pre-determined PK effect and/or the pre-determined PD effect, based on data received via a user interface device.

According to some embodiments, wherein the pre-determined PD effect pertains to a pre-determined PD profile, which ranges between a minimal level of the desired effect and a level of an undesired effect.

According to some embodiments of the invention, the pre-determined PD profile ranges between a minimal level of the desired effect to a minimal level of the undesired effect.

According to some embodiments, the pre-determined PD profile ranges between a minimal level of the desired effect to a level higher than a minimal level of the undesired effect.

According to some embodiments, defining at least one of the desired effect and/or the undesired effect comprises receiving instructions from the subject.

According to some embodiments, the biomarker includes an invasively-detected biomarker and a non-invasively-detected biomarker.

According to some embodiments, non-invasively-detected biomarkers include a heart rate, an oxygenation level (SpO2), a blood pressure, a respiratory rate, a body temperature, an inhalation volume, a facial expression, muscle twitches, cramps, spasms, sweating, hand-eye coordination, eye vascular expansion, reddening of the conjunctiva and/or sclera, a variation in intra-ocular pressure, a motor skill, ataxia, sinus tachycardia, a tremor, cardiac arrhythmias, a skin conductance/impedance level, a seizure, an electromyography (EMG), an electrocardiogram (ECG), a photo-plethysmogram (PPG), a galvanic skin response (GSR), Blue-Brown visual inhibition, H-mask visual inhibition, Auditory Latent inhibition, Visual Latent inhibition, Stroop color word, Simple reaction (conflict task), Cognitive Set switching, Logical reasoning, Decision making time, Rapid info processing, Perceptual maze, Simulated driving, Visual search, Time estimation, Time perception, Visual search, Attentional search, Symbol copying, Letter cancellation, Alphabetic cross-out, D2 cancellation, Brickenkamp D2, digit copying test (DDCT), symbol-digit substitution (SDST), digit-symbol substitution test (DSST), Digit Vigilance, Vigilance, Auditory vigilance test, Wesnes/Warburton Vigilance task, Rapid info processing, CRT+Tracking Divided attention, Selective attention, Focused attention Task, Emotional attention Task, Auditory Flutter fusion, Flash fusion, critical flicker fusion (CFF), Continuous attention, Paired associate learning, Wordlist learning, 15 word test, Introductory conditioning, Delayed word recall, Delayed word recognition, Delayed picture recognition, Word presentation, Word recognition, Numeric working memory, Numerical memory, Memory scanning, Auditory Brown/Peterson, Visual Brown/Peterson, Visual spatial memory, Fragmented picture test, Pauli test, Block Span, Digit span, Digit Span (forward), Digit Span (backward), WAIS vocabulair, WAIS similarity, Word fluency, Verbal fluency, Performance time (Delayed word recogn.), Performance time (Numeric working memory), Performance time (Digit vigilance), Performance time (Rapid info processing), Performance time (Delayed picture recognition), Performance time (Visual information processing), Simple Reaction Time CRT, Complex RTvisual, Visual choice RT, VRT, Visual response speed, ART, Acoustic RT, Wire Maze Tracing, Archimedian spiral, Critical tracking task, Trail making, Tracking Complex, Tracking Wiener Geraet, Flexibility of closure, WAIS block design, WAIS picture comparison, Digit copying, Manipulative motor, Feinmotorik, Graphological analysis, tapping, Hand arm lateral reach coordination, Visual arm random reach, Motor control & coordination, Motor behavior.

According to some embodiments, the desired effect corresponds to a symptom that includes pain, migraine, depression, cognitive function deficit, attention deficit, hyperactivity, anxiety disorders, diarrhea, nausea, vomiting, insomnia, delirium, appetite variations, sexual dysfunction, spasticity, increased intra ocular pressure, bladder dysfunction, tics, Tourette symptoms, post traumatic stress disorder (PTSD) symptoms, inflammatory bowel disease (IBD) symptoms, irritable bowel syndrome (IBS) symptoms, hyper tension, hemorrhagic symptoms, septic and cardiogenic shock, drug addiction and craving, withdrawal symptoms, tremors and other movement disorders.

According to some embodiments, the PD effect is a psychotropic effect and/or a somatic effect.

According to some embodiments, the psychotropic effect corresponds to a symptom that includes paranoia, anxiety, panic attack, euphoria, pseudo-hallucinatory, ataxia, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence and depression.

According to some embodiments, the somatic effect corresponds to a symptom that includes nausea, muscle twitches, muscle relaxation cramps, spasms, sweating, ataxia, a motor activity variation, dry mouth and a sensation of cold or hot hands and feet, increased heart rate, increased cerebral blood flow, dilation of bronchial passages, dilation of blood vessels, eye redness and pupil dilation, dry mouth, thirst, hunger or food craving.

According to some embodiments, the method presented herein is for pulmonary delivering to a subject at least a first pharmacologically active agent and a second pharmacologically active agent, at least one of which being in at least one plant material, the method comprising independently delivering the agents to the subject using the device configured to vaporize at least a first pre-determined vaporized amount of the first agent and at least a second pre-determined vaporized amount of the second agent, wherein the heating is effected such that the first pre-determined vaporized amount is delivered to the subject successively, concomitantly and/or at least partially overlapping with the second pre-determined vaporized amount.

According to some embodiments, the plant includes *Cannabis sativa, Cannabis indica, Cannabis ruderalis, Acacia* spp, *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp, *Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), a *Sapindaceae, Camellia* spp.,

*Malvaceae* spp., *Aquifoliaceae* spp., *Hoodia*, spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Aloe Vera, Angelica, Anise, Ayahuasca (Banisteriopsis caapi),* Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, Yohimbe, and any part and any combination thereof.

According to some embodiments, the plant includes *Cannabis sativa, Cannabis indica*, and *Cannabis ruderalis*.

According to some embodiments, the pharmacologically active agent includes $\Delta$9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

According to some embodiments, the pharmacologically active agent includes $\Delta$9-tetrahydrocannabinol (THC) and cannabidiol (CBD).

According to an aspect of embodiments of the present disclosure, there is provided a system for pulmonary delivering to a subject at least one pharmacologically active agent being in a plant material, which includes:
 a metered dose inhaler device configured to vaporize at least one pre-determined vaporized amount of the agent upon controllably heating the plant material; and
 a controller in communication with the inhaler device, configured to select the at least one pre-determined vaporized amount of the agent so as to achieve at least one pre-determined PK effect and/or at least one pre-determined PD effect induced by the agent in the subject.

According to an aspect of some embodiments of the present disclosure there is provided a method of pulmonary delivering to a subject at least a first pharmacologically active agent and a second pharmacologically active agent, at least one of which being in at least one plant material, the method includes independently delivering the agents to the subject using a metered dose inhaler device configured to vaporize at least a first pre-determined vaporized amount of the first agent and at least a second pre-determined vaporized amount of the second agent upon controllably heating the plant material, wherein the heating is effected such that the first pre-determined vaporized amount is delivered to the subject successively, concomitantly and/or at least partially overlapping with the second pre-determined vaporized amount, and wherein each of the pre-determined vaporized amounts of each of the agents induces in the subject independently at least one pharmacokinetic (PK) effect and/or at least one pharmacodynamic (PD) effect.

According to some embodiments, a time interval between delivering the first agent and delivering the second agent ranges between zero minutes to 30 minutes.

According to some embodiments, the PD effect includes a desired effect, an undesired effect, a therapeutic effect, an adverse effect and a level of a biomarker.

According to some embodiments, the pre-determined vaporized amount of the first agent affects a level of the PD effect induced by the second agent.

According to some embodiments, the pre-determined vaporized amount of the first agent increases a level of the desired effect induced by the second agent.

According to some embodiments, the pre-determined vaporized amount of the first agent reduces a level of the undesired effect induced by the second agent.

According to some embodiments, the first agent and the second agent induce a desired effect synergistically.

According to some embodiments, each of the pre-determined vaporized amounts of each of the agents is selected so as to achieve at least one pre-determined PK effect and/or at least one pre-determined PD effect induced independently by each of the agents in the subject.

According to some embodiments, each of the pre-determined vaporized amounts of each of the agents is determined based on at least one PK effect and/or at least one PD effect relating to a population.

According to some embodiments, the method further includes adjusting at least one of the first pre-determined vaporized amount and the second pre-determined vaporized amount so as to achieve the pre-determined PK effect and/or the pre-determined PD effect based on data indicative of at least one PK effect and/or at least one PD effect induced by the agent in the subject.

According to some embodiments, the method further includes generating the data by monitoring the at least one PK effect and/or the at least one PD effect induced by at least one of the first agent and the second agent in the subject.

According to some embodiments, the method further includes pulmonary delivering at least two pre-determined vaporized amounts of at least one of the first agent and the second agent according to a pre-defined regimen.

According to some embodiments, the method further includes adjusting the regimen so as to achieve the pre-determined PK effect and/or the pre-determined PD effect based on the at least one PK effect and/or the at least one PD effect induced by at least one of the first agent and the second agent in the subject.

According to some embodiments, the method further includes generating the data by monitoring the at least one PK effect and/or the at least one PD effect induced by at least one of the first agent and the second agent in the subject.

According to some embodiments, monitoring the PK effect and/or the PD effect is effected at pre-determined time intervals before during and/or after the pulmonary delivering.

According to some embodiments, the monitoring includes receiving data indicative of at least one PD effect in the subject from at least one sensor being in communication with a controller associated with the inhaler device.

According to some embodiments, the adjusting includes is based on data received via a user interface device.

According to some embodiments, the adjusting is effected in real-time.

According to some embodiments, monitoring the PK effect and/or the PD effect induced by at least one of the agent and the second agent in the subject, is effected at pre-determined time intervals before, during and/or after the pulmonary delivering.

According to some embodiments, the PK effect includes a concentration of each of the agents in a given volume of a bodily fluid and a concentration of each of the agents in a given mass of a bodily tissue.

According to some embodiments, the PD effect pertains to a pre-determined PD profile, which ranges between a minimal level of the desired effect and a level of an undesired effect.

According to some embodiments, the pre-determined PD profile ranges between a minimal level of the desired effect to a minimal level of the undesired effect.

According to some embodiments, the pre-determined PD profile ranges between a minimal level of the desired effect to a level higher than a minimal level of the undesired effect.

According to some embodiments, defining at least one of the desired effect and/or the undesired effect includes receiving instructions from the subject.

According to some embodiments, the biomarker includes an invasively-detected biomarker and a non-invasively-detected biomarker.

According to some embodiments, the non-invasively-detected biomarker includes a heart rate, an oxygenation level (SpO2), a blood pressure, a respiratory rate, a body temperature, an inhalation volume, a facial expression, muscle twitches, cramps, spasms, sweating, hand-eye coordination, eye vascular expansion, reddening of the conjunctiva and/or sclera, a variation in intra-ocular pressure, a motor skill, ataxia, sinus tachycardia, a tremor, cardiac arrhythmias, a skin conductance/impedance level, a seizure, an electromyography (EMG), an electrocardiogram (ECG), a photo-plethysmogram (PPG), a galvanic skin response (GSR), Blue-Brown visual inhibition, H-mask visual inhibition, Auditory Latent inhibition, Visual Latent inhibition, Stroop color word, Simple reaction (conflict task), Cognitive Set switching, Logical reasoning, Decision making time, Rapid info processing, Perceptual maze, Simulated driving, Visual search, Time estimation, Time perception, Visual search, Attentional search, Symbol copying, Letter cancellation, Alphabetic cross-out, D2 cancellation, Brickenkamp D2, digit copying test (DDCT), symbol-digit substitution (SDST), digit-symbol substitution test (DSST), Digit Vigilance, Vigilance, Auditory vigilance test, Wesnes/Warburton Vigilance task, Rapid info processing, CRT+Tracking Divided attention, Selective attention, Focused attention Task, Emotional attention Task, Auditory Flutter fusion, Flash fusion, critical flicker fusion (CFF), Continuous attention, Paired associate learning, Wordlist learning, 15 word test, Introductory conditioning, Delayed word recall, Delayed word recognition, Delayed picture recognition, Word presentation, Word recognition, Numeric working memory, Numerical memory, Memory scanning, Auditory Brown/Peterson, Visual Brown/Peterson, Visual spatial memory, Fragmented picture test, Pauli test, Block Span, Digit span, Digit Span (forward), Digit Span (backward), WAIS vocabulair, WAIS similarity, Word fluency, Verbal fluency, Performance time (Delayed word recogn.), Performance time (Numeric working memory), Performance time (Digit vigilance), Performance time (Rapid info processing), Performance time (Delayed picture recognition), Performance time (Visual information processing), Simple Reaction Time CRT, Complex RTvisual, Visual choice RT, VRT, Visual response speed, ART, Acoustic RT, Wire Maze Tracing, Archimedian spiral, Critical tracking task, Trail making, Tracking Complex, Tracking Wiener Geraet, Flexibility of closure, WAIS block design, WAIS picture comparison, Digit copying, Manipulative motor, Feinmotorik, Graphological analysis, tapping, Hand arm lateral reach coordination, Visual arm random reach, Motor control & coordination, Motor behavior.

According to some embodiments, the desired effect corresponds to a symptom, the symptom includes pain, migraine, depression, cognitive function deficit, attention deficit, hyperactivity, anxiety disorders, diarrhea, nausea, vomiting, insomnia, delirium, appetite variations, sexual dysfunction, spasticity, increased intra ocular pressure, bladder dysfunction, tics, Tourette symptoms, post traumatic stress disorder (PTSD) symptoms, inflammatory bowel disease (IBD) symptoms, irritable bowel syndrome (IBS) symptoms, hyper tension, hemorrhagic symptoms, septic and cardiogenic shock, drug addiction and craving, withdrawal symptoms, tremors and other movement disorders.

According to some embodiments, the PD effect is a psychotropic effect and/or a somatic effect.

According to some embodiments, the psychotropic effect corresponds to a symptom, the symptom includes paranoia, anxiety, panic attack, euphoria, pseudo-hallucinatory, ataxia, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence and depression.

According to some embodiments, the somatic effect corresponds to a symptom, the symptom includes nausea, muscle twitches, muscle relaxation cramps, spasms, sweating, ataxia, a motor activity variation, dry mouth and a sensation of cold or hot hands and feet, increased heart rate, increased cerebral blood flow, dilation of bronchial passages, dilation of blood vessels, eye redness and pupil dilation, dry mouth, thirst, hunger or food craving.

According to some embodiments, the at least one plant includes *Cannabis sativa, Cannabis indica, Cannabis ruderalis, Acacia* spp, *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp, *Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), a *Sapindaceae, Camellia* spp., *Malvaceae* spp., *Aquifoliaceae* spp., *Hoodia,* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis, Aloe Vera, Angelica, Anise, Ayahuasca (Banisteriopsis caapi)*, Barberry, Black Horehound, Blue Lotus, Burdock, Camomile/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (Peganum harmala), Thyme, Turmeric, Valerian, Wild Yam, Wormwood, Yarrow, Yerba Mate, Yohimbe, and any part and any combination thereof.

According to some embodiments, the at least one plant includes *Cannabis sativa, Cannabis indica*, and *Cannabis ruderalis*.

According to some embodiments, at least one of the first pharmacologically active agent and the second pharmacologically active agent includes Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

According to some embodiments, at least one of the first pharmacologically active agent and the second pharmacologically active agent includes Δ9-tetrahydrocannabinol (THC) and cannabidiol (CBD).

According to an aspect of some embodiments of the present disclosure there is provided a system for pulmonary delivering to a subject at least a first pharmacologically active agent and a second pharmacologically active agent, at least one of which being in at least one plant material, the system includes:
- a metered dose inhaler device configured independently deliver the agents to the subject by heating the at least one plant material to vaporize at least a first pre-determined vaporized amount of the first agent and at least a second pre-determined vaporized amount of the second agent; and
- a controller in communication with the inhaler device, configured to effect the heating of the first pre-determined vaporized successively, concomitantly and/or at least partially overlapping with the second pre-determined vaporized amount,
- wherein each of the pre-determined vaporized amounts of each of the agents is selected to induce in the subject independently at least one PK effect and/or at least one PD effect.

According to an aspect of some embodiments of the present disclosure there is provided a system that includes:
- a metered dose inhaler device for pulmonary delivering to a subject at least one pre-determined vaporized amount of at least one pharmacologically active agent being in a plant material, by controllably heating the plant material so as to vaporize the at least one pre-determined vaporized amount of the agent; and
- a controller in communication with the inhaler device, configured to control the pre-determined vaporized amount based on data indicative of at least one pharmacodynamic effect induced by the agent in the subject.

According to some embodiments, the data is obtainable via at least one sensor configured for monitoring the pharmacodynamic effect and/or via a user interface device configured for inputting data obtainable from at least one sensor for monitoring the pharmacodynamic effect.

According to some embodiments, the controller is configured to receive operation setting data pertaining to the pre-determined vaporized amount from a remote control device.

According to some embodiments, the controller is configured to receive the data from the sensor and/or the user interface device.

According to some embodiments, the controller is in direct and/or indirect communication with the sensor and/or the interface device.

According to some embodiments, the controller is configured to control the pre-determined vaporized amount by controlling at least one of an airflow, a heating temperature, a heating rate, a heating pattern, a heating duration and any combination thereof.

According to some embodiments, the controller is configured to control the pre-determined vaporized amount by controlling pulmonary delivering timing.

According to some embodiments, the controlling is effected in real-time.

According to some embodiments, the controller is configured for adjusting the pre-determined vaporized amount so as to achieve a pre-determined pharmacokinetic effect and/or a pre-determined pharmacodynamic effect based on the pharmacodynamic effect.

According to some embodiments, controller is configured for effecting the adjusting the pre-determined vaporized amount in real-time.

According to some embodiments, the controller is configured for effecting a pre-defined regimen that includes delivering at least two pre-determined vaporized amounts.

According to some embodiments, controller is configured for adjusting the regimen so as to achieve a pre-determined pharmacokinetic effect and/or a pre-determined pharmacodynamic effect based on the pharmacodynamic effect.

According to some embodiments, the controller is configured for effecting the adjusting the regimen in real-time.

According to some embodiments, the system includes at least one sensor configured for monitoring the pharmacodynamic effect.

According to some embodiments, the system includes a user interface device.

According to some embodiments, the user interface device includes an output device for providing information to at least one the subject, a practitioner, a memory unit and a remote device.

According to some embodiments, the user interface device includes a smartphone device.

According to some embodiments, the controller is configured for monitoring at least one of the at least one pre-determined pharmacokinetic effect and/or the at least one pre-determined pharmacodynamic effect, based on data received via the user interface device.

According to some embodiments, the controller is configured for effecting the adjusting the pre-determined vaporized amount in real-time.

According to some embodiments, the sensor includes a touch screen, an accelerometer, a proximity sensor, an infrared sensor, a camera, a magnetometer, a user location and orientation sensor, a gyroscope, a compass, a microphone, a thermometer, a humidity sensor, a heart rate sensor, a blood pressure sensor, a skin conductance/impedance sensor, a blood oxygenation level (SpO2), an inhalation volume sensor and an airflow sensor.

According to some embodiments, the system includes at least one dose unit, the dose unit includes the plant material.

According to some embodiments, the system includes a plurality of the dose units, the inhaler device is configured for using at least one of the dose units.

According to some embodiments, each of the dose units includes a plant material having a different composition of the at least one pharmacologically active agent.

According to some embodiments, the controller is configured to control the pre-determined vaporized amount by selecting at least one of the dose units according to the composition of the at least one pharmacologically active agent.

According to some embodiments, the inhaler device configured by the controller for pulmonary delivering to a subject at least a first pharmacologically active agent and a second pharmacologically active agent, at least one of which being in at least one plant material, the device is configured to vaporize at least a first pre-determined vaporized amount of the first agent and at least a second pre-determined vaporized amount of the second agent, wherein the heating is effected such that the first pre-determined vaporized amount is delivered to the subject successively, concomitantly and/or at least partially overlapping with the second pre-determined vaporized amount.

According to some embodiments, the plant includes *Cannabis sativa, Cannabis indica, Cannabis ruderalis, Acacia* spp, *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnata, Lophophora williamsii, Phalaris* spp., *Duboisia hopwoodii, Papaver somniferum, Psychotria viridis,* spp., *Salvia divinorum, Combretum quadrangulare, Trichocereus pachanoi, Heimia salicifolia, Stipa robusta, Solandra* spp., *Hypericum perforatum, Peganum harmala, Tabernaemontana* spp, *Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (Rubiaceae), a Sapindaceae, *Camellia* spp., Malvaceae spp., Aquifoliaceae spp., Hoodia, spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* Aloe Vera, Angelica, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, Yohimbe, and any part and any combination thereof.

According to some embodiments, the plant includes *Cannabis sativa, Cannabis indica,* and *Cannabis ruderalis.*

According to some embodiments, the pharmacologically active agent includes Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

According to some embodiments, the pharmacologically active agent includes Δ9-tetrahydrocannabinol (THC) and cannabidiol (CBD).

According to an aspect of some embodiments of the present disclosure there is provided a method of pulmonary delivering to a subject at least one pharmacologically active agent being in a plant material; the method includes:
  pulmonary delivering the agent to the subject from a metered dose inhaler device configured to vaporize at least one pre-determined vaporized amount of the agent upon controllably heating the plant material;
  monitoring at least one pharmacokinetic effect and/or at least one pharmacodynamic effect induced by the agent in the subject;
  adjusting the at least one pre-determined vaporized amount so as to achieve at least one pre-determined pharmacokinetic effect and/or at least one pre-determined pharmacodynamic effect based data generated through the monitoring.

According to an aspect of some embodiments of the present disclosure there is provided a method of recording at least one pharmacokinetic effect and/or at least one pharmacodynamic effect, induced by pulmonary delivering to a subject at least one pharmacologically active agent being in a plant material; the method includes:
  pulmonary delivering a pre-determined vaporized amount of the agent to the subject from a metered dose inhaler device configured to vaporize the pre-determined vaporized amount of the agent upon controllably heating the plant material;
  optionally, determining at least one pharmacokinetic effect in the subject at pre-determined time intervals before during and/or after the pulmonary delivering;
  determining at least one pharmacodynamic effect in the subject at pre-determined time intervals before during and/or after the pulmonary delivering;
  wherein the pharmacodynamic effect includes a desired effect, an undesired effect, a therapeutic effect, an adverse effect and a level of a biomarker.

According to an aspect of some embodiments of the present disclosure there is provided a method of pulmonary delivering at least one pharmacologically active agent to a patient (also referred to herein interchangeably as user of subject), the method comprising pulmonary delivering the agent to the patient from a metered dose inhaler device configured to release at least one pre-determined vaporized amount of the agent upon controllably heating a solid form of a substance comprising the agent, wherein the at least one pre-determined vaporized amount of the agent is selected so as to exhibit at least one pre-selected pharmacokinetic profile and/or at least one pre-selected pharmacodynamic profile of the agent in the patient.

According to some embodiments, the method further comprises:

determining at least one pharmacokinetic parameter and/or at least one pharmacokinetic variable and/or at least one pharmacodynamic parameter induced by the pulmonary delivering the agent in the patient from the device;

based on the pharmacokinetic parameter and/or the pharmacokinetic variable and/or the pharmacodynamic parameter, determining the pre-determined vaporized amount which exhibits the pre-selected pharmacokinetic profile and/or the pre-selected pharmacodynamic profile of the agent in the patient; and configuring the device to deliver the at least one pre-determined vaporized amount of the agent.

According to some of any of the embodiments described herein, each of the pharmacokinetic parameter and/or the pharmacokinetic variable and/or the pharmacodynamic parameter is determined for an individual patient, such that the pre-determined vaporized amount is determined personally for the patient.

According to some of any of the embodiments described herein, the pulmonary delivering comprises:

determining at least one personal pharmacodynamic and/or at least one personal pharmacokinetic parameter in an individual patient, so as to determine if pulmonary delivering the at least one pre-determined vaporized amount of the agent exhibits the pre-selected pharmacodynamic and/or the pre-selected pharmacokinetic profile in said individual patient;

if pulmonary delivering the at least one pre-determined vaporized amount of the agent does not exhibit the pre-selected pharmacodynamic and/or pharmacokinetic profile in said individual patient, determining an adjusted vaporized amount of the agent that exhibits the pre-selected pharmacodynamic and/or pharmacokinetic profile in said individual patient; and re-configuring the device to deliver the adjusted vaporized amount, whereby, upon the re-configuring, the adjusted vaporized amount is the pre-determined vaporized amount.

According to some of any of the embodiments described herein, the personal pharmacodynamic parameter is selected from the group consisting of a personally perceived therapeutic effect, a personally perceived adverse effect and a (presence or a level of a) biomarker.

According to some of any of the embodiments described herein, the biomarker is selected from the group consisting of an invasively-detected biomarker and a non-invasively-detected biomarker.

According to some of any of the embodiments described herein, the non-invasively-detected biomarker is selected from the group consisting of a heart rate, an oxygenation level (SpO2), a blood pressure, a respiratory rate, a body temperature, an inhalation volume, a facial expression, muscle twitches, cramps, spasms, sweating, hand-eye coordination, eye vascular expansion, reddening of the conjunctiva and/or sclera, a variation in intra-ocular pressure, a motor skill, ataxia, sinus tachycardia, a tremor, cardiac arrhythmias, a skin conductance/impedance level, a seizure, an electromyography (EMG), an electrocardiogram (ECG), a photo-plethysmogram (PPG), a galvanic skin response (GSR), Blue-Brown visual inhibition, H-mask visual inhibition, Auditory Latent inhibition, Visual Latent inhibition, Stroop color word, Simple reaction (conflict task), Cognitive Set switching, Logical reasoning, Decision making time, Rapid info processing, Perceptual maze, Simulated driving, Visual search, Time estimation, Time perception, Visual search, Attentional search, Symbol copying, Letter cancellation, Alphabetic cross-out, D2 cancellation, Brickenkamp D2, digit copying test (DDCT), symbol-digit substitution (SDST), digit-symbol substitution test (DSST), Digit Vigilance, Vigilance, Auditory vigilance test, Wesnes/Warburton Vigilance task, Rapid info processing, CRT+Tracking Divided attention, Selective attention, Focused attention Task, Emotional attention Task, Auditory Flutter fusion, Flash fusion, critical flicker fusion (CFF), Continuous attention, Paired associate learning, Wordlist learning, 15 word test, Introductory conditioning, Delayed word recall, Delayed word recognition, Delayed picture recognition, Word presentation, Word recognition, Numeric working memory, Numerical memory, Memory scanning, Auditory Brown/Peterson, Visual Brown/Peterson, Visual spatial memory, Fragmented picture test, Pauli test, Block Span, Digit span, Digit Span (forward), Digit Span (backward), WAIS vocabulair, WAIS similarity, Word fluency, Verbal fluency, Performance time (Delayed word recogn.), Performance time (Numeric working memory), Performance time (Digit vigilance), Performance time (Rapid info processing), Performance time (Delayed picture recognition), Performance time (Visual information processing), Simple Reaction Time CRT, Complex RTvisual, Visual choice RT, VRT, Visual response speed, ART, Acoustic RT, Wire Maze Tracing, Archimedian spiral, Critical tracking task, Trail making, Tracking Complex, Tracking Wiener Geraet, Flexibility of closure, WAIS block design, WAIS picture comparison, Digit copying, Manipulative motor, Feinmotorik, Graphological analysis, tapping, Hand arm lateral reach coordination, Visual arm random reach, Motor control & coordination, Motor behavior.

According to some of any of the embodiments described herein, the personally perceived therapeutic effect corresponds to a symptom, the symptom being selected from the group consisting of pain, migraine, depression, cognitive function deficit, attention deficit, hyperactivity, anxiety disorders, diarrhea, nausea, vomiting, insomnia, delirium, appetite variations, sexual dysfunction, spasticity, increased intra ocular pressure, bladder dysfunction, tics, Tourette symptoms, post traumatic stress disorder (PTSD) symptoms, inflammatory bowel disease (IBD) symptoms, irritable bowel syndrome (IBS) symptoms, hyper tension, hemorrhagic symptoms, septic and cardiogenic shock, drug addiction and craving, withdrawal symptoms, tremors and other movement disorders.

According to some of any of the embodiments described herein, the personally perceived adverse effect is a psychotropic adverse effect and/or a somatic adverse effect.

According to some of any of the embodiments described herein, the psychotropic adverse effect corresponds to a symptom, the symptom being selected from the group consisting of paranoia, anxiety, panic attack, euphoria, pseudo-hallucinatory, ataxia, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence and depression.

According to some of any of the embodiments described herein, the somatic adverse effect corresponds to a symptom, the symptom being selected from the group consisting of nausea, muscle twitches, muscle relaxation cramps, spasms, sweating, ataxia, a motor activity variation, dry mouth and a sensation of cold or hot hands and feet, increased heart rate, increased cerebral blood flow, dilation of bronchial passages, dilation of blood vessels, eye redness and pupil dilation, dry mouth, thirst, hunger or food craving.

According to some of any of the embodiments described herein, the pulmonary delivering further comprises:
configuring the device to deliver an adjusted vaporized amount of the agent, the adjusted vaporized amount is selected so as to exhibit a re-selected pharmacodynamic profile of the agent in the patient,
whereby, upon the configuring, the adjusted vaporized amount is the pre-determined vaporized amount and the re-selected pharmacodynamic profile is the pre-selected pharmacodynamic profile.

According to some of any of the embodiments described herein, the device is configured to deliver the pre-determined vaporized amount such that a deviation of an actual vaporized amount of the agent, from the pre-determined vaporized amount of the agent, is less than 20% of the pre-determined vaporized amount.

According to some of any of the embodiments described herein, a deviation of an actual pharmacokinetic profile from the pre-selected pharmacokinetic profile is less than 40% of the pre-selected pharmacokinetic profile.

According to some of any of the embodiments described herein, a deviation of a perceived pharmacodynamic profile from the pre-selected pharmacodynamic profile at at least one time point is less than 25% of the pre-selected pharmacodynamic profile.

According to some of any of the embodiments described herein, the pre-selected pharmacodynamic profile is selected from the group consisting of:
a pharmacodynamic profile within a level lower than a minimal level of a therapeutic effect,
a pharmacodynamic profile ranging within a minimal level of the therapeutic effect to a maximal level of the therapeutic effect in which an adverse effect is not exhibited or perceived, and
a pharmacodynamic profile within a level higher than a minimal level of an adverse effect.

According to some of any of the embodiments described herein, the pharmacodynamic profile ranges within a minimal level of the therapeutic effect to a maximal level of the therapeutic effect in which an adverse effect is not exhibited or perceived (within a therapeutic window).

According to some of any of the embodiments described herein, a deviation of the perceived pharmacodynamic profile from the pre-selected pharmacodynamic profile at at least one time point is less than 25% below the pre-selected pharmacodynamic profile.

According to some of any of the embodiments described herein, the pharmacokinetic variable is selected from the group consisting of a body weight, a body height, a gender, an age, a body mass index and a lean body mass.

According to some of any of the embodiments described herein, the pharmacokinetic parameter is selected from the group consisting of a maximal plasma concentration ($C_{max}$), a time for reaching a maximal plasma concentration ($T_{max}$) and total exposure over time ($AUC_{0 \to \infty}$).

According to some of any of the embodiments described herein, the pharmacokinetic parameter and/or the pharmacodynamic parameter is determined while monitoring at least one additional parameter selected from the group consisting of:
a vital sign selected from the group consisting of a heart rate, an oxygenation level (SpO2), a blood pressure, a respiratory rate and a body temperature;
a pulmonary function selected from the group consisting of forced expiratory volume (FEV1), maximum mid-expiratory flow (MMEF), diffusing capacity of the lung for carbon monoxide (DLCO), forced vital capacity (FVC), total lung capacity (TLC) and residual volume (RV);
a hematological marker selected from the group consisting of a hemoglobin level, a hematocrit ratio, a red blood cell count, a white blood cell count, a white blood cell differential and a platelet count;
a coagulation parameter selected from the group consisting of a prothrombin time (PT), a prothrombin ratio (PR) and an international normalized ratio (INR);
a kidney function marker selected from the group consisting of a creatinine clearance (CCr), a blood urea nitrogen level (BUN) and a glomerular filtration rate (GFR); and
a liver function marker selected from the group consisting of an aspartate aminotransferase (AST) level, a serum glutamic oxaloacetic transaminase (SGOT) level, an alkaline phosphatase level, and a gamma-glutamyl transferase (GGT) level.

According to some of any of the embodiments described herein, the method as described herein is for pulmonary delivering at least two pharmacologically active agents to the patient, wherein the device is configured to deliver independently a pre-determined vaporized amount of each of the at least two pharmacologically active agents.

According to some of any of the embodiments described herein, the method is for delivering the at least two pharmacologically active agents at a pre-determined time interval.

According to some of any of the embodiments described herein, the method is for delivering each of the at least two pharmacologically active agents independently at a pre-determined vaporized amount, wherein the substance comprises the at least two pharmacologically active agents.

According to some of any of the embodiments described herein, the method is for delivering a plurality of pre-determined vaporized amounts of the pharmacologically active agent, the plurality of pre-determined vaporized amounts being the same or different from one another.

According to some of any of the embodiments described herein, the plurality of pre-determined vaporized amounts are delivered from the device at pre-determined time intervals, the time intervals being the same or different.

According to some of any of the embodiments described herein, the device is in communication with a patient interface circuitry.

According to an aspect of some embodiments of the present disclosure there is provided a metered dose inhaler device configured for pulmonary delivering a pre-determined vaporized amount of at least one pharmacologically active agent to a patient, upon controllably heating a solid form of a substance comprising the agent, wherein:
the pre-determined vaporized amount is for exhibiting a pre-selected pharmacokinetic profile and/or a pre-selected pharmacodynamic profile of the agent in the patient; and
the pre-determined vaporized amount of the agent is determined by determining at least one pharmacokinetic parameter and/or at least one pharmacokinetic variable and/or at least one pharmacodynamic parameter induced by the pulmonary delivering of the agent in the patient from the device.

According to some of any of the embodiments described herein, the device is configured for use in communication with a patient interface circuitry.

According to some of any of the embodiments described herein, the device is capable of releasing the pre-determined vaporized amount such that a deviation of an actual vaporized amount of the agent, from the pre-determined vaporized amount of the agent, is less than 20% of the pre-determined vaporized amount.

According to some of any of the embodiments described herein, the device is capable of releasing the pre-determined vaporized amount such that a deviation of an actual pharmacokinetic profile from the pre-selected pharmacokinetic profile is less than 40% of the pre-selected pharmacokinetic profile.

According to some of any of the embodiments described herein, the device is capable of releasing the pre-determined vaporized amount such that a deviation of a perceived pharmacodynamic profile from the pre-selected pharmacodynamic profile at at least one time point is less than 25% of the pre-selected pharmacodynamic profile.

According to some of any of the embodiments described herein, the pulmonary delivering, the agent, the pre-determined vaporized amount, the pre-selected pharmacokinetic profile and/or the pre-selected pharmacodynamic profile of the agent in the patient, the at least one pharmacokinetic parameter and/or at least one pharmacokinetic variable and/or at least one pharmacodynamic parameter, the re-selected pharmacodynamic profile, the adjusted vaporized amount and the determining of any of the foregoing, are as described in any one of the respective embodiments.

According to an aspect of some embodiments of the present disclosure there is provided a patient interface circuitry used with a metered dose inhaler device, the device being configured for pulmonary delivering a plurality of pre-determined vaporized amounts of at least one pharmacologically active agent to a patient, the patient interface circuitry comprising:
- a controller;
- an input;
- a communication module;
- wherein:
  - the plurality of pre-determined vaporized amounts are delivered from the device at pre-determined time intervals, the amounts and/or the time intervals being the same or different;
  - the plurality pre-determined vaporized amounts and the pre-determined time intervals comprise a dose, a dosing and/or a regimen, and the input is configured to receive the dose and/or regimen;
  - the input configured to interact with the patient in real time during pulmonary delivering the agent so as to obtain feedback from the patient;
  - the controller is configured to iteratively modify, according to the feedback, the dose and/or regimen to thereby derive an adjusted dose and/or regimen that comprises an adjusted pre-determined vaporized amount and adjusted time intervals; and
  - the communication module is configured to communicate the adjusted dose, the adjusted dosing and/or the adjusted regimen to the MDI device.

According to some of any of the embodiments described herein, the dose and/or regimen is selected to exhibit at least one pre-selected pharmacokinetic profile and/or at least one pre-selected pharmacodynamic profile of the agent in the patient.

According to some of any of the embodiments described herein, the patient interface circuitry is configured on a personal portable device, a handheld device, a wearable device, a wrist device or an integrated eyewear device.

According to some of any of the embodiments described herein, the personal portable device is selected from the group consisting of a smartphone, a handheld device, a wearable device, a wrist device or an integrated eyewear device.

According to some of any of the embodiments described herein, the patient interface circuitry comprises a memory in communication with the controller, the memory being configured to store the dose and/or regimen and usage data of the patient.

According to some of any of the embodiments described herein, the controller is configured to modify the dose and/or regimen in response to the usage data.

According to some of any of the embodiments described herein, the patient interface circuitry is configured to provide a tool set for obtaining at least one personal pharmacodynamic and/or at least one personal pharmacokinetic parameter in the patient.

According to some of any of the embodiments described herein, the personal pharmacodynamic parameter is selected from a group consisting of a personally perceived therapeutic effect, a personally perceived adverse effect and a biomarker.

According to some of any of the embodiments described herein, the tool set comprises at least one interactive application for assisting the patient in articulating a level of at least one of the personally perceived therapeutic effect and/or a level of the personally perceived adverse effect and/or a level of the biomarker.

According to some of any of the embodiments described herein, the interactive application is a game installed on a smartphone on which the patient interface is configured.

According to an aspect of some embodiments of the present disclosure there is provided a system comprising:
- a metered dose inhaler device for pulmonary delivering at least one pre-determined vaporized amount of at least one pharmacologically active agent to a patient; and
- a patient interface circuitry in communication with the device;
- wherein at least one of the patient interface circuitry and the device is configured to modify an operation setting according to at least one of direct and indirect input received in real time from the patient using the device, the operation setting comprising a dose and/or regimen for the pulmonary delivering the agent to the patient.

According to some of any of the embodiments described herein, the system is configured for adjusting the operation setting while maintaining the dose and/or regimen within a personalized safety range defined per the patient in which harm to the patient is prevented.

According to some of any of the embodiments described herein, the operation setting further comprises one or more protocols for timing the transfer of the dose and/or regimen and/or the usage data between the system components.

According to some of any of the embodiments described herein, the operation setting defines a timing schedule for the patient interface circuitry for reminding the patient to use the device.

According to some of any of the embodiments described herein, the system comprises at least one sensor for measuring at least one personal pharmacodynamic parameter in the patient.

According to some of any of the embodiments described herein, the patient interface is configured on a personal smartphone, and the sensor is a standard component of the smartphone.

According to some of any of the embodiments described herein, the sensor is selected from a group consisting of a touch screen, a camera, an accelerometer and a microphone.

According to some of any of the embodiments described herein, the sensor is a flow sensor comprised within the device, the sensor configured for detecting an inhalation volume of the patient for estimating the at least one personal pharmacodynamic parameter in the patient based on a correlation between the inhalation volume and the personal pharmacodynamic parameter.

According to some of any of the embodiments described herein, the personal pharmacodynamic parameter correlated with the inhalation volume is a pain level.

According to some of any of the embodiments described herein, the direct input comprises a willful indication provided by the patient using the patient interface circuitry.

According to some of any of the embodiments described herein, the indirect input comprises a personally perceived therapeutic effect and/or a personally perceived adverse effect obtained by the patient interface circuitry from the patient.

According to some of any of the embodiments described herein, the system further comprises a physician interface in communication with the patient interface circuitry and the device, the physician interface configured for selecting of the operation setting by a physician.

According to some of any of the embodiments described herein, the system further comprises a database server in communication with at least one of the device, the physician interface and the patient interface circuitry.

According to some of any of the embodiments described herein, the physician interface is configured to communicate with the database server for generating the dose and/or the regimen for the patient, and wherein the operation setting includes the dose and/or the regimen.

According to some of any of the embodiments described herein, the operation setting is modified according to usage data of the patient.

According to some of any of the embodiments described herein, the device comprises a substance dispenser configured to provide the agent, and a controller for actuating the dispenser for pulmonary delivery of the vaporized agent to the patient.

According to an aspect of some embodiments of the present disclosure there is provided a method of operating a metered dose inhaler device configured for pulmonary delivering at least one pharmaceutically active agent to a patient, the method comprising:
selecting a dose and/or regimen for pulmonary delivering the agent to the patient using the device;
obtaining, in real-time during pulmonary delivering the agent, an indication relating to at least one personal pharmacodynamic and/or at least one personal pharmacokinetic effect in the patient; automatically adjusting the dose and/or regimen according to the indication.

According to some of any of the embodiments described herein, the personal pharmacodynamic parameter is selected from the group consisting of a personally perceived therapeutic effect, a personally perceived adverse effect and a (presence and/or a level of a) biomarker.

According to some of any of the embodiments described herein, the personally perceived therapeutic effect is a reduction in a level of a symptom and the personally perceived adverse effect is a psychotropic effect and/or a somatic adverse effect.

According to some of any of the embodiments described herein, the dose and/or regimen is pre-selected to exhibit an initial build up of the agent in the patient, and/or to maintain a pre-selected pharmacokinetic profile and/or a pre-selected pharmacodynamic profile of the agent in the patient for a time period which is at least as long as the pulmonary delivering the agent.

According to some of any of the embodiments described herein (for the method, device, circuitry or system), the device is configured to deliver at least one pre-determined vaporized amount of the agent upon controllably heating a solid form of a substance comprising the agent.

According to some of any of the embodiments described herein (for the method, device, circuitry or system) the substance is a plant material.

According to some of any of the embodiments described herein (for the method, device, circuitry or system) the plant is selected from the group consisting of *Cannabis sativa*, *Cannabis indica*, *Cannabis ruderalis*, *Acacia* spp, *Amanita muscaria*, *Yage*, *Atropa belladonna*, *Areca catechu*, *Brugmansia* spp., *Brunfelsia latifolia*, *Desmanthus illinoensis*, *Banisteriopsis caapi*, *Trichocereus* spp., *Theobroma cacao*, *Capsicum* spp., *Cestrum* spp., *Erythroxylum coca*, *Solenostemon scutellarioides*, *Arundo donax*, *Coffea arabica*, *Datura* spp., *Desfontainia* spp., *Diplopterys cabrerana*, *Ephedra sinica*, *Claviceps purpurea*, *Paullinia cupana*, *Argyreia nervosa*, *Hyoscyamus niger*, *Tabernanthe iboga*, *Lagochilus inebriens*, *Justicia pectoralis*, *Sceletium tortuosum*, *Piper methysticum*, *Catha edulis*, *Mitragyna speciosa*, *Leonotis leonurus*, *Nymphaea* spp., *Nelumbo* spp., *Sophora secundiflora*, *Mucuna pruriens*, *Mandragora officinarum*, *Mimosa tenuiflora*, *Ipomoea violacea*, *Psilocybe* spp., *Panaeolus* spp., *Myristica fragrans*, *Turbina corymbosa*, *Passiflora incarnata*, *Lophophora williamsii*, *Phalaris* spp., *Duboisia hopwoodii*, *Papaver somniferum*, *Psychotria viridis*, spp., *Salvia divinorum*, *Combretum quadrangulare*, *Trichocereus pachanoi*, *Heimia salicifolia*, *Stipa robusta*, *Solandra* spp., *Hypericum perforatum*, *Peganum harmala*, *Tabernaemontana* spp., *Camellia sinensis*, *Nicotiana tabacum*, *rusticum*, *Virola theidora*, *Voacanga africana*, *Lactuca virosa*, *Artemisia absinthium*, *Ilex paraguariensis*, *Anadenanthera* spp., *Corynanthe yohimbe*, *Calea zacatechichi*, *Coffea* spp. (*Rubiaceae*), a *Sapindaceae*, *Camellia* spp., *Malvaceae* spp., *Aquifoliaceae* spp., *Hoodia*, spp. *Chamomilla recutita*, *Passiflora incarnate*, *Camellia sinensis*, *Mentha piperita*, *Mentha spicata*, *Rubus idaeus*, *Eucalyptus globulus*, *Lavandula officinalis*, *Thymus vulgaris*, *Melissa officinalis*, *Aloe Vera*, *Angelica*, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Sinicuichi (Mayan Sun Opener), Spearmint, Sweet Flag, Syrian Rue (*Peganum harmala*), Thyme, Turmeric, Valerian, Wild Yam, Wormwood, Yarrow, Yerba Mate, Yohimbe, and any part and any combination thereof.

According to some of any of the embodiments described herein (for the method, device, circuitry or system) the plant is selected from the group consisting of *Cannabis sativa, Cannabis indica*, and *Cannabis ruderalis*.

According to some of any of the embodiments described herein (for the method, device, circuitry or system) the pharmacologically active agent is selected from the group consisting of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), cannabidivarin (CBDV), tetrahydrocannabivarin (THCV) and cannabitriol (CBT).

According to some of any of the embodiments described herein (for the method, device, circuitry or system) the pharmacologically active agent is selected from the group consisting of Δ9-tetrahydrocannabinol (THC) and cannabidiol (CBD).

According to some of any of the embodiments described herein any of the method, device, circuitry or system described herein is for use in the treatment of a medical condition in a subject in need thereof.

According to some of any of the embodiments described herein (for the method, device, circuitry or system) the medical condition or a symptom associated therewith is ameliorated by pulmonary delivering the at least one pharmaceutically active agent.

Unless otherwise defined, all technical and/or scientific terms used herein have the same meaning as commonly understood by one of ordinary skill in the art to which the disclosure pertains. Although methods and materials similar or equivalent to those described herein can be used in the practice or testing of embodiments of the disclosure, some methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 (Background Art) is a photograph of a metered-dose inhaler device (Syqe Inhaler Exo™), according to some embodiments of the present disclosure.

Figure 2:
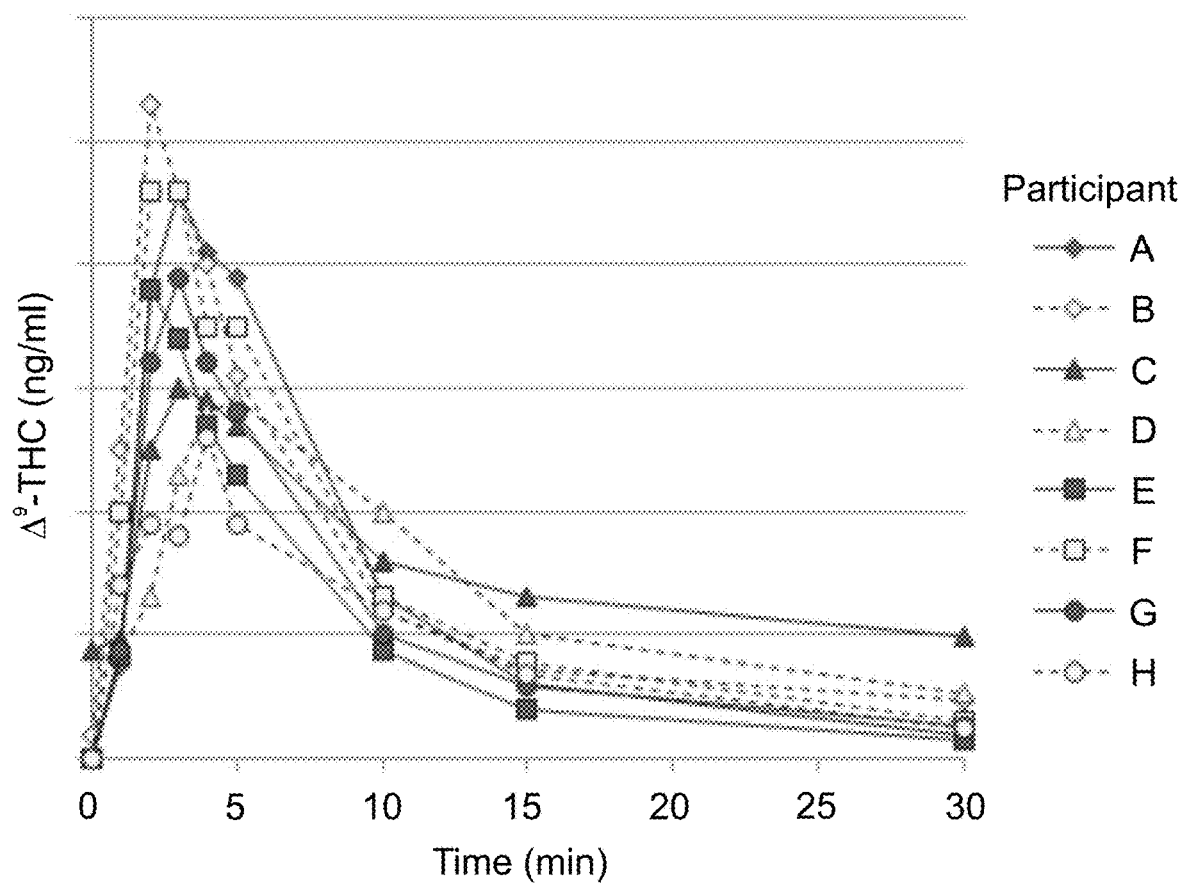

FIG. 2 presents comparative plots showing the Δ$^9$-THC plasma levels following single dose inhalation of 15.1±0.1 mg of ground *Cannabis* flos, containing 3.08±0.02 mg Δ$^9$-THC, using a metered-dose inhaler device according to some embodiments of the present disclosure.

Figure 3:
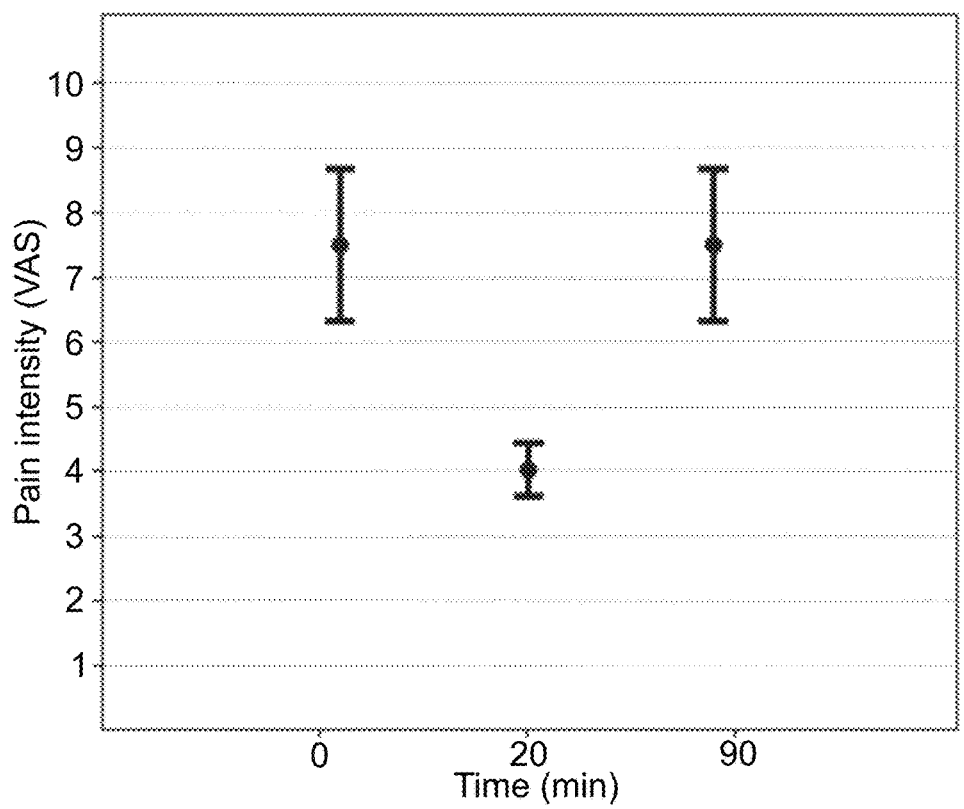

FIG. 3 presents a graph showing visual analog scale (VAS) pain intensity following single dose inhalation of 15.1±0.1 mg of ground *Cannabis* flos, containing 3.08±0.02 mg Δ$^9$-THC.

Figure 4:
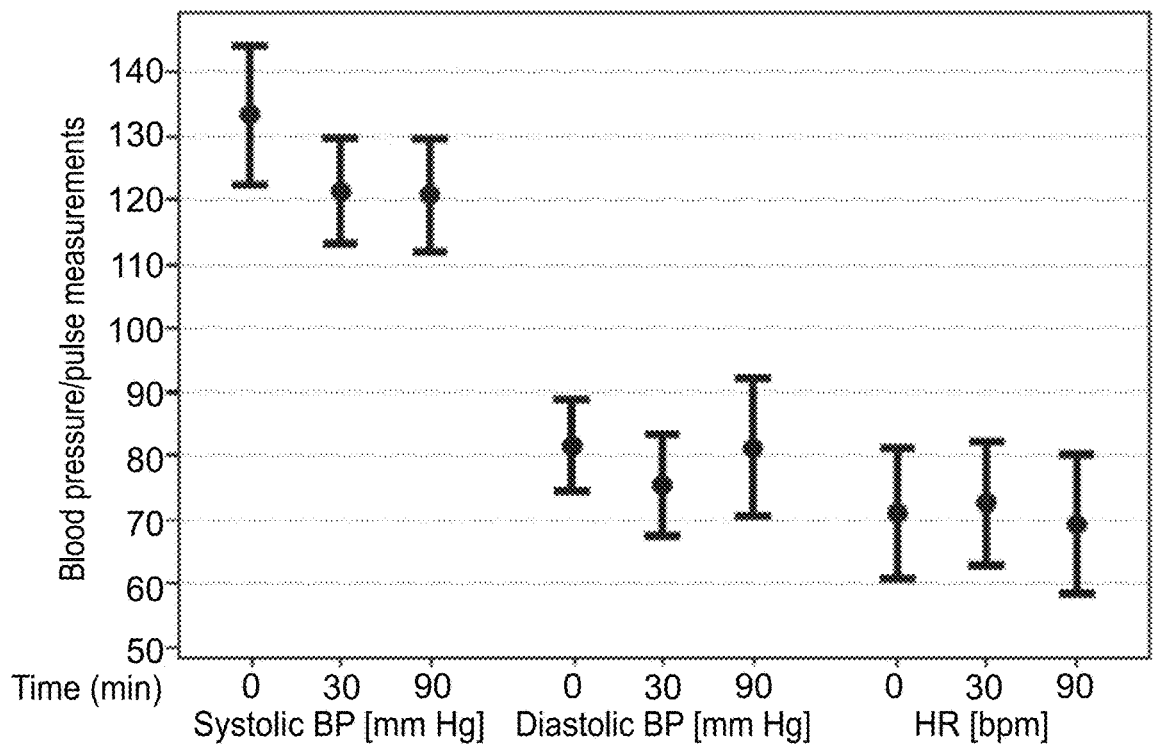

FIG. 4 presents a graph presenting blood pressure and heart rate following single dose inhalation of 15.1±0.1 mg ground *Cannabis* flos, containing 3.08±0.02 mg Δ$^9$-THC.

Figure 5:
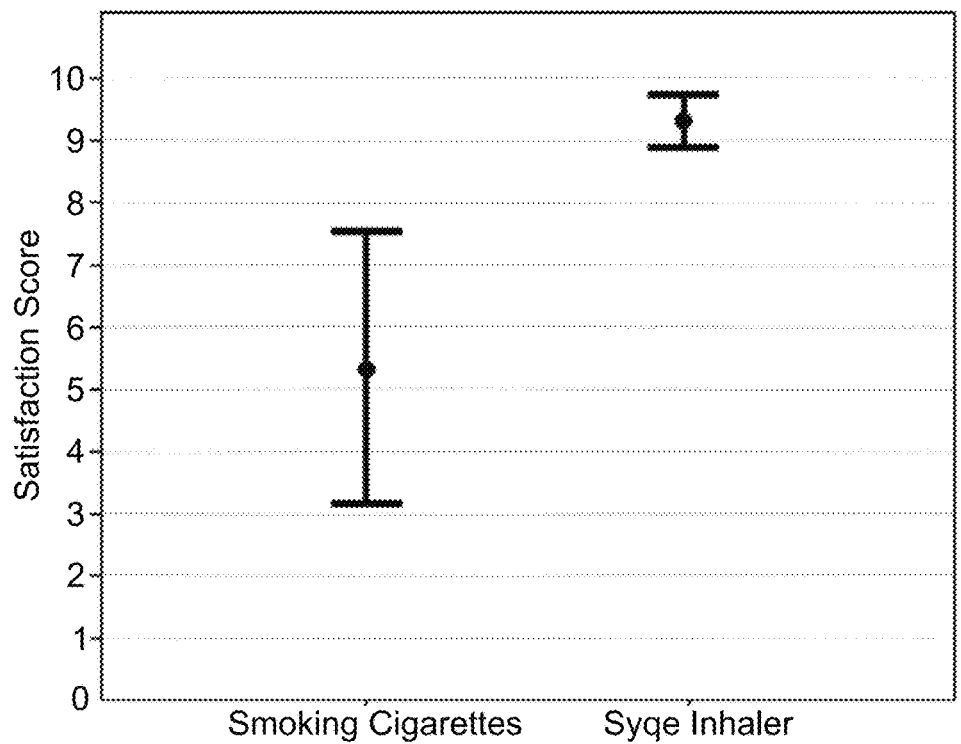

FIG. 5 presents a graph showing satisfaction score for inhalation of ground *Cannabis* flos compared to smoking *Cannabis* flos.

Figure 6:
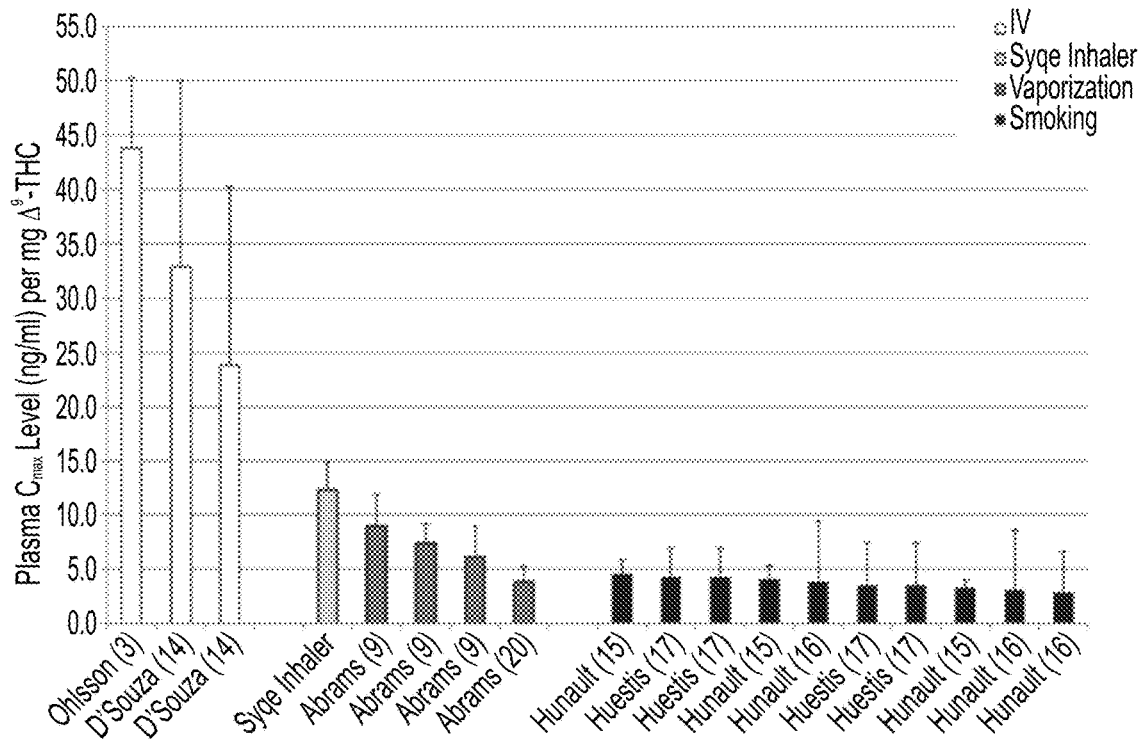

FIG. 6 is a bar graph presenting mean and 95% confidence limits of plasma $C_{max}$ levels per mg Δ$^9$-THC administered by intravenous, vaporization and smoking modes of delivery (Background Art, see, Example 2 hereinbelow), compared to Δ$^9$-THC plasma $C_{max}$ obtained by inhalation using a device according to some embodiments of the present disclosure. Numbers in parentheses represent related references as indicted in Example 2 hereinbelow.

Figure 7:
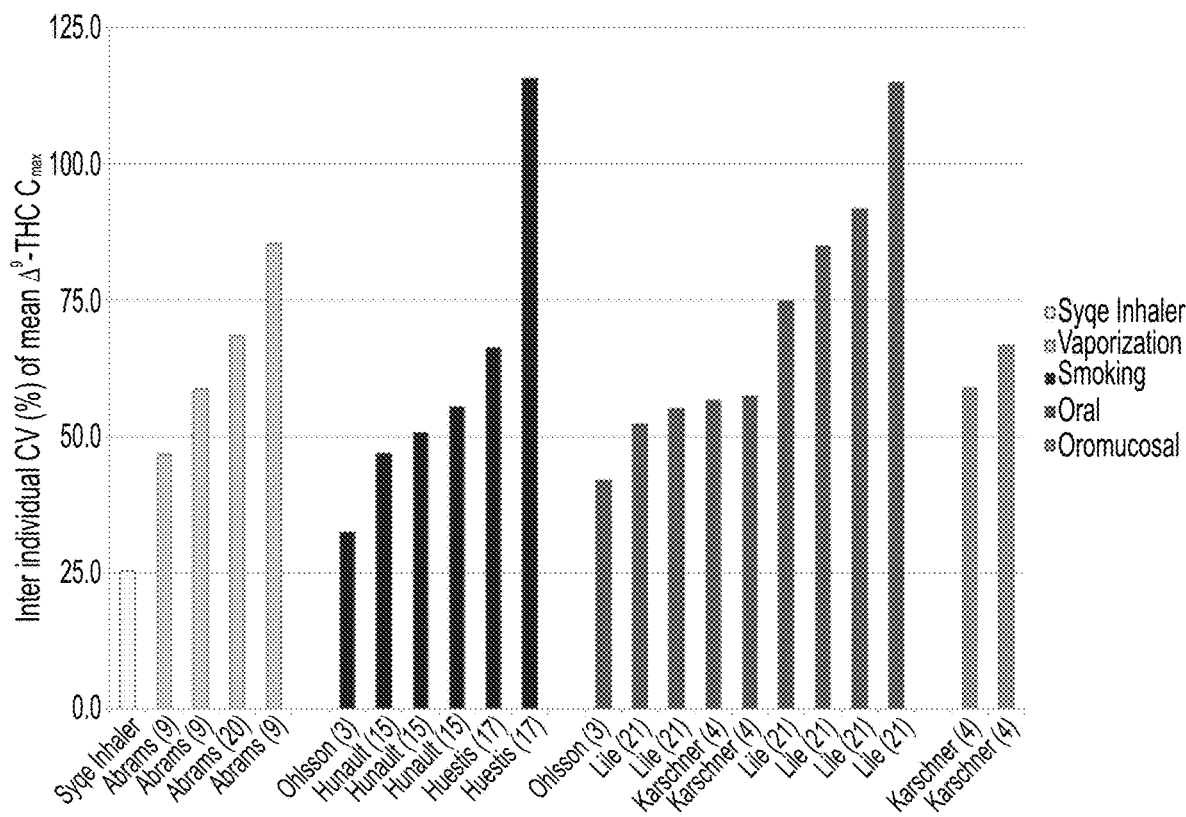

FIG. 7 is a bar graph presenting inter-individual variability (coefficient of variation, CV (%)) of Δ$^9$-THC plasma $C_{max}$ obtained by vaporization, smoking, oral and oromucosal methods of delivery (Background art, see, Example 2 hereinbelow) compared to Δ$^9$-THC plasma $C_{max}$ obtained by inhalation using a device according to some embodiments of the present disclosure. Numbers in parentheses represent related references, as indicated in Example 2 hereinbelow.

Figure 8:
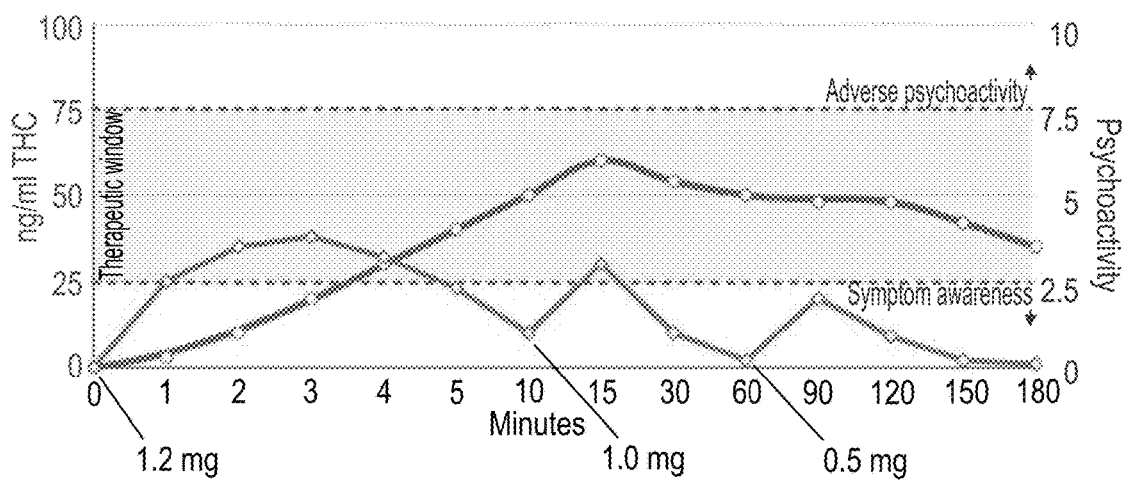

FIG. 8 presents a representative example of a pulmonary delivering of three pre-determined vaporized amounts (the calculated dosing) over a time period of 3-hours, as determined for Patient X.

Figure 9:
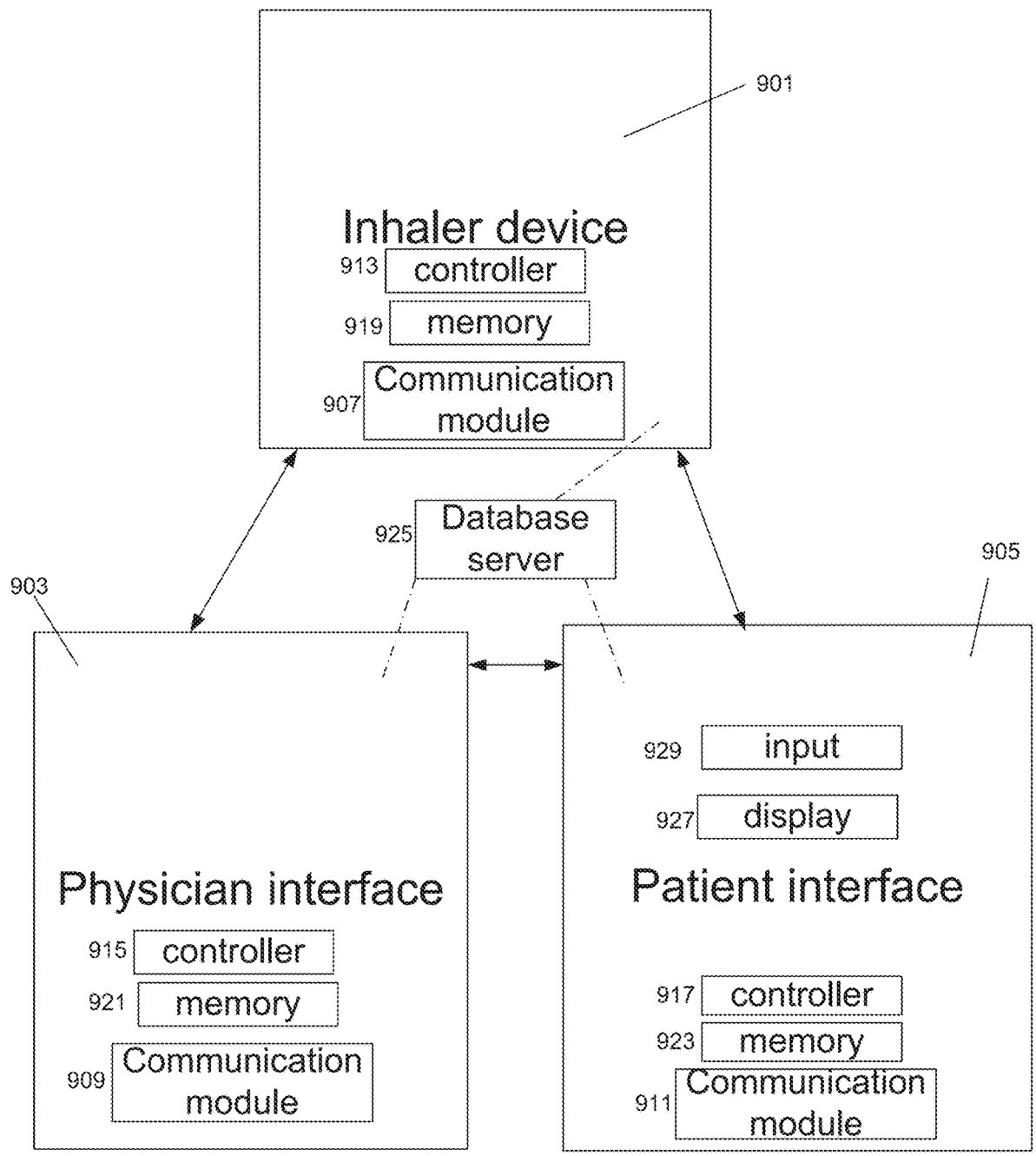

FIG. 9 is a schematic diagram of a system comprising an inhaler device, a physician interface and/or a patient interface, according to some embodiments of the present disclosure.

Figure 10:
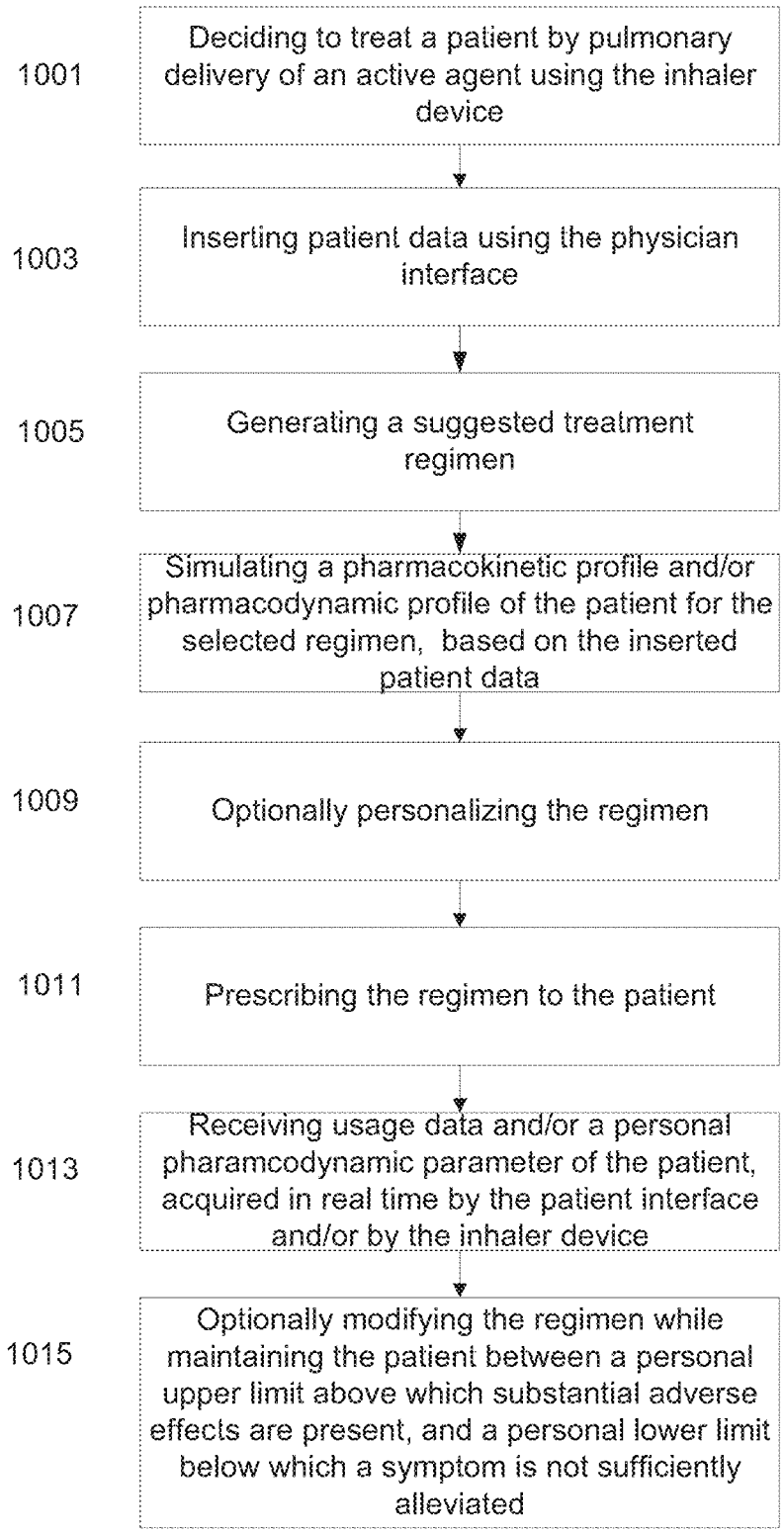

FIG. 10 is a flowchart of a method for prescribing a personalized regimen to a patient, according to some embodiments of the present disclosure.

FIGS. 11A, 11B, 11C and 11D are a schematic diagram (FIG. 11A) and print screens (FIGS. 11B, 11C and 11D) of a physician interface for selecting and prescribing a regimen to a patient, according to some embodiments of the present disclosure.

Figure 12:
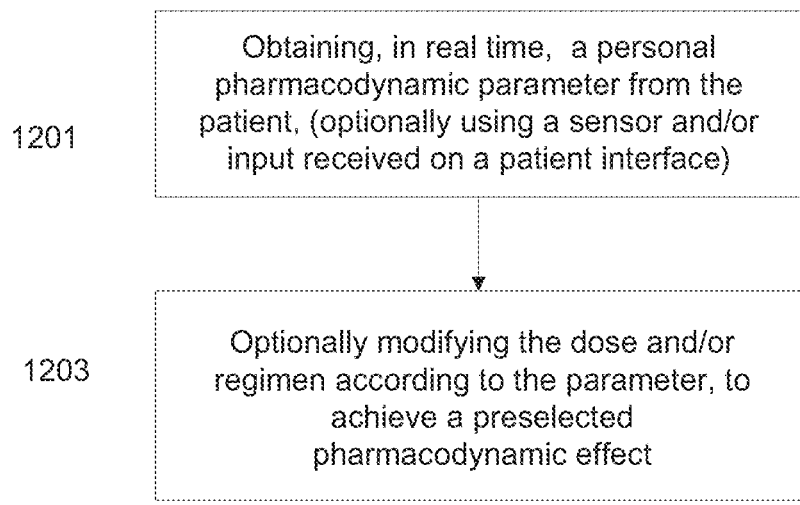

FIG. 12 is a flowchart of a method for obtaining a personal pharmacodynamic (PD) parameter from a patient and modifying a regimen accordingly, according to some embodiments of the present disclosure.

FIGS. 13A, 13B, 13C, 13D and 13E are print screens of a patient interface (FIGS. 13A, 13C, 13E), and graphic representations of an expected pharmacodynamic and pharmacokinetic profiles of the patient before and after a personal PD effect is obtained (FIGS. 13B and 13D respectively), according to some embodiments of the present disclosure.

Figure 14:
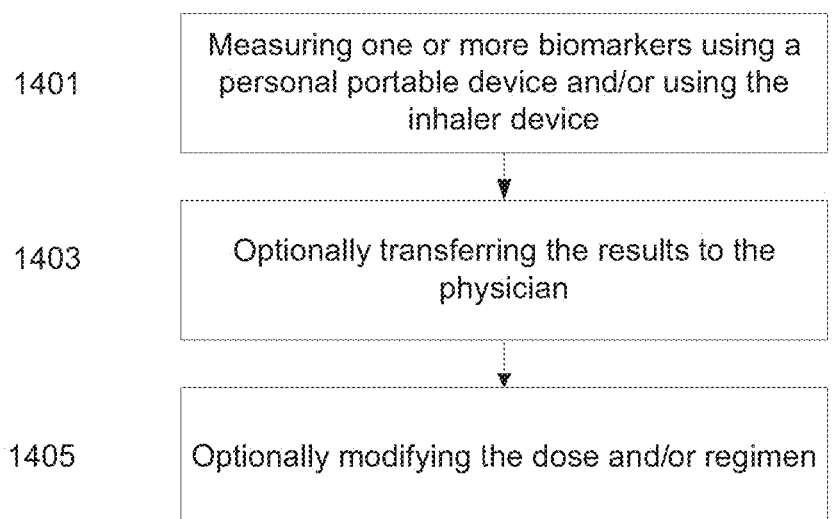

FIG. 14 is a flowchart of a method for obtaining one or more biomarkers using a personal portable device and/or using the inhaler device, and optionally modifying the dose and/or regimen accordingly, according to some embodiments of the present disclosure.

Figure 15A:
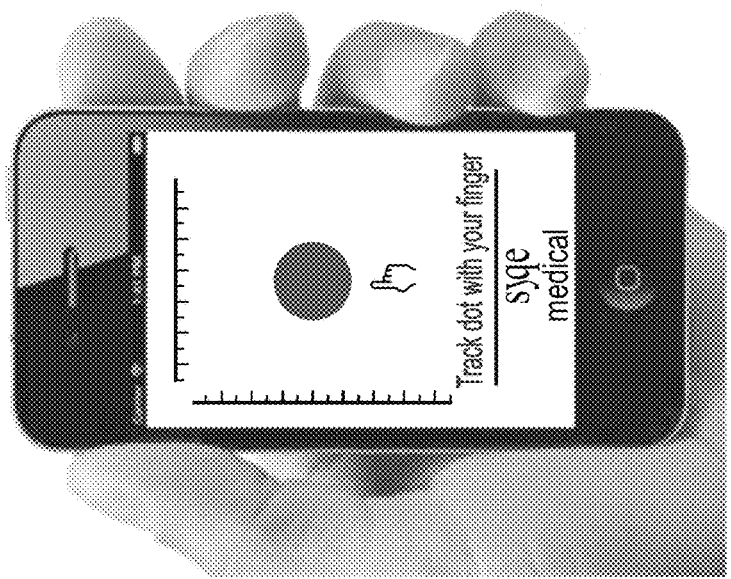
Figure 15B:
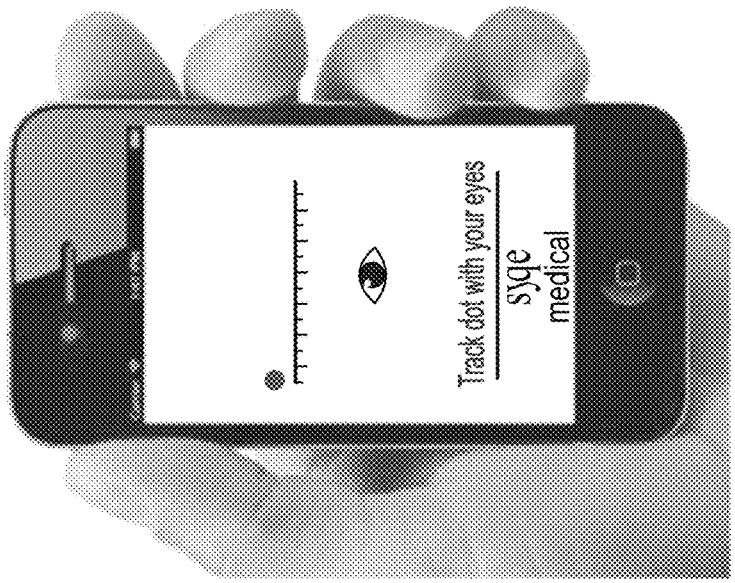
Figure 15C:
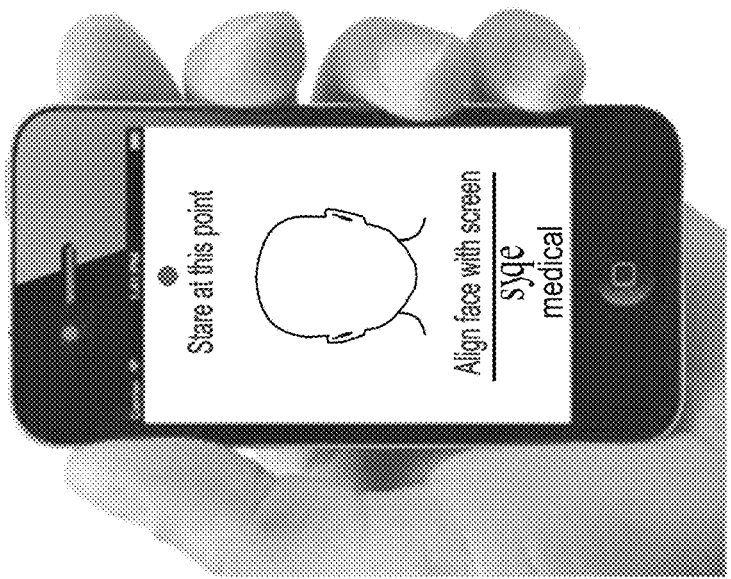

FIGS. 15A, 15B and 15C are print screens of a patient interface comprising various applications for obtaining biomarkers and/or for assisting a patient in determining a perceived therapeutic and/or adverse effect, according to some embodiments of the present disclosure.

Figure 16:
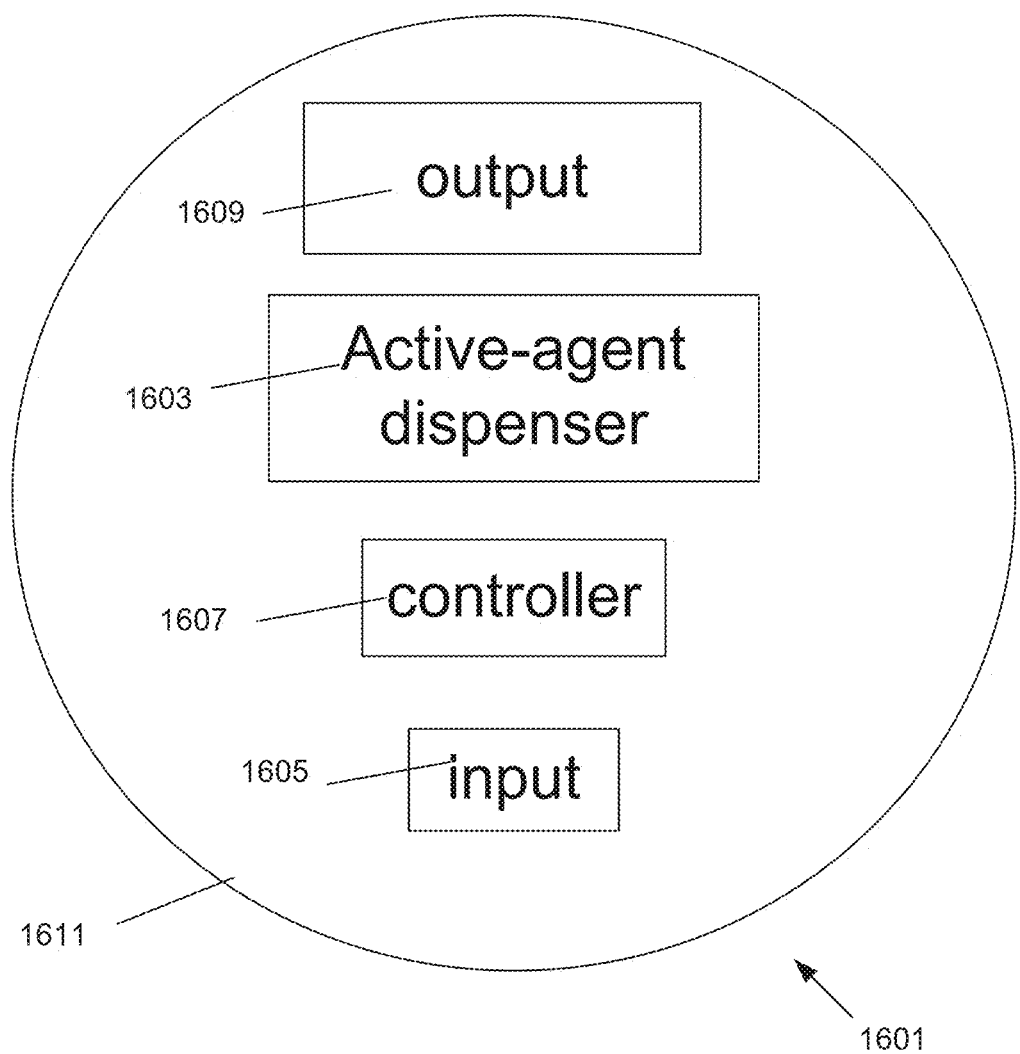

FIG. 16 is a schematic diagram of a metered dose inhaler device configured to provide automated controlled pulmonary delivery of one or more active agents, according to some embodiments of the present disclosure.

FIGS. 17A-17D are a schematic diagrams of a configuration of an inhaler device (FIG. 17A), and a cartridge, also referred to herein interchangeably as "dose unit" or "dose cartridge", of an inhaler device optionally comprising discrete doses (FIG. 17B), and other optional features thereof (FIGS. 17C-17D), according to some embodiments of the present disclosure.

Figure 18:
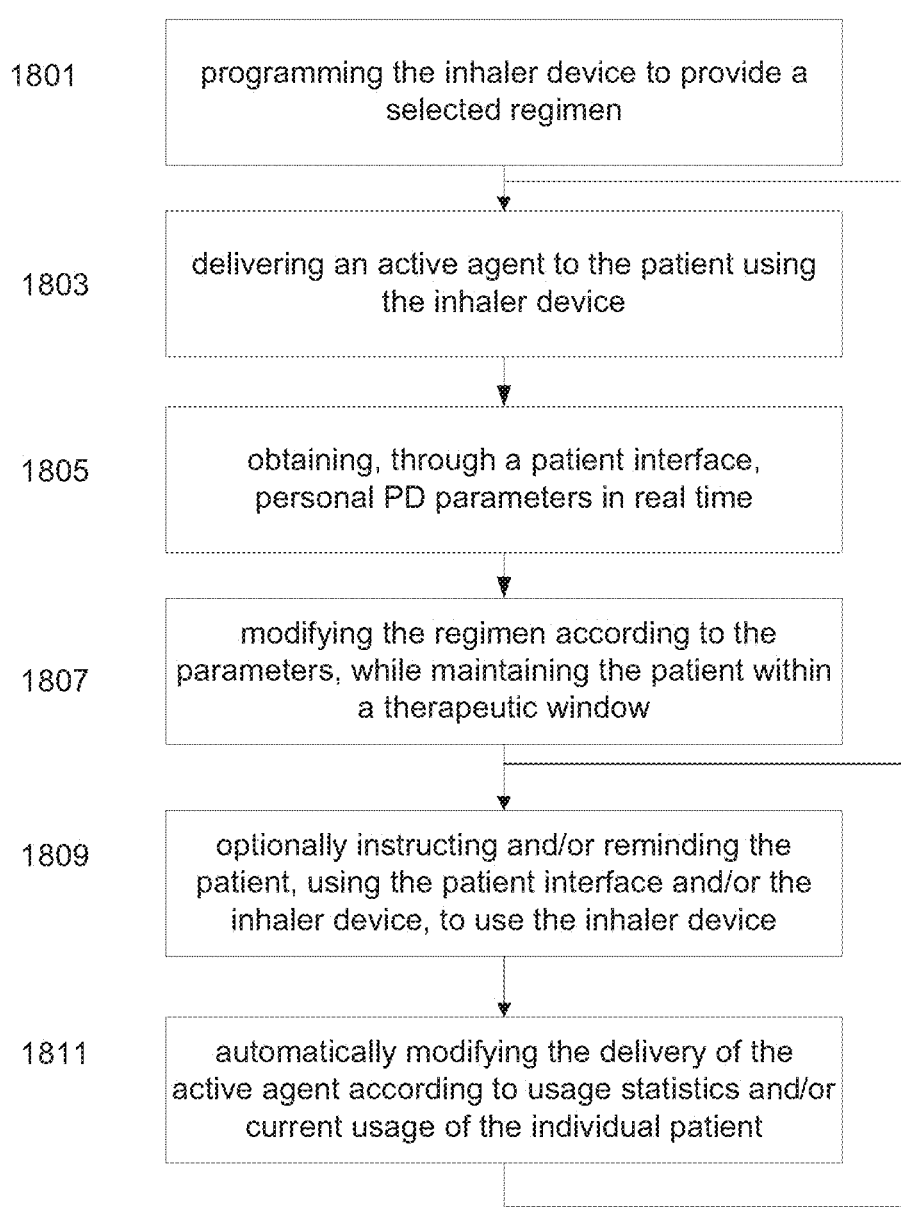

FIG. 18 is a flowchart of a method of treating an individual patient using a system according to FIG. 9, while maintaining the patient within a personalized therapeutic window, according to some embodiments of the present disclosure.

Figure 19:
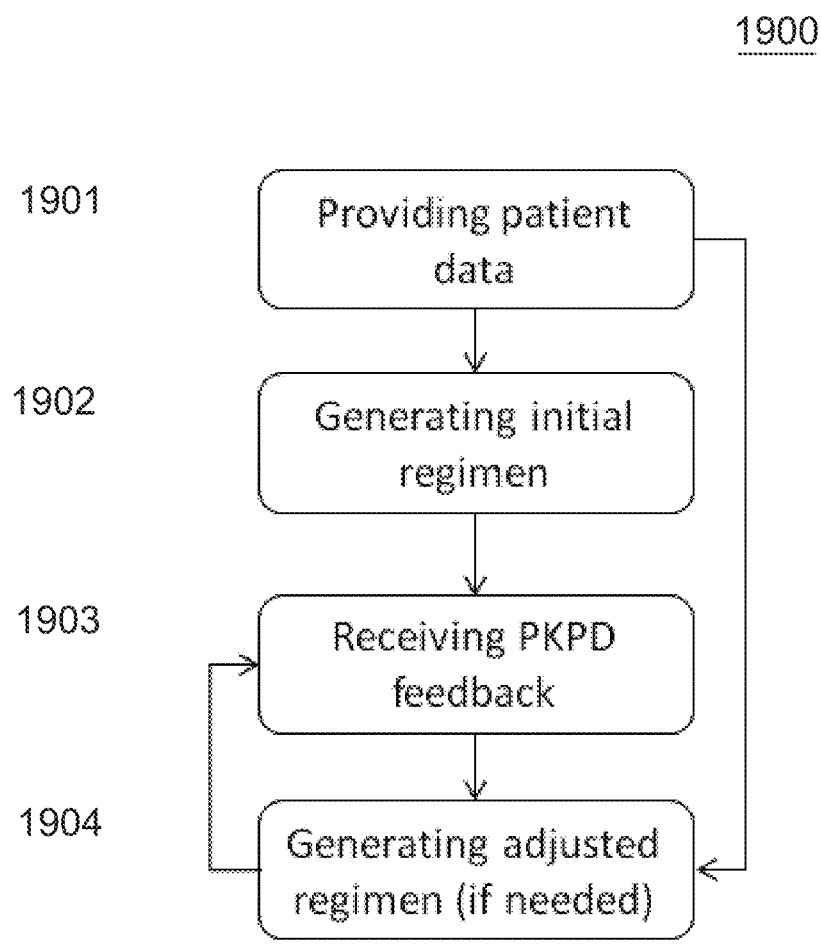

FIG. 19 presents a flowchart of a procedure for determining and administering a personal dosing and/or regimen for treating neurological pain in a human subject.

Figure 20:
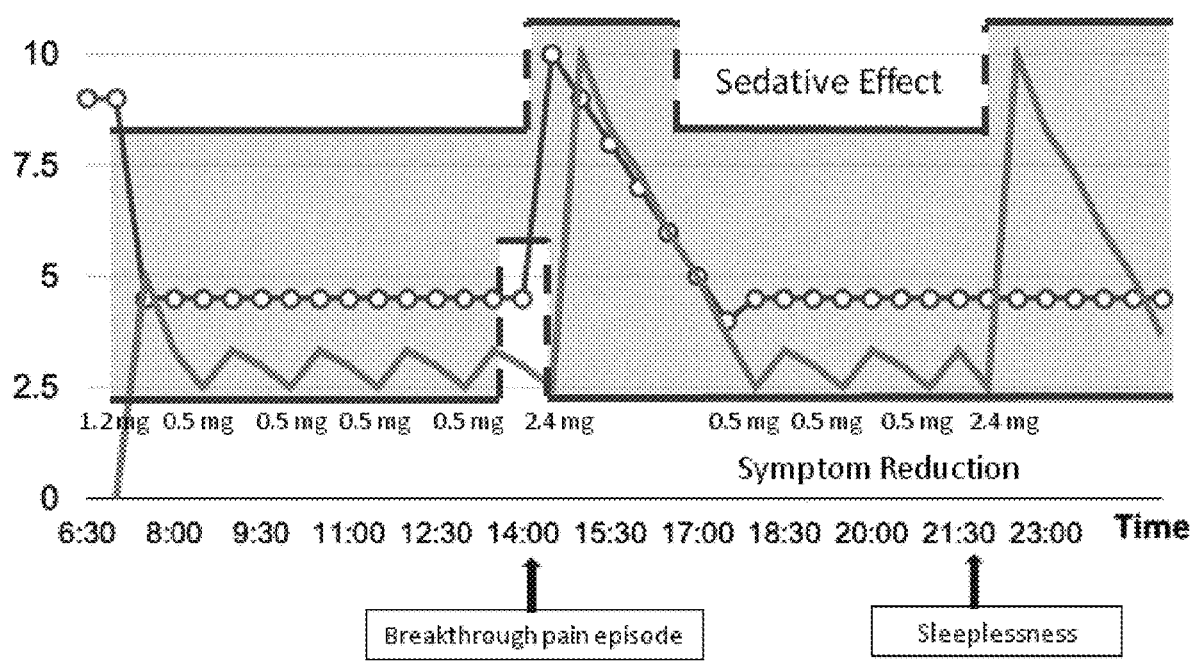

FIG. 20 is a graphical representation of a regimen for the treatment of pain and sleeplessness by pulmonary delivering of an active agent, wherein the red line represents pain level, and the green line represent blood level of the active agent, wherein the active agent is pain reliving as well as sedative.

Figure 21:
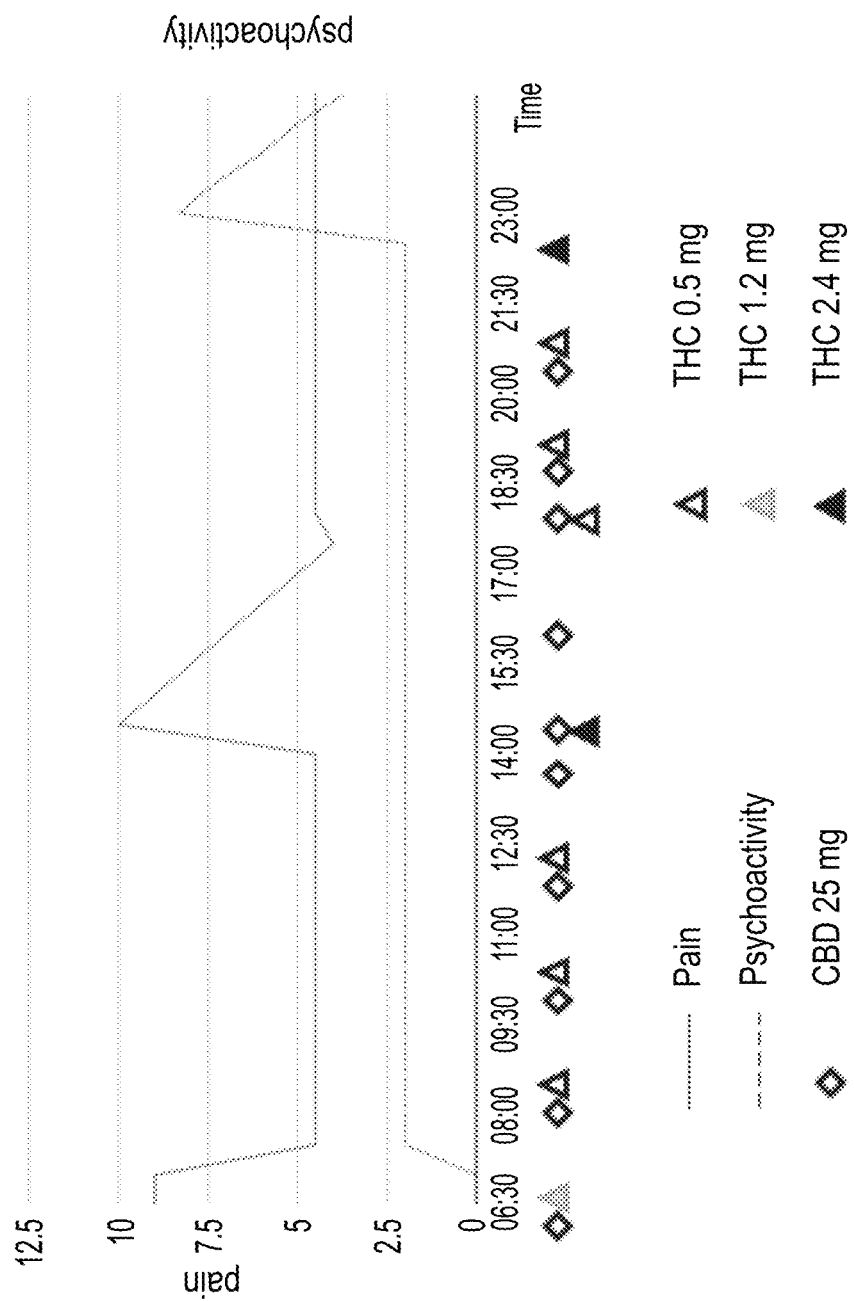

FIG. 21 is a graphical representation of a regimen for the treatment of pain by pulmonary delivering of a combination of two active agents, THC and CBD, wherein the dashed line represents the level of the adverse (psychotropic) effect, and the solid line represent the pain level, and wherein THC is inhaled by using a dose unit of 0.5 mg (empty triangle), 1.2 mg (grey triangle) and 2.4 mg (black triangle), and CBD is inhaled by using a dose unit of 25 mg (empty diamond).

DESCRIPTION OF SPECIFIC EMBODIMENTS OF THE INVENTION

The present invention, in some embodiments thereof, relates to pharmacology and, more particularly, but not exclusively, to methods, devices and systems for controlled pulmonary delivery of active agents.

Before explaining at least one embodiment of the invention in detail, it is to be understood that the invention is not necessarily limited in its application to the details set forth in the following description or exemplified by the Examples.

As discussed hereinabove, difficulties associated with controlled delivery of pharmaceutically active agents from natural substances, according to accepted pharmacological practices, limit the medicinal use of some clinically evaluated natural substances, such as active substances found in plants and herbs; the most prominent example being cannabis. Lack of accurate and precise dose determination and control capabilities is one of the major obstacles for the addition of natural substances as major players in the armamentarium of pharmaceuticals available for the treatment of many medical conditions. Moreover, lacking a method to administer active agents from natural substances according to standard and accepted pharmaceutical protocols and regulations deters practitioners from prescribing treatments based thereon.

Standard pharmacological regulations dictate that a treatment of a medical condition using a pharmaceutically active agent must be based on a therapeutically effective dose, which is administered according to a therapeutically effective regimen, while making all efforts to maintain a balance between the therapeutic effects and the adverse effects.

Figure 1:
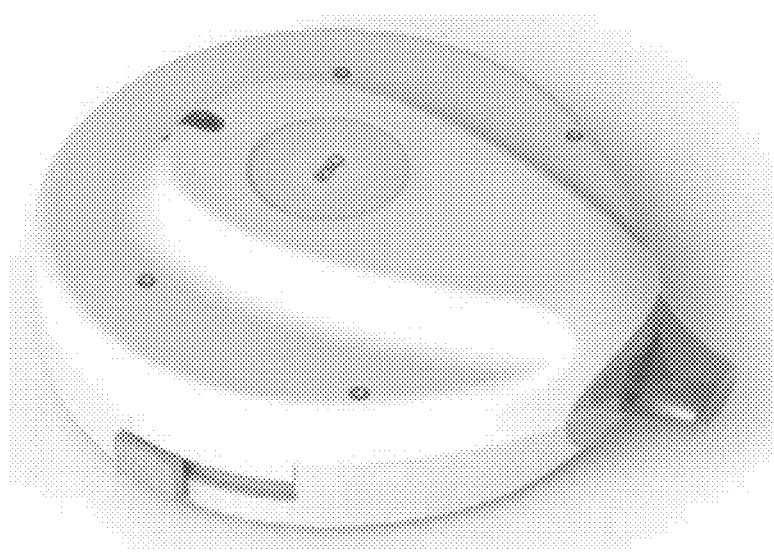

As further discussed hereinabove, a metered dose inhaler (MDI) device, capable of delivering plant-derived active agents, such as cannabinoids from cannabis, accurately and consistently, has been disclosed in WO 2012/085919. FIG. 1 presents a representative example of such an inhalation device. While conceiving the present disclosure, it has been postulated that such an MDI device may bridge the gap between the use of natural substances comprising promising pharmaceutically active agents, and standard yet strict pharmacological regulations for use of any pharmaceutically active agent in the treatment of any medical condition.

While reducing the present invention to practice, the present inventors have conducted a pharmacokinetic ("PK") and pharmacodynamic ("PD") study ("PK/PD study") of pulmonary delivering (inhalation) a cannabinoid from cannabis to a human subject, which has been conducted according to well accepted pharmacological protocols, and which demonstrated that an accurate and precise MDI device can be used to administer at least one cannabinoid from cannabis. This study also demonstrated that the MDI device used therein is far more effective and more efficient in releasing accurate and reproducible doses of vaporized pharmaceutically active agent(s) from cannabis, compared to other known methods and devices known in the art. As used herein, the terms "pharmacokinetic/pharmacodynamic" and "PK/PD" mean pharmacokinetic and/or pharmacodynamic.

The results of the study open the way to pulmonary delivering a wide range of natural plant materials, under widely accepted pharmaceutical practices and regulations, while using that precise MDI device. Such pulmonary deliveries may be used in the treatment of a wide range of medical conditions in which vaporizable agents in said natural plant materials are beneficial for treating the medical condition and/or ameliorating a symptom of the condition.

This PK/PD study has demonstrated a capability of providing the analytical means to determination and personalization of a therapeutically effective dose and/or regimen for treating neurological pain in a human subject. Such dose and/or regimen are able to maintain the treatment within the limits of the therapeutic window of THC in the human subject, namely the dose and/or regimen can afford an accurate and/or reproducible pharmacokinetic profile that affords a pre-selected or pre-determined pharmacodynamic profile of THC in the subject in need thereof.

As used herein, the terms "therapeutic window" and "pharmaceutical window" are interchangeable and refer to the range of pharmacodynamic effects induced by a range of doses of one or more pharmaceutically active agents, providing a balance between one or more desired (positive) effect(s) and one or more adverse (negative) effect(s). According to some embodiments, the pharmaceutical/therapeutic window is referred to as a pharmacodynamic profile. The window may relate to a given point in time or may span a period of time of any length, including for example minutes, hours, days or longer, shorter or to any intermediate period of time. The desirability and undesirability of an effect can be defined based on a variety of criteria, and include without limitation, medical practices, rules and regulations, cultural and demographic norms, genetic factors and personal preferences and tolerances. For example, the desirability and undesirability of an effect can be defined based on the purpose of treatment and based on generally acceptable values and optionally may take into account other parameters such as patient preference, capacity and activity. It is noted that a given effect may be regarded as desired in some cases, but be regarded as undesired in other cases, and vice versa.

According to some embodiments of the present invention, the methods, devices and systems provided herein are capable of vaporizing a pre-determined vaporized amount of an active agent that induced one or more pre-determined pharmacodynamic effects in a given subject or a population of subjects, wherein the pre-determined pharmacodynamic effect pertains to a pre-determined pharmacodynamic profile that may range between a minimal level of a desired effect and any level of an undesired effect.

In some embodiments this a pharmaceutical window spans pharmacodynamic effects ranging from the lowest level of an effective treatment of a medical condition (therapeutic effect; e.g., pain relief) to a highest level of tolerable adverse effects (e.g., tolerable psychotropic effect as described herein). Optionally, the therapeutic window may be correlated to a selected balance between therapeutic and adverse effects. For example, the undesired effects are sufficiently tolerable or even minimized, while the desired effects reach at least a minimal acceptable level or a minimal mandatory level (e.g. life preserving or preserving the function of an organ or system of the user). Optionally, an adverse effect may be limited according to a probability of serious or irreparable damage to the subject's like or well-being. However, several alternative balances may be obtainable and one may choose between the optional therapeutic windows them based on user preferences.

Herein throughout, the term "patient" is used interchangeably with the terms "subject", "user" and "a person in need thereof" to refer to the entity that uses any of the devices and systems provided herein and being the subject of any of the methods provided herein.

A therapeutic window can be correlated, via a pharmacokinetic profile, to a range of amounts of one or more pharmaceutically active agents. For example, a therapeutic window may be defined as a range of amounts of one or more pharmaceutically active agent spanning from an amount that confers a desired effect (a therapeutic effect, in which case the amount is a therapeutically effective amount or therapeutic dose) and an amount that causes more than an acceptable or tolerable level of undesired effects (e.g., adverse effects). Hence, for example, a pharmaceutically active agent having a narrow therapeutic window should be administered with great care and control so as to stay between the therapeutically effective amount and the amount that causes an adverse effect.

A therapeutic index can be expressed in terms of a therapeutic ratio (TR), which is the ratio of the toxic dose (TD) or lethal dose (LD) to the effective dose (ED). The higher the TR, the safer the drug is. For example, tetrahydrocannabinol (THC) has a therapeutic index of 1000 and is therefore considered to be a safe active agent, while digoxin, a cardiac glycoside, has a therapeutic index is approximately 2:1, meaning it is a drug that requires high levels of drug monitoring. Accordingly, a therapeutic window is affected, in some embodiments, by the therapeutic index of the one or more pharmaceutically active agents and the combinations thereof.

According to an aspect of some embodiments of the present disclosure, there is provided a method of pulmonary delivering at least one pharmacologically active agent to a patient, which is carried out by pulmonary delivering the agent to the patient using a metered dose inhaler device, wherein the device is configured to release at least one pre-determined vaporized amount of the agent upon controllably heating a substance that contains the agent, wherein the amount is set so as to achieve at least one pre-determined effect in a subject, such as a pre-determined pharmacodynamic effect.

According to an aspect of some embodiments of the present disclosure, there is provided a method of vaporizing at least one pharmacologically active agent being in a plant material and being suitable for pulmonary delivery to a patient, which is carried out by using a metered dose inhaler device, wherein the device is configured to release at least one pre-determined vaporized amount of the agent upon controllably heating the plant material, wherein the amount is set so as to achieve at least one pre-determined pharmacokinetic effect and/or at least one pre-determined pharmacodynamic effect induced by said agent in the subject upon pulmonary delivering the agent to the patient.

According to an aspect of some embodiments of the present disclosure, there is provided a use of a metered dose inhaler device for vaporizing at least one pharmacologically active agent being in a plant material suitable for pulmonary delivery to a patient, wherein the device is configured to release at least one pre-determined vaporized amount of the agent upon controllably heating the plant material, wherein the amount is set so as to achieve at least one pre-determined pharmacokinetic effect and/or at least one pre-determined pharmacodynamic effect induced by said agent in the subject, upon pulmonary delivering the agent to the patient.

It is to be understood that the pharmaceutically active agent can be in a solid or a liquid form, and further noted that the agent is contained in a solid form of a substance described herein. According to some embodiments of the present disclosure, the pharmaceutically active agent is vaporizable by heat, thereby can be released from the substance by being heat-induced vaporization.

According to some embodiments, the substance that contains at least one vaporizable active agent is, for example, a plant material. In some embodiments, the active agent is a naturally occurring agent, namely the agent occurs (produced) naturally in the plant. Alternatively, the substance is an organic material which contains, or consists of, for example, one or more natural plant materials, or a synthetic material which may comprise at least one vaporizable active agent. In some embodiments, the solid form of a substance comprises a plurality of vaporizable active agents derived or extracted from natural or organic sources, such as plants, fungi, bacteria and the likes.

In some embodiments, the substance is a natural plant matter. In an embodiment of the present disclosure, the plant matter is processed without damaging the vaporizable active agent in the plant matter. Optionally, the plant matter retains a macroscopic plant structure.

The amount of the substance used in the MDI device may be determined based on the contents of the vaporizable agent contained therein, and on the pre-determined vaporized amount required to be released therefrom. The amount of the substance used in the MDI device may range from 20 to 500 mg, 10 to 200 mg, 9 to 150 mg, 8 to 100 mg, 7 to 50 mg, 5 to 20 mg, 1 to 10 mg, 10 to 70 mg, 10 to 60 mg, 12 to 50 mg, 12 to 40 mg, 15 to 40 mg, 12 to 30 mg or 12 to 25 mg.

The terms "pharmaceutically active agent", "biologically active agent", "active agent" and "agent" are used herein interchangeably and refer to a compound, a polymer, a conjugate or a complex, or any combination thereof, which exerts a physiological or psychological effect when administered to a subject. Typically, the pharmaceutically active agent or biologically active substance exerts a desired physiological or psychological effect upon pulmonary delivering thereof via a systemic pathway (e.g., blood, lymph) to a target organ. The agent may be of natural origin or synthetic. Non-limiting examples of active agents include CNS active agents, chemotherapeutic agents, sedative or analgesic agents and a psychotropic agent. In the context of embodiments of the present disclosure, the pharmaceutically active agent is a naturally occurring agent found in a naturally occurring substance (e.g., a natural plant substance, as described herein), or a metabolite thereof. These terms also encompass, unless otherwise indicated, two or more agents.

According to some embodiments of the present disclosure, the method is carried out using an MDI which is capable of delivering reproducibly and accurately an amount of at least one vaporizable agent by heating a solid form of a substance. Such requirements of an MDI are met by, for a non-limiting example, an MDI as disclosed in U.S. patent application Ser. No. 13/997,302 or WO 2012/085919, both of which is incorporated herein by reference in its entirety as if fully set forth herein. According to some embodiments of the present disclosure, the MDI device is a device as described in WO 2012/085919, including any one of the embodiments described therein, and any combination thereof.

The term "vaporized amount", as used herein, refers to the amount of an agent that is in vapor form, whereas the vapor form/amount is obtained by means of a heating elements in the MDI device. It is noted herein that in some embodiments the amount of vaporized agent in the context of the present disclosure is not an estimated amount but rather represents the actual amount vaporized upon said heating.

The term "pre-determined vaporized amount" refers to an amount that is purposely or knowingly released from the MDI device, the magnitude of which is determined by choice or by design of a dose and/or regimen protocol, as described herein. In the context of some embodiments, the term "dose" represents a pre-determined vaporized amount. It is noted that a pre-determined vaporized amount is correlated to an available amount present in the device, and that one can pre-measure the available amount present in the device, or measure the available amount present in the device in conjunction to the administration event, and thereby preset, reset, adjust and/or readjust the pre-determined vaporized amount accordingly.

Initial Dose Determination and Device Calibration:

According to some embodiments, the method is performed such that the pre-determined vaporized amount is selected/controlled so as to exhibit a pre-selected (also referred to herein as pre-determined) pharmacokinetic profile and/or a pre-selected or pre-determined pharmacodynamic profile of the agent in the patient.

In some embodiments, the pre-determined vaporized amount is selected/determined arbitrarily, while the MDI device is configured to vaporize and deliver this amount consistently and accurately throughout any number of uses and inhalations, using any source of the active agent (substance; plant material, combination of plant material with another material etc.). According to some embodiments, a pre-determined vaporized amount of an agent can be determined based on a measurement of the amount of the agent per unit mass of the substance from which the agent is to be vaporized. Such measurement can be carried out by standard procedures; thereby various batches and sources of the substance can be standardized according to the relative amount of the agent per unit mass of the substance.

It is noted herein that according to some embodiments of the present disclosure, by exhibiting a pre-selected pharmacokinetic and/or pharmacodynamic profile, it is meant that the vaporized amount of the agent has been pre-determined based on pharmacokinetic/pharmacodynamic (PK/PD) studies conducted in at least one subject by pulmonary delivering the agent using an MDI device which is configured to release a consistent and accurate vaporized amount of the agent upon heating a solid substance comprising the same. It is also noted herein that according to some embodiments of the present disclosure, by exhibiting a pre-selected pharmacokinetic profile, it is meant that at least one desired pharmacokinetic profile has been identified and that at least one pre-determined vaporized amount of the agent has been shown to effect that desired pharmacokinetic profile in a subject. It is also noted herein that according to some embodiments of the present disclosure, by exhibiting a pre-selected pharmacodynamic profile, it is meant that at least one desired pharmacodynamic profile has been identified and that at least one pre-determined vaporized amount of the agent has been shown to effect that desired pharmacodynamic profile in a subject.

In some embodiments of the present disclosure, the terms "pre-selected" and "pre-determined" refers to, or used interchangeably with, the terms "intended", "desired" or "desirable", or with the terms "effective", "needed" and "therapeutic".

It is also noted herein that the identification of a desired pharmacokinetic profile and/or a desired pharmacodynamic profile, is typically afforded by conducting PK/PD studies for a particular pharmaceutically active agent in a particular subject or a group thereof. It is also noted herein that the ability to conduct standard and widely accepted PK/PD studies in a particular subject or a group thereof for a pharmaceutically active agent, which is delivered by inhalation (pulmonary delivery) upon controllably and reproducibly releasing a vaporized amount of the agent by heating a solid sample of a substance, is made possible (enabled) by, for example, an MDI device such as disclosed in WO 2012/085919, which can use a plant material as a source of the active agent(s).

In some embodiments, the term "pre-determined vaporized amount" is also used herein to describe the amount of the agent that is determined based on pharmacokinetic/pharmacodynamic (PK/PD) data, namely a vaporized amount that has been determined by determining PK/PD effects (parameters) for the agent in one or more patients.

In some embodiments, configuring the MDI device to release a pre-determined amount as defined herein means, in some embodiments, calibrating the device to exhibit a pre-selected PK and/or a pre-selected PD profile.

According to some of any of the embodiments of the present disclosure, the method is carried out by adjusting the pre-determined vaporized amount so as to achieve a pre-determined pharmacokinetic effect and/or a pre-determined pharmacodynamic effect based on data indicative of at least one pharmacokinetic effect and/or at least one pharmacodynamic effect induced by the agent in the subject.

In some embodiments, the method further includes generating the indicative data by monitoring at least one pharmacokinetic effect and/or at least one pharmacodynamic effect induced by the agent in the subject.

According to some of any of the embodiments of the present disclosure, the method is carried out by monitoring and/or determining at least one pharmacokinetic effect and/or at least one pharmacokinetic variable and/or at least one pharmacodynamic effect, as these terms are defined herein, which are induced by pulmonary delivering the pharmaceutically active agent to a patient using the MDI device;

based on the pharmacokinetic effect and/or the pharmacokinetic variable and/or the pharmacodynamic effect, determining the pre-determined vaporized amount which exhibits the pre-selected pharmacokinetic profile and/or the pre-selected pharmacodynamic profile of the agent in the patient; and adjusting the MDI device to deliver the pre-determined vaporized amount of the agent.

As used herein, the phrase "pharmacokinetic profile" refers to a bodily concentration of a pharmaceutically active agent, or a metabolite thereof (e.g., an active metabolite), namely, a concentration of the agent or a metabolite thereof in a physiological system of an organism (whole body, blood, plasma, lymph, tissue, organ and the likes) to which the compound has been administered, as a function of time. Typically, a pharmacokinetic (PK) profile is considered from a time point of administration of the compound to a time point at which the compound is no longer detectable in the organism or to any intermediate period of time between administration of the compound and a time at which it is no longer detectable in the organism (e.g. due to excretion); hence, a PK profile describes the bodily concentration in a specific physiological system of a specific compound between administration and dissipation, as affected by the mechanisms of liberation, absorption, distribution, metabolism and excretion/secretion of the compound. Since each organism, and each individual organism within a genus of an organism, reacts differently to the administration of the agent, a PK profile may be different, and in some cases highly variable from subject to subject, and may be different within an individual subject based on a current physiological state, medical condition, environmental conditions and even the time of day.

According to some embodiments of the present disclosure, a pharmacokinetic profile is achieved by providing a subject with one or more of:

A dose—a single amount of a compound or an agent that is being administered thereto; and/or A regimen—a plurality of pre-determined doses that can be different in amounts or similar, given at various time intervals, which can be different or similar in terms of duration. In some embodiments, a regimen also encompasses a time of a delivery period (e.g., agent administration period, or treatment period).

Alternatively, a regimen is a plurality of predetermined plurality pre-determined vaporized amounts given at pre-determined time intervals.

It is noted that the PK profile can be determined according to a change of a PK effect (parameter) as a function of time, or of a combination of PK effects a function of time.

A PK profile is typically assessed on a concentration on a time scale, using directly and/or indirectly measured PK effects. For example, a PK profile may be a plasma concentration of a given pharmaceutically active agent in a subject as a function of time.

The term "pre-selected pharmacokinetic profile", as used herein, refers to a PK profile, which has been selected as desirable. A pre-selected PK profile may be selected since it has been found effective in accomplishing a desired pharmacodynamic effect in a subject, as described in any one of the respective embodiments (e.g., to maintain a subject within a therapeutic window, as described herein).

The terms "pharmacokinetic parameter", "pharmacokinetic effect", as used herein interchangeably, refer to a measurable and quantifiable physiological effect in a subject, which pertains to the presence of a pharmaceutically active agent in a subject. PK effects are direct or indirect expressions of a group of physiological processes that include absorption, distribution, metabolism, and excretion (ADME) of a pharmaceutically active agent in a subject.

PK effects typically include, without limitation:

$C_t$, which is the concentration of an agent, as determined, measured or assessed in a specific physiologic system (e.g., in the plasma), after its administration (delivery, e.g., pulmonary delivery) of a dose or a regimen to a subject;

$C_{max}$, which is the peak concentration of an agent, as determined, measured or assessed in a specific physiologic system (typically in the plasma), after its administration to the subject;

$T_{max}$, which is the time passed between administration and arriving at $C_{max}$;

Area under the curve ($AUC_{0 \to \infty}$; zero to infinity), which is the integral of the concentration curve as a function of time, typically after a single dose or in steady state;

$C_{min}$, which is the lowest concentration of the agent in the organism before the next dose is administered;

$T_{min}$, which is the time passed until $C_{min}$ is detected, or until the next dose is administered;

$C_{last}$, which is the last observed quantifiable concentration;

$\lambda_z$, which is the terminal phase rate constant;

Elimination half-life ($t_{1/2}$), which is the time required for the concentration of the agent to reach half of any selected value;

Elimination rate constant ($k_E$), which is the rate at which an agent is removed from the organism;

Administration rate ($k_{in}$), which is the rate of administration required to balance elimination;

Clearance, which is the volume of plasma cleared of the agent per unit time;

Bioavailability, which is the systemically available fraction of a agent; and

Fluctuation, which is the peak trough fluctuation within one dose, or one regimen interval, at steady state.

As a tool for assessing the PK profile in a member of a population (a subject) of similar individual subjects (similar in the biological sense, as in a group of humans), PK variables, which have been found to be correlated to a PK profile in a sub-set of the population, may be used to generalize (extrapolate) the PK profile for each of the individuals comprising the entire population.

The term "pharmacokinetic variable", as used herein, refers to a property of a subject that is not necessarily dependent on a pharmaceutically active agent or a method of delivery a pharmaceutically active agent to a subject, and provide information pertaining to factors that affect the pharmacokinetic and pharmacodynamic profiles of an active agent in the subject.

Pharmacokinetic variables typically include, without limitation, body weight, body height, body mass index (BMI), waist-to-hip ratio, lean body mass (LBM), age and gender, race, background illnesses, patient history (e.g. previous exposure to the agent or other agents) and concurrent medication. It is to be understood that PK variables depend on genetic and epigenetic composition of each individual subject, and therefore can be used to predict PK/PD profiles in an individual subject to a certain degree of accuracy. However, personalization/individualization of a treatment based on administration of a pharmaceutically active agent is typically based on personal PK/PD effects/parameters data acquisition that is used to determine the dose and regimen for an individual subject. In general, deviation of individual parameters from average parameters set for a wide population are notably small.

In the context of some embodiments of the present disclosure, the term "treatment" refers to any one of: a single pulmonary administration of an agent at a given dose; a fixed and limited series of pulmonary administrations of an agent, given at the same or different doses at the same or different dose intervals (regimen); a chronic treatment which is administered as the limited series, but without a planned termination of the treatment (continuous treatment); and/or any combination thereof. Typically, a series of pre-determined doses given at pre-determined intervals, is referred to herein as a treatment regimen, or a regimen.

According to some embodiments of the method presented herein, pulmonary delivering the agent comprises a single dose delivered as one pre-determined vaporized amount released by the MDI device in a single inhalation session or the dose can be administered to a patient as several concomitant inhalations. Alternatively, a series of doses, each administered in one or more pre-determined vaporized amount, and given at a pre-determined time intervals, is referred to herein as a regimen. A regimen is therefore defined by one or more doses, administered in one or more pre-determined vaporized amounts, at pre-determined time intervals, wherein each of the pre-determined vaporized amounts, the doses and the time intervals can be the same or different.

In the context of embodiments of the present disclosure, a PK profile of a given pharmaceutically active agent is a result of the dose and/or regimen by which an agent is administered to a patient, or, alternatively, according to some embodiments, the PK profile is a mean to afford a particular, a pre-selected or otherwise desired pharmacodynamic profile of the agent in the patient.

As used herein, the term "pharmacodynamic profile" refers to the effect of a pharmaceutically active agent in a subject as a function of time. Accordingly, the term "pharmacodynamic profile" refers to a sum of all biological expressions and responses of an organism as a function of time, upon administration of a pharmaceutically active agent. A pharmacodynamic profile is typically a direct or indirect result of pharmacokinetic effect(s) at any given time point, or a pharmacokinetic profile of the agent in the patient, over any given time period.

A pharmacodynamic profile represents a change/variation of directly and/or indirectly determined pharmacodynamic effect(s) as a function of time.

The terms "pharmacodynamic parameter", "pharmacodynamic effect", as used herein interchangeably, refer to a group of effects pertaining to a subject and a pharmaceutical active agent, which are manifested in the subject upon administering the agent to the subject. Typically, pharmacodynamic parameters depend on the subject's PK variables and on the subject's PK effects.

Pharmacodynamic parameters can typically be determined by, without limitation, a therapeutic (desirable) effect (e.g., personally perceived therapeutic effect), an adverse (undesirable) effect (e.g., a personally perceived adverse effect), and by means of determining a level of a biomarker (which is indicative of a therapeutic and/or an adverse effect), as these terms are described hereinbelow. A pharmacodynamic profile which can be a pre-selected (desired) pharmacodynamic profile, according to some embodiments of the present disclosure, is defined by the therapeutic window of a given agent in a given subject, as this term is defined herein.

A pharmacodynamic (PD) profile is typically a time-dependent assessment and/or measurement on a scale going from no response, through the onset of a desired therapeutic effect (below a therapeutic effect threshold), via the therapeutic window, through the onset of an adverse effect (above an adverse effect threshold), and up to a toxic effect.

According to some embodiments of the present disclosure, the pulmonary delivering and/or the PK/PD study (measurement of any pharmacokinetic and/or pharmacodynamic parameters) may optionally be conducted while monitoring at least one additional physiological parameter selected from the group consisting of:

a vital sign selected from the group consisting of a heart rate, an oxygenation level (SpO2), a blood pressure, a respiratory rate and a body temperature;

a pulmonary function selected from the group consisting of forced expiratory volume (FEV1), maximum mid-expiratory flow (MMEF), diffusing capacity of the lung for carbon monoxide (DLCO), forced vital capacity (FVC), total lung capacity (TLC) and residual volume (RV);

a hematological marker selected from the group consisting of a hemoglobin level, a hematocrit ratio, a red blood cell count, a white blood cell count, a white blood cell differential and a platelet count;

a coagulation parameter selected from the group consisting of a prothrombin time (PT), a prothrombin ratio (PR) and an international normalized ratio (INR);

a kidney function marker selected from the group consisting of a creatinine clearance (CCr), a blood urea nitrogen level (BUN) and a glomerular filtration rate (GFR); and a liver function marker selected from the group consisting of an aspartate aminotransferase (AST) level, a serum glutamic oxaloacetic transaminase (SGOT) level, an alkaline phosphatase level, and a gamma-glutamyl transferase (GGT) level.

The results of such a PK/PD study, conducted for one or more subjects, can therefore be used to determine an initial pre-determined vaporized amount of at least one pharmacologically active agent that would, once administered by an MDI device configured for pulmonary delivery thereof, give rise to an initial pre-selected pharmacokinetic profile and/or an initial pre-selected pharmacodynamic profile of the agent in a particular patient, and can further be used to calibrate and preset similar MDI devices so as to deliver an initial pre-determined vaporized amount to achieve similar consistent initial results.

PD effects and profiles can also be determined or estimated based on statistical data pertaining to a population, as this term is referred to herein above in the context of PK effects, based on the approximation that when one or more certain criteria and variables are optionally considered, such as age, weight etc., the PD effect induce by a given active agent in one subject, can infer the PD effect of the agent in another subject.

As presented herein, the accuracy and consistency of the inhaler device in vaporizing and delivering at least one active agent as a pre-determined vaporized amount, allows it to be used to conduct PK/PD studies in one or more subjects. Such studies are based on the ability to record PK/PD effects accurately and consistently.

Accordingly, there is provided a method of recording at least one pharmacokinetic effect and/or at least one pharmacodynamic effect, induced by pulmonary delivering to a subject at least one pharmacologically active agent being in a plant material; the method is effected by:

pulmonary delivering a pre-determined vaporized amount of the agent to the subject from a metered dose inhaler device configured to vaporize the pre-determined vaporized amount of the agent upon controllably heating the plant material;

optionally, determining at least one pharmacokinetic effect in the subject at pre-determined time intervals before during and/or after the pulmonary delivering;

determining at least one pharmacodynamic effect in the subject at pre-determined time intervals before during and/or after the pulmonary delivering;

wherein the pharmacodynamic effect is selected from the group consisting of a desired effect, an undesired effect, a therapeutic effect, an adverse effect and a level of a biomarker.

Personalization:

As discussed hereinabove, some PK/PD studies or some parts thereof are based on population parameters and on cohorts, yielding average or standardized dose and/or regimen data, while in reality a PK/PD profile may vary from patient to patient, and even within an individual patient, depending on a current physiological condition, mental state, medical condition and environmental conditions. Therefore, a pre-determined vaporized amount of an agent (preset dose and/or regime) may be found inadequate for a particular individual at any given time and for any individual reason. Hence, in order to provide an optimized treatment for a given individual, in any of the methods presented herein, each of the pharmacokinetic and/or pharmacodynamic parameter and/or variables may further be determined for an individual patient, such that the pre-determined vaporized amount is derived individually for the patient.

It is noted that according to some embodiments of the present disclosure, while a patient may start the pulmonary delivering using an initial pre-determined vaporized amount which has not been determined based on the patient's personal/individual parameters and variables, the method includes an optional step at which the patient's personal parameters and variables are considered in the determination of the pre-determined vaporized amount. Thus, according to some of any of the embodiments of the present disclosure, the method may include personalization of the pre-determined vaporized amount that affords the pre-selected PK/PD profile. The personalization step presented below can replace a pre-calibration of the MDI device; or as a complementary step after calibration of the MDI device.

Accordingly, the pharmacokinetic effect(s) and/or the pharmacokinetic variable(s) and/or the pharmacodynamic effect(s) are independently determined for an individual patient, such that the pre-determined vaporized amount is determined personally for that patient. It is noted herein that a personal pharmacokinetic parameter can be obtained directly by conducting a PK study in the patient by monitoring the concentration of the agent in the patient (e.g., using blood samples and/or other means), or by applying a calculation based on personal PK variables and other personal variables that may have an effect on the PK/PD profiles in that patient.

Alternatively, according to some of any of the embodiments of the present disclosure, the method may include collecting, observing or otherwise monitoring and determining at least one personal pharmacodynamic effect and/or pharmacokinetic effect in an individual subject so as to determine if pulmonary delivering the initial pre-determined vaporized amount of the agent exhibits the pre-selected (desirable) pharmacodynamic and/or pharmacokinetic profile;

if pulmonary delivering the pre-determined vaporized amount of the agent does not exhibit the pre-selected/determined pharmacodynamic and/or pharmacokinetic profile, determining an adjusted vaporized amount of the agent that exhibits the pre-selected pharmacodynamic and/or pharmacokinetic profile; and adjusting, resetting, re-calibrating or otherwise re-configuring the device to deliver an adjusted vaporized amount, whereby, upon re-configuring the MDI device, the adjusted vaporized amount being now the pre-determined vaporized amount.

According to some embodiments of the present disclosure, the personalization of the pulmonary delivering and/or the PK/PD study may optionally be conducted while monitoring at least one additional physiological parameter, as described herein. Optionally, monitoring at least one pharmacokinetic effect and/or at least one pharmacodynamic effect induced by the agent in the subject is carried out at pre-determined time intervals before, during and/or after the pulmonary delivering.

According to some embodiments, monitoring of a pharmacokinetic effect and/or a pharmacodynamic effect is carried out by receiving data indicative of these effects in the subject from at least one sensor being in communication with a controller, as these terms are discussed hereinbelow, associated with the inhaler device presented herein.

It is noted that a personal pharmacodynamic parameter can be a personally perceived therapeutic effect, a personally perceived adverse effect and a (level or presence of a) biomarker obtained and/or measured in the individual patient. According to some embodiments, the acquisition/determination of the personally perceived therapeutic effect, the personally perceived adverse effect and/or the biomarker may be conducted voluntarily by the patient, or involuntarily by automatic means. The method, according to some embodiments thereof, is then effected by determining an adjusted vaporized amount of the agent based on the personal pharmacodynamic parameter, and configuring the device to deliver the adjusted vaporized amount; whereby the adjusted vaporized amount is the pre-determined vaporized amount. In other words, the adjusted vaporized amount is the personalized pre-determined vaporized amount, which is based on personal pharmacodynamic parameters obtained for an individual patient, after being administered a pre-determined vaporized amount determined for a general population and using population PK variables. Alternatively, an expected response can be used as a parameter for confirming the identity of a user. For example, a user is instructed to perform a task at a given time before and/or after administration, and the measured value is compared with a comparable expected value recorded for the same user, optionally under similar circumstances.

Personally Perceived Effect:

A "personally perceived effect" is a subjective assessment of a patient pertaining to an effect of a given' agent or treatment in the patient's body. The personally perceived effect may include one or more of a personally perceived therapeutic effect or a personally perceived adverse effect.

A psychotropic effect optionally corresponds to a symptom that can be perceived by the patient. It is noted that in some cases a psychotropic effect may not be accurately perceived by the patient. Examples of psychotropic symptoms include, without limitation, paranoia, anxiety, panic attack, euphoria, pseudo-hallucinatory, sedation, conscious perception variation, joviality, metacognition and introspection, an enhanced recollection (episodic memory), amnesia, a sensuality variation, a variation in awareness of sensation and a variation in libido, dizziness, ataxia, euphoria, perceptual alterations, temporal distortion, intensification of ordinary sensory experiences, short term memory, and attention, impaired reaction, skilled activity, verbal fluency, dependence, melancholy and depression.

A somatic effect sometimes corresponds to a symptom which can be perceived by the patient or measured thereby. Examples for somatic symptoms include, without limitation, pain, migraine, nausea, dry mouth and a sensation of cold or hot hands and feet, increased heart rate, increased cerebral blood flow (e.g., migraine symptoms, "head pressure"), dilation of bronchial passages (e.g., coughing and difficulty breathing), dilation of blood vessels (e.g., shivers, skin redness, blushing), eye redness and pupil dilation, dry mouth, thirst, hunger or food craving.

Desired Effects—Therapeutic Effects:

A "personally perceived therapeutic effect" is a subjective assessment of a patient pertaining to a beneficial (desired) effect of a given agent in the patient's body. In some embodiments, a desired effect includes a relief of a symptom and/or an alleviation of cause of a medical condition. For example, if the desired therapeutic effect is defined as an alleviation of pain, the patient may report a level of pain by means of a pain scale evaluation protocol. A pain scale protocol measures a patient's pain intensity and/or other features. In the context of embodiments of the present disclosure, a pain scale protocol is based on self-report (subjective), observational and/or behavioral data provided by the patient, while physiological data falls under the definition of biomarkers, namely objective data. In general, all personally perceived (subjective) assessments by a patient can be used as feedback for self-titration and personalization of a treatment.

A personally perceived therapeutic effect may be associated with or corresponds to, directly or indirectly, a symptom of the medical condition which the patient is being treated for. In some cases a patient may perceive a change in the perceived level of the symptom, and when the symptom of the medical condition is alleviated (a diminution in the level of the symptom), the person perceives this change as a therapeutic effect of agent delivered during the treatment. Hence, according to embodiments, a personally perceived therapeutic effect corresponds to a reduction in a level of a symptom such as, but not limited to, pain, migraine, depression, cognitive function deficit, attention deficit, hyperactivity, anxiety disorders, diarrhea, nausea, vomiting, insomnia, delirium, appetite variations, sexual dysfunction, spasticity, increased intra ocular pressure, bladder dysfunction, tics, Tourette symptoms, posttraumatic stress disorder (PTSD) symptoms, inflammatory bowel disease (IBD) symptoms, irritable bowel syndrome (IBS) symptoms, hyper tension, hemorrhagic symptoms, septic and cardiogenic shock, drug addiction and craving, withdrawal symptoms, tremors and other movement disorders symptoms.

In some embodiments, a personally perceived therapeutic effect may include an effect that is not associated with or corresponds to, directly or indirectly, a symptom of the medical condition which the patient is being treated for, but is nonetheless beneficial to the patient's experiencing such symptom. For example, when a symptom includes a form of discomfort (for example pain or nausea), a patient may benefit from a psychoactive state in which the discomfort may be less prominent or more tolerable. One example of such a desired effect is causing temporary moderate stupor during pain. In some embodiments, the same effect may be therapeutic or adverse, depending on a degree thereof and/or timing thereof and/or other circumstances.

Undesired Effects—Adverse Effects:

A "personally perceived adverse effect" is associated with an emergence and/or an increase in the level of an undesired symptom that is not necessarily associated with the medical condition being treated, since it is caused, directly or indirectly, by a pharmacokinetic parameter of the pharmaceutically active agent being delivered to the patient.

According to some embodiments, a personally perceived undesired effect can be a mental effect, a psychotropic effect and/or a somatic effect, wherein the mental and/or psychotropic effect is mostly related to CNS activity which encompasses perception, consciousness, cognition and behavioral effects, and the somatic effect relates to all other bodily systems, and include, without limitation, gastro-intestinal, neuromuscular, cardiovascular, convulsive, endocrine effects and the like.

A personally perceived adverse effect is a subjective assessment of the patient pertaining to the adverse effect of a given agent in the patient's body. In general, all personally perceived (subjective) adverse effect assessments by the patient can be used as feedback for personalization of the treatment and self-titration.

Biomarkers:

While perception of an effect is a subjective assessment of the effect, and typically complicated to quantify, a biomarker is a more objective and typically measurable quantitative assessment of an effect. Thus, the term "biomarker", as used herein, is a measurable indicator of the PD profile at a given time point, and typically consists of a direct and/or indirect somatic, biologic and/or chemical manifestation of the therapeutic effect and/or an adverse effect. In other words, a biomarker is any objectively measurable quantity that can be used as an indicator of the state of a medical condition, the effect of a particular agent on the state of a medical condition, or another physiological state of an organism. It is note that some of the therapeutic/adverse effects can only be assessed qualitatively, and some can be assessed indirectly by, for example, measuring an impaired reaction by applying a performance test.

In the context of embodiments of the present disclosure, biomarkers are divided into the group of invasively-detected biomarkers and the group of non-invasively-detected biomarkers. In general, all biomarker data (objective) collected in the patient by any mean, observation measurement, sensor measurement and the likes, can be used as feedback for personalization of the treatment and self-titration. It is noted that some invasively-detected biomarkers can be detected and measured non-invasively and vice versa.

Examples for non-invasively-detected biomarkers include, without limitation, heart rate, oxygenation level (SpO2), blood pressure, respiratory rate, body temperature, inhalation volume, facial expressions, involuntary skeleto-muscular responses (ataxia, tremors, muscle twitches, cramps, spasms etc.), voluntary motor skills, sweating, hand-eye coordination, eye vascular expansion, reddening of the conjunctiva and/or sclera, variations in intra-ocular pressure, sinus tachycardia, cardiac arrhythmias, skin conductance/impedance levels, seizures, electromyography (EMG), electrocardiogram (ECG), photo-plethysmogram (PPG), galvanic skin response (GSR), Blue-Brown visual inhibition, H-mask visual inhibition, Auditory Latent inhibition, Visual Latent inhibition, Stroop colour word, Simple reaction (conflict task), Cognitive Set switching, Logical reasoning, Decision making time, Rapid info processing, Perceptual maze, Simulated driving, Visual search, Time estimation, Time perception, Visual search, Attentional search, Symbol copying, Letter cancellation, Alphabetic cross-out, D2 cancellation, Brickenkamp D2, digit copying test (DDCT), symbol-digit substitution (SDST), digit-symbol substitution test (DSST), Digit Vigilance, Vigilance, Auditory vigilance test, Wesnes/Warburton Vigilance task, Rapid info processing, CRT+Tracking Divided attention, Selective attention, Focused attention Task, Emotional attention Task, Auditory Flutter fusion, Flash fusion, critical flicker fusion (CFF), Continuous attention, Paired associate learning, Wordlist learning, 15 word test, Introductory conditioning, Delayed word recall, Delayed word recognition, Delayed picture recognition, Word presentation, Word recognition, Numeric working memory, Numerical memory, Memory scanning, Auditory Brown/Peterson, Visual Brown/Peterson, Visual spatial memory, Fragmented picture test, Pauli test, Block Span, Digit span, Digit Span (forward), Digit Span (backward), WAIS vocabulair, WAIS similarity, Word fluency, Verbal fluency, Performance time (Delayed word recogn.), Performance time (Numeric working memory), Performance time (Digit vigilance), Performance time (Rapid info processing), Performance time (Delayed picture recognition), Performance time (Visual information processing), Simple Reaction Time CRT, Complex RTvisual, Visual choice RT, VRT, Visual response speed, ART, Acoustic RT, Wire Maze Tracing, Archimedian spiral, Critical tracking task, Trail making, Tracking Complex, Tracking Wiener Geraet, Flexibility of closure, WAIS block design, WAIS picture comparison, Digit copying, Manipulative motor, Feinmotorik, Graphological analysis, tapping, Hand arm lateral reach coordination, Visual arm random reach, Motor control & coordination, Motor behavior and EEG.

Comprehensive descriptions of non-invasively-detected biomarkers, in the context of pharmaceutically active agents derived from cannabis, include, without limitation, a study by Zuurman, L. et al. [*British Journal of Clinical Pharmacology*, 2009, 67(1), pp. 5-21], which is incorporated herein by reference as if full set forth herewith.

In the context of some embodiments of the present disclosure, assessment, observation or recordation of a personally perceived desired/therapeutic effect and/or a personally perceived undesired/adverse effect can be used at any time, including when a non-invasive biomarker is not available to the patient or the practitioner in order to conduct monitoring of PD effects for a defining a pre-determined vaporized amount during initial calibration, and/or for adjusting the amount during self-titration or personalization of the device used in treatment. Alternatively, a user or a practitioner may choose not to use a non-invasive biomarker for any reason. Optionally, an invasive biomarker measuring device may be used for monitoring amount at least one pharmacokinetic effect and/or at least one pharmacodynamic effect induced by the agent in the patient, especially if already installed in or on the patient, which can be accessed and provide the required information. In some embodiments at least two of a perceived effect, a non-invasive biomarker and an invasive biomarker are used to measure and/or estimate the same or different PD effects induced in a user by the one or more pharmaceutically active agents. It is noted that sensors for monitoring PD effects may be used as part of a manual and/or automatic feedback process for determining and/or adjusting a pre-determined vaporized amount of an agent off-line or in real-time.

As used herein, the term "real-time" refers to a reference (recordation, detection, measurement, reporting, depiction, reaction etc.) to an event or a series of events, wherein the reference occurs essentially at the same time and/or at the same rate, as the event(s). By "essentially at the same time and/or at the same rate" it is meant that a single event and its corresponding reference are temporally separated by a response time that ranges between zero to 30 minutes (0-30 minutes), 0-20 minutes, 0-10 minutes, 0-5 minutes, 0-1 minute, 0-45 seconds, 0-30 seconds, 0-20 seconds, 0-10 seconds, 0-5 seconds, 0-1 second, 0-750 milliseconds, 0-500 milliseconds, 0-250 milliseconds, 0-100 milliseconds, 0-50 milliseconds, 0-10 milliseconds or 0-1 millisecond.

Optionally, "real-time" refers to a reference (recordation, detection, measurement, reporting, depiction, reaction etc.) to an event or a series of events, wherein the reference occurs essentially between administration of an active agent to the dissipation of at least one pharmacodynamic effect induced in the subject by the administered agent. In some embodiments, "real-time" refers to a reference to an event or a series of events, occurring between two drug delivery inhalation events scheduled to occur between administration of an active agent to the dissipation of at least one pharmacodynamic effect induced in the subject by the administered agent. Optionally, the "real-time" event or series of events includes adjusting of the timing and/or amount of the later drug delivery inhalation event according to data indicative of one or more effect(s) of the earlier drug delivery inhalation event. In some embodiments, such dissipation means that the effect reaches a degree that is below detection for a given sensor and/or for being perceived by the user, as the case may be.

In the context of embodiments of the present invention, the term "real-time measurement" refers to a reference made by a sensor in response to an event that takes place in a subject in communication with the sensor. In some embodiments, a real-time measurement is a continuous, sporadic, regular or systematic monitoring, reporting, recordation, analysis, processing, presenting, displaying and transmitting of a pharmacodynamic effect by a designated sensor that is in communication with a subject.

While some PD effects are essentially subjective, such as the self-reported level of a symptom, the determination of some PD effects have been standardized so as to confer objectivity or at least afford a comparative scale that can be generalized across a population of subjects, as in the case of pain scales, wherein a change in the pain level is considered as a PD effect.

Pain scale protocols come in various forms and are available for neonates, infants, children, adolescents, adults, seniors, and persons whose communication is impaired. Examples for pain scale protocols include, without limitation, Alder Hey Triage Pain Score, Behavioral Pain Scale (BPS), Brief Pain Inventory (BPI), Checklist of Nonverbal Pain Indicators (CNPI), Critical-Care Pain Observation Tool (CPOT), COMFORT scale, Dallas Pain Questionnaire, Descriptor differential scale (DDS), Dolorimeter Pain Index (DPI), Edmonton Symptom Assessment System, Faces Pain Scale-Revised (FPS-R), Face Legs Activity Cry Consolability scale, Lequesne algofunctional index, McGill Pain Questionnaire (MPQ), Neck Pain and Disability Scale—NPAD, Numerical 11 point box (BS-11), Numeric Rating Scale (NRS-11), Oswestry disability index (ODI), Palliative Care Outcome Scale (PCOS), Roland-Morris Back Pain Disability Questionnaire (RMDQ), Support Team Assessment Schedule (STAS), Wong-Baker FACES Pain Rating Scale, Visual analog scale (VAS), Disease-Specific Pain Scale (DSPI), Pediatric Pain Questionnaire (PPQ), Premature Infant Pain Profile (PIPP), Schmidt Sting Pain Index, Starr sting pain scale, Pain Self-Efficacy Questionnaire (PSEQ), Patient-Specific Functional Scale (PSFS), Colorado Behavioral Numerical Pain Scale (for sedated patients), AUSCAN: Disease-Specific, to assess hand osteoarthritis outcomes, WOMAC: Disease-Specific, to assess knee osteoarthritis outcomes, Osteoarthritis Research Society International-Outcome Measures in Rheumatoid Arthritis Clinical Trials (OARSI-OMERACT) Initiative, and the likes.

For a non-limiting example, the Numeric Rating Scale (NRS-11) is an 11-point scale for patient self-reporting of pain for adults and children 10 years old or older, which provides a numerical Pain Level: 0 is No Pain; 1-3 is Mild Pain (nagging, annoying, interfering little with ADLs); 4-6 is Moderate Pain (interferes significantly with Activities of daily living or ADLs); and 7-10 is Severe Pain (disabling; unable to perform ADLs).

For another non-limiting example, the visual analogue scale or visual analog scale (VAS) is a psychometric response scale, which can be used in questionnaires or interactive patient interfaces; it is a measurement instrument for subjective characteristics or attitudes that cannot be mechanically, chemically or physically measured. When responding to a VAS question, respondents specify their level of agreement to a statement by indicating a position along a continuous line between two end-points. This continuous (or "analogue") aspect of the scale differentiates it from discrete scales such as the Likert scale. There is evidence showing that visual analogue scales have superior metrical characteristics than discrete scales, thus a wider range of statistical methods can be applied to the measurements. The VAS can be compared and correlated to other linear scales such as the Likert scale or Borg scale, whereas the sensitivity and reproducibility of the results are broadly very similar, although the VAS may be more practical and useful than the other scales in some cases.

A technology that allows pain to be measured objectively, and combines several of the abovementioned biomarkers, is provided for example in WO 2009/063463 and WO 2010/134068, which are incorporated herein by reference as if full set forth herewith. This technology is designed for pain classification and monitoring in responsive, awake, semi-awake or sedated subjects.

Other non-invasive biomarker level determination technologies, such as automatic facial expression recognition systems for estimation of pain level [Ashraf, A. B. et al., *Image and Vision Computing*, 2009, 27(12), p. 1788-1796; Hu, Y. et al., *Conference: IEEE International Conference on Automatic Face and Gesture Recognition—FGR*, 2008, p. 1-6] and ultraminiature cordless EMG measurement systems [Yamaguchi, T. et al., *Oral Surg Oral Med Oral Pathol Oral Radiol Endod.*, 2007 104(5), p. e22-7], for estimation of pain and other biomarkers, can be integrated into the methods presented herein via interfaces and systems as presented hereinbelow.

Invasively-detected biomarkers include any indicator that requires a sensor to be placed inside the body of the patient, including skin penetration, or requires a sample taken from within the body of the patient in order to quantify the indicator. For example, blood extraction from a vein of the patient using a needle, or via skin pricking, in order to measure the concentration of any indicator or factor (biomarker), is regarded as an invasive measurement, and thus these biomarkers are regarded as invasively-detected biomarkers.

Self-Titration:

In cases where a patient experiences for any reason inadequacy of a preset dose and/or regimen, regardless if the pre-determined vaporized amount of the agent (the preset dose and/or regimen) have been derived individually for that patient or not, this patient may wish to readjust the pre-determined vaporized amount of the agent (dose and/or regimen) according to a current physiological condition, a mental condition, or for any other reason. This option is regarded as self-titration of the agent, and be part of a manual feedback process for determining a pre-determined vaporized amount of an agent.

Hence, when the PD profile requires re-selection, the pulmonary delivery of the active agent from the MDI device further includes steps that allow the patient to self-titrate the pre-determined vaporized amount, or a practitioner to alter and readjust the pre-determined vaporized amount of the agent as needed.

According to some of any embodiments of the present disclosure, the pulmonary delivering of the pharmaceutically active agent further includes configuring the device to deliver an adjusted vaporized amount of the agent, whereas the adjusted vaporized amount is selected so as to exhibit a re-selected pharmacodynamic profile of the agent in the patient, whereby, upon the configuring, the adjusted vaporized amount becomes the pre-determined vaporized amount and the re-selected pharmacodynamic profile is regarded as a pre-selected pharmacodynamic profile.

In some embodiments, the readjustment is effected without re-determining a PK and/or a PD effect in the patient.

Automatic Feedback:

According to some embodiments, the adjustment or re-adjustment of the pre-determined vaporized amount of an agent (dose and regimen thereof) includes an automatic feedback process based on personal pharmacodynamic parameter data.

Personal pharmacodynamic parameter data optionally include at least one personally perceived therapeutic effect and at least one personally perceived adverse effect; and may further include at least one biomarker level datum.

As discussed hereinabove, the automatically obtained level of a biomarker may be an invasively-detected biomarker and a non-invasively-detected biomarker. According to embodiments of the present disclosure, the automatically obtained level of a biomarker is that of a non-invasively-detected biomarker.

Thus in some of any of the embodiments of the present disclosure, the method further includes:

automatically measuring, acquiring or otherwise determining at least one personal pharmacodynamic parameter in the patient in the form of a perceived therapeutic and/or perceived adverse effect and/or a level of at least one biomarker, collectively referred to herein as personal pharmacodynamic feedback data or information;

automatically re-determining an adjusted vaporized amount of the agent based on the automatically acquired personal pharmacodynamic feedback data, or in general adjust the dose and regimen according to the acquired personal pharmacodynamic feedback data;

automatically configuring the device to deliver the adjusted vaporized amount, to thereby exhibit a pre-selected or a re-selected PK and/or PD profile in the patient;

whereby for that particular person, the adjusted vaporized amount becomes the pre-determined vaporized amount of the pharmaceutically active agent and the re-selected PK and/or PD profile becomes the pre-selected PK and/or PD profile.

It is noted herein that automatic determination of any PD effect, or the automatic determination of the vaporized amount of the pharmaceutically active agent, can be fully or partially applied in any of the embodiments of the present disclosure, including the initial calibration of the MDI device, the re-configuration of the device during the personalization process, and/or the self-titration process.

Co-Administration:

It is noted herein that the method and/or device, according to some of any embodiments of the present disclosure, is suitable for pulmonary delivering of more than one pharmacologically active agent to a patient, wherein the device is configured to deliver independently a pre-determined vaporized amount of each the agents controllably, accurately and reproducibly.

According to some embodiments, co-administration of more than one active agent is carried out so as to achieve a desired balance between therapeutic (desired; positive; wanted) effects and adverse (undesired; negative; unwanted) effects. Such balance may be achieved for example when one active agent, while having some or no direct therapeutic effect, has the capacity to lower an adverse effect caused by the other co-administered active agent. In another example, different active agents induce similar and cumulative desired effects and different non-cumulative undesired effects; in which case such two such agents can be co-administered to induce a cumulative (e.g., double) desired effect while inducing substantially lower (e.g., single) undesired effect, compared to a 2-fold dose of each given individually. Optionally, the second agent has an effect that reduces and/or changes the nature of an adverse effect of the first agent. In such cases, the amount of the first agent (and the desired effect itself) may be increased, without increasing, and optionally while decreasing, the undesired effects thereof. This approach allows a higher dose for achieving a desired effect in treatment while maintaining low levels of adverse effects.

According to some embodiments, these two or more agents can be contained in the same substance or in more than one substance. In some embodiments, at least one of the agents is in at least one plant material. Hence, according to some embodiments, the device and method presented herein are configured for delivering each of at least two pharmacologically active agents independently at a pre-determined vaporized amount, wherein the substance being heated in the device comprises both or all these pharmacologically active agents. Alternatively, the device comprises more than one substance, which comprises the pharmacologically active agents.

In some embodiments, a method of pulmonary delivering to a subject at least a first pharmacologically active agent and a second pharmacologically active agent is provided, wherein at least one of the agents being in at least one plant material; the method is carried out by independently delivering the agents to the subject using a metered dose inhaler device configured to vaporize at least a first pre-determined vaporized amount of the first agent and at least a second pre-determined vaporized amount of the second agent upon controllably heating the plant material, wherein heating is effected such that the first pre-determined vaporized amount is delivered to the subject successively, concomitantly and/or at least partially overlapping with the second pre-determined vaporized amount, and wherein each of the pre-determined vaporized amounts of each of the agents induces in the subject independently at least one pharmacokinetic effect and/or at least one pharmacodynamic effect.

According to an aspect of some embodiments of the present disclosure, there is provided a method of pulmonary delivering to a subject at least a first pharmacologically active agent and a second pharmacologically active agent, at least one of which being in at least one plant material; the method is carried out by:
  independently delivering the agents to the subject using a metered dose inhaler device configured to vaporize at least a first pre-determined vaporized amount of the first agent and at least a second pre-determined vaporized amount of the second agent upon controllably heating the at least one plant material,
  wherein heating is effected such that the first pre-determined vaporized amount is delivered to the subject successively, concomitantly and/or at least partially overlapping with the second pre-determined vaporized amount, and wherein each of the pre-determined vaporized amounts of each of the agents induces in the subject independently at least one pharmacokinetic effect and/or at least one pharmacodynamic effect.

A pulmonary delivery of more than one active agent to a subject (a patient) is generally known in the art as co-administration. The term "co-administration" as used herein, refers to a concomitant administration of more than one active agent to a subject, whereas in the context of embodiments presented herein, the term "concomitant" means that the co-administered active agents are present in the subject (PK), or otherwise induce an effect (PD), at similar, identical or partially overlapping periods of time. In some embodiments, the time interval between delivering at least one agent (first) and delivering at least one other agent (second) ranges between zero minutes to 30 minutes.

In the context of co-administration of more than one active agent, the terms "substantially simultaneous" and "rapid succession" correspond to the term "concomitant" and "partially overlapping", as used herein, namely meaning that the period of time between an inhalation of a first agent and an inhalation of a second agent is sufficiently short to be regarded as a single inhalation. Optionally, a number of inhalations takes place within 5-30 minutes. Optionally, each inhalation in such "rapid succession" delivers to the user a different amount or a composition of one or more pharmaceutically active agents. Optionally, two or more of the inhalations provide the same composition and amount of the one or more pharmaceutically active agents. In some embodiments, an inhalation of a second agent is performed at such timing that a first active agent inhaled previously still induces at least one PD effect in the subject. In some embodiments, co-administration of more than one active agent by delivery thereof in rapid succession means that the inhaled agents have essentially the same effect as they would have had if inhaled in a single inhalation.

According to some embodiments, a time interval between delivering the first agent and delivering the second agent ranges between zero minutes to 30 minutes.

According to some embodiments, each of these agents can be delivered at a pre-determined vaporized amount. Hence, the device and the method presented herein are capable of and designed for delivering the plurality of pre-determined vaporized amounts, wherein these vaporized amounts may be the same or different.

According to some embodiments, each of these agents can be delivered at a pre-determined time interval. Hence, the device and the method presented herein are capable of and designed for delivering the plurality of pre-determined vaporized amounts at pre-determined time intervals, wherein these time intervals may be the same or different.

According to some embodiments, the device and method presented herein are capable of and designed for delivering a plurality of pre-determined vaporized amounts of each of the pharmacologically active agents, wherein the pre-determined vaporized amounts and the pre-determined time intervals may each be the same or different from one another.

In some embodiments, the co-administration is based on interdependencies between one or more PD effects induced by individual agents, namely a PD effect of one agent influences the level of a PD effect induced by the other agent. For example, in some embodiments, the pre-determined vaporized amounts of the first agent affects a level of the pharmacodynamic effect induced by the second agent. Optionally, the pre-determined vaporized amount of the first agent increases a level of a desired effect induced by the second agent (potentiation). Optionally, the pre-determined vaporized amount of the first agent reduces a level of the undesired effect induced by the second agent. Optionally, the first agent and the second agent induce a desired effect synergistically.

In some embodiments, the method of pulmonary delivering more than one active agent, a presented hereinabove, further includes:

adjusting at least one of the first pre-determined vaporized amount and the second pre-determined vaporized amount so as to achieve the pre-determined pharmacokinetic effect and/or the pre-determined pharmacodynamic effect based on data indicative of at least one pharmacokinetic effect and/or at least one pharmacodynamic effect induced by the agent in the subject.

In some embodiments, the method further includes generating indicative data by monitoring at least one pharmacokinetic effect and/or at least one pharmacodynamic effect induced in the subject by at least one of the first agent and the second agent.

As a non-limiting example, a co-administration of THC and CBD can be carried out using the device and methods provided herein. In this example, a pain management regimen is effected by inhalation of THC in doses of 5 mg pre-determined vaporized amounts taken six times a day. This is combined with three inhalations per day of 300 mg CBD to treat inflammation. The two pharmacologically active agents may be administered simultaneously or sequentially, namely in 6-9 inhalation sessions.

According to an aspect of some embodiments of the present disclosure, there is provided a method of vaporizing at least a first pharmacologically active agent and a second pharmacologically active agent, at least one of which being in at least one plant material and being suitable for pulmonary delivery to a patient, which is carried out by using a metered dose inhaler device configured to vaporize at least a first pre-determined vaporized amount of the first agent and at least a second pre-determined vaporized amount of the second agent upon controllably heating the plant material, wherein upon pulmonary delivering the agents to the subject, the heating is effected such that the first pre-determined vaporized amount is delivered to the subject successively, concomitantly and/or at least partially overlapping with the second pre-determined vaporized amount, and wherein upon pulmonary delivering the agents to the subject, each of the pre-determined vaporized amounts of each of the agents induces in the subject independently at least one pharmacokinetic effect and/or at least one pharmacodynamic effect.

According to an aspect of some embodiments of the present disclosure, there is provided a use of a metered dose inhaler device for vaporizing at least a first pharmacologically active agent and a second pharmacologically active agent, at least one of which being in at least one plant material and being suitable for pulmonary delivery to a patient, wherein the device is configured to vaporize at least a first pre-determined vaporized amount of the first agent and at least a second pre-determined vaporized amount of the second agent upon controllably heating the plant material, and wherein upon pulmonary delivering the agents to the subject, the heating is effected such that the first pre-determined vaporized amount is delivered to the subject successively, concomitantly and/or at least partially overlapping with the second pre-determined vaporized amount, and wherein upon pulmonary delivering the agents to the subject, each of the pre-determined vaporized amounts of each of the agents induces in the subject independently at least one pharmacokinetic effect and/or at least one pharmacodynamic effect.

Method of Treatment

According to an aspect of some embodiments of the present disclosure, there is provided a method of treating a patient suffering from a medical condition that is treatable by pulmonary delivering a vaporizable pharmaceutically active agent. The method, according to some of any of the embodiments of the present disclosure, is carried out by pulmonary delivering the agent to the patient from a metered dose inhaler device configured to release at least one pre-determined vaporized amount of the agent upon controllably heating a solid form of a substance comprising the agent. According to some embodiments, the pre-determined vaporized amount of the agent is selected to exhibit at least one pre-selected pharmacokinetic profile and/or at least one pre-selected pharmacodynamic profile of the agent in the patient.

Non-limiting representative medical conditions, treatable by pulmonary delivering a vaporizable pharmaceutically active agent, include neuropathic pain, phantom pain, nociceptive pain, psychogenic pain (psychalgia or somatoform pain), asthma, chronic obstructive pulmonary disease (COPD), Crohn's disease, multiple sclerosis (MS), generalized epilepsy with febrile seizures plus (GEFS+), spasticity, Dravet's Syndrome, seizures, epilepsy, psychiatric disorders, anxiety disorders, posttraumatic stress disorder (PTSD), insomnia, delirium, increased intra ocular pressure, bladder dysfunction, tics, Tourette symptoms, appetite variations, sexual dysfunction, inflammatory bowel disease (IBD), irritable bowel syndrome (IBS), hyper tension, septic and cardiogenic shock, drug addiction and craving, tremors and other movement disorders.

According to some of any of the embodiments of the present disclosure, the method is carried out by use of an MDI device which is configured to release a pre-determined vaporized amount such that a deviation of an actual vaporized amount of the agent, from the pre-determined vaporized amount of the agent, is 20% or less, 15% or less, 10% or less, or 5% or less of the pre-determined vaporized amount.

According to some of any of the embodiments of the present disclosure, the method is carried out such that a deviation of an actual pharmacokinetic profile from the pre-selected pharmacokinetic profile is 40% or less than of the pre-selected pharmacokinetic profile. Alternatively, the deviation is 35% or less, 30% or less, 25% or less, or 20% or less. It is noted that the deviation can be in the pharmacokinetic profile or in one or more pharmacokinetic parameters composting the profile, e.g., $C_t$ or $C_{max}$. Such deviations are expected to be low due to the low inter-variability of PK effects obtained when using an accurate, consistent and precise MDI device.

According to some of any of the embodiments of the present disclosure, the method is carried out such that a deviation between the perceived PD profile from the pre-selected PD profile at any given time point is 25% or less, 20% or less, 15% or less, 10% or less, or 5% or less. The deviation between the perceived PD profile from the pre-selected PD profile at any given time point can be assessed by determining a PD effect, as discussed hereinabove. The deviation is expected to be low also due to the low inter-variability of PK effects discussed hereinabove.

Since the device can be configured to deliver any accurate amount consistently so as to exhibit a pre-selected or predetermined PD effect in the patient, the device and the method presented herein can effect a pre-selected or pre-determined PD profile which can be finely controlled so as to be:

within a level lower than a minimal level of a desired effect (for example below the therapeutic window; see, FIG. 8, area below the lower horizontal dashed line);

ranging within a minimal level of said desired effect to a maximal level of said desired effect in which an undesired effect is tolerable and/or acceptable, namely substantially low or not exhibited or not perceived (for example within the therapeutic window; see, FIG. 8, area between the lower and upper horizontal dashed lines); and within a level higher than a minimal level an undesired effect (for example above the therapeutic window; see, FIG. 8, area above the lower horizontal dashed line).

In some embodiments, a minimal level of an adverse effect correlates to a maximal level of a therapeutic effect in which an adverse effect is not detected or perceived.

In some embodiments, the level of the pharmacodynamic profile that is higher than the minimal level of an adverse effect, is one wherein the higher level of the adverse effect is an acceptable level of the adverse effect. Any one of personal, medicinal and legal factors may determine the acceptability of the level of the adverse effect, such as, for example, personal preference, habits and endurance, pharmaceutical and professional safety considerations, as well as legal and social consideration.

In some embodiments, a "minimal level of a therapeutic effect" means a minimal detectable therapeutic effect. Optionally, such a minimal level is at least sufficient to justify treating a person with a given dose and/or regimen with one or more substances. Such justification may be based on, for example, the type and severity of adverse effects and on the effect that the treatment may have at the minimal level on the wellbeing of the patient. Optionally, the minimal therapeutic effect means a minimal effect that is perceived by the individual being treated. Optionally, justification for administering a dose and/or regimen aiming to achieve PK/PD effects below the therapeutic window may be to achieve a prophylactic treatment or reduce the consequences of an acute pain (breakthrough pain) and/or to prevent emergence of tolerance to the treatment.

As discussed hereinabove, according to some of any of the embodiments of the present disclosure, the pre-selected PD profile corresponds to the therapeutic window of the agent in the patient, namely ranges within a minimal level of the therapeutic effect to a maximal level of the therapeutic effect in which an adverse effect is acceptable.

At any pre-selected PD profile, the method and device provide high accuracy and reproducibility; hence, according to some of any of the embodiments of the present disclosure, the deviation of the perceived pharmacodynamic profile from the pre-selected pharmacodynamic profile at any given time point is 25% or less, 20% or less, 10% or less or 5% or less below the pre-selected PD profile, and/or 25% or less, 20% or less, 10% or less or 5% or less above said pre-selected PD profile.

A non-limiting examples of a medical condition treatable by pulmonary delivering a vaporizable pharmaceutically active agent, is pain, which is treatable by THC vaporized from cannabis.

A Metered Dose Inhaler (MDI) Device:

According to another aspect of some embodiments of the present disclosure, there is provided a metered dose inhaler (MDI) device configured for pulmonary delivery of a pre-determined vaporized amount of at least one pharmacologically active agent to a patient, wherein:

the device is configured to deliver said pre-determined vaporized amount of said agent upon controllably heating a solid form of a substance comprising said agent;

the pre-determined vaporized amount is selected such that it affords a pre-selected pharmacokinetic profile and/or a pre-selected pharmacodynamic profile of the agent in the patient; and the pre-determined vaporized amount is derived by measuring at least one pharmacokinetic parameter and/or at least one pharmacodynamic parameter induced by the pulmonary delivering of the agent in the patient from the MDI device (PK/PD studies).

According to an aspect of some embodiments of the disclosure, there is provided a method for controlling a metered dose inhaler; the method is effected by:

heating plant material so as to vaporize at least one pre-determined vaporized amount of at least one pharmacologically active agent being in the plant material; and controlling the pre-determined vaporized amount based on data indicative of at least one pharmacodynamic effect induced by the agent in the subject.

According to an aspect of some embodiments of the disclosure, there is provided a method of operating an MDI for pulmonary delivering to a subject of at least one pharmacologically active agent being in a plant material; the method is effected by:

selecting at least one pre-determined vaporized amount of the agent so as to achieve at least one pre-determined pharmacokinetic effect and/or at least one pre-determined pharmacodynamic effect induced by the agent in the subject; and vaporizing, the at least one pre-determined vaporized amount of the agent using the metered dose inhaler device for controllably heating the plant material.

According to some embodiments of the invention, the MDI device is further configured for communication with a patient interface circuitry and be integrated in a system designed to allow PK/PD data acquisition and input, patient records' storage, automatic or manual calibration, adjustment, resetting and re-determination of the initial presetting of the device by the patient and/or by a practitioner, as will be described in details hereinbelow.

As discussed hereinabove, and demonstrated in the PK/PD study presented in the Examples section below, inter-variability of PK/PD among the cohort of the study was notably low, and afforded by use of the accurate and consistent MDI device, according to embodiments of the present disclosure.

According to some of any of the embodiments of the present disclosure, the method and device presented herein are also characterized by a high accuracy, consistency, precision and reproducibility, which are expressed by a minimal deviation between the actual vaporized amount of the agent being inhaled by the patient, and the pre-determined vaporized amount of the agent.

According to some of any of the embodiments of the present disclosure, the MDI device for controlled vaporization of at least one active pharmaceutically active agent from at least one type of substance by application of heat, comprises:

At least one cartridge (also referred to herein as a "dose unit") containing a substance that comprises at least one active pharmaceutically active agent;

a heating element adapted to apply heat to the substance to vaporize the pharmaceutically active agent; and a mechanism adapted for moving the cartridge relative to a controller for powering the heating element.

In an embodiment of the invention, the device further comprises substance organized as plurality of cartridges arranged in a tape, a daisy or a magazine, the substance comprising the active pharmaceutically active agent. Optionally, the active pharmaceutically active agent is a restricted pharmaceutically active agent. Optionally or additionally, the active pharmaceutically active agent is selected from the group comprising: tetrahydrocannabinol (THC), salvinorin A, benzoylmethylecgonine, dimethyltryptamine, psilocybin. Optionally or additionally, the substance is organized with a pre-determined amount of the active pharmaceutically active agent per unit area of the each cartridge in the tape, the daisy or the magazine. Optionally or additionally, a thickness of the cartridge ranges from about 0.2 mm to about 2.0 mm. Optionally or additionally, the tape, the daisy or the magazine comprises about 5 grams to about 100 grams of the substance. Optionally or additionally, the tape, the daisy or the magazine comprises a sufficient amount of the active pharmaceutically active agent for at least two treatments. Optionally or additionally, the cartridge comprises a first material layer coupled to the substance, the first layer comprising apertures large enough to let gas escape but small enough to contain residue of the heated substance. Optionally or additionally, a diameter of the apertures ranges from 25 μm-500 μm. Optionally or additionally, the cartridge comprises a second material layer coupled to the substance, the second layer adapted to transmit heat to the substance without substantially distributing the heat across the second layer. Optionally or additionally, the heating element and the substance are held between the first and the second layers.

In an embodiment of the invention, the device further comprises an inhaler unit, the inhaler unit comprising a mouthpiece for inhalation of the pharmaceutically active agent, the mouthpiece forming fluid communication with a vapor chamber of the device, the vapor chamber comprising the vaporized active pharmaceutically active agent.

Optionally, the mouthpiece comprises a one-way valve to control fluid flow away from the vapor chamber. Optionally or additionally, the device further comprising a sensor in fluid communication with the mouthpiece, the sensor adapted to estimate an air flow rate and send a signal to a controller, the controller adapted for vaporizing the pharmaceutically active agent according to the airflow rate.

In an embodiment of the invention, the device further comprises a controller configured to synchronize the application of heat with the movement of a cartridge and/or with airflow rate effected by inhalation.

In an embodiment of the invention, the device further comprises circuitry for controlling (controller) activation of the heating element.

In an embodiment of the invention, the device further comprises a communication interface for communicating to one or more external computers and/or systems and/or patient/physician interfaces.

In an embodiment of the invention, the device further comprises a dose display meter for providing visual output of the vaporization of the pharmaceutically active agent.

In an embodiment of the invention, the device is portable and weights no more than 300 grams.

In an embodiment of the invention, the device further comprises a memory adapted to hold at least one of prescription data and usage data, the memory coupled to the controller, the controller adapted to control at least one of the heating element and the mechanism according to the dose and/or regimen data.

In an embodiment of the invention, the device further comprises a unique ID adapted for tracking the device use by an associated patient.

In an embodiment of the invention, the device further comprises a sensor adapted to detect a physical breach of the device.

There is provided in accordance with an embodiment of the invention, a method for controlled vaporization of an active pharmaceutically active agent from a substance, the substance is organized as a cartridge, the method comprising;

applying heat to an area of the cartridge to vaporize a predetermined amount of the active pharmaceutically active agent and; moving the cartridge relative to a heat source.

Alternatively, the heating element is comprised within the cartridge, and the cartridge is moved relative to electrical contacts for powering the heating element.

In an embodiment of the invention, the method further comprises adjusting at least one of timing and speed of the moving to vaporize the active pharmaceutically active agent according to a delivery profile. Optionally, the substance comprises a macroscopic plant structure.

In an embodiment of the invention, the vaporizing comprises vaporizing during pulmonary delivery.

In an embodiment of the invention, the applying heat comprises applying heat to reach a target temperature in less than 500 milliseconds after a start signal.

There is provided in accordance with an embodiment of the invention, a method for controlled vaporization of at least one active pharmaceutically active agent from at least one type of substance by application of heat, the method comprising:

heating up multiple areas of substance organized as one or more cartridges with one user trigger, to release the at least one active pharmaceutically active agent.

Optionally, the areas comprise different active pharmaceutically active agents.

There is provided in accordance with an embodiment of the invention, a method of manufacturing a cartridge of substance comprising an active pharmaceutically active agent, the cartridge adapted for use with a device for automatically applying localized heat to vaporize the pharmaceutically active agent, the method comprising:

grinding the substance without substantially physically damaging the active pharmaceutically active agent;

sieving the ground substance to isolate small particles;

measuring the concentration of active pharmaceutically active agents the small particles; and pressing the small particles into the cartridge.

In an embodiment of the invention, sieving is performed a plurality of times to isolate particles of different sizes.

In an embodiment of the invention, a size of particles ranges from about 100 μm to about 700 μm.

In an embodiment of the invention, pressing is performed on a material having apertures with a size smaller than the size of the small particles.

In an embodiment of the invention, the method further comprises marking the cartridge with the concentration of the active pharmaceutically active agent.

There is provided in accordance with an embodiment of the invention, a cartridge for therapeutic drug delivery comprising substance comprising an active pharmaceutically active agent, said substance organized with a predetermined amount of the active pharmaceutically active agent per unit area of said tape (cartridge), and a heating element comprised therein.

In an embodiment of the invention, a plurality of cartridges is organized as a roll of tape, a daisy or a magazine.

Illustrative Application:

According to some embodiments and aspects of the present disclosure, each and any method, device, interface, system or sub-system presented herein can be used for treating a medical condition treatable by a pharmacologically active agent, which is vaporizable from a solid substance. In some embodiments of the present disclosure, the substance is a plant material.

Some plants which can be used in the context of the present disclosure, include, without limitation, *Cannabis sativa, Cannabis indica, Cannabis ruderalis, Acacia* spp., *Amanita muscaria, Yage, Atropa belladonna, Areca catechu, Brugmansia* spp., *Brunfelsia latifolia, Desmanthus illinoensis, Banisteriopsis caapi, Trichocereus* spp., *Theobroma cacao, Capsicum* spp., *Cestrum* spp., *Erythroxylum coca, Solenostemon scutellarioides, Arundo donax, Coffea arabica, Datura* spp., *Desfontainia* spp., *Diplopterys cabrerana, Ephedra sinica, Claviceps purpurea, Paullinia cupana, Argyreia nervosa, Hyoscyamus niger, Tabernanthe iboga, Lagochilus inebriens, Justicia pectoralis, Sceletium tortuosum, Piper methysticum, Catha edulis, Mitragyna speciosa, Leonotis leonurus, Nymphaea* spp., *Nelumbo* spp., *Sophora secundiflora, Mucuna pruriens, Mandragora officinarum, Mimosa tenuiflora, Ipomoea violacea, Psilocybe* spp., *Panaeolus* spp., *Myristica fragrans, Turbina corymbosa, Passiflora incarnate, Lophophora williamsii, Phalaris* spp., *Duboisia hopwoodii, Papaver somniferum, Psychotria viridis*, spp., *Salvia divinorum, Combretum quadrangulare, Trichocereus pachanoi, Heimia salicifolia, Stipa robusta, Solandra* spp., *Hypericum perforatum, Peganum harmala, Tabernaemontana*spp., *Camellia sinensis, Nicotiana tabacum, rusticum, Virola theidora, Voacanga africana, Lactuca virosa, Artemisia absinthium, Ilex paraguariensis, Anadenanthera* spp., *Corynanthe yohimbe, Calea zacatechichi, Coffea* spp. (*Rubiaceae*), a *Sapindaceae, Camellia* spp., *Malvaceae* spp., *Aquifoliaceae* spp., *Hoodia,* spp. *Chamomilla recutita, Passiflora incarnate, Camellia sinensis, Mentha piperita, Mentha spicata, Rubus idaeus, Eucalyptus globulus, Lavandula officinalis, Thymus vulgaris, Melissa officinalis,* any part and any combination thereof.

Other plants and plant materials, which can be used beneficially to vaporize at least one pharmaceutically active agent in the context of embodiments of the present disclosure include, without limitation, Aloe Vera, Angelica, Anise, Ayahuasca (*Banisteriopsis caapi*), Barberry, Black Horehound, Blue Lotus, Burdock, Camomille/Chamomile, Caraway, Cat's Claw, Clove, Comfrey, Corn Silk, Couch Grass, Damiana, Damiana, Dandelion, Ephedra, Eucalyptus, Evening Primrose, Fennel, Feverfew, Fringe Tree, Garlic, Ginger, Ginkgo, Ginseng, Goldenrod, Goldenseal, Gotu Kola, Green Tea, Guarana, Hawthorn, Hops, Horsetail, Hyssop, Kola Nut, Kratom, Lavender, Lemon Balm, Licorice, Lion's Tail (Wild Dagga), Maca Root, Marshmallow, Meadowsweet, Milk Thistle, Motherwort, Passion Flower, Passionflower, Peppermint, Prickly Poppy, Purslane, Raspberry Leaf, Red Poppy, Sage, Saw Palmetto, Sida Cordifolia, Siniсuichi (Mayan Sun Opener), Spearmint, Sweet Flag, Syrian Rue (Peganum harmala), Thyme, Turmeric, Valerian, Wild Yam, Wormwood, Yarrow, Yerba Mate, Yohimbe, and any part and any combination thereof.

In some embodiments, the active agent is a terpenoid, alkaloid or cannabinoid. For example, in some embodiments, the active agent is a diterpenoid such as, but not limited to salvinorin A from salvia. In other embodiments, the active agent is an alkaloid such as, but not limited to, benzoylmethylecgonine from the coca plant, or the active agent is a tryptamine such as psylocibin from mushrooms. In alternative embodiments the active substance is dimethyltryptamine (DMT) from a variety of plants. In further embodiments, the active substance is nicotine from tobacco. In further embodiments, the active substance is a terpenoid, e.g., limonene, α-pinene, β-myrcene, linalool, β-caryophyllene, caryophyllene, nerolidol or phytol, present in various plant forms.

According to some embodiments, the plant material is selected from the group consisting of *Cannabis sativa, Cannabis indica,* and *Cannabis ruderalis,* and according to some embodiments, the plant is *Cannabis sativa*.

Cannabis is a natural source for vaporizable cannabinoids, which constitute a class of diverse chemical compounds that act on cannabinoid receptors found in cells of humans and other animals. Cannabinoids, which include endocannabinoids (produced in animals), phytocannabinoids (found in cannabis and some other plants) and synthetic cannabinoids (manufactured chemically), are known to bind to naturally receptor proteins, and repress neurotransmitter release in the brain. The primary psychoactive compound of cannabis, is the phytocannabinoid Δ9-tetrahydrocannabinol (THC).

Cannabidiol (CBD) is another major constituent of the plant, representing up to 40% in extracts of the plant resin. There are at least 85 different cannabinoids isolated from cannabis, exhibiting varied effects, which include cannabigerols (CBG), cannabichromenes (CBC), cannabinol (CBN), cannabinodiol (CBDL), cannabicyclol (CBL), cannabielsoin (CBE), cannabitriol (CBT), Cannabidivarin (CBDV), Tetrahydrocannabivarin (THCV) and other miscellaneous types.

Tetrahydrocannabinol (Delta-9-tetrahydrocannabinol; Δ9-THC; THC) is the primary psychoactive component of the Cannabis plant. Δ9-THC and Δ8-THC mimic the action of anandamide, a neurotransmitter produced naturally in mammals. These two THC's produce the psychoactive effects associated with cannabis by binding to the CB1 and CB2 cannabinoid receptors in the brain; it has been reported to exhibit approximately equal affinity for the CB1 and CB2 receptors. THC appears to ease moderate pain (analgesic) and to be neuroprotective, while studies also show that THC reduces neuroinflammation and stimulates neurogenesis.

Cannabidiol (CBD) is not considered to be psychoactive, and was thought not to affect the psychoactivity of THC. However, recent evidence shows that smokers of cannabis with a higher CBD/THC ratio were less likely to experience schizophrenia-like symptoms. This is supported by psychological tests, in which participants experience less intense psychotic-like effects when intravenous THC was co-administered with CBD.

Cannabidiol has a different affinity for CB1 and CB2 receptors compared to THC (CBD has a greater affinity for the CB2 receptor than for the CB1 receptor), but acts as an indirect antagonist of cannabinoid agonists. Recently it was found to be an antagonist at the putative new cannabinoid receptor, GPR55, a GPCR expressed in the caudate nucleus and putamen. Cannabidiol has also been shown to act as a 5-HT1A receptor agonist, an action that is involved in its antidepressant, anxiolytic, and neuroprotective effects. CBD is also reported to relieve convulsion, inflammation, anxiety, and nausea.

CBD is known to play a role in preventing the short-term memory loss associated with THC in mammals. CBD has been suggested as a therapeutic agent in the treatment of schizophrenia. Researchers discovered CBD's ability to "turn off" the activity of ID1, the gene responsible for metastasis in breast and other types of cancers, including the particularly aggressive triple negative breast cancer.

Hence, accordion to some embodiments of the present disclosure, the pharmacologically active agent is a cannabinoid selected from the group consisting of Δ9-tetrahydrocannabinol (THC), cannabidiol (CBD), cannabigerols (CBG), cannabichromenes (CBC), cannabinol (CBN), cannabinodiol (CBDL), cannabicyclol (CBL), cannabielsoin (CBE), Cannabidivarin (CBDV), Tetrahydrocannabivarin (THCV) and cannabitriol (CBT), and according to some embodiments, the pharmacologically active agent is selected from the group consisting of Δ9-tetrahydrocannabinol (THC) and cannabidiol (CBD).

As mentioned above, pulmonary delivery of cannabinoids from cannabis via smoking is the most prevalent route of administration used by majority of the patients prescribed on cannabis. The substantially lower oral mode and/or oromucosal routes of delivery of cannabis or extracts thereof is partially attributed to the slow and erratic absorption of cannabinoids with oral administration, leading to delayed onset and often unsatisfactory magnitude of analgesia. However, although smoking proves a rapid and efficient method of cannabinoid delivery resulting in first onset of effects after about 7 minutes, the bioavailability of tetrahydrocannabinol (THC) is heterogeneous and ranges between 2 to 56% due mainly, to variability in the depth of inhalation, puff duration, breath-hold time, and the fact that about 30% of the THC dose is assumed to be destroyed by pyrolysis during smoking.

As discussed hereinabove, in order to improve the efficiency, accuracy and consistency of cannabinoid administration by inhalation, while avoiding the risks of smoking-related diseases caused by noxious pyrolytic byproducts, some embodiments of the present disclosure are based on the use of a combustion-free and smokeless MDI device, such as that taught in WO/2012/085919, which has been shown to be most suitable for pulmonary administration of cannabinoids from cannabis.

In some embodiments, the pulmonary delivery method described herein utilizes THC or, more specifically, $\Delta^9$-THC as the pharmaceutically active agent. In some embodiments, the THC dose (pre-determined vaporized amount) is about 0.1-10 mg, which has been shown to be salutary analgesics for a heterogeneous variety of neuropathic pain conditions. Such low THC dose can be vaporized accurately and consistently from natural cannabis in an amount that ranges from 5 to 50 mg, 6 to 50 mg, 7 to 40 mg, 8 to 40 mg, 8 to 30 mg, 9 to 40 mg, 9 to 35 mg, 10 to 35 mg, 11 to 30 mg, 12 to 30 mg, 12 to 27 mg, or 12 to 25 mg, depending on the total amount of $\Delta^9$-THC available in the cannabis. In some preferred embodiments, the cannabis contains about 20% $\Delta^9$-THC, and the amount of cannabis used in the inhaler for each dose ranges from 15.0 to 25.0 mg.

In some embodiments, a single dose of 3.08±0.02 mg of total available $\Delta^9$-THC in a cannabis sample containing about 20% $\Delta^9$-THC, delivered in a single inhalation, elevated the $C_{max}$ plasma level of $\Delta^9$-THC in a patient to 38±10 ng/ml and provided a 45% reduction of pain intensity which reversed within 90 minutes.

As demonstrated by the PK/PD study presented in the Example section that follows below, loading the MDI with about 15 mg cannabis aliquots and heating each to about 190° C. for less than about 3 seconds, yielded about 52% of the total $\Delta^9$-THC available for inhalation in the plant material. Such a high yield of $\Delta^9$-THC is outstanding when compared to $\Delta^9$-THC yield measured in different types of smoking procedures known in the art. For example, it has been reported that $\Delta^9$-THC's plasma levels afforded by smoking vary widely and have been estimated only at about 20-37% of the total $\Delta^9$-THC available for inhalation in the plant material, wherein the remainder is lost through combustion (23-30%) and side-stream smoke (40-50%). Furthermore, even by applying commonly used vaporizers and vaporization techniques, such as the Volcano®, heating a dose of 200 mg crude flower tops of cannabis, containing 18% THC, to 200° C., resulted in a THC delivery of only 22%. This difference in the extraction efficiency between the various vaporizers known in the art, and the MDI device and the methods described herein is based inter alia on various unique mechanical attributes of the MDI, which allows the accuracy and consistency required for PK/PD calibration thereof.

Among other advantageous properties of the methods ad devices presented herein, which involve, according to some embodiments thereof, vaporization of cannabinoids from cannabis at temperatures of 155-218° C., it has been shown that polynuclear aromatic hydrocarbons as well as carbon monoxide, benzene, toluene and particulate tar levels were dramatically reduced in the cannabis vapor phase. This finding is in sharp contrast to products produced in smoking cannabis. While combustion products were not monitored, the noxious intake from the MDI device used in accordance with the present disclosure is expected to be very little if any, based on the following observations: (1) each dose consisted of a small amount (about 15 mg) of high THC concentration (about 20%) cannabis; (2) unlike the combusted cannabis, which turned to ash, the residual material, after evaporation, obtained a consistent amber colored appearance; (3) no burning sensation of the upper respiratory track was reported by patients; (4) no increase of cannabinol (a product of THC oxidation) was measured in residues; and (5) no transformation of $\Delta^9$- to $\Delta^8$-THC was detected in residues.

The present inventors have demonstrated a PK/PD profile of $\Delta^9$-THC similar to that previously reported in the art using purified and thus quantified $\Delta^9$-THC. As demonstrated in the Examples section that follows, the inhalation method employed by the present inventors has successfully obtained pulmonary delivery of THC that was characterized by rapid absorption, followed by bi-phasic decline in plasma concentration over time: a phase of rapid decline corresponding to the distribution of THC to tissues and extensive storage, followed by a phase of prolonged release from adipose tissue to the blood and elimination. The present inventors compared the peak plasma concentration ($C_{max}$) of $\Delta^9$-THC obtained by smokeless inhalation in accordance with the method described herein to $C_{max}$ levels known in the art for various delivery routes of cannabis. As discussed in the Examples section hereinunder, the inhalation method described herein yielded the highest increase of $C_{max}$ per mg of THC available in the cannabinoid material used—mean of 12.3 ng/ml/mg THC compared to 6.1-9.0 for Volcano vaporizer and 0.6-4.6 for regular smoking cigarettes. In addition, the inter-individual variability in peak THC concentrations obtained by the method described herein was considerably lower compared to inter-individual variability obtained in the art: 25.3% versus 47-85% for vaporizer, 32-115% for smoking cigarettes, 42-115% for oral administration and 59-67% for oromucosal route of delivery.

Thus, in some embodiments, a high resolution in determining and controlling the amount of a pharmaceutically active agent is provided by the pulmonary delivering method described herein. In some embodiments, individual preselected vaporized amounts (doses) of, e.g., THC, are released electronically (by heating a pre-weighed portion of cannabis), in amount increments of 0.1 mg, ranging from 0.1 to 6.0 mg, 0.3 to 1.7 mg, 0.1 to 2.0 mg, from 0.2 to 1.9 mg, from 0.2 to 1.8 mg, from 0.3 to 1.8 mg, from 0.3 to 1.6 mg, from 0.4 to 1.6 mg, from 0.5 to 2.0 mg, from 0.6 to 2.0 mg or from 0.3 to 0.9 mg, including any subranges and any intermediate values therebetween.

In accordance with embodiments of the method provided herein, predictive PK/PD protocols are developed for vaporized cannabinoids, based on clinical data, accumulated individually for each patient as well on a cohort of patients, which account for the dose and regimen administered, based on individual and population parameters, as described hereinabove. These protocols accurately simulate the PK profile of a patient after delivering a pre-determined dose, or pre-determined regimen, and in parallel predict the PD profile which is composed of symptom relief (therapeutic effect) and psychoactive levels (adverse effect). Once a sub therapeutic level, and the adverse psychoactive level are correlated with PK and patient parameters, a relatively narrow therapeutic window is derived, in which the MDI device can precisely maintain in the patient, by automating specific pre-selected vaporized amounts (doses and/or regimen).

By inputting patient data, the protocol calculates the recommended dose and regimen for that specific patient in order to stay within the therapeutic window for a specific duration.

In an embodiment, the calculated dose and regimen to stay within the therapeutic window for 3 hours in a 35 years old male patient having a BMI of 22 is 1.2 mg at t=0; 1.0 mg at t=10 minutes; and 0.5 mg at t=60 minutes (see, FIG. 8).

According to these embodiments, the device selectively administers different doses at different time intervals so as to prevent adverse effects while still alleviating symptoms.

A System for Pulmonary Delivery:

As discussed hereinabove, the method and device presented herein are highly suitable for personalization, self-titration, mechanization and automatization of an otherwise complex and challenging mode of administration and treatment of a variety of medical conditions; while any personalized treatment protocol presents challenges, a treatment based on pulmonary delivery of active agents vaporized by heat from natural substances is a task which has not been achieved hitherto.

Once the problem of accuracy, consistency and reproducibility is solved by using a the MDI device disclosed herein; and once the need for calibrating and presetting the device to stay within a desired therapeutic window, based on widely accepted PK/PD experimental parameters has been served, as disclosed herein, the present inventors have conceived an integrated system that can control the device using input collected from a variety of sources so as to provide a highly personalized and effective treatment for any given patient, also in real-time.

According to an aspect of some embodiments of the disclosure, there is provided a system that includes:
  a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and
  a controller associated with the inhaler device, and configured to control the pre-determined vaporized amount.

According to an aspect of some embodiments of the disclosure, there is provided a system of pulmonary delivering to a subject at least one pharmacologically active agent being in a plant material; the system includes:
  a metered dose inhaler device configured to vaporize at least one pre-determined vaporized amount of the agent upon controllably heating the plant material; and
  a controller configured to select the at least one pre-determined vaporized amount of the agent so as to achieve at least one pre-determined pharmacokinetic effect and/or at least one pre-determined pharmacodynamic effect induced by the agent in the subject.

According to an aspect of some embodiments of the disclosure, there is provided a system for pulmonary delivering to a subject at least a first pharmacologically active agent and a second pharmacologically active agent, at least one of which being in at least one plant material; the system includes:
  a metered dose inhaler device configured independently deliver the agents to the subject by heating the at least one plant material to vaporize at least a first pre-determined vaporized amount of the first agent and at least a second pre-determined vaporized amount of the second agent; and
  a controller configured to effect the heating of the first pre-determined vaporized successively, concomitantly and/or at least partially overlapping with the second pre-determined vaporized amount,
  wherein each of the pre-determined vaporized amounts of each of the agents is selected to induce in the subject independently at least one pharmacokinetic effect and/or at least one pharmacodynamic effect.

According to an aspect of some embodiments of the disclosure, there is provided a system that includes:
  a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and
  a controller associated with the inhaler device, and configured to control the pre-determined vaporized amount,
  wherein the controller is configured to receive operation setting data pertaining to the pre-determined vaporized amount from a remote control device. In some embodiments, the remote control device is configured to receive data indicative of at least one pharmacodynamic effect induced by the agent in the subject, and further configured to determine and transmit operation setting data pertaining to the pre-determined vaporized amount.

According to an aspect of some embodiments of the disclosure, there is provided a system that includes:
  a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant; and
  a controller associated with the inhaler device, and configured to control the pre-determined vaporized amount based on data indicative of at least one pharmacodynamic effect induced by the agent in the subject.

According to an aspect of some embodiments of the invention, there is provided a system that includes a metered dose inhaler device for pulmonary delivering at least one pre-determined amount of at least one pharmacologically active agent to a subject. The system further includes at least one sensor for monitoring at least one pharmacodynamic effect in the subject induced by the agent, e.g. a psychoactive effect; and a processing unit associated with the inhaler device and with said at least one sensor. In some embodiments, the processing unit is configured to determine the pre-determined amount based on the data received from the sensor. The amount, which is being determined and controlled, may be a single dose or a regimen.

The indicative data is obtainable from a variety of sources, such as statistical data of a pharmacodynamic effect induced by the agent in a population, a user history, preferences and habits, a physician prescription and the like. In some embodiments, the indicative data is obtainable via at least one sensor configured for monitoring pharmacodynamic effects in a subject and/or via a user interface device configured for inputting data obtainable from such as sensors. In some embodiments, the controller is configured to receive indicative data pertaining to a pharmacodynamic effect from a sensor and/or a user interface device.

According to some embodiments, the controller is in direct and/or indirect communication with a sensor and/or an interface device, namely the controller can be associated via direct communication with the source of the indicative data (sensor and/or interface device), or be associated therewith via a remote control device.

According to some embodiments, the system includes an inhaler device as described hereinabove, a controller as described hereinabove, and at least one sensor and/or a user interface as described hereinabove, each configured independently to provide to the controller data indicative of at least one PD effect induced by the active agent in the subject.

According to an aspect of some embodiments of the disclosure, there is provided a system that includes, without limitation:
- a metered dose inhaler device for pulmonary delivering to a subject at least one pre-determined vaporized amount of at least one pharmacologically active agent being in a plant material by controllably heating the plant material so as to vaporize a pre-determined vaporized amount of the agent from the plant;
- at least one sensor for monitoring at least one pharmacodynamic effect in the subject induced by the agent and/or a user interface device for inputting data obtained from at least one sensor for monitoring at least one pharmacodynamic effect in the subject induced by the agent; and
- a controller associated with the inhaler device and with the at least one sensor.

In some embodiments, the controller used in the system described herein is configured to control the pre-determined vaporized amount by controlling the heating of the substance (e.g., plant material). Controllably heating the plant material is effected, for example, by controlling at least one of a heating temperature, a heating pattern (which part of the plant material to heat), a heating rate (how many times the plant material is exposed to heat), a heating duration (how long the plant material is exposed to heat in any given heating event), and any combination thereof.

In some embodiments, the controller is configured to control the pre-determined vaporized amount by controlling the airflow in the inhaler device, for example by controlling duct opening, valves and shutters in the inhaler device.

In some embodiments, the controller is configured to control the pre-determined vaporized amount by controlling the timing of one or more inhalation events. For example, the pre-determined vaporized amount is delivered in more than one inhalation event, and the controller is configured to generate at least one alert signal to the subject to use the inhaler device at indicated time points, at indicated time intervals and any other schedule so as to complete the pulmonary delivery of the pre-determined vaporized amount to the subject.

In some embodiments, by controlling the abovementioned heating and airflow parameters in the inhaler device, the controller is used to adjust the pre-determined vaporized amount so as to achieve a pre-determined pharmacokinetic effect and/or a pre-determined pharmacodynamic effect based on the pharmacodynamic effect. In some embodiments, the controller is configured for effecting the adjustment of the pre-determined vaporized amount in real-time.

In general, the controller is used to carry out more complex treatment plans, such as a regimen, a delivery of more than one active agent, each having a different dose and/or regimen, and/or other dose and timing related adjustments. In some embodiments, a controller can be configured for adjusting the regimen so as to achieve a pre-determined pharmacokinetic effect and/or a pre-determined pharmacodynamic effect based on the pharmacodynamic effect. In some embodiments, the controller is configured for effecting a pre-defined regimen that comprises delivering at least two pre-determined vaporized amounts. In some embodiments, the controller is configured for real-time adjustment of various operational settings of the inhaler device and parameters of the pulmonary delivery.

According to some embodiments, the system further includes or may be in communication with a user interface device, which can be used to input information and data into the controller, and/or to display, transmit or otherwise output data and information from the controller. In some embodiments, the user interface comprises an output device for providing information to at least one of the following: the subject, a practitioner, a memory unit and a remote device (a server, a display, a remote monitoring system/device and the like). In some embodiments, the user interface device includes a smartphone device. A smartphone may include a touchscreen, a microphone, a speaker, a GPS receiver, an accelerometer, a thermometer, a light detector and the like.

In some embodiments, the controller is configured for monitoring at least one of the at least one pre-determined pharmacokinetic effect and/or the at least one pre-determined pharmacodynamic effect, based on data received via the user interface device. Accordingly, the controller is configured for adjusting the pre-determined vaporized amount in real-time.

FIG. 9 is a schematic diagram of a system comprising an MDI device (also referred to herein as "inhaler device"), a physician interface and/or a patient interface, according to some embodiments of the invention.

In some embodiments, MDI device 901 is configured to communicate with a physician interface 903 and/or with a patient interface 905. In some embodiments, MDI device 901 is configured to receive input from one or both of the interfaces 903 and/or 905. Additionally or alternatively, MDI device 901 is configured to send output to one or both of the interfaces 903 and/or 907.

In some embodiments, communication between the system components is performed via one or more data transfer means such as a USB connection, a cable connection, a wireless connection, and/or any suitable wired and/or wireless communication protocol.

In some embodiments, communication between the system components is performed through one or more communication modules, such as communication module 907 of MDI device 901, communication module 909 of physician interface 903, and/or communication module 911 of patient interface 905.

In some embodiments, MDI device 901 comprises a controller 913, configured, for example, to activate heating of the substance to thereby vaporize the active agent, control the heating profile and/or activation of heat, control a cartridge feed mechanism of the MDI device, read data from a memory 919 of MDI device 901, control power usage, and/or other functions. In some embodiments, controller 913 communicates with a memory 919. Optionally, memory 919 is configured to store prescription data, personal usage data, patient details, personal PD effects obtained from the patient, dose and/or regimen modifications, parameters obtained from the patient in response to a change in a dose and/or regimen, and/or other values or information. In some embodiments, controller 913 activates pulmonary delivery of the active agent according to dose and/or regimen data stored in memory 919. In some embodiments, memory 919 is configured to store usage data and/or feedback data from the patient with respect to a specific dose and/or regimen and/or with respect to a pre-selected (desired) PD profile of the active agent in the patient.

In some embodiments, physician interface 903, comprising, for example, one or more of a controller 915, a memory 921 and/or a communication module 909, is configured on a personal computer (tablet computer, laptop computer, desktop computer, or others), a mobile device such as a smartphone, a handheld device, a wearable device, a wrist device or an integrated eyewear device, a clinic or hospital monitor and/or any other suitable device. Optionally, the physician is provided with remote access to MDI device 901. Additionally or alternatively, physician activates MDI device 901 directly. In some embodiments, the physician pre-programs (pre-calibrates or presets) MDI device 901 with a pre-determined vaporized amount (dose and/or regimen) suitable for an individual patient. In some embodiments, data is sent from physician interface 903 to patient interface 905, for example for instructing the patient or for effecting preset adjustments.

In some embodiments, patient interface 905, comprising, for example, one or more of a controller 917, a memory 923 and/or a communication module 911, is configured on a personal computer (tablet computer, laptop computer, desktop computer, or others), a mobile device such as a smartphone, and/or on MDI device 901 itself.

In some embodiments, patient interface 905 receives an input 929. The input may be received from one or more of the patient, the physician interface, the database server, the MDI device. Examples of various types of inputs may include a dose and/or regimen defined by the physician and received on the physician interface, a current personal PD effect of the patient, inserted by the patient and/or obtained from the patient, personal usage statistics recorded for example on the database server and/or on the memory of the MDI device, an indication of inhalation duration and/or inhalation volume sensed by the MDI device, and/or other types of input.

In some embodiments, patient interface 905 comprises a display 927. Optionally, the display is an interactive display, for example a touch screen of a smartphone, a handheld device, a wearable device, a wrist device or an integrated eyewear device.

In some cases, certain functions such as transferring data to the physician, accessing the database to acquire information such as user/patient instructions, and/or other functions are enabled by patient interface 905, while other function such as modifying the pre-determined vaporized amount (dose) and/or regimen (plurality of doses), viewing protocols of other patients, and/or other functions are not permitted by patient interface 905. Optionally, the physician sets the patient interface access definitions per an individual patient.

In some embodiments, patient interface 905 and/or MDI device 901 are configured to notify the patient every time a pulmonary delivery (an inhalation) is due.

Optionally, the notice is provided automatically based on a scheduled regimen stored in the memory. Additionally or alternatively, the notice is set by the patient. Additionally or alternatively, the notice is issued by the physician.

In some embodiments, one or more of the system components communicates with a database server 925, by receiving input from the database and/or sending out information to the database. In some embodiments, the database comprises individual data of the patient, for example including medical history of the patient, data transmitted by MDI device 901, input data from the physician, input data from the patient, and/or other information. Optionally, the database server is configured to perform calculations on the data.

In some embodiments, database server 925 comprises collective data, including, for example, one or more of clinical experiment results, results of other patients, research data, and/or other data. Optionally, database server 925 communicates with a plurality of treatment systems being used by various patients. Data from various interactions between patients and the MDI device is collected in the central database, continuously learning individual usage patterns of patients and recommending dose and/or regimen accordingly. Utilizing the collective user database may improve generating of accurate predictive dose and/or regimen for current and new patients, improving the overall therapeutic success rate of the treatment.

In some embodiments, according to personal feedback data obtained from the patient using MDI device 901 and/or by patient interface 905, the pre-determined vaporized amount (dose and/or regimen) is automatically modified by controller 917 of the patient interface and/or by controller 913 of the MDI device to compensate for inadequate settings or misuse of the MDI device, for example in a situation in which the patient does not use the MDI device when instructed to, and/or use the MDI device is carried out at a timing different than the preset regimen. One or more actions may be taken in response, for example postponing the next dose, increasing or decreasing the next dose (and/or following doses), and/or otherwise altering the regimen.

In some embodiments, a patient using MDI device 901 may wish to schedule their dose and/or regimen in a way in which possible adverse effects least interfere with the patient's daily activities. While certain adverse effects are tolerable in a home setting or at certain time of day, and are an acceptable trade off for symptom relief, these adverse effects may be undesirable when the patient is engaged in activities such as driving, attending a meeting, and/or other activities. Optionally, using patient interface 905 and/or by directly activating MDI device 901, the patient schedules a dose and/or regimen in a manner that least interferes with their planned activities.

Additionally or alternatively, MDI device 901 and/or patient interface 905 are configured to actively impose a certain dose and/or regimen, for example based on input from the patient. In an example, the patient inserts their planned daily activities and timing of those activities, and the dose and/or regimen is automatically modified accordingly. Optionally, the dose and/or regimen is automatically modified to ensure that the patient is in a suitable condition to perform the planned activity, for example ensuring that during driving the level of an adverse effect is relatively low or not perceived.

In some embodiments, the patient may voluntarily modify the dose and/or regimen, for example using patient interface 905. Optionally, the extent of modifications is limited, to prevent a condition in which the patient is at risk, for example preventing overdosing.

In some embodiments, the patient may simply use MDI device 901, even when not specifically instructed to. In such a case, the next dose and/or regimen may be automatically modified in response to the usage. Optionally, the patient is notified about modifications in the dose and/or regimen through patient interface 905. Additionally or alternatively, the physician is notified about such changes, for example through physician interface 903.

FIG. 10 is a flowchart of a method for prescribing a regimen to a patient using an MDI device for delivery of at least one active agent, according to some embodiments of the invention.

In some embodiments, a physician may decide to treat a patient by effecting a pulmonary delivery of one or more active agents by an MDI device (1001).

In some embodiments, patient data such as one or more of, for example, PK variables (e.g., age, gender, BMI etc.), pathophysiological status, pharmocogenetic and/or pharmacogenomic variables and/or other parameters are inserted to the system (1003), for example by the physician and/or other clinical personnel. Optionally, the patient's parameters and personal variables are inserted using the physician interface.

In some embodiments, a suggested dose and/or regimen is generated (1005). Optionally, the dose and/or regimen is generated automatically, for example by software of the physician interface. Additionally or alternatively, the dose and/or regimen is planned by the physician. In some embodiments, the dose and/or regimen is generated by matching the inserted patient data to a pre-defined dose and/or regimen using data from a database, or according to personal feedback data, or for example according to a look up table.

In some embodiments, a simulation of an expected PK/PD profile of the patient for the selected dose and/or regimen is produced (1007). In some embodiments, an expected PK/PD profile, including for example therapeutic effects and/or adverse effects is simulated. In some embodiments, by correlating between the pharmacodynamic profile and/or pharmacokinetic profile and the patient's personal data, a therapeutic window is selected. Optionally, the PK/PD profile simulations and/or the pre-selected therapeutic window are graphically displayed to the physician, for example on a display of the physician's interface. When considering the simulations, a physician may decide to modify the dose and/or regimen to better suit (personalized) it to the patient (1009). In some cases, the physician may decide to change proposed dose and/or regimen parameters such as one or more of dose, dosing, regimen or total treatment duration, and/or other treatment parameters.

In some cases, treating includes administering two or more substances, simultaneously or sequentially, to obtain a desired therapeutic effect in the patient. The system, according to some of any of the embodiments of the present disclosure, provides the ability to use the MDI for delivering more than one pharmaceutically active agents (from one or more substances) at any ratio or pre-determined vaporized amounts so as to exhibit a pre-selected PD profile (e.g., maintaining an individual patient within the therapeutic window calculated per the patient). In some embodiments, different doses are selectively administered according to a regimen so as to prevent adverse effects while still alleviating symptoms.

In some embodiments, the selected (and optionally refined) dose and/or regimen is prescribed to the patient (1011).

In some embodiments, as a follow up and over a time period in which the patient is treated (e.g., over several hours, over a day, over a week, over a month, and/or intermediate, longer or shorter periods), the physician receives one or more indications such as indications relating to the patient's general usage of the device, indications relating to dose and/or regimen administered to the patient, substance consumed by the patient, one or more personal PD effects of the patient, for example relating to the presence of adverse effects, such as the psychoactive level and/or indications relating to the symptom intensity such as the pain level, and/or a level of one or more biomarkers and/or other indications (1013). Optionally, one or more indications are provided in real-time. Additionally or alternatively, the indications are provided at the end of a pulmonary delivery of the agent. Additionally or alternatively, the indications are provided on demand of the physician. Additionally or alternatively, the patient decides when to send indications to the physician.

In some embodiments, the indications are transmitted to the physician by the MDI device and/or by the patient interface, automatically and/or in response to an instruction from the physician and/or the patient. Optionally, one or more indications are stored in the database for future reference.

In some embodiments, based on the provided indications, the dose and/or regimen is adjusted or otherwise modified (1015). Optionally, modification is performed in real-time. In some embodiments, a specific dose and/or regimen is modified, optionally in real-time. In some embodiments, the dose and/or regimen is modified while taking into account upper and lower PD effect limits defined individually per the patient. An upper limit may allow dose and/or regimen above which substantial adverse effects are present. A lower limit may allow dose and/or regimen below which a symptom, which was intended to be treated by delivery of the active agent, is not sufficiently alleviated.

FIGS. 11A, 11B, 11C and 11D are a schematic diagram (FIG. 11A) and print screens (FIGS. 11B, 11C and 11D) of a physician interface for selecting and prescribing a dose and/or regimen to a patient, according to some embodiments of the invention.

Figure 11A:
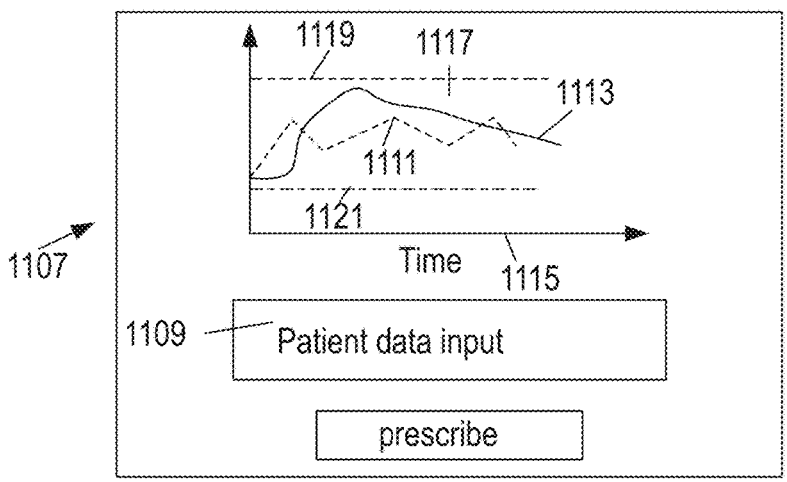

FIG. 11A illustrates a general display 1107 of a physician interface. In some embodiments, patient data is inserted by the physician through input 1109.

In some embodiments, a graphical display of an expected and/or pre-selected pharmacokinetic profile 1111 and/or an expected and/or pre-selected pharmacodynamic profile 1113 is presented to the physician. Optionally, one or more of the profiles are shown, separately or together, with respect to a time series 1115, including, for example, a duration (e.g., an hourly scale) over which a patient is treated. In some embodiments, a therapeutic window 1117 is defined, setting an upper limit 1119 and a lower limit 1121.

In some embodiments, the dose and/or regimen is selected so as to have the expected and/or pre-selected PK/PD profiles fit within a range of the therapeutic window 1117.

In some embodiments, a limit is defined as a constant value, presented as a straight line, for example as shown in FIG. 11A. Alternatively, a limit may comprise a varying set of values, and be presented as a curved line. For example, lower limit 1121 represents a desirable therapeutic effect, upper limit 1119 represents an acceptable adverse effect, and a higher $C_{max}$ threshold of the pharmacokinetic profile may be set for an initial part of the treatment, for example to accelerate symptom relief, and the $C_{max}$ threshold may decrease as the treatment continues as desired. In some embodiments, a dose and/or regimen is selected and/or adjusted to achieve an initial build up of the active agent in the patient, for example at an initial part of the treatment, and then to provide on-going dosing for maintaining the patient in a steady state (maintenance dosing). In general, an initial build up of the agent is based on a relatively large amount of the agent compared to the amounts given at the maintenance dosing.

In some embodiments, for example when refining a pre-determining vaporized amount of the agent (dose and/or regimen) for an individual patient, a physician may perform one or more of raising and/or lowering of limit 1119 and/or limit 1121, raising and/or lowering the peaks of profile 1113 and/or of profile 1111, extending and/or shortening a treatment duration along the time axis, and/or other modifications.

It is noted that the graphic representation is shown herein as an example, and that various graphic representations such as a bar graph may be used. In some embodiments, the profile 1111 and/or profile 1113 may be presented in a non-continuous manner, for example as a set of points.

Figure 11B:
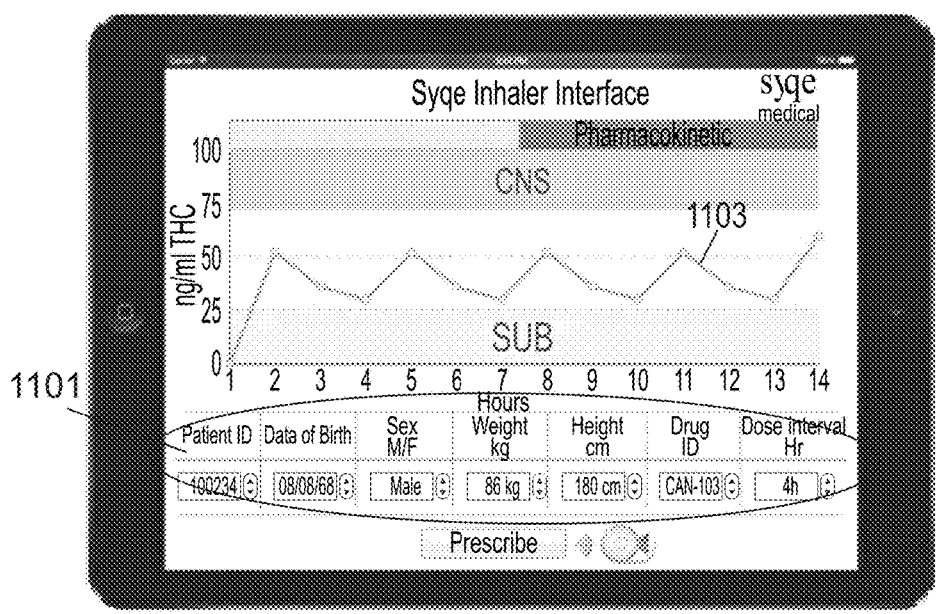

FIG. 11B illustrates a simulation of an expected pharmacokinetic profile of a patient using a pre-determined vaporized amount delivered according to a pre-determined regimen, according to some embodiments. In this example for a physician interface screen, a physician may fill in patient data 1101 (such as gender, weight, height, administered drug, patient ID and/or other data), and obtain a pharmacokinetic profile extrapolation of the individual patient, as shown for example by graph 1103, simulating the plasma concentration of an active agent in the patient over time.

Figure 11C:
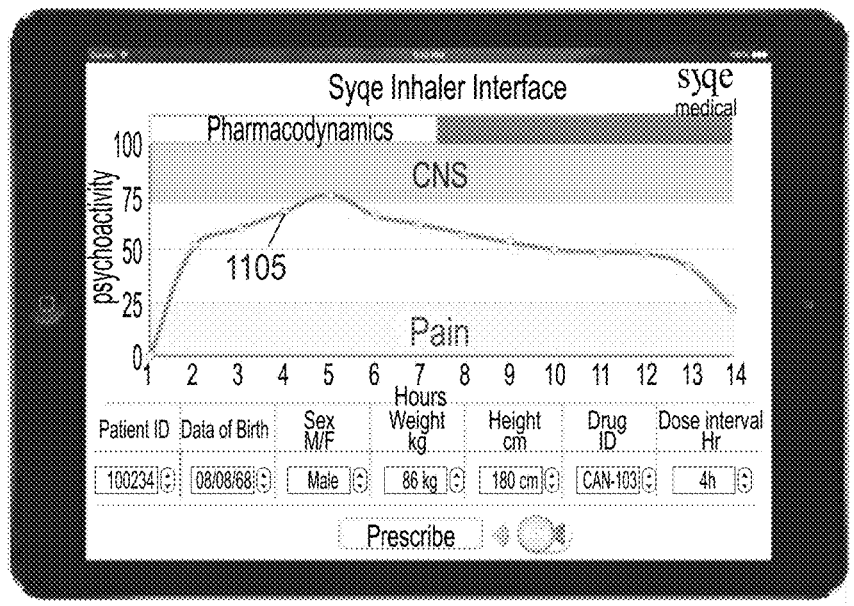

Similarly, FIG. 11C illustrates an expected pharmacodynamic profile extrapolation 1105 of the individual patient, showing an adverse effect level in the patient over time.

Figure 11D:
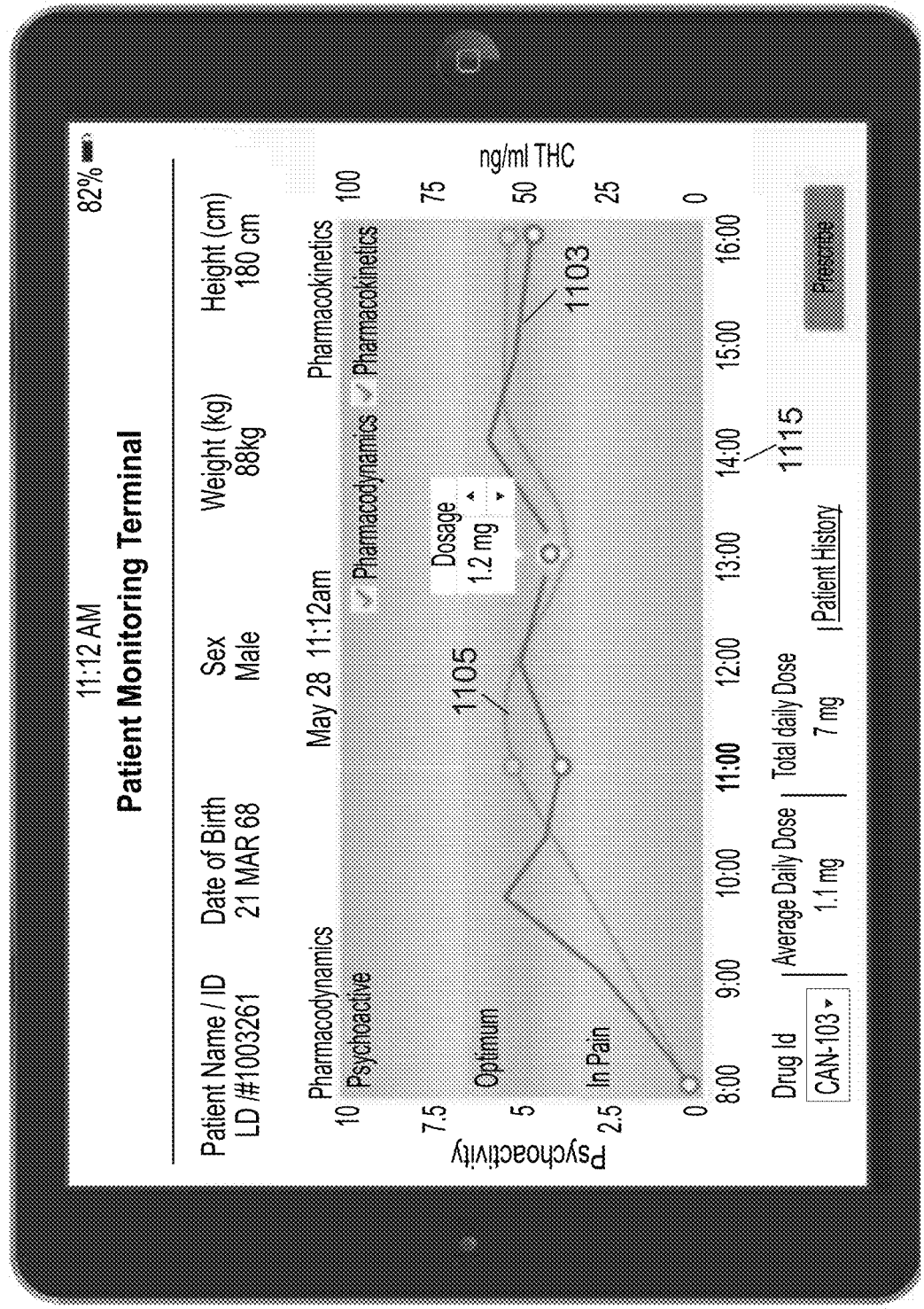

FIG. 11D shows a physician interface print screen, according to some embodiments of the invention. A simulated pharmacokinetic profile is represented by graph 1103 and a simulated pharmacodynamic profile is represented by graph 1105, which are displayed on a time series axis 1115, in this example representing an 8-hour period. A pharmacodynamic parameter scale of the patient is visually divided into sections indicating, for example, an "in pain" state (below a therapeutic effect level), indicating "optimum" state (within the therapeutic window) and indicating, for example, "psychoactive" state (above an adverse effect level) as defined per the individual patient, and the simulated PK/PD profiles as graphs are shown with respect to these sections. In this simulation, a first dose is provided at 8:00, resulting in a change of both the pharmacodynamic and pharmacokinetic parameters, going up from the "in pain" section into the "optimum" section. A second dose, provided at 11:00, is shown to maintain the patient within "optimum" (the therapeutic window).

FIG. 12 is a flowchart of a method for obtaining feedback data from a patient and modifying/adjusting a dose and/or regimen accordingly, according to some embodiments of the invention.

In some embodiments, a personal PD effect of the patient is obtained (1201).

In some embodiments, the PD effect relates to an adverse effect such as a psychoactive level, a therapeutic effect such as a pain level, and/or a change in any of those levels thereof. The PD effect may include an absolute quantification of the level, and/or a relative quantification of the level, assessed, for example, with respect to a level measured before a delivery of single dose and/or before a delivery of dosing and/or regimen. The PD effect may be obtained before, during and/or after a delivery of single dose and/or before, during and/or after a delivery of dosing and/or regimen and/or before, during and/or after a general time period over which treatment is provided to the patient.

In some embodiments, the PD effect is provided directly by the patient, for example using the patient interface. In some embodiments, the patient can manually adjust a visual representation of the PD effect, based on a personal determination of the level of the PD effect. In an example, the patient may raise or lower a bar on a graph indicating a pain level, for example on a touch screen of a cellular phone and/or any other personal device on which the patient interface is configured.

In some embodiments, patients who are unable to articulate levels of the PD effect may utilize an interactive set of tools to assist them in determining their current level of the PD effect, for example as further described herein.

Additionally or alternatively to a conscious, personally perceived PD effect indicated by the patient, a personal PD effect such as a biomarker is obtained by the patient interface and/or by the system, for example using a sensor. In some embodiments, one or more standard components of a cellular phone and/or personal computer on which the patient interface is configured as acts as a sensor for obtaining the parameter. Some components which may be used as sensors for obtaining PD effects from the patient may include: a touch screen, may be used for example to assess dexterity, eye-hand coordination, and/or a memory and cognition state; a gyroscope, accelerometer, proximity sensor and/or gesture sensor such as IR sensor may be used, for example, to assess motor skills; a camera and/or light source may be used, for example, to detect visual tracking, saccade variance, eye vascular expansion, pupil dilation and/or pulsation; an RGB illumination may be used, for example, to assess environmental perception; a magnetometer and/or GPS may be used, for example, to assess orientation; a speaker and/or microphone may be used, for example, to assess auditory and/or vocal skills; a temperature and/or humidity sensor may be used, for example, to assess a body temperature.

In some embodiments, the MDI device is configured to obtain personal feedback data. In an example, the MDI device comprises a flow sensor and/or a pressure sensor.

Optionally, a breathing related indication of the patient is obtained using the flow and/or pressure sensor. In some embodiments, the sensor is adapted to detect a volume of inhalation. Since a correlation may exist between inhalation volume and a PD effect, such as a pain level, in some embodiments, a flow and/or pressure measurement is initiated to determine a PD effect in the patient.

Once one or more personal PD effects are obtained, the dose and/or regimen may be modified accordingly (1203). In some embodiments, the dose and/or regimen is modified, on one hand, to improve or otherwise change a condition of the patient based on the provided indication, and, on the other hand, to achieve a pre-selected pharmacodynamic profile, such as maintaining the patient within the therapeutic window—between a lower limit of a therapeutic effect that provides symptom relief, and a higher limit of an adverse effect in which the adverse effect level is still tolerable. In some embodiments, the MDI device can be configured such that when below a minimal therapeutic effect, input by the patient may increase the dose and/or adjust the regimen in frequency and/or in quantity. Optionally, the dose and/or regimen is modified to obtain a level above a minimal therapeutic effect. Additionally or alternatively, the dose and/or regimen is modified as much as the maximal level of an adverse effect permits.

FIGS. 13A, 13B, 13C, 13D and 13E are print screens of a patient interface (FIG. 13A, FIG. 13C and FIG. 13E), and graphic representations of an expected pharmacodynamic and pharmacokinetic profiles of the patient before and after input of personal PD effect of the patient is obtained (13B and 13D respectively), according to some embodiments of the invention.

Figure 13A:
Figure 13B:
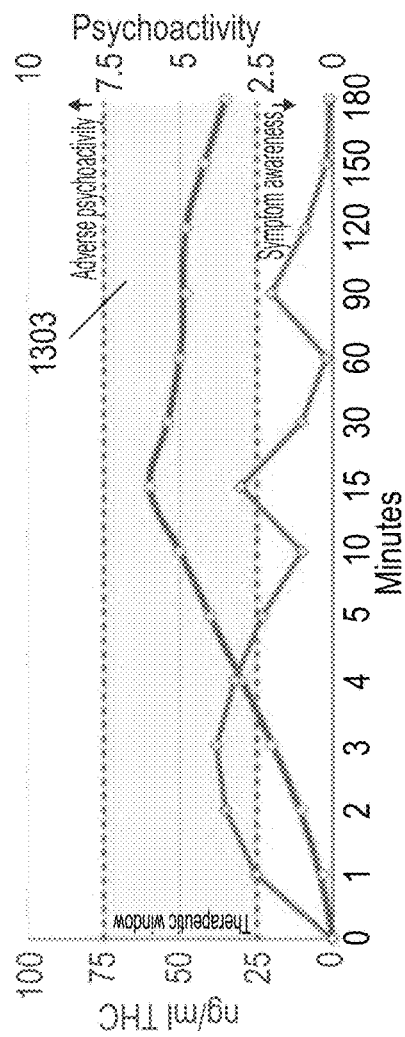

FIG. 13B presents an example for a calculated 3-hours regimen for a certain patient (Patient X, 35 years old and has a BMI of 22). According to an example for a calculated regimen, to maintain Patient X within the therapeutic window for 3 hours effected a PK profile presented by the red curve in FIG. 13B, Patient X is required to be subjected to pulmonary delivery of an active agent using a metered-dose MDI device according to some embodiments of the present disclosure, at the following times and doses: 00 minutes—1.2 mg; 10 minutes—1.0 mg; 60 minutes—0.5 mg. The blue curve represents an example for a calculated PD profile at the indicated doses. As seen, the calculated regimen maintains Patient X within limit levels, namely below the adverse effect level and above the therapeutic effect level, namely at a therapeutic window 1303 ranging between 2.5 to 7.5 on the adverse psychoactivity effect scale.

Figure 13C:
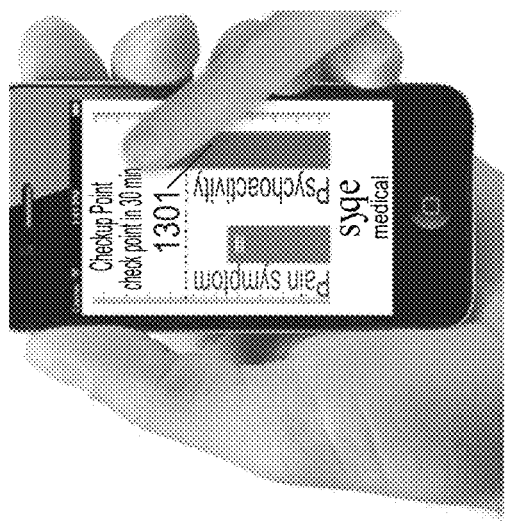
Figure 13D:
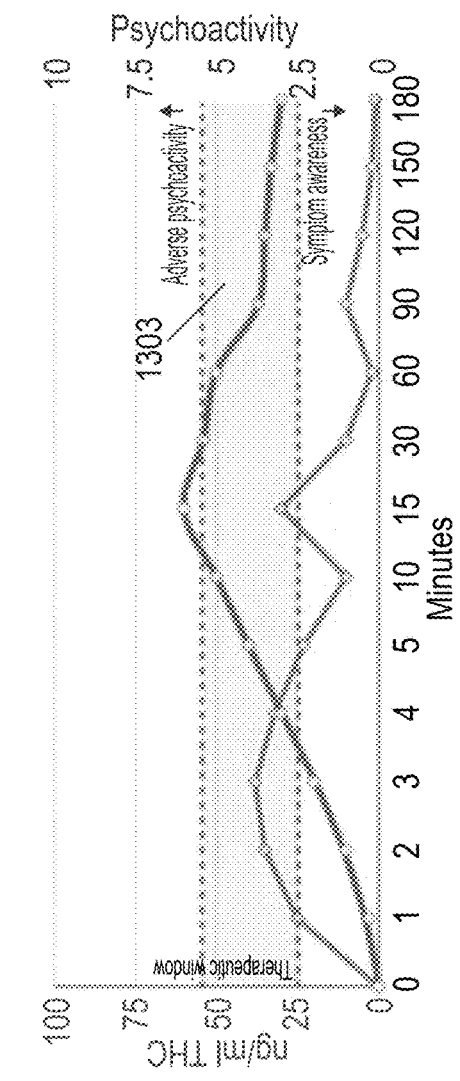

In FIG. 13C, during and/or after treatment, Patient X indicates a wish to alter the adverse effect limit, for example by raising a psychoactivity level bar 1301 on the patient interface screen. By raising the bar, the patient may indicate he is willing to increase the tolerable level of an adverse psychoactive effect. The therapeutic window, as shown in FIG. 13D, is then redefined based on the patient's input—for example, the window is narrowed to a range of 2.5 to 5 on the psychoactivity scale. The currently administered dose and/or regimen may then be modified accordingly. For example, a pre-determined vaporized amount that is planned for pulmonary delivering at, for example, 60 minutes from the initial pulmonary delivering is reduced from 0.5 mg to 0.3 mg, in attempt to lower the level of an adverse effect (psychoactive effect) the patient is experiencing.

In some embodiments, the dose and/or regimen is automatically modified, based on the patient's input. Additionally or alternatively, the patient input and/or the simulated profiles are transferred, automatically and/or on demand of the patient, to the physician, and the physician modifies the regimen.

It is noted that the sensitivity of a patient to the therapeutic and/or an adverse effect may vary throughout the day for a patient, e.g., demonstrating higher pain sensitivity in the evening, diminished cognitive abilities in the morning, thus less susceptive to a therapeutic effect in the evening, or more susceptive to an adverse effect in the morning.

Additionally or alternatively to an adverse effect level, a patient may indicate their therapeutic effect level and/or other conditions, and the dose and/or regimen will be modified accordingly.

Figure 13E:
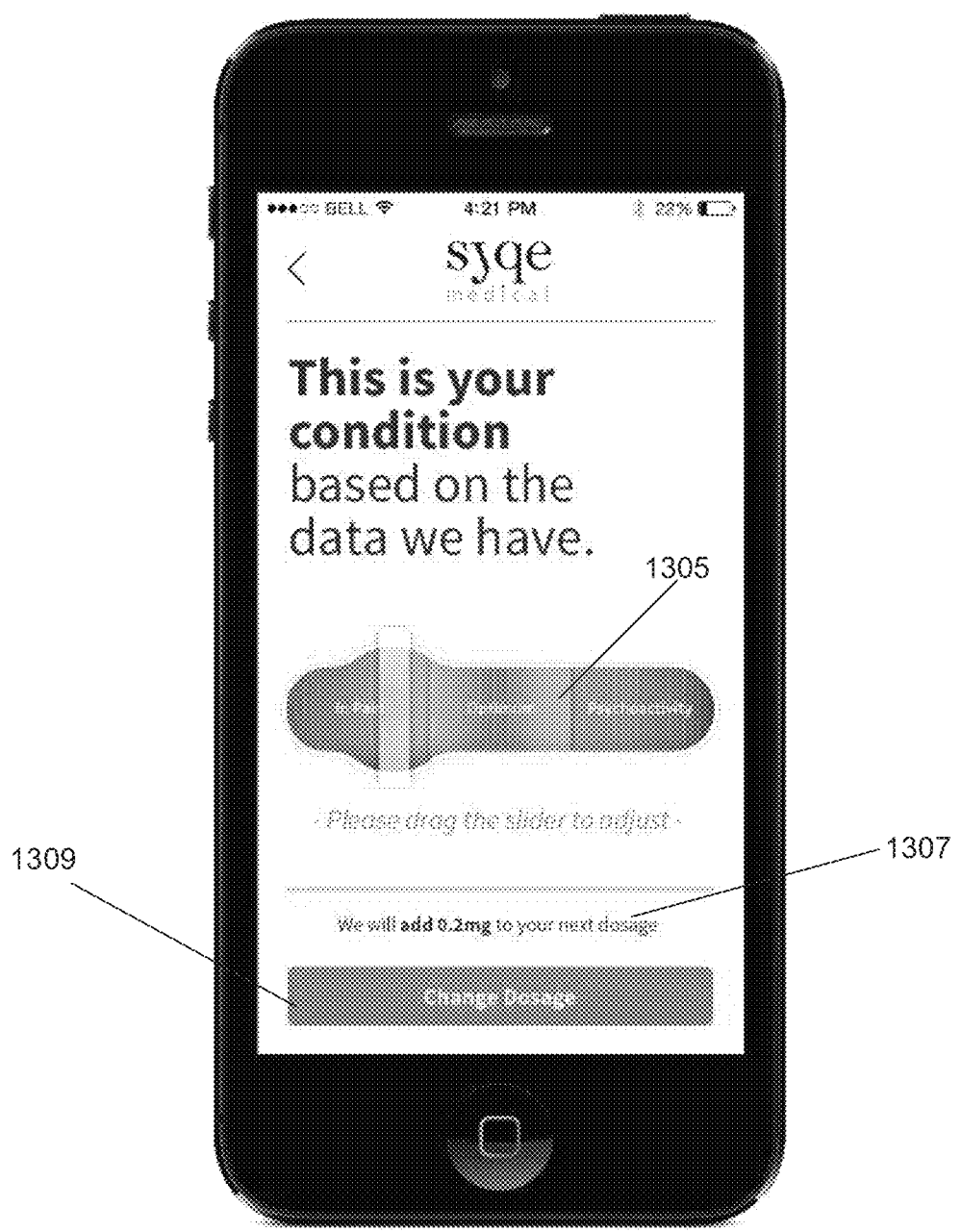

FIG. 13E shows a patient interface application including an adjustable slider 1305, moveable by the patient. In some embodiments, the application presents to the patient an estimation of a current condition, calculated based on one or more of following: the pre-determined dose and/or regimen, previous input obtained from the patient, for example including biomarkers and/or other direct and/or indirect personal PD effects, treatment and effect history for the individual patient, usage record of the patient, a medical condition of the patient, information from a collective database, and/or other information.

During treatment and/or following treatment, the patient may drag the slider to reflect their perceived PD profile. For example, if the patient experiences a complete therapeutic effect (e.g., patient is no longer in pain), the patient may move the slider to an "optimal" state (e.g., to a "psychoactive" state).

Using input obtained from the patient, the patient interface may automatically modify the next dose and/or regimen. In some embodiments, an indication of the modification 1307 is displayed to the patient, for example notifying the patient that the next dose is increased in amount. Optionally, the application is configured to request confirmation 1309 from the patient to change the dose and/or regimen.

In some embodiments, the input from the patient and/or the modified settings are automatically transferred to the physician interface. In some cases, the physician may decide to manually change the newly defined dose and/or regimen settings.

FIG. 14 is a flowchart of a method for measuring one or more biomarkers using a personal portable device and/or using the MDI device, and modifying the dose and/or regimen accordingly, according to some embodiments of the invention.

In some embodiments, one or more biomarkers are measured (1401). In some embodiments, the biomarkers indicate the existence and/or extent of adverse effects in a treated patient. Optionally, the biomarker measures are used for determining a therapeutic window for an individual patient, and/or for controlling the dose and/or regimen to maintain the patient within the therapeutic window.

Adverse effects, such as cognitive impairment and other psychoactive effects, may differ between patients given various genetic and biological traits. Therefore, in some embodiments, individual biomarkers, such as CNS biomarkers, are obtained from the patient, using, for example, one or more sensors in the system, and/or one or one more sensors configured in the patient interface device, such as cellular phone sensors for example as described hereinabove.

Non-invasive biomarker assessment methods may include one or more of saccadic eye movement assessment (such as saccadic movement), memory testing, adaptive tracking, finger tapping assessment, body sway assessment, visual analog scale match, and/or other assessment methods.

In some embodiments, various known in the art non-invasive biomarker tests such as cognitive tasks may be performed, including, for example, reaction time, attention, visuospatial span, name recall, narrative recall, face recall, name-face association, construction, verbal fluency, object naming, implicit memory, logical reasoning and/or other cognitive tasks.

In some embodiments, the biomarker measures are communicated to the physician (1403). Optionally, the PD effect measures are stored in a memory of the MDI device and/or a memory of the patient interface. Additionally or alternatively, the PD effect measures are uploaded to a database. Optionally, the PD effect measures are compared to PD effect measures stored in the database, including, for example, previous PD effect measures of the individual patient, PD effect measures of other patients, PD effect measures from literature, etc.

In some embodiments, the dose and/or regimen is modified according to the PD effect measures (1405).

FIGS. 15A, 15B and 15C are print screens of a patient interface comprising various applications for obtaining PD effect data and/or for assisting a patient in determining a vaporized amount of the agent (dose and/or regimen), according to some embodiments of the invention.

In the application shown herein by way of example, which may be installed on a personal portable device such as a cellular phone and/or a tablet computer, a patient interactively performs one or more tasks, which may be incorporated as a part of a game or the like, based on a personal PD effect which can be assessed based on the task. In some embodiments, an adverse effect level, such as a psychoactive level of the patient, is automatically deduced by the application. Additionally or alternatively, the application assists the patient in articulating their perceived therapeutic and/or adverse effect, which can then be provided as an input to the system.

The tasks shown herein for example include tracking a target with a finger (FIG. 15A), visually tracking a target (FIG. 15B), aligning a target (FIG. 15C).

Other applications may include various personal PD effect measurements using activities and methods known in the art, such as simulated driving, card sorting, arithmetic skill testing, time estimation, symbol copying, adaptive tracking, reaction time, picture and/or wording skills, and/or other applications, for example as described hereinabove.

FIG. 16 is a schematic diagram of a metered dose MDI device configured to provide automated controlled pulmonary delivery of one or more active agents, according to some embodiments of the invention.

In some embodiments, device 1601 comprises substance dispenser 1603, e.g., a dispenser for the substance that contains the pharmaceutically active agent and allows the pharmaceutically active agent to be vaporized therefrom. In some embodiments, the substance dispenser comprises, or is in communication with, a source of at least one substance from which the active agent originates, and a mechanism for processing the substance to obtain a deliverable active agent, for example as described hereinabove.

The substance may comprise various forms, such as, for example, a solid bulk, solid particles or a powder. Optionally, the substance is contained within a cartridge, a capsule, and/or other containers. In some embodiments, the processing mechanism includes one or more of, for example, heating (e.g., for vaporizing), turning to aerosol, causing a chemical reaction, for example by mixing with other materials, releasing substance from a container such as by breaking open a capsule, pressure propellant, mobilizing and/or other types of processing. Alternatively, the active agent is already in a ready to use form and does not require any processing before delivering to the user by heating the substance.

In some embodiments, MDI device 1601 comprises input module 1605. Optionally, input module 1605 is configured to receive data pertaining to a dose and/or a regimen according to which the active agent will be delivered to the patient. Additionally or alternatively, input module 1605 is configured to receive one or more indications from a sensor (not shown in this figure), comprised within device 1601 and/or configured externally to device 1601.

In some embodiments, MDI device 1601 comprises a controller 1607, configured to initiate and/or modify and/or cease the pulmonary delivery of the pharmaceutically active agent. In some embodiments, controller 1607 operates substance dispenser 1603, for example activating heating of the substance by a heating element. In some embodiments, controller 1607 activates delivery of a pre-determined vaporized amount of the agent, such as the dose and/or regimen received as input. In some embodiments, controller 1607 controls the flow of the active agent, for example by activating one or more valves. In some embodiments, the controller is adapted to release the agent based on a current flow rate.

In some embodiments, MDI device 1601 comprises an output 1609. Optionally, output 1609 is configured as a mouthpiece to be engaged by the patient. Alternatively, to a mouthpiece, output 1609 may be configured as a breathing mask, a pacifier-like attachment for infants, and/or other structures suitable for delivering the flow of vapors to the patient.

In some embodiments, components of device 1601 such as the substance dispenser and/or the controller and/or other components are contained within a housing 1611. Optionally, the housing is shaped and sized to be used as a handheld device.

In some embodiments, MDI device 1601 comprises a flow control mechanism.

Optionally, the flow of vapors is controlled using one or more valves. In some embodiments, the flow is selected and/or modified per the individual patient, for example by timing the delivery and allowing flow of the active agent to the patient only during inhalation of the patient, indicated for example by a sensor incorporated in the MDI device. In some embodiments, the device is configured to modify the flow to allow the patient to instinctively identify when to cease inhalation, inhale deeper, and/or otherwise change the breathing rhythm and/or intensity. In an example, a pulse of increased flow volume is delivered by the device to indicate to the patient to cease inhalation.

In some embodiments, the flow is selected and/or modified to reduce an amount of active agent that remains trapped within the outflow tract of the device, and is not delivered to the patient. In some cases, the amount of trapped active agent is reduced to a known, predefined amount by controlling the flow.

In some embodiments, the flow is controlled by controller 1607. Optionally, the flow is controlled according to data received on input module 1605, data acquired by a sensor, and/or other indications.

A potential advantage of a device comprising a flow control mechanism which is operable per an individual patient may include improved accuracy of delivery to the patient, with respect to timing and/or pre-determined vaporized amounts of active agent delivered by the device, improving the performance of the system/MDI device.

Figure 17A:
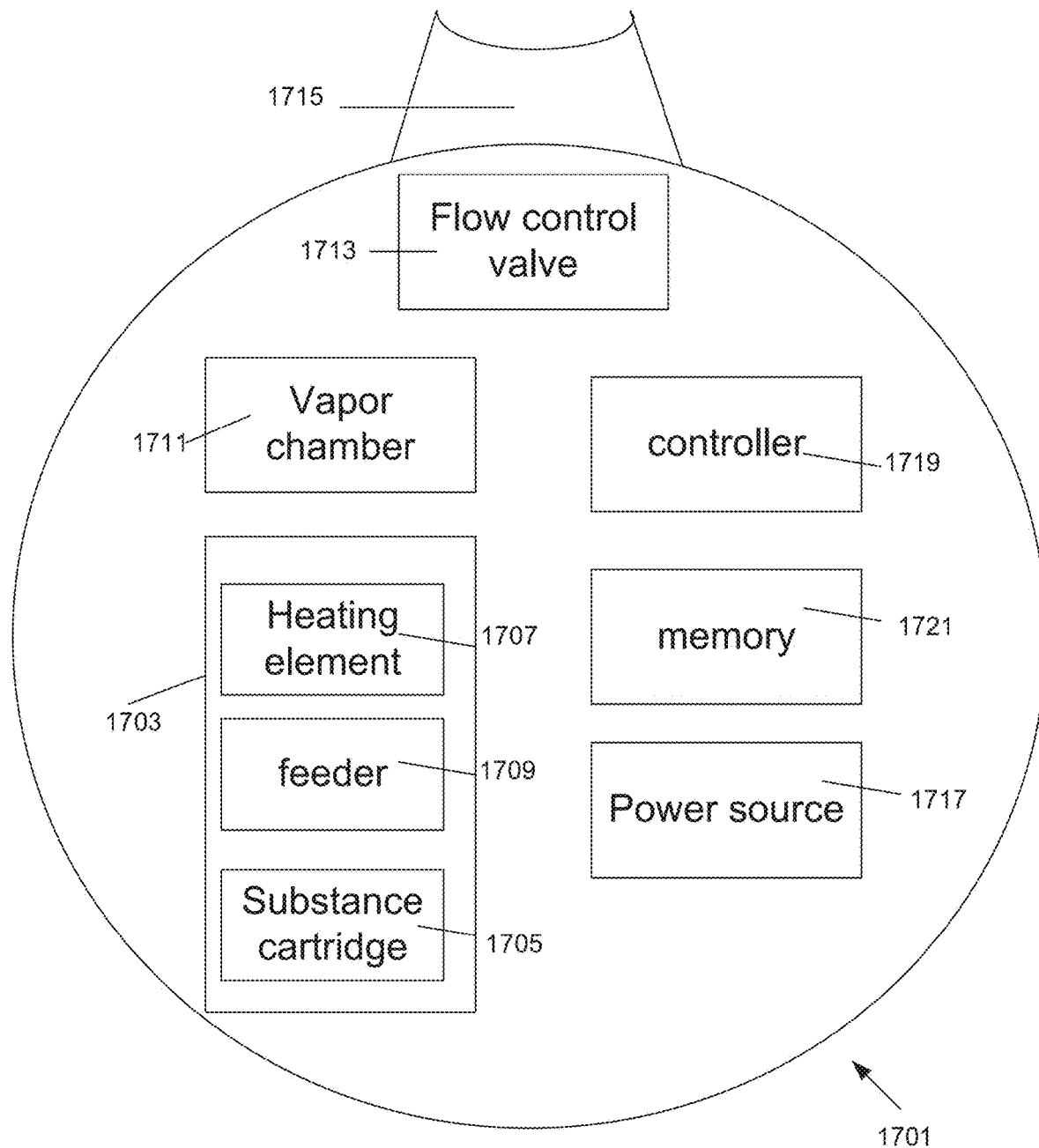

FIG. 17A is a schematic diagram of a configuration of an MDI device 1701, according to some embodiments of the invention.

In this configuration, the substance dispenser 1703 comprises a substance cartridge 1705, a heating element 1707, and a feeder 1709 which moves the substance cartridge relative to the heating element 1707, for example to be in contact with or in proximity to the heating element.

In some embodiments, the heating element is configured to provide localized heating, for example by conduction, convection and/or radiation. In some embodiments, a substance is heated sufficiently quickly to a temperature suitable for forming vapors of a vaporizable pharmaceutically active agent contained therein. In some embodiments, the substance is organized as a moving element, which can be selectively and/or locally activated. Optionally, the substance is organized into compacted shapes. Optionally, each shape represents a pre-determined vaporized amount.

In some embodiments, the vapors released from the substance collect within a vapor chamber 1711, from which they travel to the patient through an outflow tract.

Optionally, a valve 1713 is positioned along the tract to control the rate of flow.

In some embodiments, device 1701 comprises a mouthpiece 1715 from which the vapors are delivered to the patient in response to inhalation. Alternatively, mouthpiece 1715 can be attached to other elements, for example, to a mask and/or nasal cannula, optionally with supplemental oxygen, for example, to deliver therapy to debilitated patients. Optionally, mouthpiece is in fluid communication with valve 1713.

In some embodiments, device 1701 comprises a power source 1717, for example a battery, a manually wound spring, and/or a wall socket plug.

In some embodiments, device 1701 comprises a controller 1719, for example as described hereinabove, configured to control one or more of valve 1713, power source 1717, and/or the substance dispenser 1703 as a whole and/or separately control the components of the substance dispenser. In some embodiments, controller 1719 verifies that a substance cartridge is authorized for use.

In some embodiments, controller 1719 is in communication with memory 1721, which can be read by the controller and/or be written in.

Figure 17B:
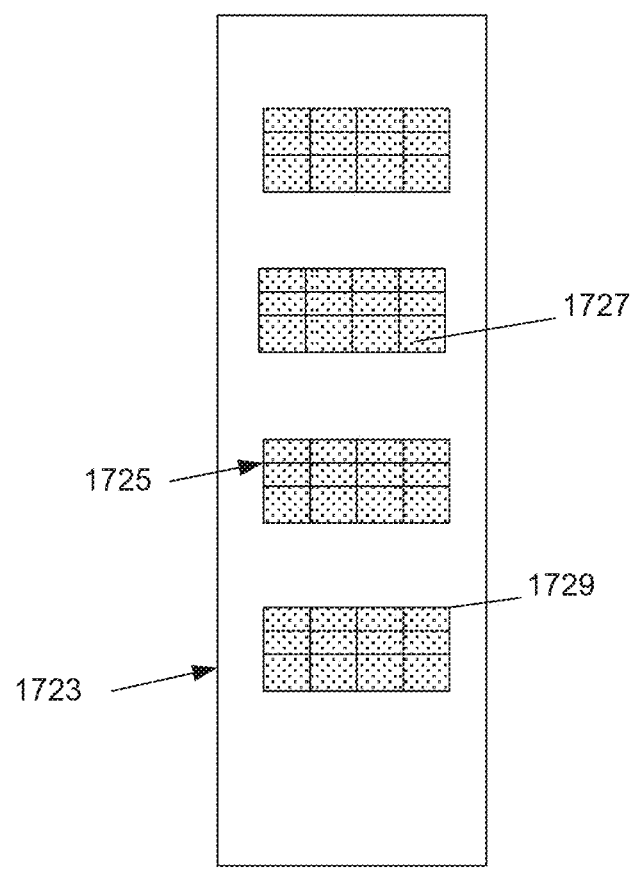

FIG. 17B shows a cartridge 1723, comprising a plurality of discrete substance cartridges 1725. Each cartridge 1725 contains one or more substances 1727 intended for vaporization (e.g. plant material), enclosed within a heating element 1729 which functions as the housing of the cartridge. In some embodiments, heating element 1729 is shaped as cage-like a net of wires which encases the substance. In some embodiments, to vaporize the active agent, electrical current is passed through heating element 1729, heating the substance contained within the specific individual cartridge.

According to some embodiments, the system provided herein includes at least one dose unit that includes plant material that contains the active agent. In some embodiments the system comprises a plurality of dose units, and the controller is configured to use at least one of the dose units for vaporizing the active agent from the dose unit.

In some embodiments, the system comprises a plurality of dose units, each of which comprises a plant material having a different composition of at least one pharmacologically active agent. In some embodiments a subset of the dose units have the essentially the same active agent(s) composition. In some embodiments, a plurality of does units have the same agents but at different amount ratios. According to some embodiments, the controller of the system is configured to select at least one of the dose units based on its active agent composition. For example, the controller can be used to select a dose unit having a plant material that includes one active, and then select another dose unit to vaporize a different active agent. The controller can also be used to effect a different heating temperatures for different durations so as to vaporizer different agents from the same dose unit, based on their varied vaporization temperatures. In some embodiments, the controller is configured to select a sequence of dose units having the same or different composition for inhalation at the same time or in rapid succession, thereby providing a combination of agents and/or higher amount than can be delivered with a single dose unit.

Figure 17C:
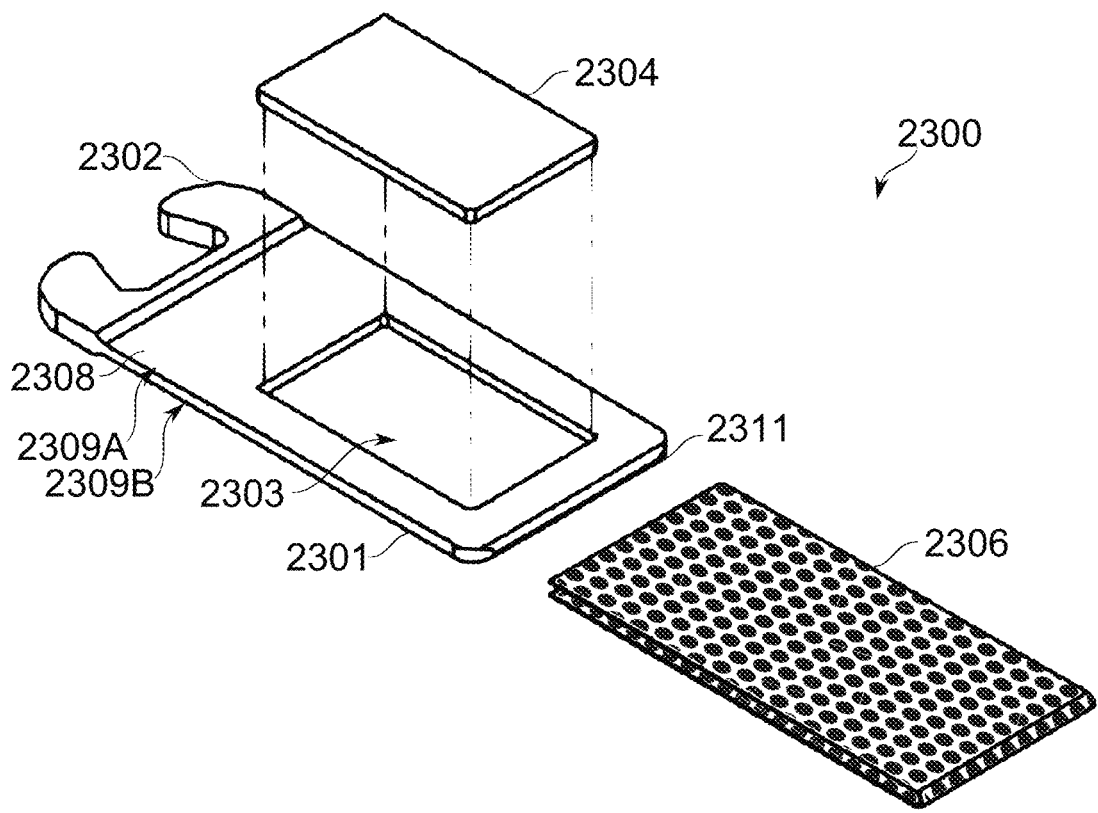
Figure 17D:
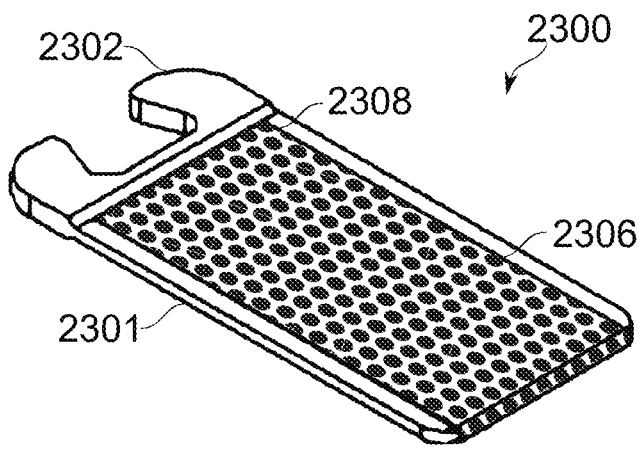

Reference is now made to FIGS. 17C-17D, which are schematic views of a dose unit 2300 (dosing substance vaporization cartridge), disassembled and assembled, according to some embodiments.

FIGS. 17C-17D present schematic illustrations of a dose unit (dosing substance vaporization cartridge, or cartridge), according to some embodiments, showing dose unit 2300 having substance 2304 containing one or more active agents and fitting into aperture 2303 in frame 2308 which forms a part of housing 2301 (FIG. 17C), and a resistive heating element 2306 in thermal contact with and extending across two opposite surfaces of substance 2304 (FIG. 17D). In some embodiments resistive heating element 2306 extends across only one surface of substance 2304, while in other embodiments it extends over more than two opposite surfaces thereof.

In some embodiments, pre-measured or known amounts of a substance containing one or more active agents is assembled upon and/or within a dose unit 2300. Optionally, dose unit 2300 comprises:

- substance 2304, optionally formed, for example, by flattening, for rapid vaporization;
- mechanical support for substance 2304 (for example, support by enclosure within aperture 2303 in frame 2308 of housing 2301, which is optionally frame shaped);
- means for facilitating transport of dose unit 2300 (for example, latch mandibles 2302); and/or
- means for heating (vaporizing) substance 2304 (for example, a resistive heating element 2306, for example a mesh).

Optionally at least a portion of dose unit 2300 comprising at least a portion of substance 2304 (or at least all heated portions of substance 2304), is permeable to the passage of air, such that air may pass through the substance when heating and carry with it the heat-vaporized agent.

Optionally, the dose unit is disposable. Potential advantages of a disposable dose unit include: containment of active agent residue for disposal; close integration of dosage support and transport for reliable dosage transport within a dosing apparatus; and/or reduced need to maintain and/or monitor portions of the dosing system (such as a vaporizing heating element) which are subject to conditions that could degrade performance over time.

Optionally, the dose unit is for use in a single inhalation. Potential advantages of a single-use dose unit include improving the precision and/or reliability in controlling the vaporized amount of the bioactive agent under inhaler settings. For example, the concentration and/or dispersal of an active agent in the substance 2304 may be controlled during manufacture at some degree of precision. In general, the degree of variation in the output of the device (e.g., the amount of vaporized and inhaled active agent) may be maintained within a tolerance of less than +/−15% of the intended output. Other factors that may have an effect on variations in the device's output include ambient conditions, user's use habits and user's current condition.

In some embodiments, dose unit 2300 comprises a housing 2301 having aperture or receiving chamber 2303. Optionally, housing 2301 comprises a flattened and elongated strip, while receiving chamber 2303 comprises an aperture framed by the strip (frame 2308). During preparation of dose unit 2300, substance 2304 is inserted into receiving chamber 2303. Optionally, the substance is shaped to fit receiving chamber 2303 before or during insertion such that it conforms to the flattened shape of receiving chamber 2303. It is a potential advantage for substance 2304 to be held in a flattened format, since a greater surface area and/or uniform thickness potentially allow faster and/or more evenly distributed heating and/or airflow during vaporization and delivery.

In some embodiments, substance 2304 dimensions are, for example, about 6×10 mm across the exposed surface area, and about 1 mm thick. Optionally, the thickness of substance 2304 is in the range of about 0.1-1.0 mm, or a greater, lesser, or intermediate thickness. Optionally, the face area of substance 2304 is in the range of about 20-100 mm$^2$; for example 20 mm$^2$, 40 mm$^2$, 50 mm$^2$, 60 mm$^2$, 80 mm$^2$, or another greater, lesser, or intermediate face area. Substance 2304 is optionally formed into a square or substantially square shape (for example, about 8×8×1 mm); optionally substance 2304 is oblong with a side ratio of, for example, 1:2, 1:3, 1:4, 1:10, or another larger, smaller, or intermediate ration of side lengths. Optionally, substance 2304 is, for example, about 30×2×0.5 mm in dimension. Corresponding substance 2304 by weight is about 15 mg in some embodiments. In some embodiments, substance 2304 weight is selected from within a range of about 1-100 mg, or another range having the same, larger, smaller, and/or intermediate bounds.

It is a potential advantage to surround substance 2304 with a framing housing 2301 for greater mechanical stability. For example, substance 2304 potentially comprise individual substance particles, such that substance 2304 is liable to shed particles, particularly if moved or bent. Enclosure within cartridge frame 2308 allows substance 2304 to be moved within the system without applying stresses directly thereto. In some embodiments, the overall length and width of the cartridge is about 20×10 mm, or another larger, smaller, or intermediate size. During manufacture, a framing housing is a potential advantage for formation of a substance sample of the correct size for fitted occlusion of a conduit through which airflows to pick up volatiles released during heating of the substance.

In some embodiments, vaporization of an active agent comprises heating by resistive heating element 2306 or other form of resistive heating element. The resistive mesh optionally comprises a material which displays substantial resistive heating; for example, nichrome (typical resistivity of about 1-1.5 µΩ·m), FeCrAl (typical resistivity of about 1.45 µΩ·m), stainless steel (typical resistivity of about 10-100 µΩ·m), and/or cupronickel (typical resistivity of about 19-50 µΩ·m). According to the choice of material (e.g., metal), parameters such as heating element length and width, thickness, aperture size and/or aperture pattern are adjusted to comprise a total resistance across the resistive heating element which is, for example, in the range from about 0.05-1Ω, 0.5-2Ω, 0.1-3Ω, 2-4Ω, or within another range having the same, higher, lower, and/or intermediate bounds.

Optionally, during assembly, resistive heating element 2306 is attached to housing 2301, in a position overlying substance 2304 on one or more sides. For example, the resistive heating element 2306 has a U shape that extends both sides of frame 2308 from dorsal surface 2309A to fold around housing end 2311, and extend back along ventral surface 2309B. Optionally, resistive heating element 2306 extends around chamber 2303 such that substance 2304 contained within chamber 2303 is enclosed by the heating element 2306. In some embodiments, resistive heating element 2306 (e.g. mesh) comprises a plurality of separate panels, for example, a panel on each side of the cartridge. Optionally, the panels are electrically connected, one to the other. A potential advantage of two-sided mesh enclosure of substance 2304 is increased speed and/or uniformity of vaporization upon application of a current to heating element 2306. In some embodiments, the heating element is embedded wholly or partially within substance 2304. Optionally, a heating element is embedded partially or wholly within frame 2308 of housing 2301; for example, the housing 2301 is originally molded with heating element 2306 in place, and/or heating element 2306 is pressed into place under high temperature at another stage of manufacturing.

In some embodiments, resistive heating element 2306 comprises a ratio of open (aperture) to closed (mesh material) surface area of between about 1:1 (50%) and 1:3 (33%). In some embodiments, the ratio is in the range of about 10-20%, about 20-40%, about 30-50%, about 40-70%, about 60-80%, about 70-90%, or another range of ratios having the same, larger, smaller, and/or intermediate bounds. In some embodiments, the apertures of the mesh are in the range of about 10 µm, about 25 µm, 32 µm, 50 µm, 75 µm, 100 µm, 200 µm, 300-750 µm, 700-1200 µm, or another larger, smaller, or intermediate range. Optionally, at least two apertures have different size and/or shape. In some embodiments, the mesh is a 400/0.03 316 stainless steel mesh, with 0.033 mm holes, 400 holes per square inch, wherein each hole is about 0.033 mm (33 µm), a 0.03 mm thick wire.

In some embodiments, resistive heating element 2306 comprises an etched resistive foil (for example a foil etched into a continuous ribbon or other shape, and backed by a polymer such as polyimide and/or silicone rubber). Optionally a backed resistive foil is perforated through the backing to allow airflow during volatilization of the dosing substance. In some embodiments, a fuse is added to the resistive foil, for example as an added component, and/or as a region of ribbon manufactured deliberately thin, so as to provide a method of destroying the heating element after use (by sending an appropriately high current through the heating element for a sufficient period of time).

In some embodiments, resistive heating element 2306 is secured to cartridge housing 2301 by pressing the mesh onto the housing using a temperature high enough for the housing to melt and/or soften such that the mesh becomes embedded in the material of the housing. In some embodiments, the housing comprises an inert, thermally resistant, non-conducive material. In some embodiments, the housing material used comprises, for example, a liquid crystal polymer (LCP), polyether ether ketone (PEEK), Ultem, Teflon, Torlon, Amodel, Ryton, Forton, Xydear, Radel, Udel, Polypropylene, Propylux, Polysulfone, or another polymer material.

A potential advantage of LCP and/or PEEK is good resistance to temperature higher than a temperature needed to vaporize a substance held in the cartridge. In some embodiments, bonding of mesh and housing occurs at a temperature of about 280° C. (or another temperature high enough to melt and/or soften LCP or PEEK). LCP and PEEK provide the potential advantage of good thermal stability at lower temperatures, for example, at a vaporization temperature of about 230° C.

A potential advantage of providing a heating element, such as resistive heating element 2306, for each individual dose unit is to provide uniformity of performance between uses. Potentially, a portion of the bioactive agent with which a heating element comes into contact remains stuck to the heating element after cool down. This buildup has the potential to affect vaporization performance. Remote heating (by radiation and/or indirect conductance, for example) potentially produces a system having relatively high thermal inertia (needing greater heating power) compared to direct conductive heating by a contact electrode; the problem of contact electrode contamination is removed by designing it for single use. A lowered requirement for heating potentially increases safety and/or device longevity. Potentially, a lowered requirement for heating also lowers demands on power delivery, allowing embodiments with increased portability, greater charge life, and/or lowered expense (for example, for systems having battery-powered heating elements).

In some embodiments, dose unit 2300 (cartridge) comprises a locking member for use in cartridge transport. The locking member comprises, for example, latch mandible 2302. The locking allows engagement by one or more matching members of a dosing system transport mechanism, for securing and/or movement of the cartridge. Cartridge movement and/or securing against unwanted movement may occur during the cartridge life cycle, for example: when the cartridge is placed into a queue of cartridges comprising a plurality of cartridges arranged for use, when the cartridge is advanced in the queue, when a cartridge is selected for use, when a cartridge is moved into position for use, when a cartridge is actually used, and/or when a cartridge is discarded, or, alternatively, moved to a "used" position in the cartridge queue.

The produced vapors are optionally collected in a vapor chamber and delivered to the patient.

A potential advantage of individually heated cartridges may include more accurate control over the pre-determined vaporized amounts of active agent being delivered to the patient, for example in comparison to a moving strip of cartridges heated by a stationary heating element. Individual loading and heating of a specific cartridge at certain timing may improve the accuracy of the MDI device.

FIG. 18 a flowchart of a method of treating an individual patient using a system according to FIG. 9, while maintaining the patient within a therapeutic window, according to some embodiments of the invention.

In some embodiments, the MDI device is programmed with a pre-determined vaporized amount (dose and/or regimen) (1801). Optionally, the dose and/or regimen is set in the inhaler device by the physician, manually (such as by activating buttons on the device itself) and/or using the physician interface. Additionally or alternatively, the dose and/or regimen is set in the MDI device according to instructions sent from the patient interface.

In some embodiments, the MDI device is optionally configured for selecting at least one pre-determined vaporized amount for an inhalation session, which can include a plurality of inhalations, based on the dose unit's contents, and controlling at least one of heating and airflow in the device to control the pre-determined vaporized amount of an active agent provided to the user. In other words, based on the properties of the substance, which is packed into the dose unit, namely the amount of active agent(s) available therein for vaporization, the device can be configured to vaporize some or all of the available active agent(s) in the substance in a single or a plurality of inhalations, wherein the controllability over the vaporized amount in each inhalation is afforded by control over the heating level and duration, and the airflows output and duration in the device.

In some embodiments, the MDI device is activated to deliver the active agent to the patient (1803). In some embodiments, direct and/or indirect feedback data from the patient is obtained in real-time (1805). Optionally, feedback data is obtained during a pulmonary delivering (an inhalation session). A treatment may typically start with a pulmonary delivery, and end between 5-20 minutes thereafter, for example when the pre-selected pharmacodynamic profile has fully manifested for the active agent and/or at a later time. Additionally or alternatively, feedback data is obtained over a series of pulmonary deliveries, for example over a time period of 1 hour, 3 hours, 5 hours, 9 hours, 12 hours or intermediate, longer or shorter time periods. A protocol may include 5-10 pulmonary deliveries per day, in time intervals ranging between 15-180 minutes between successive pulmonary deliveries.

In some embodiments, the feedback data which is obtained from the patient includes personal PD effects such as therapeutic effects, for example symptom intensity, and/or adverse effects, for example a psychoactive state of the patient.

In some embodiments, the patient interface interacts with the patient to obtain the feedback data. In some embodiments, questions to the patient relating their current state are displayed on a screen, and the patient answers the questions. Such a question may be presented, for example, in the form of a bar indicating a pain level, for example, which the patient raises and/or lowers. Additionally or alternatively, feedback data is obtained by one or more applications, such as games, which the patient interacts with. Optionally, non-invasive biomarkers levels are estimated by analyzing the patient's input when interacting with the user interface. Additionally or alternatively, feedback data from the patient is obtained by measuring various biomarkers using one or more sensors, for example by utilizing components of a smartphone, a handheld device, a wearable device, a wrist device or an integrated eyewear device, to act as non-invasive biomarker sensors.

In some embodiments, the personal PD effects are obtained periodically, for example semi-daily, daily, weekly, monthly, per demand such as before a dose and/or a series of doses, before and/or after alterations in dosing and/or regimen, or others.

In some embodiments, in response to the PD effects, a dose and/or regimen is modified (1809). Optionally, the dose and/or regimen is modified to achieve a desired effect, for example reduce pain level of the patient, while maintaining the patient within a therapeutic window. In some embodiments, the dose and/or regimen is iteratively modified by the patient interface. Modifications may take place a plurality of times, for example during, between or after one or more pulmonary deliveries, and/or over a total treatment time period (days, weeks, months, years) over which the patient is treated. The modification is limited by safety cutoffs, such as doses which may put the patient at risk.

In some embodiments, the patient interface and/or the MDI device remind the patient to perform one or more pulmonary deliveries (1811). Such a reminder may be provided as a visual signal (for example light indication), a sound, a vibration, a notification on a portable/handheld device, e.g. smartphone, a handheld device, a wearable device, a wrist device or an integrated eyewear device, or a combination thereof.

In some embodiments, usage data of the patient is recorded and stored in the MDI device memory and/or in the patient interface memory. Optionally, the delivery of the active agent is modified, potentially in real-time, according to usage data. For example, in a case in which the patient missed one or more pulmonary deliveries, the dose and/or regimen may be automatically modified to set a delivery of, for example, an increased amount of active agent in the following one or more pulmonary deliveries.

In some embodiments, any one or more of the actions described in 1801-1811 may be repeated. Advantageously, obtaining personal PD effects and/or usage data from the patient repetitively may provide for ongoing adjustment of the dose and/or regimen, providing a flexible, precise and accurate personalized treatment to the patient based on an actual effect of the treatment on the individual patient.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present disclosure.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Pharmacokinetic Studies

A study was conducted in order to characterize the inter-individual variability of $\Delta^9$-THC plasma levels during the absorption phase, upon using a hand-held metered-dose MDI device configured for pulmonary delivering pre-determined amounts of the active agent $\Delta^9$-THC from a solid substance (cannabis-derived plant substance) upon heating the substance.

The study was used to further evaluate the pharmacodynamic effect of pulmonary delivery of $\Delta^9$-THC on pain reduction from baseline using a 10 cm visual analog scale (VAS) pain scale (0 being no pain; and 10 being worst possible pain); for monitoring adverse effects, blood pressure and heart rate, and for estimating the degree of satisfaction with the use of the MDI on a 0-10 scale.

Study Cohort:

The study was conducted at the Pain Research Unit of Rambam Health Care

Campus in Haifa, Israel. Cohort patients were enrolled in the study after meeting the following criteria:
(a) Aged 18 years or older.
(b) Suffering from neuropathic pain of any type for at least 3 months.
(c) Stable analgesic regimen for at least 60 days that included medicinal cannabis.
(d) Normal liver function (defined as aspartate aminotransferase level less than three times the normal level), normal renal function (defined as a serum creatinine level lower than 133 μmol/L), and normal hematocrit (higher than 38%).
(e) Negative pregnancy test (defined by β human chorionic gonadotropin pregnancy test), when applicable.
(f) possession of a valid license from the Israeli Ministry of Health to receive medicinal cannabis.

Exclusion criteria were presence of significant cardiac or pulmonary disease, history of a psychotic disorder, pregnancy or breastfeeding, or presence of a non-neuropathic pain.

PK/PD Study Protocol:

The PK/PD study was carried out based on a single-dose open-label design protocol. The medical history of all patients was evaluated, and they were physically examined by the study physician. Routine medications were continued throughout the trial. Patients were required to abstain from using cannabis for 12 hours prior to the trial.

Following 3 successful demonstrative pulmonary delivery, the participants inhaled a single dose vaporized from 15.1±0.1 mg of *Cannabis* flos for about 3 seconds.

Blood samples were drawn immediately before and at 1, 2, 3, 4, 5, 15, 30, 60, 90 and 120 minutes after inhalation for monitoring plasma levels of $\Delta^9$-THC and its active metabolite 11-hydroxy $\Delta^9$-THC (11-OH-THC). The whole blood was collected in 13×75 mm purple-top Vacutainer® tubes containing EDTA. Samples were kept on ice and centrifuged within 30 minutes. Plasma was aliquoted into 3.6 ml polypropylene Nunc cryotubes (Thomas Scientific), stored frozen at −20° C. and analyzed within 6 weeks. The plasma cannabinoid's concentration analysis was performed at NMS Labs (Willow Grove, PA, USA) by multi-dimensional gas chromatography/mass spectrometry method.

Pain intensity reduction was assessed as a therapeutic effect by asking participants to indicate the intensity of their current pain on a 100 mm visual analog scale (VAS) between 0 (no pain) and 100 (worst possible pain) at baseline (prior to the inhalation) and at 20 and 90 minutes following the pulmonary delivery of the pharmaceutically active agent from cannabis. Adverse effects, in the form of psychotropic symptoms, were recorded at 5, 15, 30, 60 and 120 minutes post pulmonary delivery, along with those spontaneously reported by the participants. Adverse effects were evaluated according to standardized criteria in terms of severity, frequency, duration and relationship to the study's active agent. Adverse effects were graded using the NIH Division of AIDS table for scoring severity of adult adverse experiences. Blood pressure and pulse rate were also recorded before, during and after the pulmonary delivery.

Satisfaction from the experience of pulmonary delivery of vapors, compared to the current method of use (smoking), was assessed by using a 100 mm VAS ruler anchored by "not at all" at 0 and "very much" at 100 and 120 minutes following treatment.

PK/PD Study Medication:

The crude substance employed was pharmaceutical-grade *Cannabis* flos (Bedrocan BV, Veendam, The Netherlands) containing 19.9% dronabinol ($\Delta^9$-THC), 0.1% cannabidiol (CBD) and 0.2% cannabinol (CBN). The crude substance was free of pesticides and heavy metal (less than 0.2 ppm lead, less than 0.02 ppm mercury and less than 0.02 ppm cadmium). Foreign materials (stalks, insects and other vermin) were removed from the crude substance. Microbiological purity was confirmed (total aerobic microbial count of less than 10 CFU/gram, total yeast and moulds count of less than 10 CFU/gram and absence of *P. aeruginosa*, *S. aureus* and bile-tolerant gram negative bacteria).

The *Cannabis* flos substance was gently grounded while retaining all compounds in raw form, resulting in a physically modified substance containing 20.4% of the active Δ9-THC. The grounded cannabis was provided in preloaded cartridges containing 15.1±0.1 mg each.

MDI Device:

The study's MDI device was a battery operated palm sized hand held metered dose MDI (Syqe MDI™), designed to vaporize multiple doses of pharmaceutically active agent(s), resulting in pulmonary delivery of vaporizable active agent(s) (see, Background Art FIG. 1 and WO/2012/085919). The MDI consisted of a multi-cartridge daisy, cartridge counter, indication light and power switch. Each cartridge was preloaded with pre-weighed 15.1±0.1 mg of the substance (*Cannabis* flos) prepared as described above, each containing about 3.08±0.02 mg $\Delta^9$-THC based on substance analysis. The vaporization and pulmonary delivery process was instantaneously triggered by the inhalation force of the patient and lasted about 3 seconds. The transition to the next pulmonary delivery was performed by sliding the dose indicator. Each cartridge was heated to about 190° C. in about 470 ms, and was precisely sustained for 2,530 ms. The efficiency of the THC vaporization process was 52.7±2.7% (data not shown), indicating a low variability between pulmonary delivered doses. The device allowed for inhalation ranges between 1 to 30 L/minute, engaging real-time flow control and an automated anatomic dead space elimination mechanism, assuring all vapors pass the trachea post inhalation.

The device required minimal user training. The device electronically controlled and logged the entire pulmonary delivery process, allowing for storing and uploading of treatment data logs. The MDI device further allowed for "single dose" resolution, instantaneous administration, and required no preprocessing or any user intervention other than the inhalation.

Pharmacokinetic Parameters Data and Statistical Analysis:

The peak THC concentration ($C_{max}$) and time to attain $C_{max}$ ($T_{max}$) were derived directly from the experimental data (blood samples). Area under the plasma THC concentration time curve (AUC) was determined by linear trapezoidal non-compartmental analysis (WinNonlin Pro software version 2.0; Pharsight, Mountain View, CA, USA). The AUC was extrapolated to infinity ($AUC_{0 \rightarrow infinity}$) by the addition of $C_{last}/\lambda_Z$, where $C_{last}$ and $\lambda_Z$ are the last measured THC concentration and the terminal slop on the Ln scale, respectively. For those participants who demonstrated a residual plasma THC level at time zero ($C_0 > 0$), the $AUC_{0 \rightarrow infinity}$ was obtained from the equation: $AUC_{0 \rightarrow infinity} = AUC_{0 \rightarrow last} + C_{last}/\lambda_Z - C_0/\lambda_Z$ where $C_0/\lambda_Z$ is the residual AUC contributed from previous doses [see, Rowland M, Tozer T N. "Clinical Pharmacokinetics: Concepts and Applications". 3th ed., Williams and Wilkins, Media, PA, 1995].

Results are reported herein as mean values±1 standard deviation (±SD). For each one of the measured effects (VAS pain intensity, systolic and diastolic blood pressure, heart rate and satisfaction score), the mean and 95% confidence interval (CI) at different time points was plotted. Differences between VAS pain intensity values and satisfaction scores, before and after inhalation, were tested by two-tailed paired Student t-test. Blood pressure and heart rate values were compared among different time points by one-way ANOVA. P-values<0.05 were accepted as significant. All statistical analyses were performed using Minitab Statistical Software, version 16.

Eight patients participated in the study. Patients' demographic and baseline characteristics data are presented in Table 1.

TABLE 1

| | Participant | | | | | | | |
|---|---|---|---|---|---|---|---|---|
| | A | B | C | D | E | F | G | H |
| Gender | M | M | M | M | F | F | F | M |
| Age (years) | 35 | 41 | 44 | 25 | 41 | 53 | 69 | 28 |
| Weight (Kg) | 122 | 73 | 80 | 58 | 89 | 56 | 85 | 71 |
| BMI | 35.6 | 21.8 | 26.4 | 17.9 | 30.8 | 23.3 | 34 | 23.7 |
| Cause of pain | | | | | | | | |
| Spinal cord injury | | | ✓ | | | | | |
| CRPS | ✓ | ✓ | | | | | ✓ | ✓ |
| Lumbosacral radiculopathy | | | | | ✓ | ✓ | | |
| Pelvic neuropathic pain | | | | ✓ | | | | |
| Duration of pain (months) | 32 | 87 | 30 | 36 | 36 | 75 | 147 | 48 |
| Cannabis use | | | | | | | | |
| Dosing: (gr Cannabis/month) | 20-30 | 20-30 | 20-30 | 15-20 | 2-5 | 20-30 | 15-20 | 30-40 |
| Concomitant medications | | | | | | | | |
| Opiates | | ✓ | | | | | ✓ | ✓ |
| Antidepressants | ✓ | ✓ | | | | | ✓ | ✓ |
| Anticonvulsants | ✓ | ✓ | | | | | ✓ | ✓ |
| Benzodiazepines | ✓ | | | | | | | |
| Steroids | | ✓ | | | | | | |
| NSAID. Beta Blockers. Others | ✓ | | ✓ | ✓ | ✓ | | ✓ | |

Participants were predominately men (62.5%), ranging in age from 25 to 69 years (mean age±SD=42±14). Mean weight and body mass index±SD were 79±21 kg and 27±6, respectively. All participants suffered from neuropathic pain: 4 had Complex Regional Pain Syndrome (CRPS), 2 had lumbosacral radiculopathy, 1 had pelvic neuropathic pain and 1 had pain related to spinal cord injury. Median time from the diagnosis of neuropathic pain to study enrollment was 48 months (range: 30-147). All patients were treated routinely with Cannabis flos, inhaled by smoking 2-3 times a day.

The median monthly dose was 20-30 grams (range: 2-5 grams up to 30-40 grams monthly dose).

Table 2 presents pharmacokinetics data obtain for $\Delta^9$-THC following a single dose inhalation of 15.1±0.1 mg Cannabis flos, containing 3.08±0.02 mg $\Delta^9$-THC, self-administered by 8 adult patients as described herein (see, Table 1 hereinabove). The inter-individual variability in plasma cannabinoids levels upon the single dose inhalation is presented in FIG. 2 and Table 2 below.

TABLE 2

| Participant | $C_{max}$ (ng/L) | $T_{max}$ (minutes) | AUC (ng · min/L) |
|---|---|---|---|
| A | 46 | 3 | 495 |
| B | 53 | 2 | 825 |
| C | 29 | 3 | 850 |
| D | 30 | 5 | 491 |
| E | 38 | 2 | 284 |
| F | 46 | 2 | 724 |
| G | 39 | 3 | 712 |
| H | 26 | 4 | 473 |
| Mean | 38 | 3 | 607 |
| SD | 10 | 1 | 200 |

Two patients had residual plasma THC, above the limit of quantization, at baseline. In the remaining six patients, THC was firstly detected in the blood sample drawn 1 minute post-inhalation. THC mean plasma $C_{max}$ for the entire group was 38±10 ng/ml and occurred after 3±1 minutes. Mean THC-$AUC_{0 \rightarrow infinity}$ was 607±200 ng·min/ml. No measurable plasma levels of the active metabolite (11-OH-THC) were monitored within the time frame of the blood sampling (0-120 minutes). The mean baseline VAS pain intensity was 7.5±1.4. A significant analgesic response was noted 20 minutes after inhalation (difference of 3.4 points, 95% CI: [2.1, 4.9], P=0.001). The VAS values reported at 90 minutes post-dosing showed virtually identical results as at baseline, as shown in FIG. 3.

The adverse effects were minimal, reversible and well tolerated. Seven patients (87.5%) experienced light headedness for the first 10 minutes following inhalation, but the effect receded rapidly thereafter. Three patients fully recovered within 15 minutes and all the others—within 30 minutes post-inhalation.

As depicted in FIG. 4, comparing to baseline, a borderline significance decrease in the mean systolic blood pressure (BP) was noted 30 minutes following inhalation which persisted for 90 minutes (from 133±13 to 122±10 and 121±11 mm Hg at 30 and 90 minutes post-inhalation, respectively; P=0.068). No significant differences in mean diastolic blood pressure and heart rate were measured during the study period (for diastolic BP: from 82±9 to 75±10 and 81±12 mm Hg at 0, 30 and 90 minutes post-inhalation, respectively; P=0.410). For heart rate: from 71±12 to 72±11 and 69±13 bpm at 0, 30 and 90 minutes post-inhalation, respectively; P=0.873).

As shown in FIG. 5, all patients selected pulmonary delivery using the MDI device as their preferred mode of treatment compared to smoking, their current mode of use (satisfaction score of 9.37±0.52 compared to 5.37±2.61, 95% CI for mean difference: [1.72, 6.28]; P=0.004).

The adverse effects observed in the study were minimal, reversible and receded rapidly, in accordance with clinical studies involving low doses of THC released from cannabis and delivered by inhalation, as mentioned above. No participant withdrew because of tolerability issues.

Example 2

Comparative Analyses

The data obtained in the studies described in Example 1 were analyzed comparatively to smoking, oromucosal, oral and intravenous administration of $\Delta^9$-THC and inhalation using the commercially available Volcano® vaporizer.

Plasma $C_{max}$ Levels Per mg of $\Delta^9$-THC Administration:

The present inventors have compared THC yields obtained via pulmonary delivery according to the method described herein to data published in the art (Background art), the comparative results being graphically presented in FIG. 6.

Thus, intravenous administration of $\Delta^9$-THC, as a reference mode of delivery, yielded the highest plasma $C_{max}$ levels per mg of $\Delta^9$-THC administered-43.8 (as reported by Ohlsson, et al. Clin Pharmacol Ther. 1980; 28(3):409-16; the column denoted "Ohlsson (3)" in FIG. 6), and 32.8, 23.8 ng $\Delta^9$-THC/ml plasma (as reported by D'Souza et al., Neuropsychopharmacology, 2004; 29(8):1558-72; the column denoted "D'Souza (14)" in FIG. 6).

Among the alternative modes of administration of $\Delta^9$-THC, the pulmonary delivery method described herein yielded the highest increase of $C_{max}$ per mg of $\Delta^9$-THC available in the cannabis substance used—mean of 12.3 ng/ml/mg $\Delta^9$-THC compared to 6.1-9.0 for Volcano® vaporizer (columns denoted "Abrams (9)" and "Abrams (20)"; Abrams et al. Clin Pharmacol Ther. 2007; 82(5):572-8; Abrams et al., Clin Pharmacol Ther. 2011; 90(6):844-51, respectively), and 0.6-4.6 for regular smoking cigarettes (columns denoted "Ohlsson (3)", "Hunault (15)", "Hunault (16)", and "Huestis (17)": Hunault et al. Psychopharmacology (Berl). 2008; 201(2):171-81; Hunault et al., Toxicol Appl Pharmacol. 2010; 246(3):148-53; Huestis et al., Clin Pharmacol Ther. 1992 July; 52(1):31-41).

The rate of absorption and distribution of THC by smoking could lead $C_{max}$ to be an artifact of the sampling protocol; that is, random sampling over a large number of individual peaks and valleys after each puff could have produced artificial peak responses. This constrain led researchers to use a continuous withdrawal pump with adjustable speeds for fast sequential blood sampling in order to characterize the absorption phase of marijuana smoking. They reported a mean $C_{max}$ increase of 3.54 or 4.28 ng/ml per mg $\Delta^9$-THC observed after the first puff of a 1.75% or 3.55% $\Delta^9$-THC cigarette, respectively. The smoking protocol consisted of a 2 seconds long inhalation, a 10 seconds long holding-in period and a 72 seconds long exhalation and rest period.

The results obtained by the present inventors were higher by a factor of 2.9-3.5 compared to those obtained by Huestis et al., which may be indicative for one or more of: a 33% longer inhalation period, the lack of side-stream smoke and the minimal pyrolytic destruction of THC during the vaporization process in the MDI device (FIG. 6).

Inter-Individual Variability in $C_{max}$ of THC:

FIG. 7 presents data of inter-individual variability in peak plasma $\Delta^9$-THC concentrations obtained by the method described herein and comparative data known in the art (Background Art). As seen in FIG. 7, $C_{max}$ inter-individual variability of the MDI device according to embodiments of the present disclosure was 25.3%.

Several studies have reported coefficient of variation (CV) values of 47-85% for vaporizer (columns denoted "Abrams (9)" and "Abrams (20)" in FIG. 7), 32-115% for smoking cigarettes (columns denoted "Ohlsson (3)", "Hunault (15)", and "Huestis (17)"), 42-115% for oral administration (Ohlsson (3), Karschner (4), and Lile (21); Karschner et al., Clin Chem. 2011; 57(1):66-75; Lile et al., J Clin Pharmacol. 2013; 53(7):680-90), and 59-67% for oromucosal route of delivery (Karschner (4)), as illustrated in FIG. 7.

Most of the studies presented in FIG. 7 were conducted under controlled dosing and experimental conditions. In "real life" conditions, a higher inter-individual variability is expected.

The relatively low $C_{max}$ inter-variability may be attributed to features of the tested MDI device that ensure a complete, high efficient delivery of the vaporized agent(s) to the lungs, independent of the inhalation pattern of the individual patient.

Example 3

Therapeutic Window Determining and PD-Profile Personalization

In accordance with the personalized pulmonary delivery method described herein, a dose and a regimen was calculated to maintain the treatment within a pre-determined therapeutic window for an individual patient, referred to herein as "Patient X", for 3 hours, using an algorithm specifically developed for a metered-dose inhaler device used according to some embodiments of the present disclosure. The therapeutic window calculations were based on THC concentration in the plasma and body (PK profile of THC) as known in the art, combined with the PK variables of Patient X (e.g., BMI, age, gender etc.), as described hereinabove.

A dosing (a plurality of pre-determined vaporized amounts) and a regimen (time intervals between doses) were determined for Patient X by an algorithm that simulates a pharmacokinetic profile of that patient based on the above-presented and other PK studies conducted in a population of subjects and population PK variables, optionally in combination with PK effects defined as described hereinabove for the MDI device, and in parallel stimulates the pharmacodynamic profile, which is expected to be exhibited, considering a desired therapeutic effect level and a tolerable adverse effect level. The resulting predicted PD profile therefore commensurate a therapeutic window that would allow Patient X both the therapeutic effect of symptom treatment (pain relief) and tolerable psychotropic activity levels (CNS related adverse psychotropic effects).

The algorithm provides a desired dosing and regimen to achieve a desired PD profile, based on the PK effects and variables.

FIG. 8 presents a representative example of a pulmonary delivering of three pre-determined vaporized amounts (the calculated dosing) over a time period of 3-hours, as calculated for Patient X. Patient X is 35 years old male exhibiting a BMI of 22.

According to the predicted PK/PD profiles, in order to maintain the effect of THC within the therapeutic window for 3 hours, as presented by the red curve in FIG. 8, Patient X needed to inhale THC vaporized from cannabis using the metered-dose MDI device used in Examples 1 and 2 hereinabove, according to some embodiments of the present disclosure, at the following time intervals and pre-determined vaporized amounts (the calculated dosing and regimen): at 00 minutes—1.2 mg; at 10 minutes—1.0 mg; and at 60 minutes—0.5 mg. The blue curve represents the calculated PD profile at the indicated dosing. As seen, the calculated regimen maintains Patient X within tolerable adverse CNS activity levels, namely below the adverse effect level and above the minimal level of symptom awareness (namely, above the minimal therapeutic effect).

The MDI device and algorithm used in the pulmonary delivering method described herein provide the ability to use such an MDI device for pulmonary delivering active agents at a pre-determined vaporized amount(s) (pre-determined dosing and regimen), wherein the MDI device is calibrated and configured based on PK/PD data and personal PK variables and/or data, so as to obtain desirable pre-selected PK profile, which is selected so as to obtain a pre-selected (desirable) PD profile, and maintain the effects of the agent within a pre-determined therapeutic window which has been selected for an individual patient.

The following is an example for a procedure for determining and administering a personal dosing and/or regimen for treating a human subject by pulmonary delivery using an inhaler device, according to some embodiments of the present disclosure. The procedure is depicted in flowchart 1900 presented in FIG. 19.

Providing patient data (see, 1901 in FIG. 19) may include information about the patient's properties, including for example one or more of the patient's age, gender, weight, BMI, expected activity, etc., a recommended dosage and/or regimen and/or a syndrome or indication for which treatment is administered. Optionally, providing patient data (1901) also includes PK/PD data from one or more previous uses of an inhaler for the same active agent(s) and possibly also for the same indication. Optionally, providing patient data (1901) includes a correlation or set of correlations between a dose and the PK profile and/or PD profile of the patient over a period of time as recorded in one or more previous deliveries of the same one or more pharmaceutically active substances. Optionally, providing patient data (1901) includes data assembled from PK/PD profiles of a plurality of users or a population to which the user belongs.

Optionally, providing patient data (1901) includes treatment instructions and/or treatment preferences. Some examples for treatment instructions or preferences may include no dose during a given temporal window; allowing more drowsiness generally (e.g., for bedridden patients) or at a given time (e.g., initial treatment and/or during the night and/or when dealing with extreme symptoms); requiring alertness in given timeframe (e.g., when a patient expects to need alertness), and the like. Such instructions may be given a weighted value; for example, a patient may be less adamant on some instructions then others, for example the patient may prefer having more drowsiness in the evening, but may indicate that he must be alert for a test at 10 AM.

The instruction may have a relative effect in the sense that some effects may be tolerated to a certain degree only in order to comply with a given instruction. For example a patient may instruct that he must be alert for driving unless pain is above a certain given value.

Still encompassed by optional providing patient data (1901), treatment instructions may be provided at any time during a period of treatment; for example, before beginning treatment a patient may provide treatment instructions and/or treatment preferences. At any time thereafter, a patient may input additional indications and/or preferences. For example, a patient may, at any time, use a user interface associated with the device to instruct regarding a future (e.g. next) dose (or more than one dose). Such instruction may include that a dose will not be taken in a given window of time, or must be taken before a given time point, etc. Optionally such instruction may include an adjustment of the user's acceptable and/or preferred therapeutic window what constitutes a sufficient therapeutic effect and/or what constitutes a maximal level (tolerable) of an adverse effects.

Optionally, providing patient data (1901) is updated to reflect when a dose was inhaled, the dose amount and/or how the device operated in the inhalation event (e.g., if inhalation was successful or failed due to a device malfunction and/or improper usage). This may be taken as an indication of user status and/or device malfunction and/or amount of active substance inhaled (efficiency factor). Such data may be used to adjust the regiment and/or issue a notification to the user and/or medical practitioner.

Optionally, when a regimen calls for the user to administer a dose, the user may be prompted to do so, visually and/or by sound, via at least one user interface. When prompted, the user may have the option to defer by selecting a "snooze" option and optionally set the next time when he would take the next dose. In response, the device may readjust the regimen (e.g., next dose size and timing) and/or provide a notification to the user that this would not be possible or is likely to have a given adverse effect.

Optionally, if a user misses a time slot allotted for a given dose, one or more of the following may take place: (a) the regimen is adjusted to compensate for the delay; (b) a notification is given to the user (possibly by way of an alarm and/or vibration); (c) a notification is given to a care giver and/or a medical practitioner.

Generating initial dosing and/or regimen (see, 1902 in FIG. 19) may be effected as follows:

Based on recommended dosing and/or regimen (see details below) and patient data (1901), an initial dosing and/or regiment (1902) is proposed. The initial dosing and/or regimen (1902) may include the recommended dosage according to known standards and/or may be adjusted by taking into account data related to the patient's previous treatment(s) using an inhaler and the treatment instructions and/or preferences.

Taking into account the recommended dosing and/or regimen, treatment instructions may include some constraints that are more stringent than others. For example, a maximal allowed dose may not be exceeded regardless of user's preferences, and the device may be configured not to allow overdosing. Similarly, a minimal mandatory dose may be prescribed and should not be avoided regardless of user's preferences, and the device may be configured to issue a non-compliance alert to the user and/or care giver and/or medical staff in such cases. Optionally, the constraints may be imposed in advance (e.g., based on a therapeutic index of the one or more active substances and/or in accordance with a plan plotted or approved by a physician) and/or periodically or on an ongoing basis (for example as a result of specific events encountered by the user's use of the device).

Optionally, generating initial regimen (1902) is effected for a patient when first assigned with an inhaler and a regimen. In such case the patient is required to inhale the first dose or first several doses under supervision (e.g., for a period of 2 hours or more). During this time period the patient's symptoms and PD effects are observed, recorded and measured before the first dose and then occasionally at least for the supervised period. Additionally or alternatively, one or more inhalations are monitored by blood tests to extract some PK effects or a full PK profile. This may include administration of several different doses in order to establish a personalized initial dosing and/or regimen. When PK effects are taken and analyzed, a first correlation (blood concentration over time as a function of the pre-determined vaporized amount/dose) may be recorded. This correlation may remain the same for a given patient as long as no major weight change or changes in kidney and/or liver function occurs. A second correlation, such as a PD effect as a function of blood concentration over time, may be used as it is known for the population at large. Based on the two correlations an individual initial dose/PD correlation over time may be determined per patient. Optionally, a direct correlation is measured and used for a given patient, between a PD effect over time as a function off the pre-determined vaporized amount/dose.

Receiving PKPD feedback (see, 1903 in FIG. 19) is effected to include at least one of several classes of user indications/information, including user semi-controlled (voluntarily or involuntarily) indication and user uncontrolled (involuntarily) indication.

Receiving PKPD feedback (1903) may include receiving user-controlled indication and/or information, wherein the user may provide input regarding the perceived and/or sensed effect and/or a desired range of effect. For example, inputting one or more responses to interrogation via the device's user interface and/or by a practitioner (e.g., grade a degree of pain and/or a degree to a psychoactive effect), while the user has control on the input he provides. A response may include grading on a scale (e.g., a scale of pain from 1 to 10), a Yes/No response (e.g., whether nausea was removed or if food was eaten without vomiting) and/or a temporal description of an effect ("when did you notice that pain began to dissipate?", "how did the pain feel during the time from inhalation to interrogation?" etc.). The interrogation may be periodic (e.g., once a day or every several hours or upon inhalation or as a requirement before inhalation) and may be limited to only a part of the period of treatment. For example, interrogation may cover the initial 6, 12 or 24 hours in order to determine a regimen and then repeated periodically (e.g., once a day or once a week or once a month or upon desire) in order to confirm the regimen and/or readjust it in view of progress.

Receiving PKPD feedback (1903) may include receiving user semi-controlled indication, wherein the user may participate in measuring the user's status; while user compliance is needed for these indications, the user has little or no control on the result. For example, a user may be instructed to attach a sensor to his body that communicates with the device or allow sensing a property (e.g., eye redness). Optionally and alternatively, a user interface may test the user, for example by following pupils and/or instructing the user to perform a task. Examples for tasks may include, without limitation, following a mark on a screen with your eyes; dragging a mark on a screen through a pattern without touching walls; completing mental tasks (such as solving mathematical equations or answering questions); testing memory by games; and testing concentration.

Receiving PKPD feedback (1903) may include receiving user uncontrolled indication, wherein the inhaler or a device associated with the inhaler may sense one or more properties of a user as an indication of the user's status and use that as an indication of one or more effects of the inhaled dose regimen on the user. For example, sensing mouth temperature during inhalation and/or pupil size without prompting the user, each of which may indicate PD effect and thus serve as a PD effect; sensing tremor or a variation in tremor; and sensing heart rate and/or blood pressure, for example by interaction with a sensor worn by the user and/or implanted in the user.

Optionally and alternatively, sensing airflow properties in the device may be used as an indication of the user's status, wherein such air flow properties may include one or more of flow rate and/or the rate of increase in flow rate and or a degree and/or rate of variation in flow during an inhalation event. For example, considering changes from one or more baseline values, which may indicate for example an improvement or a decline in wellbeing (e.g. as manifested by strength and/or pain that may affect the inhalation properties/patterns for the user) and/or concentration or attention.

Generating adjusted regimen (see, 1904 in FIG. 19) is effected if needed, to generate an adjusted dosing and/or regimen. An adjusted dosing and/or regimen may be required when one or more of the following occurs:

1. One or more treated symptoms is not sufficiently alleviated;
2. One or more psychoactive effects exceed a given threshold
3. The therapeutic/adverse effect balance is below a given threshold; and/or
4. A change in circumstances that needs to be taken into account occurs (e.g. breakthrough pain or a missed inhalation event).

It is noted that a given activity of an agent may be regarded as a desired effect or an undesired effect inter alia in different circumstances and for different subjects. For example, an active agent that is analgesic, sedative and/or hallucinogenic it may be that the analgesic property is a therapeutic effect and the hallucinogenic property is an adverse effect. As for sedation, in some circumstances this might be a desired effect of treatment while in others it may be undesired.

Optionally and alternatively, in generating adjusted regimen (1904), the dosing and/or regimen includes a second active agent (or more than two agents) that is co-administered in order to reduce an undesired side effect of the drug.

An example for a regimen for treating the symptoms of neuropathic pain, occasional breakthrough pain (BTH) episodes and sleeplessness due to pain is presented in FIG. 20.

FIG. 20 is a graphical representation of a regimen for the treatment of pain and sleeplessness by pulmonary delivering of an active agent, wherein the red line represents the pain level, and the green line represent the blood level of the active agent, wherein the active agent is pain reliving as well as sedative, and is inhaled by using various doses during wakefulness.

As can be seen in FIG. 20, pulmonary delivering a pre-determined vaporized amounts (the calculated dosing) over a day from wakefulness at about 6:30 am to sleep after 22:30, wherein the patient is, for instance, a 35 years old male exhibiting a BMI of 22. The patient suffers from chronic neuropathic pain, occasional breakthrough pain (BTH) episodes (once in the presented day) and sleeplessness due to pain, particularly difficulty in falling asleep. According to the above, PK/PD profiles are predicted and an initial regimen is proposed, in order to maintain the effect of the active agent (such as THC) within the therapeutic window for at least 12 hours. The regimen includes a first dose of, for example, 1.2 mg taken at 7 AM in view of pain increase through the night, when no treatment was administered, followed by 0.5 mg every 1.5 hours.

In this example, the therapeutic effect requires a minimal value, which is determined based on a minimal dose needed for perceiving an effective therapeutic, effect, and a maximal dose, which is determined according to at least one or more PK/PD effects and optionally as a function of the minimal value. The minimal value may vary according to the symptoms/disease being treated. The maximal value may vary, for example, according to time of day and patient schedule and preferences.

FIG. 20 also shows that this regimen reduced pain (red line) from a high value before 7 am to a value that is maintained within the allowed window until about 14:30 when the patient experienced a BTH of severe pain. In response, the therapeutic window is adjusted. The high threshold of the dose increases in this example, because in view of the severe pain, some excess psychoactive effect becomes tolerable and even desired. Additionally, the bottom range of the window moved up because the required dose needed to alleviate the pain became higher.

As can further be seen in FIG. 20, a BTH episode is handled by administering an inhalation of 2.4 mg, which results in the expected reduction in pain with concomitant high sedative effect. Once pain returned to a tolerable level, the initial therapeutic window is reestablished and the initial regimen is resumed. This return to the initial regimen and re-establishment of the therapeutic window may be abrupt, as shown, or gradual. Additionally, the top value and bottom value of the window may change simultaneously or at separate times, as shown.

As can further be seen in FIG. 20, at a time designated by the patient (in advance or in real-time) as bedtime, the dosing is adjusted. This is because the PD effect of drowsiness changed from an adverse effect to a therapeutic effect. The patient administers a dose of 2.4 mg about 30 minutes prior to intended sleep time. Before awaking, the dose may be adjusted gradually or abruptly so that any late night inhalation would not be likely to have an excessive effect in the morning.

Example 4

Pulmonary Delivery Protocol

Following is an example for use of the method, device and system presented herein, according to some embodiments of the present disclosure.

An MDI device, for example as described herein in FIG. 16 and/or FIGS. 17A-17D, is loaded with a plurality of pre-weighted cartridges, each containing a substance that comprises one or more vaporizable pharmaceutically active agent(s). The MDI is pre-calibrated and preset to release a pre-determined vaporized amount of the pharmaceutically active agent according to PK/PD data obtained for a population and/or PK effects of a particular patient, as described hereinabove.

The system, for example as described hereinabove in FIG. 9, is pre-loaded with personal information pertaining to the patient (e.g., PK variables) and his or her medical condition and history, data pertaining to the pre-determined vaporized amount and time intervals for pulmonary delivery of the agent (dosing and regimen), data pertaining to a pre-selected pharmacokinetic profile and/or a pre-selected pharmacodynamic profile, data pertaining to a desired therapeutic effect and a tolerable adverse effect (therapeutic window) selected or determined for the patient, data pertaining to safety thresholds for various conditions (toxicity, sleeping, alert and motor skills, cognitive functions, resting, etc.), and data pertaining to past uses of the system, if available.

During initial use, the patient is using the system to run a set of initialization tests for the patient to determine baseline state prior to exposure to the active agent, using a plurality of non-invasive objective (measurable biomarkers) and subjective (reported perception) data collection procedures of various personal PD effects. These baseline tests are run periodic, namely hourly, semi-daily, daily, weekly, monthly, per demand and before dose/regimen administration and alterations. It is noted that personal PD effects can be obtained prior to the pulmonary delivery, namely before any agent has been delivered to the patient, and are therefore regarded as base-line values of the personal PD effects. For example, if a personal PD effect is a pain level, the system records the pain level under the influence of zero amount of the agent.

The patient then uses the MDI device while being monitored on all or some of the biomarkers, objective and subjective, following a pulmonary delivery of a pre-determined vaporized amount of the agent or a plurality of pre-determined vaporized amounts of the agent, delivered at pre-determined time intervals (a pre-determined dosing/regimen).

In some embodiments, monitoring comprises determining personal PD effects. Various parameters may be voluntarily provided by the patient via, e.g., a patient interface, while others may be independently collected by the system, via sensors and/or a practitioner interface. Personally perceived parameters such as a perceived therapeutic effect (for example a pain level) and a perceived adverse effect (for example a psychoactive level) are inserted to the system, for example by the patient interacting with a patient interface display. An application for obtaining personally perceived parameters may, for example, visually present a graph to the patient, such as a bar graph, which the patient can modify based on his perceived notion of the effects.

Other personal PD effects may include presence and/or levels of biomarkers.

In some embodiments, presence and/or level of biomarkers is determined using one or more sensors. Optionally, the sensors are common components of a mobile personal device, such as a smartphone, a handheld device, a wearable device, a wrist device or an integrated eyewear device, which are utilized to collect indications based on which biomarkers can be deduced. Alternatively, biomarkers are detected and measured via external elements paired to the mobile personal device.

Components which may be used as sensors for obtaining a parameter from the patient may include: a touch screen, may be used for example to assess dexterity, eye-hand coordination, and/or a memory and cognition state; a gyroscope, accelerometer, proximity sensor and/or gesture sensor such as IR sensor may be used, for example, to assess motor skills; a camera and/or light source may be used, for example, to detect visual tracking, saccade variance, eye vascular expansion, pupil dilation and/or pulsation; an RGB illumination may be used, for example, to assess environmental perception; a magnetometer and/or GPS may be used, for example, to assess orientation; a speaker and/or microphone may be used, for example, to assess auditory and/or vocal skills; a temperature and/or humidity sensor may be used, for example, to assess a body temperature.

Additional biomarkers may be determined with the aid of one or more applications, configured, for example, on the patient interface and/or the MDI device, which are designed to test the patient cognitive, mental, motoric and/or physical condition.

Biomarker assessment methods may include one or more of saccadic eye movement assessment (such as saccadic movement), memory testing, adaptive tracking, finger tapping assessment, body sway assessment, visual analog scale match, and/or other assessment methods. In some embodiments, the applications are designed to test the patient using various known in the art cognitive tasks, including, for example, reaction time, attention, visuospatial span, spatial-temporal reasoning, name recall, narrative recall, face recall, name-face association, construction, verbal fluency, object naming, implicit memory, logical reasoning and/or other cognitive tasks.

In some embodiments, the collected parameters are stored in a memory of the patient interface, for example as described in FIG. 9. Optionally, the collected parameters are transferred to the physician's interface, for example as described in FIG. 9. In some cases, the parameters are transferred in real-time, during use of the MDI device.

During use, if the patient's symptoms are not mitigated and/or adverse effects above a certain threshold are present, according to objective and/or subjective measures, or for any other reason, the dose and/or the regimen may be modified. In some embodiments, the patient initiates a dose/regimen modulation by entering personally perceived PD effects via the patient interface. The systems may perform a series of data collection pertaining to other PD effects, objective and subjective, analyze the data in correlation to the personally perceived PD effects entered by the patient and to safety cutoff values, and either alerts the patient to the allowed, recommended and/or prescribed dose/regimen comparatively. For example, the system may alert the patient/practitioner to a non-safe dose/regimen or to an ineffective dose/regimen, and/or alert the patient/practitioner to a different dose/regimen according to the prescribed dose/regimen or past experiences logged in the database of the system, and/or notify the patient to ramifications of any given dose/regimen per time of day, activity and location ("too early in the day", "too far from home", "in a moving vehicle" and the likes). The PD-based personalization of the dose/regimen is monitored and recorded for future reference, and may be translated to a re-determined initial vaporized amount and regimen.

Thereafter, the patient interface automatically modifies the dose and/or regimen, while restricting the modulation by the safety thresholds and/or other thresholds, such as thresholds initially defined by the physician. Additionally or alternatively, the physician, upon receipt of the personal PD effects, modifies the dose and/or regimen, for example using the patient interface, and instructions are transferred to the patient interface and/or to the MDI device. Optionally, the physician re-selects a personal PD profile for the patient and/or re-selects a personal dosing/regimen to suit a therapeutic window of the patient. Additionally or alternatively, the patient and/or physician operate the MDI device manually (for example by activating buttons or switches on the device), to set the desired dosing and/or regimen.

Example 5

Treatment Using a Combination of Active Agents

According to some embodiments of the present disclosure, active agent combination treatment may include active agents that provide a synergistic effect, active agents that provide the same effect but each with different advantages or disadvantages, active agents that potentiate or attenuate other one another or other active agents (e.g., alter the effective therapeutic window or therapeutic index of one-another), active agents that provide contradictory effect, such as, for example, THC is counteracted by CBD, and active agents that have counteractive but desired effects and need to be spaced apart.

The potential benefits of a combination treatment which is effected, according to some embodiments, for example, by use of the presently described device, include, without limitation, precise dosing for each of the plurality of active agents and for each inhalation event and precise proportion between active agents and/or inhalation events.

For example, in some embodiments, the ability to deliver complex regimens that involve varying doses and/or varying administration time intervals for each agent. For example, the device may include a repository or one or more magazines of dose units, at least some of which comprising different amount and/or combination of one or more active agents. Accordingly, a dose unit or a set of dose units may be selected to provide a desired result or combination. Additionally or alternatively, the combination is provided by controlling the amount of active agent allowed to vaporize from one or more of the dose units, effected by temperature and duration of heating the substance comprising the agents (e.g., the plant material) and/or by controlling airflow through the substance.

Other advantages of the presently provided combination treatment may include increased compliance and reduction in user errors, effected at least by precise monitoring thereof, and regimen adjustments performed in real-time to correct errors and/or respond to unexpected events.

Control over the combination treatment may include simultaneous or substantially simultaneous delivery of more than one active agent, which may be carried out for example using:
  i. A dose unit having more than one active agents;
  ii. A plurality of dose units having different active agent combinations used controllably in rapid succession; and/or
  iii. Simultaneous use of a plurality of dose units having different active agents.

The timing between inhalation events of two or more different active agents or active agent compositions may be selected based upon their PK and/or PD effects and the desired overlap or lack thereof between active agents, optionally taking into account an effect that one active agent might have on the PK and/or PD effects of the other when present in the user at the same time. Optionally, care is given to reduce the number of inhalations to improve patient comfort and/or compliance.

A co-administration regimen, according to some embodiments of the present disclosure, includes, for example one or more of:
  i. Each active agent having its own independent regimen;
  ii. Active agents are delivered in dependent fashion (e.g., second active agent is delivered within a given time period after the administration of the first active agent);
  iii. Active agents given on demand, for example, an immediate dose is delivered upon user request to treat breakthrough pain or to reduce a psychoactive effect;

A simultaneous delivery of two (or more) active agents may include the use of:
  a. A plant (e.g. cannabis) having more than one naturally occurring active agents therein (note: plant variety may be chosen to provide a desired active agent ratio);
  b. Mixing more than one plant materials having different drug combinations; for example each comprising a different active agent or having a first active agent in excess compared to the other plant material that comprises a second active agent in excess;
  c. A combination of extracted active agents, or optionally adding an one or more extracts comprising one or more active agents to a plant material also comprising one or more active agents;

A co-administration regimen can be delivered, according to some embodiments of the present disclosure, by providing different dose units comprising different active agents within the device and controlling the relative vaporization timing thereof so as to allow selective vaporization of the different active agents or active agents composition, each for different inhalation events (e.g., by selecting a dose unit having a desired composition and/or by matching a plurality of dose units to provide a desired amount/combination of active agents).

Some active agents' combinations, which can be effectively delivered using the device and methods provided herein, according to embodiments of the present disclosure, include, without limitation, nicotine and THC, caffeine and THC and CBD and THC.

An example for a combination treatment for attenuating THC-induced psychoactivity include, without limitation, a dose of 10-60 mg CBD administered by inhalation prior to, during or after inhalation of THC or on appearance/observation/perceiving of THC induced psychoactivity, using repeated inhalation at intervals of up to 1 minute for a maximum of six doses (totaling up to 360 mg of CBD a day) or until symptom reduction.

An alternative combination treatment for attenuating THC-induced psychoactivity include, without limitation, a dose of 10-40 mg limonene administered by inhalation prior to, during or after inhalation of THC or on appearance/observation/perceiving of THC induced psychoactivity, using repeated inhalation at intervals of up to 1 minute for a maximum of six doses (totaling up to 240 mg of limonene a day) or until symptom reduction.

Table 3 below presents dosing regimen useful in treating disorders and diseases responsive to co-administration of THC and CBD using the device and methods presented herein. The regimens represent Peri-Disorder/event, episodic and chronic (12 hour treatment period) treatment for average patient size.

TABLE 3

| Disorder/Disease | Regimen |
| --- | --- |
| Neo-Natal Ischemic Brain Injury | CBD: 1-10 mg/kg x2-6/day, each followed at 5-20 minute interval by THC: 0.1-0.5/kg (kg = body weight) |
| Impaired Sucking reflex—Failure to Thrive | CBD: 1-10 mg/kg x2-6/day, each followed at 5-20 minute interval by THC: 0.1-0.5/kg |
| Autism | CBD: 10-60 mg x2-6/day, each followed at 5-20 minute interval by THC: 0.2-2 mg |
| ADHD | CBD: 10-60 mg x2-6/day, each followed at 5-20 minute interval by THC: 0.2-2 mg |
| Epilepsy | Prevention: CBD: 10-60 mg x2-6/day, each followed at 5-20 minute interval by THC: 0.2-2 mg x2-6/day Attack: CBD: 10-60 mg x2-6/day, each followed at 5-20 minute interval by THC0.5-5 mg. If needed, THC administration may continue at the same dosage range till sedation |
| Migraine/cluster headache | Prevention: CBD: 10-60 mg/2-6 followed at 5-20 minute interval by THC: 0.2-2 mg x2-6/day Attack: CBD: 10-60 mg/2-6 followed at 5-20 minute interval by THC0.5-5 mg till sedation |
| Alzheimer's Disease | CBD: 10-60 mg x2-6/day, each followed at 5-20 minute interval by THC: 0.2-2 mg |
| Stroke | CBD: 10-60 mg x2-6/day, each followed at 5-20 minute interval by THC: 0.2-2 mg |
| neurodegenerative disorders | CBD: 10-60 mg x2-6/day, each followed at 5-20 minute interval by THC: 0.2-2 mg |
| Dystonia | CBD: 10-60 mg x2-6/day, each followed at 5-20 minute interval by THC: 0.2-2 mg |

Following is an example for treatment of a patient having back pain using a combination of THC and CBD. Treatment is administered using a device according to the present disclosure. The regimen is performed in order to maintain the patient within the following therapeutic window:
1. Pain is to be maintained below a given threshold, at least as long as the patient is awake.
2. Psychoactive effects are to be maintained below a given threshold that will allow the patient a desired level of activity and awareness.
3. The psychoactivity level may be increased in cases of breakthrough pain and during nighttime when drowsiness is preferred.

FIG. 21 is a graphical representation of a regimen for the treatment of pain by pulmonary delivering of a combination of two active agents, THC and CBD, wherein the dashed line represents the level of the adverse (psychotropic) effect, and the solid line represent the pain level, and wherein THC is inhaled by using a dose unit of 0.5 mg (empty triangle), 1.2 mg (grey triangle) and 2.4 mg (black triangle), and CBD is inhaled by using a dose unit of 25 mg (empty diamond).

As can be seen in FIG. 21, the patient is provided with a dose unit containing a 25 mg dose of CBD about 20 minutes before each dose of THC, beginning when the patient wakes up in the morning. The first dose unit contains 1.2 mg THC. This is more than the usual dose because it is required to remove residual pain buildup that occurred during the night. This is followed by using a dose unit containing 25 mg CBD plus 0.5 mg THC paired doses about once every two hours. As seen in FIG. 21, the pain level decreases and remains constant while psychoactivity is kept at a low level.

As can further be seen in FIG. 21, at about 2 PM, after the patient takes a CBD precursor dose, breakthrough pain is manifested unexpectedly. This event is input into the device system via the user interface, and accordingly the user is instructed (with or without physician intervention) to administer to himself a dose of 2.4 mg THC. This large THC dose is taken concomitantly with an additional dose 25 mg CBD in order to reduce or prevent a predicted increase in psychoactivity, and about two hours after administering the large THC dose, yet another CBD dose is administered.

As can further be seen in FIG. 21, once the breakthrough pain has diminished, the combined dosing of 25 mg CBD plus 0.5 mg THC is resumed. It is noted that in the first instance the combined dosing is taken in view of the excess THC taken earlier due to breakthrough pain.

Finally, as can be seen in FIG. 21, drowsiness is desired before bedtime and hence the psychoactivity threshold shifts to allow a higher level of the adverse effect. Accordingly, the last dose is a high 1.2 mg THC dose taken alone without a CBD precursor.

Example 6

User/Physician Interface Input and Output

The following is a presentation of user interface input categories, according to some embodiments of the present disclosure.

Generally and optionally the user interface can provide feedback from the user, indicative of one or more of:
1. User identity;
2. Perceived or measured therapeutic or adverse effects pertaining to the treatment/dosage/regimen;
3. Instructions/requests from the user regarding timing and/or acceptable and/or desired therapeutic or adverse effects.

The user identity can be monitored by user response (password, pattern entry or other challenge request) or by biometric means (facial and/or voice recognition, fingerprint, retina scan). Use activity (device holding/grasping, inhaling, inactive) can be monitored by heat sensing, electric charge and accelerometry.

The perceived or measured therapeutic or adverse effects may include one or more of treatment related effects (pain/nausea/PD level) and/or side effects (PD), and may be provided in different classes of indications.

Optionally the user may be interrogated periodically (e.g., once a day or every several hours or upon preparation for inhalation or as a requirement before inhalation) and may be limited to only a part of the period of treatment. For example, interrogation may cover the initial 6, 12 or 24 hours in order to determine a regimen and then repeated periodically (e.g. once a day or once a week or once a month or upon desire) in order to confirm the regimen and/or readjust it in view of progress.

Optionally the user may interact with the interface at will.

The user interface can be used for user-controlled indication/information. Examples include voluntarily data input, or in response to an interrogation by the device and/or a practitioner (e.g., a response to a request to grade a degree of pain and/or a degree to a psychoactive effect).

A user semi-controlled indication is exemplified by a user who participates in measuring his own status. In such cases some user compliance is required for these indications, but the user has little or no control on the consequences as these are expressed in the device's output and response, such as the determination of the pre-determined vaporized amount.

Examples include:
a user subjecting himself to a sensor (e.g., eye redness or heart rate sensor);
a user performing a test, such as playing a game, or instructing the user to perform a task, such as for example, following a mark on a screen with his eyes while having his pupils monitored, dragging a mark on a screen through a pattern without touching walls; completing mental tasks such as solving mathematical equations or answering verbose questions; playing memory and/or concentration games; etc.

A user uncontrolled indication includes a user interface which is associated with sensing one or more user properties for providing an indication of the user's status and use that information to control the determination of the pre-determined vaporized amount, the dose and/or the regimen, thereby controlling one or more therapeutic/adverse effects in the user.

Examples include:
Sensing mouth temperature or pupil size that may indicate a high PD effect;
Sensing tremor or a variation in tremor;
Sensing heart rate and/or blood pressure, for example by interaction with a sensor worn by the user and/or implanted in the user;
Sensing airflow properties in the device as induced by the user. Such airflow properties may include one or more of flow rate and/or the rate of increase in flow rate and or a degree and/or rate of variation in flow during an inhalation event. For example considering changes from one or more baseline values, which may indicate for example an improvement or a decline in wellbeing (e.g. as manifested by strength and/or pain that may affect the inhalation properties/patterns for the user).

Optionally, the user may provide instructions/requests via the user interface to the device in advance and/or during the inhalation session.

Examples include:
Defining a given regimen/sensed effect as to be saved in order that it may be repeated in future uses. For example, one psychoactive state may be defined by the user as a desired "default" condition while another may be defined as "sufficiently pain free" and yet another as "good for performance of specific tasks (e.g., driving). Such designations may be subject to constraints imposed by the device based for example on a physician's input or a maximal allowed dosage for a period of time and the like. Optionally, in subsequent inhalations the user may be prompted to indicate how well this desired effect was met, in order to improve the dosing regimen on an ongoing basis;
General regimen requests (e.g. sleep times where drowsiness becomes a desired affect and no longer an undesired side effect; times where special awareness is needed, such as work or study or driving sessions);
Optionally a dose request or a regimen request or a dosing regimen proposed by the user is sent to a physician for approval before being implemented by the device. Optionally the request is sent only when the device cannot execute the request without exceeding pre-entered constraints. Optionally some constraints are made rigid and cannot be exceeded regardless of a physician approval (e.g., lethal dosage);
The user interface may allow a user to chart/plan his psychoactive state throughout the day manually (e.g., on a touch screen or an image that is captured by the device, etc.), and have the device adapt the regimen accordingly. A user may draw the levels of psychoactivity on a time based chart representing a desired psychoactivity throughout the day. Optionally, the user defines the psychoactivity state and treatment state, namely the user is involved in determining the therapeutic window, and the device calculates an adequate regimen that is known or expected to achieve the desired PKPD balance, as long as it also falls within any optional pre-imposed constraints;
Unplanned changes (e.g., unexpected need to perform a task that requires a heightened awareness or other schedule change or sudden medical requirement like breakthrough pain);
Snoozing the device or missing a session. Optionally the device imposes a limitation on the amount of time allowed for snoozing;

According to some embodiments, the device provides temporal and location dependent treatment, which is based on sensors in communication with the device and patient's personal treatment information. The sensors provide time and location data (based on GPS/WiFi or the like) and/or location data is provided via a user interface and boundaries are determined in which a particular therapeutic window is in effect, thereby selecting a time/location-dependent dose and/or regimen, as well as specific time/location-dependent set of alerts.

Setting specific location and/or time dependent constraints on dose/regimen/device operation via, e.g., GPS-based or WiFi-based or input-based geographic location information (e.g., geo-fencing). For example, in some areas different dose and/or regimen boundaries are imposed (e.g., work versus home). For example, a default degree of freedom is prescribed by a physician when providing the device. One or more other degrees of freedom may be set in advance or calculated upon request. These degrees of freedom may be manifested as boundaries in a treatment (therapeutic window). Optionally, the treatment window may be location dependent. For example, a user's workplace may be designated as area which will not allow the user to reach a certain psychoactive state, while a user's home address, and optionally during late evening and nighttime, be considered as a free psychoactivity area (other types of places are contemplated for any sort of default pre-setting). Optionally, the alerts provided by a user interface are location sensitive, such that for example sound or volume may be restricted in a workplace; and A user's interface equipped with a database for storing, analyzing and using information regarding the user's preferences, dated activities and locations and the like.

User interface output may include automated text messages provided for example by email or text messages to the user, a care giver of physician, or a medical treatment center.

The output may be available generally or individually to individual users.

Following are some specific examples of interest:

Outputs and/or alerts, provided for the patient, a caregiver or any pre-designated individual or system, designed to assist and/or protect a user when in a relatively high psychoactive state. The following may be performed when an adverse effect is perceived, and/or anticipated and/or upon request by the user, such as alerts to designated recipients (e.g., relatives or neighbors) when certain psychoactive levels are reached;

Setting an adverse effect (psychoactive) level-dependent message such as "do not disturb" on the user's personal smartphone and other devices. For example, when the user experiences a certain adverse effect level, calls from pre-selected callers are blocked and/or responded automatically with a text message to indicate that the user is not available, thus potentially reducing anxiety during the treatment session;

When an acute adverse effect is anticipated (e.g., based on a regimen and/or during a treatment session) an 'anticipating alert" may be given. In such case, the interface may guide the user to a safe environment, offer the possibility of communicating the situation to pre-selected recipient, suggest to have food/beverage ready in order to mitigate the adverse effect, prepare an antidote dose from the device as an emergency precaution, and/or provide a notification to a care giver and/or physician;

Visual real-time representation of the adverse effect level of a user may be provided, for example as a graph, chart, number, bar, line or any other visual representation. Optionally this representation may be viewed by a user and/or a physician and/or a care giver at all times. The visual representation may include data derived from one or more of the inhaler regarding a dose taken, and PK/PD algorithms which simulate the psychoactive PD, the user's history for inhaler use and its effect and sensed information.

The physician interface may include, for example, the regimen as provided by the physician. This regimen may be imposed on the user or subject to the user's acceptance. Optionally, the regimen includes a degree of freedom that allows the user and/or the device to modify a regimen without physician intervention or approval. In such cases the physician may be notified before and/or after the treatment session.

The physician interface may also be configures to present a set of specific alerts when a user reaches certain adverse effect levels (e.g., specific psychoactive levels), or when the use is about to reach specific adverse effect levels, so physician can track all the available parameters while user is in that state. Optionally, the physician can set a "personalized message" to be sent to the user once the user reaches/about to reach specific adverse effect levels.

The physician may be able to approve/reject/modify dosing regimens selected or requested by the user.

According to embodiments of the present disclosure, a user/physician interface for obtaining input in any category can include any interface that allows the above examples (including user control or lack thereof and visual schematics, sound, text etc.). Sensors can be integrated in the inhaler device or otherwise be associated or in communication therewith. The sensors can be dedicated sensors or advantage may be taken from a device for other use (e.g., communication with a pacemaker for cardiac related properties).

Environmental sensors can provide information on user activity as an indication for the user's PD and/or wellbeing. Examples include heart-rate sensors, pace/motion/velocity sensors, and GPS location.

Example 7

Regimen of an Active Agent

Following is a table detailing dosing and/or regimen and indications for pulmonary delivery of an active agent, THC from a cannabis plant, according to some embodiments of the present disclosure.

Table 4 below lists dosing and/or regimen according to syndromes (symptoms, events, disorders and diseases), which are treatable and/or therapeutically responsive to THC. A dose, individual or part of a regimen, corresponds to a single pre-determined vaporized amount of THC.

Different treatments may include prophylactic treatment (pre-disorder/event treatment), namely pulmonary delivery of THC via the device presented herein when an event is expected, based on time and/or circumstance wherein a pre-event dose may be prescribed; acute or episodic treatment, namely pulmonary delivery of THC via the device presented herein when an episode occurs and the duration of the symptom(s) (the time period until symptom(s) subside); semi-chronic or chronic treatment, namely pulmonary delivery of THC via the device presented herein regardless of perception of an acute symptom or when an event/symptom(s) may last for an extended period of time.

Treatments are presented in Table 4 below based on the above groups and for average patient size, for a 12 hour treatment period.

TABLE 4

| Syndrome | THC Dose |
| --- | --- |
| Neurological | |
| Neo-Natal Ischemic Brain Injury | 0.1-0.5/kg x2-6/day |
| Impaired Sucking reflex—Failure to Thrive | 0.1-0.5/kg x2-6/day |

TABLE 4-continued

| Syndrome | THC Dose |
|---|---|
| Autism | 0.2-2 mg x2-4/day |
| ADHD | 0.2-2 mg x2-4/day |
| Epilepsy | Prevention-0.2-2 mg x2-4/day |
| | Attack—0.5-5 mg till sedation |
| Migraine | Prevention-0.2-0.2 mg x2-6 |
| | Attack—0.5-5 mg till sedation |
| Alzheimer's Disease | 0.2-2 mg x2-4/day |
| Stroke | 0.2-2 mg x2-4/day |
| neurodegenerative disorders | 0.2-2 mg x2-4/day |
| Dystonia | 0.2-2 mg x2-4/day |
| Huntington's Disease | 0.2-2 mg x2-4/day |
| Tourette's Syndrome | 0.2-2 mg x2-4/day |
| Parkinson's Disorder | 0.2-2 mg x2-4/day |
| Sleep Apnea | 0.2-2 mg/day prior to sleep |
| Tinnitus | 0.2-2 mg x2-4/day |
| Vertigo | 0.2-2 mg x2-4/day |
| Neuropathic Pain | 0.2-5 mg x2-4/day |
| Ophthalmology | |
| Glaucoma | 0.2-2 mg x2-4/day |
| Macular degeneration | 0.2-2 mg x2-4/day |
| Endocrinology | |
| Diabetes Mellitus | 0.2-2 mg x2-4/day |
| Pre Menstrual Syndrome | 0.2-2 mg x2-4/day |
| Psychiatric | |
| Depression | 0.2-2 mg x2-4/day |
| Schizophrenia | 0.2-2 mg x2-4/day |
| Anxiety Disorders (Panic , OCD and PTSD) | 0.2-2 mg x2-4/day |
| Autoimmune/Inflammatory mediated Diseases | |
| Arthritis | 0.2-2 mg x2-4/day |
| Osteoporosis/pain | 0.2-2 mg x2-4/day |
| Multiple Sclerosis | 0.2-2 mg x2-4/day |
| Amyotrophic Lateral Sclerosis (ALS) | 0.2-2 mg x2-4/day |
| ankylosing spondylitis | 0.2-2 mg x2-4/day |
| psoriasis | 0.2-2 mg x2-4/day |
| psoriatic arthritis | 0.2-2 mg x2-4/day |
| Allergy, Pruritus | 0.2-2 mg x2-4/day |
| Autoimmune Retinopathy | 0.2-2 mg x2-4/day |
| Autoimmune chronic active hepatitis | 0.2-2 mg x2-4/day |
| Celiac | 10-60 mg/2-6/day |
| Autoimmune pancreatitis (AIP) | 0.2-2 mg x2-4/day |
| Insulin-dependent diabetes mellitus | 0.2-2 mg x2-4/day |
| Meniere's Disease | 0.2-2 mg x2-4/day |
| Musculoskeletal | |
| Fibromyalgia | 0.2-2 mg x2-4/day |
| Osteoporosis | |
| Cardiovascular | |
| Myocardial Infarct | During Attack—0.5-5 mg till sedation with monitoring of blood pressure |
| Pulmonary | |
| Asthma | 0.2-2 mg x2-4/day |
| Chronic Obstructive Pulmonary Disease | 0.2-2 mg x2-4/day |
| Gastroenterology | |
| Inflammatory Bowel Disease | 0.2-2 mg x2-4/day |
| Inflammatory Bowel Syndrome | 0.2-2 mg x2-4/day |
| Urology/Gynecology | |
| Irritable bladder | 0.2-2 mg x2-4/day |
| Dysmenorrhea | 0.2-2 mg x2-4/day |
| Appetite/Weight | |
| CINV | 0.2-2 mg x2-4/day |
| HIV wasting | 0.2-2 mg x2-4/day |
| Anorexia Nervosa | 0.2-2 mg x2-4/day |

Example 8

Plants Comprising Psychoactive Agent(s)

Psychoactive agents affect the central nervous system in various ways by influencing the release of neurotransmitters (chemical messengers within the nervous system, such as acetylcholine, serotonin, dopamine, norepinephrine), or mimicking their actions. Psychoactive agents can be classified based on their effects, such as, without limitation, sedative agents, stimulating agents, excitants and enhancers of mental alertness and physical activity; agents that reduce fatigue, appetite enhancers/suppressants, hallucinogenic agents, perception-altering agents, mood-altering agents, depressants and stimulants.

The following are some examples for plants that can be used as a source for vaporizable active agent(s) according to embodiments of the present disclosure, for having medicinal as well has psychoactive properties.

Opium poppy (*Papaver sornniferurn*; Papaveraceae) is known for its analgesic, sedative, hypnotic and hallucinogenic effects in mammals. The active agents in opium include alkaloids, whereas more than 30 alkaloids have been identified in opium, including morphine, codeine, thebaine, papaverine, and more. Medicinal uses of opium and/or active agents originating in opium include analgesics, severe pain management (particularly morphine), insomnia in conjunction to pain or not (laudanum), cough suppression (codeine), and diarrhea control and paregoric.

Kava (*Piper methysticum*; Piperaceae) is known for its sedative, depressant and hypnotic activity. The active agents in Kava include kavalactones, such as kavain, yangonin, 10-methoxyyangonin, 11-methoxyyangonin, 11-hydroxyyangonin, desmethoxyyangonin, 11-methoxy-12-hydroxydehydrokavain, 7,8-dihydroyangonin, 5-hydroxykavain, 5,6-dihydroyangonin, 7,8-dihydrokavain, 5,6,7,8-tetrahydroyangonin, 5,6-dehydromethysticin, methysticin and 7,8-dihydromethysticin. Kavain has a modest analgesic effect, about twice that of aspirin, and acts as a mild anaesthetic and tranquilizer. Various kavalactones produce a various psychoactive effect, and have been shown useful as tranquilizers and sleep promoters. It has been shown that leaves, stem, and bark can be used as muscle relaxant to relieve stiffness and muscle fatigue, and plant extracts have been used as anti-anxiety medicine.

*Datura* spp (*Datura stramonium*, Jimson weed; Solanaceae; Nightshade family) is known for its aphrodisiac and hallucinogen effects in mammals. The active agents in datura include tropane alkaloids such as atropine, hyoscyamine, scopolamine and more. Uses of datura (whole plant and parts thereof) and/or active agents originating from datura include arousal of sexual drive, stimulation and thereafter suppression of the central nervous system and induced hallucinations.

Peyote (*Lophophora williamsii* cactaceae) contains some 30-40 different potent alkaloids, with mescaline being the most active hallucinogen in the group. Peyote is typically used as a sexual stimulant and as a hallucinogen.

Ayahuasca (Vine of the Soul, *Banisteriopsis caapi*; Yagé) includes many alkaloids which induce hallucinogenic activity in human and share structural similarities with serotonin. It has been used as an anti-depressant and to induce hallucination.

Other plants comprising active agent(s) with known psychoactive properties include, without limitation:

Angiosperm families, such has Solanaceae (nightshade), *Atropa belladonna* (belladonna)(hallucinogen), *Datura* spp.

(jimsonweed)(hallucinogen), *Mandragora officinarum* (mandrake)(hallucinogen), *Nicotiana* spp. (tobacco)(stimulant/depressant), *Rubiaceae* (coffee), *Papaver somniferum* (Opium poppy)(depressant), *Erythroxylaceae coca* (coca) (stimulant), *Convolvulaceae* (morning-glory), *Cactaceae*, *Lophophora williamsii* (peyote)(hallucinogen), *Piperaceae*, *Piper methysticum* (kava)(depressant), *Malphiginaceae* and *Banisteriopsis* sp. (ayahuasca) (hallucinogen).

Table 5 summarizes some of the plants comprising active agents which can be used in the context of some embodiments of the present disclosure.

TABLE 5

| Group | Subgroup | Chemical class | Examples |
|---|---|---|---|
| Sedatives | Phyto-compounds | Terpenoids | *Mentha piperita*, *Zanthoxyumschinifolium* *Mentha X* *Kaempferia galanga* *Lactuca virosa* *Cichorium intybus* *Galphimia glauca* (*cav.*) *Kuntze* (*Malpighiaceae*) *Aquilaria sinensis* *Nardostachys jatamansi* *Myricaria elegans Royle* (*Tamaricaceae*) |
| Sedatives | Phyto-compounds | Flavonoids | *Albizzia* *Zizyphus vulgaris* *Ziziphus jujuba Mill* var. *spinosa* (*Bunge* *Zizyphus. jujuba* is *Valeriana officinalis* *Chamomilla* *recutita* (*L*) *Eremostachys laciniata* (*L*) *Bunge* *Lamiaceae* |
|  |  | Alkaloids | *Salvia plebeia* (*Labiatae*). *S. plebeia*). *Zizyphus vulgaris* *Atropa bell-donna L* *Datura stramonium* *L.*(*Solanaceae*) |
|  |  | Saponins | *Zizyphus vulgaris* (*Rhamnaceae*) *Bunge* *Ziziphus jujuba* |
|  | Sedative Botanical compounds not referred to as phyto-chemicals | Quinoids Lactones Cinnamates Nitrite Valepotriates and iridoids Extracts | *Ternstroemia pringlei* *Pusatilla alpine* Subsp *Kaempferia galanga* *Ixora pavetta Vahl.* (*Rubiaceae*) *Valeriana officinalis L.* (*Valerianaceae*) *Mentha arvensis* *Linn* (*Labiatae* *Cissus quadrangularis Linn* *Zanthoxylum* *budrunga W* exhibited *Byrsocarpus coccineus* *Millettia thonningii*, *Ocinum sanctum* and *Securitaca longepedunculaca* *Ducrosia anethifolia* (*DC*) *Boiss.* (*Apiaceae*) *Lavendula angustifolia Mill*, *Melissa* *officinalis L*, *Origanum* *vulgare L*, *Crataegus* *monogyna Jaeq*, and *Crataegus oxyacantha L* *Cecropia pachystachya* *Mart.* *Casimiroa pringlei* *Citrus sinensis*, |
| Stimulants |  |  | *Citrus limon*, *Ternstroemia pringlei*, *Ternstroemia sylvatica*, *Casimiroea edulis*, *Galphimia glauca*, and *Cymbopogon citratus* *Gotu Kola*, *Centella asiatica*, *Hoodia gordonii* *Caffeine* *Catha edulis* *Ephedra sinica*, *Coca* Tea *Piper betle* *Ginseng* *Rhodiola rosea* |
| Hallucinogens |  |  | *Lophophora williamsii* (*peyote*), *Datura* spp *Mandragora officinarum* (*mandrake*), peyote, *Banisteriopsis* sp. (*ayahuasca*), *Malphiginaceae*, hallucinogen marijuana (*Cannabis*) |
| Depressants |  |  | *Papaver somniferum* (Opium poppy), *Papaveraceae*, *Piper methysticum* (*kava*), *Piperaceae* |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A cellular phone including circuitry for use as a user interface of an inhaler device for pulmonary delivery of at least one active substance for treating pain, nausea or sleeplessness, the circuitry configured for:
   collecting, from an individual user, data pertaining to at least one effect induced by the at least one active substance; the collecting comprising obtaining feedback data via interaction between the user and the user interface, the interaction including obtaining an indication of a level of a therapeutic effect on pain, nausea or sleeplessness as perceived by the user themselves, and an indication of a level of a psychoactive effect of the at least one active substance;

storing the collected feedback data in a memory;
automatically deducing a psychoactive state of the user based on the collected feedback data; and
communicating the collected feedback data to one or more of: an external device, the inhaler device, a practitioner, and the user for the generating of a suggested dose and/or regimen of the at least one active substance based on the collected feedback data, said suggested dose selected in order to balance between a reducing effect of said pain, nausea or sleeplessness and said psychoactive effect on the user.

2. The cellular phone according to claim 1, wherein the circuitry is configured to obtain the feedback data after inhalation of the user from the inhaler device.

3. The cellular phone according to claim 1, wherein one or more components of the cellular phone are configured to function as sensors for obtaining the feedback data.

4. The cellular phone according to claim 3, wherein the one or more components comprise(s) one or both of:
 (a) a touch screen for assessment of one or more of: dexterity, hand-eye coordination, memory and/or cognitive state of the user;
 (b) one or more of a gyroscope, an accelerometer, a proximity sensor and a gesture sensor for assessment of motoric skills of the user.

5. The cellular phone according to claim 3, wherein the one or more components include a camera and/or a light source for detecting one or more of: visual tracking, saccade variance, eye vascular expansion, pupil dilation, pulsation in the user.

6. The cellular phone according to claim 3, wherein the one or more components include a magnetometer for assessment of orientation of the user and/or a GPS to provide information regarding a geographic location of the user.

7. The cellular phone according to claim 3, wherein the one or more components include a speaker and/or a microphone for assessment of auditory and/or vocal skills of the user.

8. The cellular phone according to claim 3, wherein the one or more components include a temperature sensor for assessment of a user's body temperature.

9. The cellular phone according to claim 1, including one or more games and/or tasks which the user interacts with for obtaining the feedback data.

10. The cellular phone according to claim 9, wherein the tasks include manually and/or visually tracking a target.

11. The cellular phone according to claim 9, wherein the tasks include mental and/or cognitive tests.

12. The cellular phone according to claim 11, wherein the test includes a visual analog scale in which the user responds by specifying their level of agreement to a statement by indicating a position along a bar or line.

13. The cellular phone according to claim 1, configured to display a question to the user regarding the therapeutic effect and/or the adverse effect and to collect the user's response to the question.

14. The cellular phone according to claim 1, wherein the circuitry comprises a communication module configured to transfer the obtained feedback data to a physician interface.

15. The cellular phone according to claim 1, wherein the circuitry is configured to receive instructions and/or requests from the user regarding one or more of: delivery timing, acceptable adverse effects, desired therapeutic effects.

16. The cellular phone according to claim 1, wherein the circuitry is configured to generate the suggested dose and/or regimen of the at least one active substance.

17. A kit comprising:
 at least one cellular phone according to claim 1;
 at least one inhaler device in communication with the cellular phone.

18. The kit according to claim 17, wherein the inhaler device comprises a cartridge including plant material from which the at least one active substance is vaporized to be delivered to the user.

19. The kit according to claim 18, wherein the plant material comprises cannabis.

* * * * *